United States Patent
Attie et al.

(10) Patent No.: US 10,189,882 B2
(45) Date of Patent: Jan. 29, 2019

(54) METHODS FOR TREATING MYELODYSPLASTIC SYNDROMES AND SIDEROBLASTIC ANEMIAS

(71) Applicant: Acceleron Pharma Inc., Cambridge, MA (US)

(72) Inventors: Kenneth M. Attie, Boston, MA (US); Christopher Robert Rovaldi, Swampscott, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 14/958,551

(22) Filed: Dec. 3, 2015

(65) Prior Publication Data

US 2016/0289286 A1    Oct. 6, 2016

Related U.S. Application Data

(60) Provisional application No. 62/155,395, filed on Apr. 30, 2015, provisional application No. 62/088,087, filed on Dec. 5, 2014, provisional application No. 62/086,977, filed on Dec. 3, 2014.

(51) Int. Cl.

| | |
|---|---|
| *A61K 38/00* | (2006.01) |
| *C07K 14/475* | (2006.01) |
| *A61K 38/17* | (2006.01) |
| *A61K 38/18* | (2006.01) |
| *C12Q 1/6883* | (2018.01) |
| *C07K 14/71* | (2006.01) |
| *C07K 14/495* | (2006.01) |
| *A61K 35/14* | (2015.01) |
| *A61K 35/18* | (2015.01) |

(52) U.S. Cl.
CPC .......... *C07K 14/475* (2013.01); *A61K 35/14* (2013.01); *A61K 35/18* (2013.01); *A61K 38/179* (2013.01); *A61K 38/1816* (2013.01); *C07K 14/495* (2013.01); *C07K 14/71* (2013.01); *C12Q 1/6883* (2013.01); *C07K 2319/30* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,319,499 B1 | 11/2001 | Elliott |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,988,973 B2 | 8/2011 | Sherman |
| 8,058,229 B2 | 11/2011 | Seehra et al. |
| 8,216,997 B2 | 7/2012 | Seehra et al. |
| 8,343,933 B2 | 1/2013 | Knopf et al. |
| 2009/0005308 A1 | 1/2009 | Knopf et al. |
| 2009/0047281 A1 | 2/2009 | Sherman |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2011/0038831 A1 | 2/2011 | Seehra et al. |
| 2012/0028276 A1 | 2/2012 | Moore et al. |
| 2013/0243743 A1 | 9/2013 | Seehra et al. |
| 2015/0361163 A1 | 12/2015 | Kumar et al. |
| 2016/0039922 A1 | 2/2016 | Attie |
| 2016/0046690 A1 | 2/2016 | Kumar et al. |
| 2016/0289286 A1 | 10/2016 | Attie et al. |
| 2017/0037100 A1 | 2/2017 | Kumar |

FOREIGN PATENT DOCUMENTS

| | | |
|---|---|---|
| WO | WO-2004/034962 A2 | 4/2004 |
| WO | WO-2006/012627 A2 | 2/2006 |
| WO | WO-2008/076437 A2 | 6/2008 |
| WO | WO-2008/097541 A2 | 8/2008 |
| WO | WO-2010/019261 A1 | 2/2010 |
| WO | WO-2011/020045 A1 | 2/2011 |
| WO | WO-2013/059347 A1 | 4/2013 |
| WO | WO-2014/066487 A2 | 5/2014 |
| WO | WO-2015/161220 A1 | 10/2015 |
| WO | WO-2016/090077 A1 | 6/2016 |
| WO | WO-2016/183280 A1 | 11/2016 |

OTHER PUBLICATIONS

Bejar et al. Validation of a prognostic model and the impact of SF3B1, DNMT3A, and other mutations in 289 genetically characterized lower risk MDS patient samples. Abstract. Blood, vol. 118, No. 21. Abstract No. 969. (Nov. 18, 2011).*
Itoh et al. Sideroblastic anemia associated with multiple myeloma in Turner's syndrome. Abstract. Internal medicine Tokyo, Japan, vol. 31, No. 4, pp. 483-485 (Apr. 1992).*
Malcovati et al. Granulocyte JAK2 (V617F) mutation status in myeloid neoplasms with ringed sideroblasts. Abstract. Blood, vol. 108, No. 11, Part 1, pp. 256A (Nov. 16, 2006).*
Pereria et al. X-linked sideroblasticanemia (XLSA): Two new mutations identified in males. Abstract. Haematologica, vol. 95, Supp. Suppl. 2, pp. 716-717. Abstract No. 1854 (Jun. 2010).*
Akhtari, M., "When to Treat Myelodysplastic Syndromes," Oncology, vol. 25(6): 480-486 (2011).

(Continued)

*Primary Examiner* — Elizabeth C. Kemmerer
*Assistant Examiner* — Regina M DeBerry
(74) *Attorney, Agent, or Firm* — White & Case LLP

(57) ABSTRACT

In certain aspects, the present disclosure provides compositions and methods for increasing red blood cell and/or hemoglobin levels in vertebrates, including rodents and primates, and particularly in humans. In some embodiments, the compositions of the disclosure may be used to treat or prevent sideroblastic anemias and myelodysplastic syndromes or one or more complications associated sideroblastic anemias and myelodysplastic syndromes.

25 Claims, 35 Drawing Sheets
(15 of 35 Drawing Sheet(s) Filed in Color)
Specification includes a Sequence Listing.

(56) References Cited

OTHER PUBLICATIONS

Attie, et al., "A Phase 1 Study of ACE-536, A Regulator of Erythroid Differentiation, in Healthy Volunteers," American Journal of Hematology, vol. 89(7): 766-770 (2014).
Barzi, et al., "Myelodysplastic Syndromes: A Practical Approach to Diagnosis and Treatment," Cleveland Clinic Journal of Medicine, vol. 77(1): 37-44 (2010).
Bejar, et al., "Recent Developments in Myelodysplastic Syndromes," Blood, vol. 124(18): 2793-2803 (2014).
Bennett, et al., "Proposals for the Classification of the Myelodysplastic Syndromes," British Journal of Hematology, vol. 51: 189-199 (1982).
Biankin, et al., "Pancreatic Cancer Genomes Reveal Aberrations in Axon Guidance Pathway Genes," Nature, vol. 491: 399-405 (2012).
Bottomley, et al., "Siderblastic Anemia: Diagnosis and Management," Hematology Oncology Clinic of North America, vol. 28: 653-670 (2014).
The Cancer Genome Atlas Netowrk: Comprehensive Molecular Portraits of Human Breast Tumours,Nature, vol. 490: 61-70 (2012).
Cao, et al., "Recent Advances in β-thalassemias," Pediatric Reports, vol. 3(e17): 65-78 (2011).
Casadevall, et al., "Health, Economic, and Quality-of-Life Effects of Erythropoietin and Granulocyte Colony-Stimulating Factor for the Treatment of Myelodysplastic Syndromes: A Randomized, Controlled Trial," Blood, vol. 104(2): 321-327 (2014).
Cazzola, et al., "Quantitative Evaluation of Erythropoietic Activity in Dysmyelopoietic Syndromes," British Journal of Hematology, vol. 50: 55-62 (1982).
Cazzola, et al., "The Genetic Basis of Myelodysplasia and Its Clinical Relevance," Blood, vol. 122(25): 4021-4034 (2013).
Chesnais, et al., "Spliceosome Mutations in Myelodysplastic Syndromes and Chronic Myelomonocytic Leukemia," Impact Journals: Oncotarget, vol. 3(11): 1284-1293 (2012),.
Cheson, et al., "Clinical Application and Proposal for Modification fo the International Working Group (Iwg) Response Criteria in Myelodysplasia," Blood, vol. 108(2): 419-425 (2006).
Cheson, et al., "Report of an International Working Group to Standardize Response Criteria for Myelodysplastic Syndromes," Blood, vol. 96(12): 3671-3674 (2000).
Davidoff, et al., "Patterns of Erythropoiesis-Stimulating Agent Use Among Medicare Beneficiaries with Myelodysplastic Syndromes and Consistency with Clinical Guidelines," Leukemia Research, vol. 37: 675-680 (2013).
Dayyani, et al., "Cause of Death in Patients with Lower-Risk Myelodysplastic Syndrome," Cancer, vol. 116: 2174-2179 (2010).
Demetri, et al., "Quality-of-life Benefit in Chemotherapy Patients Treated With Epoetin Alfa Is Independent of Disease Response or Tumor Type: Results From a Prospective Community Oncology Study," Journal of Clinical Oncology, vol. 16(10): 3412-3425 (1998).
Dolatshad, et al., "Disruption of SF3B1 Results in Deregulated Expression and Splicing of Key Genes and Pathways in Myelodysplastic Syndrome Hematopoietic Stem and Progenitor Cells," Leukemia, vol. 29: 1092-1103 (2015).
Esposito, et al., "Labile Plasma Iron in Iron Overload: Redox Activity and Susceptibility to Chelation," Blood, vol. 102(7): 2670-2677 (2003).
Estey, E. H., "Current Challenges in Therapy of Myelodysplastic Syndromes," Current Opinion in Hematology, vol. 10: 60-67 (2003).
Fenaux, et al., "Efficacy of Azacitidine Compared with that of Conventional Care Regimens in the Treatment of Higher-Risk Myelodysplastic Syndromes: A Randomised, Open-Label, Phase III Study," The Lancet: Oncology, vol. 10: 223-232 (2009).
Furney, et al., "SF3B1 Mutations Are Associated with Alternative Splicing in Uveal Melanoma," Cancer Discovery, vol. 3(10): 1122-1129 (2013).
Galanello, et al., "Combined Iron Chelation Therapy," Annals of the New York Academy of Sciences, vol. 1202: 79-86 (2010).

Garcia-Manero, et al., "Hypomethylating Agents and Other Novel Strategies in Myelodysplastic Syndromes," Journal of Clinical Oncology, vol. 29(5): 516-523 (2011).
Giagounidis, et al., "Outcomes in RBC Transfusion-Dependent Patients with Low-/Intermediate-1-Risk Myelodysplastic Syndromes with Isolated Deletion 5q Treated with Lenalidomide: A Subset Analysis from the MDS-004 Study," European Journal of Hematology, vol. 93: 429-438 (2014).
Glaspy, et al., "Impact of Therapy with Epotin Alfa on Clinical Outcomes in Patients with Nonmyeloid Malignancies During Cancer Chemotherapy in Community Oncology Practice," Journal of Clinical Oncology, vol. 15(3): 1218-1234 (1997).
Glaspy, J. A., "Erythropoietin in Cancer Patients," The Annual Review of Mediine, vol. 60: 181-192 (2009).
Goldberg, et al., "Incidence and Clinical Complications of Myelodysplastic Syndromes Among United States Medicare Beneficiaries," Journal of Clinical Oncology, vol. 28(17): 2847-2852 (2010).
Greenberg, et al., "Myelodysplastic Syndromes: Clinical Practice Guidelines in Oncology," Journal of the National Comprehensive Cancer Network, vol. 9(1): 30-56 (2011).
Greenberg, et al., "Treatment of Myelodysplastic Syndrome Patients with Erythropoietin with or without Granulocyte Colony-Stimulating Factor: Results of a Prospective Randomized Phase 3 Trial by the Eastern Cooperative Oncology Group (E1996)," Blood, vol. 114(12): 2393-2400 (2009).
Hellstrom-Lindberg, et al., "A Validated Decision Model for Treating the Anaemia of Myelodysplastic Syndromes with Erythropoietin + Granulocyte Colony-Stimulating Factor: Significant Effects on Quality of Life," British Journal of Haematology, vol. 120: 1037-1046 (2003).
Horl, et al., "European Best Practice Guidelines 14-16 Inadequate Response to Epoetin," Nephrology Dialysis Transplantation, vol. 15(Supp. 4): 43-50 (2000).
Jacobs et al., "European Best Practice Guidelines 5 Target haemoglobin," Nephrology Dialysis Transplaantation, vol. 15[Suppl 4]: 15-19 (2000).
Je, et al., "Mutational Analysis of Splicing Machinery Genes SF3B1, U2AF1 and SRSF2 in Myelodysplasia and Other Common Tumors," International Journal of Cancer, vol. 133: 260-266 (2013).
Jelkmann, et al., "The Erythropoietin Receptor in Normal and Cancer Tissues," Critical Reviews in Oncology/Hematology, vol. 67: 39-61 (2008).
Juneja, et al., "Prevalence and Distribution of Ringed Sideroblasts in Primary Myelodysplastic Syndromes," Journal of Clinical Pathology, vol. 36: 566-569 (1983).
Kalinowski, et al., "The Evolution of Iron Chelators for the Treatment of Iron Overload Disease and Cancer," Pharmacological Reviews, vol. 57(4): 547-583 (2005).
Kantarjian, et al., "Safety and Efficacy of Romiplostim in Patients With Lower-Risk Myelodysplastic Syndrome and Thrombocytopenia," Journal of Clinical Oncology, vol. 28(3): 437-444 (2010).
Kantarjian, et al., "Survival Advantage with Decitabine Versus Intensive Chemotherapy in Patients with Higher Risk Myelodysplastic Syndrome: Comparison with Historical Experience," Cancer, vol. 109(6): 1133-1137 (2007).
Koury, et al., "Erythropoietin Retards DNA Breakdown and Prevents Programmed Death in Erythroid Progenitor Cells," Science, vol. 248: 378-381 (1990).
Krapf, et al., "Arterial Hypertension Induced by Erythropoietin and Erythropoiesis-Stimulating Agents (ESA)," Clinical Journal of the American Society of Nephrology, vol. 4: 470-480 (2009).
Leitch, H. A., "Controversies Surrounding Iron Chelation Therapy for MDS," Blood Reviews, vol. 25: 17-31 (2011).
Liboi, et al., "Erythropoietin Receptor Signals Both Proliferation and Erythroid-Specific Differentiation," Proceedings of the National Academy of Sciences, vol. 90: 11351-11355 (1993).
Lin, et al., "NUP98-HOXD13 Transgenic Mice Develop a Highly Penetrant, Severe Myelodysplastic Syndrome that Progresses to Acute Leukemia," Blood, vol. 106(1): 287-295 (2005).
List, et al., "Lenalidomide in the Myelodysplastic Syndrome with Chromosome 5q Deletion," The New England Journal of Medicine, vol. 355(14): 1456-1465 (2006).

(56) References Cited

OTHER PUBLICATIONS

Liu, et al., "Suppression of Fas-FasL Coexpression by Erythropoietin Mediates Erythroblast Expansion During the Erythropoietic Stress Response in Vivo," Blood, vol. 108(1): 123-133 (2006).

Lyons, et al., "Comparison of 24-Month Outcomes in Chelated and Non-Chelated Lower-Risk Patients with Myelodysplastic Syndromes in a Prospective Registry," Leukemia Research, vol. 38: 149-154 (2014).

Lyons, et al., "Hematologic Response to Three Alternative Dosing Schedules of Azacitidine in Patients with Myelodysplastic Syndromes," Journal of Clinical Oncology, vol. 27(11): 1850-1856 (2009).

Malcovati, et al., "Clinical Significance of SF3B1 Mutations in Myelodysplastic Syndromes and Myelodysplastic/Myeloproliferative Neoplasms," Blood, vol. 118(24): 6239-6246 (2011).

Malcovati, et al., "Impact of the Degree of Anemia on the Outcome of Patients with Myelodysplastic Syndrome and its Integration into the WHO classification-based Prognostic Scoring System (WPSS)," Haematologica, vol. 96(10): 1433-1440 (2011).

Malcovati, et al., "Prognosis Factors and Life Expectancy in Myelodysplastic Syndromes Classified According to WHO Criteria: A Basis for Clinical Decision Making," Journal of Clinical Oncology, vol. 23(30): 7594-7603 (2005).

Malcovati, et al., "Refractory Anemia with Ring Sideroblasts," Best Practice & Research Clinical Haematology, vol. 26: 377-387 (2013).

Moyo, et al., "Erythropoiesis-Stimulating Agents in the Treatment of Anemia in Myelodysplastic Syndromes: A Meta-Analysis," Annals of Hematology, vol. 87: 527-536 (2008).

Mufti, et al, "Diagnosis and Classification of Myelodysplastic Syndrome: International Working Group on Morphology of Myelodysplastic Syndrome (IWGM-MDS) Consensus Proposals for the Definition and Enumeration of Myeloblasts and Ring Sideroblasts," Haematologica, vol. 93(11): 1712-1717 (2008).

Negrin, et al., "Maintenance Treatment of the Anemia of Myelodysplastic Syndromes with Recombinant Human Granulocyte Colony-Stimulating Factor and Erythropoietin: Evidence for in Vivo Synergy," Blood, vol. 87(10): 4076-4081 (1996).

Oliva, et al., "A Review of Anemia as a Cardiovascular Risk Factor in Patients with Myelodysplastics Syndromes," American Journal of Blood Research, vol. 1(2): 160-166 (2011).

Ornstein, et al., "Combination Strategies in Myelodysplastic Syndromes," International Journal of Hematology, vol. 95: 26-33 (2012).

Ozcan et al., "Review of therapeutic options and the management of patients with myelodysplastic syndromes," Expert Review Hematol, vol. 6:165-189 (2013).

Papaemmanuil, et al., "Somatic SF3B1 Mutation in Myelodysplasia with Ring Sideroblasts," The New England Journal of Medicine, vol. 365(15): 1384-1395 (2011).

Park, et al., "Predictive Factors of Response and Survival in Myelodysplastic Syndrome Treated with Erythropoietin and G-CSF: The GFM Experience," Blood, vol. 111(2): 574-582 (2008).

Rawn, J., "The Silent Risks of Blood Transfusion," Current Opinion in Anaethesiology, vol. 21: 664-668 (2008).

Santini, et al., "Hepcidin Levels and Their Determinants in Different Types of Myelodysplastic Syndromes," PLoS One, vol. 6(8): 1-8 (2011).

Santini, V., "Clinical Use of Erythropoietic Stimulating Agents in Myelodysplastic Syndromes," The Oncologist, vol. 16(Supp. 3): 35-42 (2011).

Santini, V., "Treatment of Low-Risk Myelodysplastic Syndrome: Hematopoietic Growth Factors Erythropoietins and Thrombopoietins," Seminars in Hematology, vol. 49(4): 295-303 (2012).

Shen, et al., "DNA Methylation Predicts Survival and Response to Therapy in Patients with Myelodysplastic Syndromes," Journal of Clinical Oncology, vol. 28(4): 605-613 (2010).

Siah, et al., "Normal Iron Metabolism and the Pathophysiology of Iron Overload Disorders," The Clinical Biochemist Reviews, vol. 27: 5-16 (2006).

Slichter, S. J., "Evidence-Based Platelet Transfusion Guidelines," American Society of Hematology Education Program: 172-178 (2007).

Sloand, et al., "Alemtuzumab Treatment of Intermediate-1 Myelodysplasia Patients is Associated with Sustained Improvement in Blood Counts and Cytogenetic Remissions," Journal of Clinical Oncology, vol. 28(35): 5166-5173 (2010).

Socolovsky, et al., "Ineffective Erythropoiesis in Stat5a-/-5b-/- Mice Due to Decreased Survival of Early Erythroblasts," Blood, vol. 98(12): 3261-3273 (2001).

Steensma, D. P., "Hematopoietic Growth Factors in Myelodysplastic Syndromes," Seminars in Oncology, vol. 38(5): 635-647 (2011).

Steensma, et al., "The Myelodysplastic Syndromes: Diagnosis and Treatment," Mayo Clinic Proceedings, vol. 81(1): 104-130 (2006).

Steensma, et al., "When is Iron Overload Deleterious, and When and How Should Iron Chelation Therapy Be Administered in Myelodysplastic Syndromes?," Best Practice & Research Clinical Haematology, vol. 26: 431-444 (2013).

Suragani, et al., "Transforming Growth Factor-β Superfamily Ligand Trap ACE-536 Corrects Anemia by Promoting Late-Stage Erythropoiesis," Nature Medicine, vol. 20(4): 408-417 (2014).

Temraz, et al., "Iron Overload and Chelation Therapy in Myelodysplastic Syndromes," Critical Reviews in Oncology/Hematology, vol. 91: 64-73 (2014).

Vardiman, et al., "The 2008 Revision of the World Health Organization (WHO) Classification of Myeloid Neoplasms and Acute Leukemia: Rationale and Important Changes," Blood, vol. 114(5): 937-951 (2009).

Wang, et al., "SF3B1 and Other Novel Cancer Genes in Chronic Lymphocytic Leukemia," The New England Journal of Medicine, vol. 365(26): 2497-2506 (2011).

Weatherall, et al., "Red Cells I: Inherited Anaemias," The Lancel, vol. 355: 1169-1175 (2000).

Webb, et al., "The Development and Application of Small Molecule Modulators of SF3b as Therapeutic Agents for Cancer," Drug Discovery Today, vol. 18(1-2): 43-49 (2013).

Zeidan, et al., "There's Risk, and Then There's Risk: The Latest Clinical Prognostic Risk Stratification Models in Myelodysplastic Syndromes," Current Hematologic Malignancy Reports, vol. 8: 351-360 (2013).

Anonymous "Ferritin" www.webmd.com/a-to-z-guides/ferritin?page=2 originally published 2008.

Anonymous "Iron and Thalassemia," Accessed on the Internet Apr. 3, 2014 at <sickle.bwh.harvard.edu/thaliron.html>. Published Aug. 25, 1997.

Anonymous "Learning about Thalassemia" <http://www.genome.gov/10001221> Accessed on Internet Jul. 9, 2013. Published Jun. 28, 2010.

Camaschella, C., "Recent Advances in the Understanding of Inherited Sideroblastic Anemia", British Journal of Haematology, vol. 143:27-38 (2008).

Dore et al., "Serum erythropoietin levels in thalassemia intermedia," Annals of Hematology, vol. 67:183-186 (1993).

Haidar et al., "Paraspinal extramedullary hematopoiesis in patients with thalassemia intermedia," Eur Spine J., vol. 19: 871-878 (2010).

Kumar Mishra and Tiwari, "Iron Overload in Beta Thalassaemia Major and Intermedia Patients," MAEDICA—Journal of Clinical Medicine, vol. 8(4): 328-332 (2013).

Merck Manual. Iron-Utilization Anemias (Sideroblastic Anemias), pp. 1150-1151 (1992).

Nemeth, E., "Hepcidin in β-thalassemia," Annals of the New York Academy of Sciences, vol. 1202: 31-35. Published Aug. 2, 2010.

Tanno, T. and Miller, J.L., "Iron Loading and Overloading due to Ineffective Erythropoiesis," Advances in Hematology, vol. 2010; Article ID 358283, Chapter 2 (Abstract) (2010).

Terpos et al., "Prolonged Administration of Erythropoietin Increases Response Rate in Myelodysplastic Syndromes: a Phase II Trial in 281 Patients", British Journal of Haematology, vol. 118(1):174-180 (2002).

Vogiatzi et al., "Bone Disease in Thalassemia: A Frequent and Still Unresolved Problem," Journal of Bone and Mineral Research, vol. 24: 543-557 (2008).

(56) References Cited

OTHER PUBLICATIONS

Ward, R., "An update on disordered iron metabolism and iron overload," Hematology, vol. 15(5): 311-317 (2010).

Whatley, et al., "C-Terminal Deletions in the ALAS2 Gene Lead to Gain of Function and Cause X-Linked Dominant Protoporphyria Without Anemia or Iron Overload", American Journal of Human Genetics, vol. 83:408-414 (2008).

\* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIGURE 1

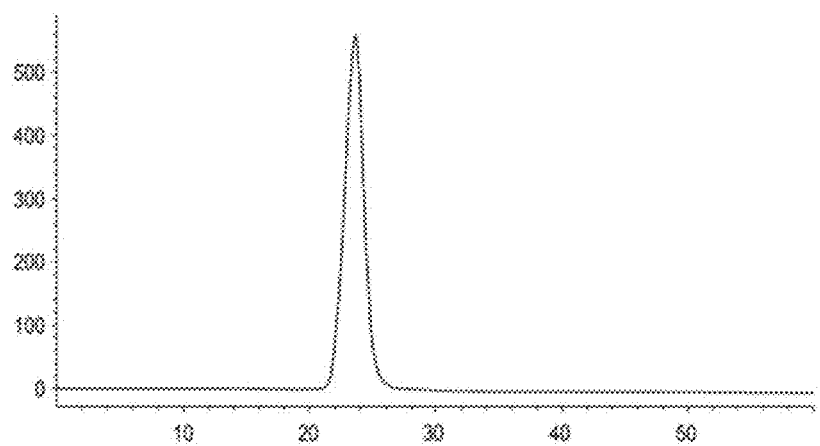
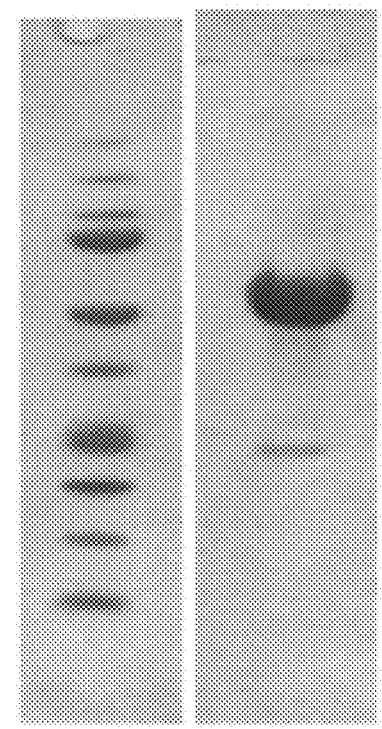
Figure 3

```
  1  MDAMKRGLCC VLLLCGAVFV SPGASGRGEA ETRECIYYNA NWELERTNQS
 51  GLERCEGEQD KRLHCYASWR NSSGTIELVK KGCWLDDFNC YDRQECVATE
101  ENPQVYFCCC EGNFCNERFT HLPEAGGPEV TYEPPPTAPT GGGTHTCPPC
151  PAPELLGGPS VFLFPPKPKD TLMISRTPEV TCVVVDVSHE DPEVKFNWYV
201  DGVEVHNAKT KPREEQYNST YRVVSVLTVL HQDWLNGKEY KCKVSNKALP
251  APIEKTISKA KGQPREPQVY TLPPSREEMT KNQVSLTCLV KGFYPSDIAV
301  EWESNGQPEN NYKTTPPVLD SDGSFFLYSK LTVDKSRWQQ GNVFSCSVMH
351  EALHNHYTQK SLSLSPGK (SEQ ID NO:38)
```

FIGURE 16

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCTCTGGGCG TGGGGAGGCT GAGACACGGG
     TCAGAAGCAA AGCGGGCCGC GGAGACCCGC ACCCCTCCGA CTCTGTGCCC

101  AGTGCATCTA CTACAACGCC AACTGGGAGC TGGAGCGCAC CAACCAGAGC
     TCACGTAGAT GATGTTGCGG TTGACCCTCG ACCTCGCGTG GTTGGTCTCG

151  GGCCTGGAGC GCTGCGAAGG CGAGCAGGAC AAGCGGCTGC ACTGCTACGC
     CCGGACCTCG CGACGCTTCC GCTCGTCCTG TTCGCCGACG TGACGATGCG

201  CTCCTGGCGC AACAGCTCTG GCACCATCGA GCTCGTGAAG AAGGGCTGCT
     GAGGACCGCG TTGTCGAGAC CGTGGTAGCT CGAGCACTTC TTCCCGACGA

251  GGGATGATGA CTTCAACTGC TACGATAGGC AGGAGTGTGT GGCCACTGAG
     CCCTACTACT GAAGTTGACG ATGCTATCCG TCCTCACACA CCGGTGACTC

301  GAGAACCCCC AGGTGTACTT CTGCTGCTGT GAAGGCAACT TCTGCAACGA
     CTCTTGGGGG TCCACATGAA GACGACGACA CTTCCGTTGA AGACGTTGCT

351  GCGCTTCACT CATTTGCCAG AGGCTGGGGG CCCGGAAGTC ACGTACGAGC
     CGCGAAGTGA GTAAACGGTC TCCGACCCCC GGGCCTTCAG TGCATGCTCG

401  CACCCCCGAC AGCCCCCACC GGTGGTGGAA CTCACACATG CCCACCGTGC
     GTGGGGGCTG TCGGGGGTGG CCACCACCTT GAGTGTGTAC GGGTGGCACG

451  CCAGCACCTG AACTCCTGGG GGGACCGTCA GTCTTCCTCT TCCCCCCAAA
     GGTCGTGGAC TTGAGGACCC CCCTGGCAGT CAGAAGGAGA AGGGGGGTTT

501  ACCCAAGGAC ACCCTCATGA TCTCCCGGAC CCCTGAGGTC ACATGCGTGG
     TGGGTTCCTG TGGGAGTACT AGAGGGCCTG GGGACTCCAG TGTACGCACC

551  TGGTGGACGT GAGCCACGAA GACCCTGAGG TCAAGTTCAA CTGGTACGTG
     ACCACCTGCA CTCGGTGCTT CTGGGACTCC AGTTCAAGTT GACCATGCAC

601  GACGGCGTGG AGGTGCATAA TGCCAAGACA AAGCCGCGGG AGGAGCAGTA
     CTGCCGCACC TCCACGTATT ACGGTTCTGT TTCGGCGCCC TCCTCGTCAT

651  CAACAGCACG TACCGTGTGG TCAGCGTCCT CACCGTCCTG CACCAGGACT
     GTTGTCGTGC ATGGCACACC AGTCGCAGGA GTGGCAGGAC GTGGTCCTGA

701  GGCTGAATGG CAAGGAGTAC AAGTGCAAGG TCTCCAACAA AGCCCTCCCA
     CCGACTTACC GTTCCTCATG TTCACGTTCC AGAGGTTGTT TCGGGAGGGT

751  GCCCCCATCG AGAAAACCAT CTCCAAAGCC AAAGGGCAGC CCCGAGAACC
     CGGGGGTAGC TCTTTTGGTA GAGGTTTCGG TTTCCCGTCG GGGCTCTTGG
```

Figure 17A

```
 801  ACAGGTGTAC ACCCTGCCCC CATCCCGGGA GGAGATGACC AAGAACCAGG
      TGTCCACATG TGGGACGGGG GTAGGGCCCT CCTCTACTGG TTCTTGGTCC

851  TCAGCCTGAC CTGCCTGGTC AAAGGCTTCT ATCCCAGCGA CATCGCCGTG
      AGTCGGACTG GACGGACCAG TTTCCGAAGA TAGGGTCGCT GTAGCGGCAC

901  GAGTGGGAGA GCAATGGGCA GCCGGAGAAC AACTACAAGA CCACGCCTCC
      CTCACCCTCT CGTTACCCGT CGGCCTCTTG TTGATGTTCT GGTGCGGAGG

951  CGTGCTGGAC TCCGACGGCT CCTTCTTCCT CTATAGCAAG CTCACCGTGG
      GCACGACCTG AGGCTGCCGA GGAAGAAGGA GATATCGTTC GAGTGGCACC

1001  ACAAGAGCAG GTGGCAGCAG GGGAACGTCT TCTCATGCTC CGTGATGCAT
      TGTTCTCGTC CACCGTCGTC CCCTTGCAGA AGAGTACGAG GCACTACGTA

1051  GAGGCTCTGC ACAACCACTA CACGCAGAAG AGCCTCTCCC TGTCCCCGGG
      CTCCGAGACG TGTTGGTGAT GTGCGTCTTC TCGGAGAGGG ACAGGGGCCC

1101  TAAATGA (SEQ ID NO:39)
      ATTTACT (SEQ ID NO:40)
```

Figure 17B

```
  1  MDAMKRGLCC VLLLCGAVFV SPGAASTREC IYYNANWELE RTNQSGLERC
 51  EGEQDKRLHC YASWRNSSGT IELVKKGCWS DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 41)
```

FIGURE 18

```
                                                                    E   T   R   E   C   I   Y   Y
  1  ATGCATGCAA TGAAGAGAGG GCTCTGCTGT GTGCTGCTGC TGTGTGGAGC
     TACGTACGTT ACTTCTCTCC CGAGACGACA CACGACGACG ACACACCTCG

E   T   R   E   C   I   Y   Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N   A   N   W   E   L   E   R   T   N   Q   S   G   L   E   R   C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E   G   E   Q   D   K   R   L   H   C   Y   A   S   W   R   N   S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S   G   T   I   E   L   V   K   K   G   C   W   D   D   D   F
201  CTCTGGCACC ATCGAGCTCG TGAAGAAGGG CTGCTGGGAC GATGACTTCA
     GAGACCGTGG TAGCTCGAGC ACTTCTTCCC GACGACCCTG CTACTGAAGT

N   C   Y   D   R   Q   E   C   V   A   T   E   E   N   P   Q   V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y   F   C   C   C   E   G   N   F   C   N   E   R   F   T   H   L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P   E   A   G   G   P   E   V   T   Y   E   P   P   P   T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG
```

Figure 19A

```
 601  AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG

801  CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851  GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901  GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951  CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 42)
      GTCTTCTCGG AGAGGGACAG GGGCCCATTT ACT (SEQ ID NO: 43)
```

Figure 19B

```
  1   ZTRECIYYNA NWELERTNQS GLERCEGEQD KRLHCYASWR NSSGTIELVK
 51   KGCWZDDFNC YDRQECVATE ENPQVYFCCC EGNFCNERFT HLPEAGGPEV
101   TYEPPPTGGG THTCPPCPAP ELLGGPSVFL FPPKPKDTLM ISRTPEVTCV
151   VVDVSHEDPE VKFNWYVDGV EVHNAKTKPR EEQYNSTYRV VSVLTVLHQD
201   WLNGKEYKCK VSNKALPAPI EKTISKAKGQ PREPQVYTLP PSREEMTKNQ
251   VSLTCLVKGF YPSDIAVEWE SNGQPENNYK TTPPVLDSDG SFFLYSKLTV
301   DKSRWQQGNV FSCSVMHEAL HNHYTQKSLS LSPGK (SEQ ID NO: 44)
```

FIGURE 20

1   STRECIYYNA NWELERTNQS GLERCEGEQD KRLHCYASWR NSSGTIELVK

51  KGCWLDDFNC YDRQECVATE ENPQVYFCCC EGNFCNERFT HLPEAGGPEV

101 TYEPPPT  (SEQ ID NO: 45)

FIGURE 21

```
                                                       E    T    R    E    C    I    Y    Y
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E    T    R    E    C    I    Y    Y
 51  AGTCTTCGTT TCGCCCGGCG CCGCCGAAAC TCGGGATCG ATTATTACA
     TCAGAAGCAA AGCGGGCCGC GGCGGCTTTG GCGCCTACA TAAATAATGT

N    A    N    W    E    L    E    R    T    N    Q    S    G    L    E    R    C
101  AAGCAAATG GGAACTGAA CGAACAACC AAACGGCT GAACGTG
     TACGATTAAC CCTTGACTT GCCTGCTTGG TTAGGCCCGA GCTTGCCACA

E    G    E    Q    D    K    R    L    E    C    Y    A    S    W    R    N    S
151  GAGGGAGAC AGGAAAACG CTCATGC TAGCCTCT GGCGAAC
     CTCCCCCTTG TCCTATTTGC GGAGGTAACG ATACGCAGCA CCTCCTTGAG

S    G    T    I    E    L    V    K    R    G    C    W    D    D    D    F
201  CTCGGAC ATGACTG TAAGAAGG GTGCTGGGAC GAGGATTCA
     GAGGCCCTGC TAACTTGACC AGTTCTTTCC CACGACCCTG CTGCTAAAGT

N    C    Y    D    R    Q    E    C    V    A    T    E    E    N    P    Q    V
251  ATGTATGA GGCAGGAG TGTGTGCCA CGAGGAGAA CCCAGGT
     TAACAATACT GGCGGTCCTT ACACAGCGCT GGCTTCTCTT AGGCGTCCAG

Y    F    C    C    E    G    N    F    C    N    E    R    F    T    H    L
301  TATTCTGT GTGGAGG AATTCTG AAGACGT TACCAT
     ATAAAGACAA CAACGCTCCC CTTAAAGACA TTACTTGCCA AATGGGTGGA

P    E    A    G    G    P    E    V    T    Y    E    P    P    P    T
351  CCGAGCG GGGGCCG AGTACTA GACCCCG CCACGGTG
     GGGGCTTCGG CCGCCGGGC TCCACTGGAT ACTTGGGGC GGGTGGCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA
```

Figure 22A

```
701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 46)
      GTCTTCTCGG AGAGGGACAG GGGCCCATTT ACT (SEQ ID NO: 47)
```

Figure 22B

```
GAXAC XCCXGAXTGX ATXTAXTACA AXGCXAAXTG GGAXCTXGAX CGXACXAACC
AXXCGGXCT XGAXCGXTGX GAXGXXGAXC AGGAXAAXCG XCTXCAXTGC TAXGCXTCXT
GGXGXAACXX CTCXGGXACX ATXGAXCTXG TXAAGAAXGG XTGCTGGGAC GAXGAXTTCA
AXTGXTAXGA XXGXCAGGAX TGTGTXGCXA CXGAXGAGAA XCCXCAGGTX TAXTTCTGXT
GXTGXGAXGG XAAXTTCTGX AAXGAXCGXT TXACXCAXXT XCCXGAXGC

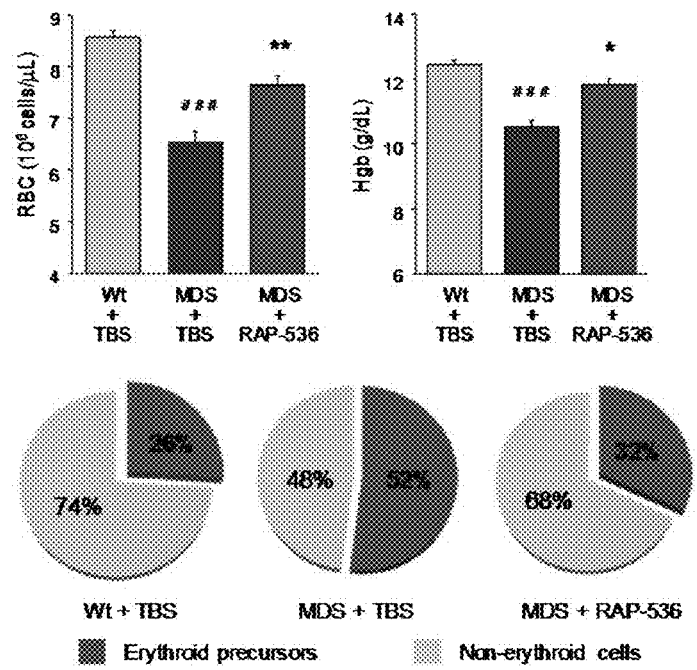
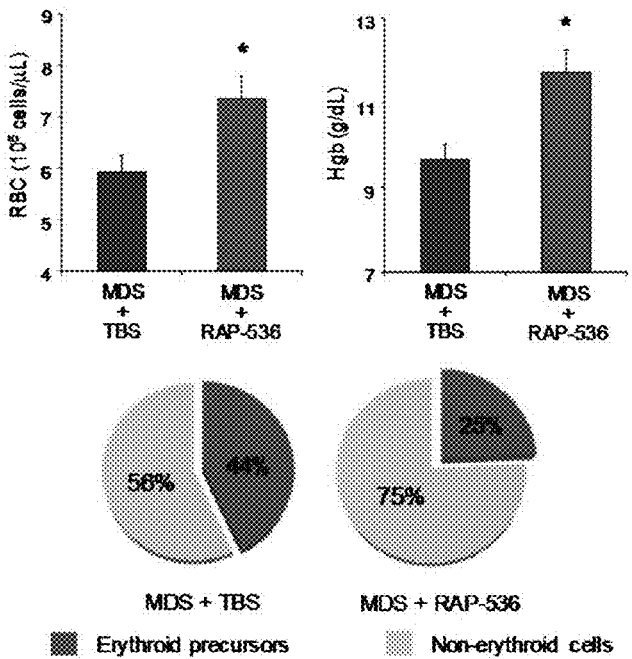
FIGURE 32

METHODS FOR TREATING MYELODYSPLASTIC SYNDROMES AND SIDEROBLASTIC ANEMIAS

CROSS-REFERENCE TO RELATED APPLICATIONS

This application claims the benefit of priority to U.S. provisional application Ser. No. 62/086,977, filed Dec. 3, 2014; U.S. provisional application Ser. No. 62/088,087, filed Dec. 5, 2014; and U.S. provisional application Ser. No. 62/155,395, filed Apr. 30, 2015. The disclosures of each of the foregoing applications are hereby incorporated by reference in their entirety.

SEQUENCE LISTING

The instant application contains a Sequence Listing which has been submitted via EFS-Web and is hereby incorporated by reference in its entirety. Said ASCII copy, created on Jun. 23, 2016, is named PHPH083101_Seq.txt, and is 110,164 bytes in size.

BACKGROUND OF THE INVENTION

The present disclosure relates to treatments for dysregulated production of blood cellular components, including red blood cells, neutrophils, and platelets. Hematopoiesis is the formation of cellular components of the blood from self-renewing hematopoietic stem cells located mainly in the bone marrow, spleen, or lymph nodes during postnatal life. Blood cells can be classified as belonging to the lymphocytic lineage, myelocytic lineage, or erythroid lineage. By a process known as lymphopoiesis, common lymphoid progenitor cells give rise to T-cells, B-cells, natural killer cells, and dendritic cells. By a process termed myelopoiesis, common myeloid progenitor cells give rise to macrophages, granulocytes (basophils, neutrophils, eosinophils, and mast cells), and thrombocytes (platelets). Finally, by a process known as erythropoiesis, erythroid progenitor cells give rise to red blood cells (RBC, erythrocytes).

Postnatal erythropoiesis occurs primarily in the bone marrow and in the red pulp of the spleen. The coordinated action of various signaling pathways controls the balance of cell proliferation, differentiation, survival, and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage-committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates. The mature red blood cell (RBC) is responsible for oxygen transport in the circulatory systems of vertebrates. Red blood cells contain high concentrations of hemoglobin, a protein that binds to oxygen in the lungs at relatively high partial pressure of oxygen ($pO_2$) and delivers oxygen to areas of the body with relatively low $pO_2$.

Erythropoietin (EPO) is widely recognized as a significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Effects of EPO are mediated by a cell-surface receptor belonging to the cytokine receptor superfamily. The human EPO receptor gene encodes a 483 amino acid transmembrane protein; however, the active EPO receptor is thought to exist as a multimeric complex even in the absence of ligand (see, e.g., U.S. Pat. No. 6,319,499). The cloned full-length EPO receptor expressed in mammalian cells binds EPO with an affinity similar to that of the native receptor on erythroid progenitor cells. Binding of EPO to its receptor causes a conformational change resulting in receptor activation and biological effects including increased proliferation of immature erythroblasts, increased differentiation of immature erythroblasts, and decreased apoptosis in erythroid progenitor cells [see, e.g., Liboi et al. (1993) Proc Natl Acad Sci USA 90:11351-11355; Koury et al. (1990) Science 248:378-381].

Various forms of recombinant EPO are used by physicians to increase red blood cell levels in a variety of clinical settings, particularly in the treatment of anemia. Anemia is a broadly-defined condition characterized by lower than normal levels of hemoglobin or red blood cells in the blood. In some instances, anemia is caused by a primary disorder in the production or survival of red blood cells (e.g., myelodysplastic syndromes). More commonly, anemia is secondary to diseases of other systems [see, e.g., Weatherall & Provan (2000) Lancet 355, 1169-1175]. Anemia may result from a reduced rate of production or increased rate of destruction of red blood cells or by loss of red blood cells due to bleeding. Anemia may result from a variety of disorders that include, for example, acute or chronic renal failure or end stage renal disease, chemotherapy treatment, a myelodysplastic syndrome, rheumatoid arthritis, and bone marrow transplantation.

Treatment with EPO typically causes a rise in hemoglobin by about 1-3 g/dL in healthy humans over a period of weeks. When administered to anemic individuals, this treatment regimen often provides substantial increases in hemoglobin and red blood cell levels and leads to improvements in quality of life and prolonged survival. However, EPO is not uniformly effective, and many individuals are refractory to even high doses [see, e.g., Horl et al. (2000) Nephrol Dial Transplant 15, 43-50]. For example, over 50% of patients with cancer have an inadequate response to EPO, and approximately 10% with end-stage renal disease are hyporesponsive to EPO [see, e.g., Glaspy et al. (1997) J Clin Oncol 15, 1218-1234; Demetri et al. (1998) J Clin Oncol 16, 3412-3425]. Although the molecular mechanisms of resistance to EPO are as yet unclear, several factors, including inflammation, iron and vitamin deficiency, inadequate dialysis, aluminum toxicity, and hyperparathyroidism may predict a poor therapeutic response. In addition, recent evidence suggests that higher doses of EPO may be associated with an increased risk of cardiovascular morbidity, tumor growth, and mortality in some patient populations [see, e.g., Krapf et al. (2009) Clin J Am Soc Nephrol 4:470-480; Glaspy (2009) Annu Rev Med 60:181-192]. Therefore, it has been recommended that EPO-based therapeutic compounds (e.g., erythropoietin-stimulating agents, ESAs) be administered at the lowest dose that allows a patient to avoid red blood cell transfusions [see, e.g., Jelkmann et al. (2008) Crit Rev Oncol. Hematol 67:39-61].

Sideroblastic anemia, which occurs in both inherited and acquired forms, is characterized by the presence of "ring sideroblasts" in bone marrow. These distinctive red blood cell precursors (erythroblasts) can be identified by the presence of perinuclear siderotic granules, which are revealed by histologic staining with Prussian blue and are indicative of pathologic iron deposits in mitochondria [see, e.g., Mufti et al. (2008) Haematologica 93:1712-1717; Bottomley et al. (2014) Hematol Oncol Clin N Am 28:653-670]. Acquired sideroblastic anemia occurs most frequently in the context of myelodysplastic syndromes (MDS), a heterogeneous group of hematopoietic stem-cell disorders estimated to affect between 30,000 and 40,000 patients per year in the United States [Bejar et al. (2014) Blood 124:2793-2803]. These disorders are characterized by ineffective hematopoiesis, abnormal "dysplastic" cell morphology, and the potential for clonal evolution to acute myeloid leukemia. As discussed below, recent advances in the genetic basis of MDS have the potential to greatly improve its diagnosis and treatment.

There is high unmet need for effective therapies for MDS, sideroblastic anemia and complications of those disorders. Endogenous EPO levels are commonly elevated in subsets of patients with MDS, thus suggesting that EPO has diminished effectiveness in these patients. It has been estimated that fewer than 10% of patients with MDS respond favorably to EPO [Estey (2003) Curr Opin Hematol 10, 60-67], while a more recent meta-analysis found that EPO response rates range from 30% to 60% depending on the study [Moyo et al (2008) Ann Hematol 87:527-536]. Compared to other MDS patients, those with ring sideroblasts tend to be at substantially lower risk of developing acute myeloid leukemia and would therefore stand to benefit for an extended period from anti-anemia therapeutic agents that do not contribute to systemic iron burden and that instead help to reduce the iron overload frequently present in such patients [see, e.g., Temraz et al., 2014, Crit Rev Oncol Hematol 91:64-73].

Thus, it is an object of the present disclosure to provide methods treating patients with MDS and sideroblastic anemias with ActRII antagonists disclosed herein and, in particular, to guide selection of MDS patients that are most likely to show therapeutically beneficial increases in red blood cells, neutrophils, and other blood cells as a result of treatment.

SUMMARY OF THE INVENTION

In part, the disclosure provides methods of treating MDS and sideroblastic anemias, particularly treating or preventing one or more complications or subtypes of MDS, including MDS patients characterized by the presence of sideroblasts in the bone marrow, with one or more ActRII antagonists.

In part the disclosure provides methods for treating or preventing disorders or complications of a disorder that is associated with germ line or somatic mutations in SF3B1, such as myelodysplastic syndrome (MDS), chronic lymphocytic leukemia (CLL), and acute myeloid leukemia (AML) as well as in breast cancer, pancreatic cancer, gastric cancer, prostate cancer, and uveal melanoma with one or more ActRII antagonists. In certain aspects the disorder may be in a subject that has bone marrow cells that test positive for an SF3B1 mutation, particularly myelodysplastic syndrome, CLL and AML. Optionally a mutation in the SF3B1 gene is in an exon, intron or 5' and/or 3' untranslated region. For example, in some embodiments, a mutation in the SF3B1 gene is in exon 14, 15, and/or 16 of SF31B. Optionally a mutation in SF3B1 causes a change in the amino acid sequence or does not cause a change in the amino acid sequence of the protein encoded by the gene. Optionally a mutation in the SF3B1 gene causes a change in the amino acid of the protein encoded by the gene selected from the following changes: K182E, E491G, R590K, E592K, R625C, R625G, N626D, N626S, H662Y, T663A, K666M, K666Q, K666R, Q670E, G676D, V701I, I704N, I704V, G740R, A744P, D781G, A1188V, N619K, N626H, N626Y, R630S, I704T, G740E, K741N, G742D, D894G, Q903R, R1041H, I1241T, G347V, E622D, Y623C, R625H, R625L, H662D, H662Q, T663I, K666E, K666N, K666T, K700E, E783K, and V701F.

In certain aspects, the disclosure provides methods for treating or preventing sideroblastic anemia in a human subject, comprising administering to a subject in need thereof a polypeptide comprising an amino acid sequence that is at least 70%, 75%, 80%, 85%, 90%, 91%, 92%, 93%, 94%, 95%, 96%, 97%, 98%, 99%, or 100% identical to amino acids 29-109 of SEQ ID NO: 1, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In other aspects, the disclosure provides methods for treating or preventing sideroblastic anemia in a human subject, comprising administering to a subject in need thereof a polypeptide comprising an amino acid sequence that is at least 70%, 75%, 80%, 85%, 90%, 91%, 92%, 93%, 94%, 95%, 96%, 97%, 98%, 99%, or 100% identical to amino acids 25-125 of SEQ ID NO: 1, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In even other aspects, the disclosure provides methods for treating or preventing sideroblastic anemia in a human subject, comprising administering to a subject in need thereof a polypeptide comprising, consisting essentially of, or consisting of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 44, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In certain aspects, the disclosure provides methods for treating or preventing one or more complications of sideroblastic anemia in a human subject, comprising administering to a subject in need thereof a polypeptide comprising an amino acid sequence that is at least 70%, 75%, 80%, 85%, 90%, 91%, 92%, 93%, 94%, 95%, 96%, 97%, 98%, 99%, or 100% identical to amino acids 29-109 of SEQ ID NO: 1, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In other aspects, the disclosure provides methods for treating or preventing and/ or one or more complications of sideroblastic anemia in a human subject, comprising administering to a subject in need thereof a polypeptide comprising an amino acid sequence that is at least 70%, 75%, 80%, 85%, 90%, 91%, 92%, 93%, 94%, 95%, 96%, 97%, 98%, 99%, or 100% identical to amino acids 25-125 of SEQ ID NO: 1, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In even other aspects, the disclosure provides methods for treating or preventing and/or one or more complications of sideroblastic anemia in a human subject, comprising administering to a subject in need thereof a polypeptide comprising, consisting essentially of, or consisting of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 44, wherein the polypeptide comprises an acidic amino acid [a naturally occurring amino acid (e.g., D or E) or an artificial amino acid] at position 79 with respect to SEQ ID NO: 1, wherein the subject is on a dosing schedule that comprising administering from 0.125 to 1.75 mg/kg (e.g., 0.75 to 1.75 mg/kg) of the polypeptide to the subject. In certain preferred embodiments, polypeptides to be used in accordance with the methods described herein are dimers (e.g., a homodimer comprising two polypeptides corresponding to the amino acid sequence of SEQ ID NO: 44 associated by covalent or non-covalent interactions). Optionally the polypeptide may bind to one or more ligand of the TGFβ superfamily. For example, in some embodiments, polypeptides described herein (e.g., ActRIIA and ActRIIB polypeptides as well as variant thereof such as GDF traps) may bind to GDF11. In other embodiments, polypeptides described herein (e.g., ActRIIA and ActRIIB polypeptides as well as variant thereof such as GDF traps) may bind to GDF8. In still other embodiments, polypeptides described herein (e.g., ActRIIA and ActRIIB polypeptides as well as variant thereof such as GDF traps) may bind to GDF11 and GDF8. Optionally the polypeptide may comprises one or more amino acid modifications selected from: a glycosylated amino acid, a PEGylated amino acid, a farnesylated amino acid, an acetylated amino acid, a biotinylated amino acid, and an amino acid conjugated to a lipid moiety. In certain preferred embodiments the polypeptide is glycosylated and has a mammalian glycosylation pattern. Optionally the polypeptide has a glycosylation pattern obtainable from a Chinese hamster ovary cell line. Optionally the methods comprises subcutaneously administered the polypeptide to the subject. Optionally the dosing schedule further comprises administering the polypeptide to the patient twice every week, once every week, once every 3 weeks, once every 4 weeks, once every 5 weeks, once every 6 weeks, once every 7 weeks, once every 8 weeks, once every 9 weeks, once every 10 weeks, once every 12 weeks, once every 14 weeks, once every 16 weeks, once every 18 weeks, once every 20 weeks, once every 24 weeks, once every 26 weeks, once every 28 weeks, once every 30 weeks, once every 32 weeks, once every 34 weeks, or once every 36 weeks In certain preferred embodiments the dosing schedule further comprises administering the polypeptide to the patient once every three weeks. Optionally the subject has undesirably high levels of endogenous EPO. Optionally the subject has previously been treated with one or more EPO receptor agonists. Optionally the subject has an inadequate response to the EPO receptor agonist. Optionally the subject is no longer responsive to the EPO receptor agonist. Optionally the EPO receptor agonist is EPO. Optionally the treatment increases red blood cell levels. Optionally the treatment increases hemoglobin levels. Optionally wherein the treatment results in a hemoglobin increase of ≥1.5 g/dL for ≥two weeks. Optionally the treatment results in a hemoglobin increase of ≥1.5 g/dL for ≥eight weeks. Optionally the subject has been administered one or more blood cell transfusions prior to the start of treatment. Optionally wherein the subject is a low transfusion burden subject. Optionally the subject is a high transfusion burden subject. Optionally the treatment decreases blood cell transfusion burden. Optionally the treatment decreases blood cell transfusion by ≥50% for at least four weeks relative to the equal time prior to start of treatment. Optionally the treatment decreases blood cell transfusion by ≥50% for at least eight weeks relative to the equal time prior to start of treatment. Optionally the patient has myelodysplastic syndrome. Optionally the patient has an International Prognostic Scoring System (IPSS) or IPSS-R score of low or intermediate. Optionally the sideroblastic anemia subject has at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% ring blasts as a percentage of bone marrow erythroid precursors in his or her bone marrow. Optionally the treatment increases neutrophil levels. Optionally the subject has bone marrow cells that test positive for one or more mutations in SF3B1. Optionally the subject has bone marrow cells that test positive for one or more mutations in DNMT3A. Optionally the subject has bone marrow cells that test positive for one or more mutations in TET2. Optionally the treatment decreases iron overload. In some embodiments, the treatment decrease tissue iron overload (e.g., iron overload in the kidney, liver, and/or spleen). In some embodiments, the treatment decrease serum iron overload.

In part the disclosure provides methods for treating or preventing disorders or complications of a disorder that is associated with germ line or somatic mutations in DNMT3A, such as myelodysplastic syndrome (MDS), chronic lymphocytic leukemia (CLL), and acute myeloid leukemia (AML) with one or more ActRII antagonists. In certain aspects the disorder may be in a subject that has bone marrow cells that test positive for a DNMT3A mutation, particularly myelodysplastic syndrome, CLL and AML. Optionally a mutation in the DNMT3A gene is in an exon, intron and/or 5' or 3' untranslated region. For example, in some embodiments, a mutation in the DNMT3A gene is in exon 10, 18, and/or 22 of DNMT3A. Optionally a mutation in DNMT3A causes a change in the amino acid sequence or does not cause a change in the amino acid sequence of the protein encoded by the gene. Optionally a mutation in the DNMT3A gene causes a change in the amino acid of the protein encoded by the gene selected from the following changes: R882C, R882H, P904L, and P905P. Optionally a mutation in the DNMT3A gene introduces a premature stop codon. For example, in some embodiments, a mutation in the DNMT3A gene that introduces a premature stop codon is selected from the following positions: Y436X and W893X.

In part the disclosure provides methods for treating or preventing disorders or complications of a disorder that is associated with germ line or somatic mutations in TET2, such as myelodysplastic syndrome (MDS), chronic lymphocytic leukemia (CLL), and acute myeloid leukemia (AML) with one or more ActRII antagonists. In certain aspects the disorder may be in a subject that has bone marrow cells that test positive for a TET2 mutation, particularly myelodysplastic syndrome, CLL and AML. Optionally a mutation in the TET2 gene is in an exon, intron and/or 5' or 3' untranslated region. For example, in some embodiments, a mutation in the TET2 gene is in exon 1, exon 4, exon 5, exon 6, exon 7, exon 8, and/or exon 9 of TET2. Optionally a mutation in TET2 causes a change in the amino acid sequence or does not cause a change in the amino acid sequence of the protein encoded by the gene. Optionally a mutation in the TET2 gene causes a change in the amino acid of the protein encoded by the gene selected from the following changes: E47Q, Q1274R, W1291R, G1370R, N1387S, and Y1724H. Optionally a mutation in the TET2 gene introduces a premature stop codon. For example, in some embodiments, a mutation in the TET2 gene that introduces a premature stop codon is selected from the following positions: R550X, Q1009X, Y1337X, R1404X, R1516X, and Q1652X.

In certain aspects, the disclosure provides methods for treating or preventing a bone marrow disorder in a subject, comprising administering to a subject in need thereof an effective amount of an ActRII antagonist, wherein the subject has bone marrow cells that test positive for one or more mutations in a gene selected from the group consisting of: SF3B1, DNMT3A, and TET2. In some embodiments, the subject tests positive for one or more SF3B1 mutations. Optionally one or more of the SF3B1 mutations are in a SF3B1 exon. Optionally one or more of the SF3B1 mutations are in a SF3B1 intron. Optionally one or more of the SF3B1 mutations are in a SF3B1 5' and/or 3' region. Optionally one or more of the SF3B1 mutations causes a deletion, addition, and/or substitution of an amino acid in the protein encoded by the mutated SF3B1 gene. Optionally one or more SF3B1 mutations causes a substitution of one or more amino acid selected from the group consisting of: K182E, E491G, R590K, E592K, R625C, R625G, N626D, N626S, H662Y, T663A, K666M, K666Q, K666R, Q670E, G676D, V701I, I704N, I704V, G740R, A744P, D781G, A1188V, N619K, N626H, N626Y, R630S, I704T, G740E, K741N, G742D, D894G, Q903R, R1041H, I1241T, G347V, E622D, Y623C, R625H, R625L, H662D, H662Q, T663I, K666E, K666N, K666T, K700E, V701F, and E783K. Optionally one or more SF3B1 mutations are in a SF3B1 exon selected from the group consisting of: exon 14, exon 15 and exon 16. In some embodiment, the subject tests positive for one or more DNMT3A mutations. Optionally one or more of the DNMT3A mutations are in a DNMT3A exon. Optionally one or more of the DNMT3A mutations are in a DNMT3A intron. Optionally one or more of the DNMT3A mutations are in a DNMT3A 5' and/or 3' region. Optionally one or more of the DNMT3A mutations causes a deletion, addition, and/or substitution of an amino acid in the protein encoded by the mutated DNMT3A gene. Optionally one or more DNMT3A mutations causes a substitution of one or more amino acid selected from the group consisting of: R882C, R882H, P904L, and P905P. Optionally the one or more DNMT3A mutations are in a DNMT3A exon selected from the group consisting of: exon 10, exon 18 and exon 22. Optionally one or more DNMT3A mutations introduces a premature stop codon. Optionally one or more DNMT3A mutations is selected from the group consisting of Y436X and W893X. In some embodiments, subject tests positive for one or more TET2 mutations. Optionally one or more of the TET2 mutations are in a TET2 exon. Optionally one or more of the TET2 mutations are in a TET2 intron. Optionally one or more of the TET2 mutations are in a TET2 5' and/or 3' region. Optionally one or more of the TET2 mutations causes a deletion, addition, and/or substitution of an amino acid in the protein encoded by the mutated TET2 gene. Optionally one or more TET2 mutations causes a substitution of one or more amino acid selected from the group consisting of: E47Q, Q1274R, W1291R, G1370R, G1370E, N1387S, and Y1724H. Optionally one or more TET2 mutations are in a TET2 exon selected from the group consisting of: exon 1, exon 4, exon 5, exon 6, exon 7, exon 8, and exon 9. Optionally one or more TET2 mutations introduces a premature stop codon. Optionally one or more TET2 mutations is selected from the group consisting of: R550X, Q1009X, Y1337X, R1404X, R1516X, and Q1652X. Optionally the subject has anemia. Optionally the subject has undesirably high levels of endogenous EPO. Optionally the subject has previously been treated with one or more EPO receptor agonists. Optionally the subject has an inadequate response to the EPO receptor agonist. Optionally the subject is no longer responsive to the EPO receptor agonist. Optionally the EPO receptor agonist is EPO. Optionally the treatment delays conversion to leukemia. Optionally the treatment delays conversion to acute myeloid leukemia. Optionally the subject is a pre-leukemia patient. Optionally the treatment increases red blood cell levels and/or hemoglobin levels in the subject. Optionally the subject has been administered one or more blood cell transfusions prior to the start of the ActRII antagonist treatment. Optionally the treatment decreases blood cell transfusion burden. Optionally the treatment decreases blood cell transfusion by greater than about 30%, 40%, 50%, 60%, 70%, 80%, 90%, or 100% for 4 to 8 weeks relative to the equal time prior to the start of the ActRII antagonist treatment. Optionally the treatment decreases blood cell transfusion by greater than about 50% for 4 to 8 weeks relative to the equal time prior to the start of the ActRII antagonist treatment. Optionally the treatment decreases iron overload. Optionally the treatment decrease iron content in the liver and/or spleen.

In certain aspects, the disclosure provides methods for treating or preventing myelodysplastic syndrome (MDS) and/or one or more complications of MDS, comprising administering to a subject in need thereof an effective amount of an ActRII antagonist, wherein the subject has bone marrow cells that test positive for one or more mutations in a gene selected from the group consisting of: SF3B1, DNMT3A, and TET2. In some embodiments, the subject tests positive for one or more SF3B1 mutations. Optionally one or more of the mutations are in a SF3B1 exon. Optionally one or more of the SF3B1 mutations are in a SF3B1 intron. Optionally one or more of the SF3B1 mutations are in a SF3B1 5' and/or 3' region. Optionally one or more of the SF3B1 mutations causes a deletion, addition, and/or substitution of an amino acid in the protein encoded by the mutated SF3B1 gene. Optionally one or more SF3B1 mutations causes a substitution of one or more amino acid selected from the group consisting of: K182E, E491G, R590K, E592K, R625C, R625G, N626D, N626S, H662Y, T663A, K666M, K666Q, K666R, Q670E, G676D, V701I, I704N, I704V, G740R, A744P, D781G, A1188V, N619K, N626H, N626Y, R630S, I704T, G740E, K741N, G742D, D894G, Q903R, R1041H, I1241T, G347V, E622D, Y623C, R625H, R625L, H662D, H662Q, T663I, K666E, K666N, K666T, K700E, V701F, and E783K. Optionally one or more SF3B1 mutations are in a SF3B1 exon selected from the group consisting of: exon 14, exon 14 and exon 16. In some embodiments, the subject tests positive for one or more DNMT3A mutations. Optionally one or more of the DNMT3A mutations are in a DNMT3A exon. Optionally one or more of the DNMT3A mutations are in a DNMT3A intron. Optionally one or more of the DNMT3A mutations are in a DNMT3A 5' and/or 3' region. Optionally one or more of the DNMT3A mutations causes a deletion, addition, and/or substitution of an amino acid in the protein encoded by the mutated DNMT3A gene. Optionally one or more DNMT3A mutations causes a substitution of one or more amino acid selected from the group consisting of: R882C, R882H, P904L, and P905P. Optionally one or more DNMT3A mutations are in a DNMT3A exon selected from the group consisting of: exon 10, exon 18, and exon 22. Optionally one or more DNMT3A mutations introduces a premature stop codon. Optionally one or more DNMT3A mutations are selected from the group consisting of Y436X and W893X. In some embodiments, the subject tests positive for one or more TET2 mutations. Optionally one or more of the TET2 mutations are in a TET2 exon. Optionally one or more of the TET2 mutations are in a TET2 intron. Optionally one or more of the TET2 mutations are in a TET2 5' and/or 3' region. Optionally one or more of the TET2 mutations causes a deletion, addition, and/or substitution of an amino acid in the protein encoded by the mutated TET2 gene. Optionally one or more TET2 mutations causes a substitution of one or more amino acid selected from the group consisting of: E47Q, Q1274R, W1291R, G1370R, G1370E, N1387S, and Y1724H. Optionally one or more TET2 mutations are in a TET2exon selected from the group consisting of: exon 1, exon 4, exon 5, exon 6, exon 7, exon 8, and exon 9. Optionally one or more TET2 mutations introduces a premature stop codon. Optionally one or more TET2 mutations is selected from the group consisting of: R550X, Q1009X, Y1337X, R1404X, R1516X, and Q1652X. Optionally the subject has anemia. Optionally the subject has undesirably high levels of endogenous EPO. Optionally the subject has previously been treated with one or more EPO receptor agonists. Optionally the subject has an inadequate response to the EPO receptor agonist. Optionally the subject is no longer responsive to the EPO receptor agonist. Optionally the EPO receptor agonist is EPO. Optionally the treatment delays conversion to leukemia. Optionally the treatment delays conversion to acute myeloid leukemia. Optionally the treatment increases red blood cell levels and/or hemoglobin levels in the subject. Optionally the subject has been administered one or more blood cell transfusions prior to the start of the ActRII antagonist treatment. Optionally the treatment decreases blood cell transfusion burden. Optionally the treatment decreases blood cell transfusion by greater than about 30%, 40%, 50%, 60%, 70%, 80%, 90%, or 100% for 4 to 8 weeks relative to the equal time prior to the start of the ActRII antagonist treatment. Optionally the treatment decreases blood cell transfusion by greater than about 50% for 4 to 8 weeks relative to the equal time prior to the start of the ActRII antagonist treatment. Optionally the treatment decreases iron overload. Optionally the treatment decrease iron content in the liver and/or spleen. Optionally the subject has a subtype of MDS selected from: MDS with refractory anemia with ring sideroblasts (RARS); MDS with refractory anemia with ring sideroblasts and thrombocytosis (RARS-T); MDS with refractory cytopenia with unilineage dysplasia (RCUD); MDS with refractory cytopenia with multilineage dysplasia and ring sideroblasts (RCMD-RS); MDS with a somatic mutation in one or more of SF3B1, SRSF2, DNMT3A, and TET2; MDS without a somatic mutation in ASXL1 or ZRSR2; MDS with iron overload; and MDS with neutropenia. Optionally the subject has an International Prognostic Scoring System (IPSS) score selected from: low, intermediate 1, or intermediate 2. Optionally the subject has sideroblasts. Optionally the subject has at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% sideroblasts as a percentage of bone marrow erythroid precursors in his or her bone marrow.

ActRII antagonists of the disclosure include, for example, agents that can inhibit ActRII receptor (e.g., an ActRIIA and/or ActRIIB receptor) mediated activation of a signal transduction pathway (e.g., activation of signal transduction via intracellular mediators, such as SMAD 1, 2, 3, 5, and/or 8); agents that can inhibit one or more ActRII ligands (e.g., activin A, activin B, activin AB, activin C, activin E, GDF11, GDF8, BMP6, BMP7, Nodal, etc.) from, e.g., binding to and/or activating an ActRII receptor; agents that inhibit expression (e.g., transcription, translation, cellular secretion, or combinations thereof) of an ActRII ligand and/or an ActRII receptor; and agents that can inhibit one or more intracellular mediators of the ActRII signaling pathway (e.g., SMADs 1, 2, 3, 5, and/or 8).

In particular, the disclosure provides methods for using an ActRII antagonist, or combination of ActRII antagonists, to treat or prevent one or more complications of MDS and sideroblastic anemias including, for example, anemia, neutropenia, splenomegaly, blood transfusion requirement, development of acute myeloid leukemia, iron overload, and complications of iron overload, among which are congestive heart failure, cardiac arrhythmia, myocardial infarction, other forms of cardiac disease, diabetes mellitus, dyspnea, hepatic disease, and adverse effects of iron chelation therapy and as other examples, to increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In particular, the disclosure provides methods for using an ActRII antagonist, or combination of ActRII antagonists, to treat or prevent complications in a subtype of MDS, including MDS patients with elevated numbers of erythroblasts (hypercellularity) in bone marrow; in MDS patients with more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% sideroblasts, as a percentage of erythroid precursors in bone marrow; in MDS patients with refractory anemia with ring sideroblasts (RARS); in MDS patients with refractory anemia with ring sideroblasts and thrombocytosis (RARS-T); in MDS patients with refractory cytopenia with unilineage dysplasia (RCUD); in MDS patients with refractory cytopenia with multilineage dysplasia and ring sideroblasts (RCMD-RS); in MDS patients with a somatic mutation in SF3B1, SRSF2, DNMT3A, TET2, or SETBP1; in MDS patients without a somatic mutation in ASXL1 or ZRSR2; in MDS patients with iron overload; and in MDS patients with neutropenia.

Also in particular, the disclosure provides methods for using an ActRII antagonist, or combination of ActRII antagonists, to treat or prevent complications of a sideroblastic anemia, including refractory anemia with ring sideroblasts (RARS); refractory anemia with ring sideroblasts and thrombocytosis (RARS-T); refractory cytopenia with multilineage dysplasia and ring sideroblasts (RCMD-RS); sideroblastic anemia associated with alcoholism; drug-induced sideroblastic anemia; sideroblastic anemia resulting from copper deficiency (zinc toxicity); sideroblastic anemia resulting from hypothermia; X-linked sideroblastic anemia (XLSA); SLC25A38 deficiency; glutaredoxin 5 deficiency; erythropoietic protoporphyria; X-linked sideroblastic anemia with ataxia (XLSA/A); sideroblastic anemia with B-cell immunodeficiency, fevers, and developmental delay (SIFD); Pearson marrow-pancreas syndrome; myopathy, lactic acidosis, and sideroblastic anemia (MLASA); thiamine-responsive megaloblastic anemia (TRIVIA); and syndromic/non-syndromic sideroblastic anemia of unknown cause.

In certain embodiments, preferred ActRII antagonists to be used in accordance with the methods disclosed herein are agents that bind to and/or inhibit GDF11 and/or GDF8 (e.g., an agent that inhibits GDF11- and/or GDF8-mediated activation of ActRIIA and/or ActRIIB signaling transduction, such as SMAD 2/3 signaling). Such agents are referred to collectively as GDF-ActRII antagonists. Optionally, such GDF-ActRII antagonists may further inhibit one or more of activin A, activin B, activin AB, activin C, activin E, GDF11, GDF8, BMP6, BMP7, and Nodal. Therefore, in some embodiments, the disclosure provides methods of using one or more ActRII antagonists, including, for example, soluble ActRIIA polypeptides, soluble ActRIIB polypeptides, GDF trap polypeptides, anti-ActRIIA antibodies, anti-ActRIIB antibodies, anti-ActRII ligand antibodies (e.g, anti-GDF11 antibodies, anti-GDF8 antibodies, anti-activin A antibodies, anti-activin B antibodies, anti-activin AB antibodies, anti-activin C antibodies, anti-activin E antibodies, anti-BMP6 antibodies, anti-BMP7 antibodies, and anti-Nodal antibodies), small-molecule inhibitors of ActRIIA, small-molecule inhibitors of ActRIIB, small-molecule inhibitors of one or more ActRII ligands (e.g., activin A, activin B, activin AB, activin C, activin E, GDF11, GDF8, BMP6, BMP7, Nodal, etc.), inhibitor nucleotides (nucleotide-based inhibitors) of ActRIIA, inhibitor nucleotides of ActRIIB, inhibitor nucleotides of one or more ActRII ligands (e.g., activin A, activin B, activin AB, activin C, activin E, GDF11, GDF8, BMP6, BMP7, Nodal, etc.), or combinations thereof, to increase red blood cell levels and/or hemoglobin levels in a subject in need thereof, treat or prevent an anemia in a subject in need thereof, treat sideroblastic anemia or MDS in a subject in need thereof, or treat one or more complications of sideroblastic anemia or MDS in a subject in need thereof and as other examples, to increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof. In certain embodiments, ActRII antagonists to be used in accordance with the methods disclosed herein do not substantially bind to and/or inhibit activin A (e.g., activin A-mediated activation of ActRIIA and/or ActRIIB signaling transduction, such as SMAD 2/3 signaling).

In part, the present disclosure demonstrates that an ActRII antagonist comprising a variant, extracellular (soluble) ActRIIB domain that binds to and inhibits GDF11 activity (e.g., GDF11-mediated ActRIIA and/or ActRIIB signaling transduction, such as SMAD 2/3 signaling) may be used to increase red blood cell levels in vivo, treat anemia resulting from various conditions/disorders, and treat sideroblastic anemia or MDS. Therefore, in certain embodiments, preferred ActRII antagonists to be used in accordance with the methods disclosed herein (e.g., methods of increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1 mutations in a subject in need thereof, etc.) are soluble ActRII polypeptides (e.g. soluble ActRIIA or ActRIIB polypeptides) that bind to and/or inhibit GDF11 (e.g., GDF11-mediated activation of ActRIIA and/or ActRIIB signaling transduction, such as SMAD 2/3 signaling). While soluble ActRIIA and soluble ActRIIB ActRII antagonists may affect red blood cell formation and/or morphology through a mechanism other than GDF11 antagonism, the disclosure nonetheless demonstrates that desirable therapeutic agents, with respect to the methods disclosed herein, may be selected on the basis of GDF11 antagonism or ActRII antagonism or both. Optionally, such soluble ActRII polypeptide antagonist may further bind to and/or inhibit GDF8 (e.g. inhibit GDF8-mediated activation of ActRIIA and/or ActRIIB signaling transduction, such as SMAD 2/3 signaling). In some embodiments, soluble ActRIIA and ActRIIB polypeptides of the disclosure that bind to and/or inhibit GDF11 and/or GDF8 may further bind to and/or inhibit one or more additional ActRII ligands selected from: activin A, activin B, activin AB, activin C, activin E, BMP6, BMP7, and Nodal.

In certain aspects, the present disclosure provides GDF traps that are variant ActRII polypeptides (e.g., ActRIIA and ActRIIB polypeptides), including ActRII polypeptides having amino- and carboxy-terminal truncations and/or other sequence alterations (one or more amino acid substitutions, additions, deletions, or combinations thereof). Optionally, GDF traps of the invention may be designed to preferentially antagonize one or more ligands of ActRII receptors, such as GDF8 (also called myostatin), GDF11, Nodal, BMP6, and BMP7 (also called OP-1). As disclosed herein, examples of GDF traps include a set of variants derived from ActRIIB that have greatly diminished affinity for activin, particularly activin A. These variants exhibit desirable effects on red blood cells while reducing effects on other tissues. Examples of such variants include those having an acidic amino acid [e.g., aspartic acid (D) or glutamic acid (E)] at the position corresponding to position 79 of SEQ ID NO:1. In certain embodiments, preferred GDF traps to be used in accordance with the methods disclosed herein (e.g., methods to increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof, etc.) bind to and/or inhibit GDF11. Optionally, such GDF traps may further bind to and/or inhibit GDF8. In some embodiments, GDF traps that bind to and/or inhibit GDF11 and/or GDF8 may further bind to and/or inhibit one or more additional ActRII ligands (e.g., activin B, activin E, BMP6, BMP7, and Nodal). In some embodiments, GDF traps to be used in accordance with the methods disclosed herein to not substantially bind to and/or inhibit activin A (e.g., activin A-mediated activation of ActRIIA and/or ActRIIB signaling transduction, such as SMAD 2/3 signaling). In certain embodiments, a GDF trap polypeptide comprises an amino acid sequence that comprises, consists of, or consists essentially of, the amino acid sequence of SEQ ID NOs: 36, 37, 41, 44, 45, 50 or 51, and polypeptides that are at least 80%, 85%, 90%, 95%, 96%, 97%, 98%, or 99% identical to any of the foregoing. In other embodiments, a GDF trap polypeptide comprises an amino acid sequence that comprises, consists of, or consists essentially of the amino acid sequence of SEQ ID NOs: 2, 3, 4, 5, 6, 10, 11, 22, 26, 28, 29, 31, or 49, and polypeptides that are at least 80%, 85%, 90%, 95%, 96%, 97%, 98%, or 99% identical to any of the foregoing. In still other embodiments, a GDF trap polypeptide comprises an amino acid sequence that comprises of the amino acid sequence of SEQ ID NOs: 2, 3, 4, 5, 6, 29, 31, or 49, and polypeptides that are at least 80%, 85%, 90%, 95%, 96%, 97%, 98%, or 99% identical to any of the foregoing, wherein the position corresponding to 79 in SEQ ID NO: 1, 4, or 50 is an acidic amino acid. A GDF trap may include a functional fragment of a natural ActRII polypeptide, such as one comprising at least 10, 20, or 30 amino acids of a sequence selected from SEQ ID NOs: 1, 2, 3, 4, 5, 6, 9, 10, 11, or 49 or a sequence of SEQ ID NO: 2, 5, 10, 11, or 49 lacking the C-terminal 1, 2, 3, 4, 5 or 10 to 15 amino acids and lacking 1, 2, 3, 4 or 5 amino acids at the N-terminus. A preferred polypeptide will comprise a truncation relative to SEQ ID NO: 2 or 5 of between 2 and 5 amino acids at the N-terminus and no more than 3 amino acids at the C-terminus. A preferred GDF trap for use in such a preparation consists of, or consists essentially of, the amino acid sequence of SEQ ID NO: 36.

Optionally, a GDF trap comprising an altered ActRII ligand-binding domain has a ratio of $K_d$ for activin A binding to $K_d$ for GDF11 and/or GDF8 binding that is at least 2-, 5-, 10-, 20, 50-, 100-, or even 1000-fold greater relative to the ratio for the wild-type ligand-binding domain. Optionally, the GDF trap comprising an altered ligand-binding domain has a ratio of $IC_{50}$ for inhibiting activin A to $IC_{50}$ for inhibiting GDF11 and/or GDF8 that is at least 2-, 5-, 10-, 20-, 25-50-, 100-, or even 1000-fold greater relative to the wild-type ActRII ligand-binding domain. Optionally, the GDF trap comprising an altered ligand-binding domain inhibits GDF11 and/or GDF8 with an $IC_{50}$ at least 2, 5, 10, 20, 50, or even 100 times less than the $IC_{50}$ for inhibiting activin A. These GDF traps can be fusion proteins that include an immunoglobulin Fc domain (either wild-type or mutant). In certain cases, the subject soluble GDF traps are antagonists (inhibitors) of GDF8 and/or GDF11.

In certain aspects, the disclosure provides GDF traps which are soluble ActRIIB polypeptides comprising an altered ligand-binding (e.g., GDF11-binding) domain. GDF traps with altered ligand-binding domains may comprise, for example, one or more mutations at amino acid residues such as E37, E39, R40, K55, R56, Y60, A64, K74, W78, L79, D80, F82 and F101 of human ActRIIB (numbering is relative to SEQ ID NO: 1). Optionally, the altered ligand-binding domain can have increased selectivity for a ligand such as GDF8/GDF11 relative to a wild-type ligand-binding domain of an ActRIIB receptor. To illustrate, these mutations are demonstrated herein to increase the selectivity of the altered ligand-binding domain for GDF11 (and therefore, presumably, GDF8) over activin: K74Y, K74F, K74I, L79D, L79E, and D801. The following mutations have the reverse effect, increasing the ratio of activin binding over GDF11: D54A, K55A, L79A and F82A. The overall (GDF11 and activin) binding activity can be increased by inclusion of the "tail" region or, presumably, an unstructured linker region, and also by use of a K74A mutation. Other mutations that caused an overall decrease in ligand binding affinity, include: R40A, E37A, R56A, W78A, D80K, D80R, D80A, D80G, D80F, D80M and D80N. Mutations may be combined to achieve desired effects. For example, many of the mutations that affect the ratio of GDF11:activin binding have an overall negative effect on ligand binding, and therefore, these may be combined with mutations that generally increase ligand binding to produce an improved binding protein with ligand selectivity. In an exemplary embodiment, a GDF trap is an ActRIIB polypeptide comprising an L79D or L79E mutation, optionally in combination with additional amino acid substitutions, additions, or deletions.

In certain embodiments, ActRII antagonists to be used in accordance with the methods disclosed herein are ActRIIB polypeptides or ActRIIB-based GDF trap polypeptides. In general such ActRIIB polypeptides and ActRIIB-based GDF trap polypeptides are soluble polypeptides that comprise a portion/domain derived from the ActRIIB sequence of SEQ ID NO:1, 4, or 49, particularly an extracellular, ligand-binding portion/domain derived from the ActRIIB sequence of SEQ ID NO:1, 4, or 49. In some embodiments, the portion derived from ActRIIB corresponds to a sequence beginning at any one of amino acids 21-29 (e.g., 21, 22, 23, 24, 25, 26, 27, 28, or 29) of SEQ ID NO:1 or 4 [optionally beginning at 22-25 (e.g., 22, 23, 24, or 25) of SEQ ID NO:1 or 4] and ending at any one of amino acids 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 [optionally beginning at 22-25 (e.g., 22, 23, 24, or 25) of SEQ ID NO:1 or 4] and ending at any one of amino acids 109-133 (e.g., 109, 110, 111, 112, 113, 114, 115, 116, 117, 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 [optionally beginning at 22-25 (e.g., 22, 23, 24, or 25) of SEQ ID NO:1 or 4] and ending at any one of amino acids 109-133 (e.g., 109, 110, 111, 112, 113, 114, 115, 116, 117, 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at any one of amino acids 21-24 (e.g., 21, 22, 23, or 24) of SEQ ID NO: 1 or 4 and ending at any of amino acids 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 and ending at any one of amino acids 118-133 (e.g., 118, 119, 120, 121, 122, 123, 124, 125, 126, 127, 128, 129, 130, 131, 132, or 133) of SEQ ID NO: 1 or 4 In some embodiments, the portion derived from ActRIIB corresponds to a sequence beginning at any one of amino acids 21-24 (e.g., 21, 22, 23, or 24) of SEQ ID NO: 1 or 4 and ending at any one of amino acids 118-134 (e.g., 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 and ending at any one of amino acids 128-133 (e.g., 128, 129, 130, 131, 132, or 133) of SEQ ID NO: 1 or 4. In some embodiments, the portion derived from ActRIIB corresponds to a sequence beginning at any of amino acids 20-24 (e.g., 20, 21, 22, 23, or 24) of SEQ ID NO: 1 or 39 and ending at any of amino acids 128-133 (e.g., 128, 129, 130, 131, 132, or 133) of SEQ ID NO: 1 or 39. In some embodiments, the portion derived from ActRIIB corresponds to a sequence beginning at any one of amino acids 21-29 (e.g., 21, 22, 23, 24, 25, 26, 27, 28, or 29) of SEQ ID NO: 1 or 4 and ending at any one of amino acids 118-134 (e.g., 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 and ending at any one of amino acids 118-133 (e.g., 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at one any of amino acids 21-29 (e.g., 21, 22, 23, 24, 25, 26, 27, 28, or 29) of SEQ ID NO: 1 or 4 and ending at any one of amino acids 128-134 (e.g., 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 and ending at any one of amino acids 128-133 (e.g., 128, 129, 130, 131, 132, or 133) of SEQ ID NO: 1 or 4. Surprisingly, ActRIIB and ActRIIB-based GDF trap constructs beginning at 22-25 (e.g., 22, 23, 24, or 25) of SEQ ID NO: 1 or 4 have activity levels greater than proteins having the full extracellular domain of human ActRIIB In a preferred embodiment, the ActRIIB polypeptides and ActRIIB-based GDF trap polypeptides comprise, consist essentially of, or consist of, an amino acid sequence beginning at amino acid position 25 of SEQ ID NO: 1 or 4 and ending at amino acid position 131 of SEQ ID NO: 1 or 4. Any of the foregoing ActRIIB polypeptides or ActRIIB-based GDF trap polypeptides may be produced as a homodimer. Any of the foregoing ActRIIB polypeptides or ActRIIB-based GDF trap polypeptides may further comprise a heterologous portion that comprises a constant region from an IgG heavy chain, such as an Fc domain. Any of the above ActRIIB-based GDF trap polypeptides may comprise an acidic amino acid at the position corresponding to position 79 of SEQ ID NO: 1, optionally in combination with one or more additional amino acid substitutions, deletions, or insertions relative to SEQ ID NO: 1. Any of the above ActRIIB polypeptides or ActRIIB-based GDF trap polypeptides, including homodimer and/or fusion proteins thereof, may bind to and/or inhibit signaling by activin (e.g., activin A, activin B, activin C, or activin AB) in a cell-based assay. Any of the above ActRIIB polypeptides or ActRIIB-based GDF trap polypeptides, including homodimer and/or fusion proteins thereof, may bind to and/or inhibit signaling by GDF11 and/or GDF8 in a cell based assay. Optionally, any of the above ActRIIB polypeptides or ActRIIB-based GDF trap polypeptides, including homodimer and/or fusion proteins thereof, may bind to and/or inhibit signaling of one or more of activin B, activin C, activin E, BMP6, BMP7, and Nodal in a cell-based assay.

Other ActRIIB polypeptides and ActRIIB-based GDF Trap polypeptides are contemplated, such as the following. An ActRIIB polypeptide or GDF trap polypeptide comprising an amino acid sequence that is at least 80% (e.g., 85%, 90%, 95%, 96%, 97%, 98%, 99%, or 100%) identical to the sequence of amino acids 29-109 of SEQ ID NO: 1 or 4, wherein the position corresponding to 64 of SEQ ID NO: 1 is an R or K, and wherein the ActRIIB polypeptide or ActRIIB-based GDF trap polypeptide inhibits signaling by activin, GDF8, and/or GDF11 in a cell-based assay. The ActRIIB polypeptide or ActRIIB-based GDF trap polypeptide as above, wherein at least one alteration with respect to the sequence of SEQ ID NO: 1 or 4 is positioned outside of the ligand-binding pocket. The ActRIIB polypeptide or ActRIIB-based GDF trap polypeptide as above, wherein at least one alteration with respect to the sequence of SEQ ID NO: 1 or 4 is a conservative alteration positioned within the ligand-binding pocket. The ActRIIB polypeptide or ActRIIB-based GDF trap polypeptide as above, wherein at least one alteration with respect to the sequence of SEQ ID NO: 1 or 4 is an alteration at one or more positions selected from the group consisting of K74, R40, Q53, K55, F82, and L79.

Other ActRIIB polypeptides and ActRIIB-based GDF trap polypeptides are contemplated, such as the following. An ActRIIB polypeptide or ActRIIB-based GDF trap polypeptide comprising an amino acid sequence that is at least 80% (e.g., 85%, 90%, 95%, 96%, 97%, 98%, 99%, or 100%) identical to the sequence of amino acids 29-109 of SEQ ID NO: 1 or 4, and wherein the protein comprises at least one N-X-S/T sequence at a position other than an endogenous N-X-S/T sequence of ActRIIB, and at a position outside of the ligand binding pocket. The ActRIIB polypeptide or ActRIIB-based GDF trap polypeptide as above, wherein the ActRIIB polypeptide or ActRIIB-based GDF trap polypeptide comprises an N at the position corresponding to position 24 of SEQ ID NO: 1 or 4 and an S or T at the position corresponding to position 26 of SEQ ID NO: 1 or 4, and wherein the ActRIIB polypeptide or ActRIIB-based GDF trap polypeptide inhibits signaling by activin, GDF8, and/or GDF11 in a cell-based assay. The ActRIIB polypeptide or ActRIIB-based GDF trap polypeptide as above, wherein the ActRIIB polypeptide or ActRIIB-based GDF Trap polypeptide comprises an R or K at the position corresponding to position 64 of SEQ ID NO: 1 or 4. The ActRIIB polypeptide or ActRIIB-based GDF trap polypeptide as above, wherein ActRIIB polypeptide or ActRIIB-based GDF trap polypeptide comprises a D or E at the position corresponding to position 79 of SEQ ID NO: 1 or 4, and wherein the ActRIIB polypeptide or ActRIIB-based GDF trap polypeptide inhibits signaling by activin, GDF8, and/or GDF11 in a cell-based assay. The ActRIIB polypeptide or ActRIIB-based GDF trap polypeptide as above, wherein at least one alteration with respect to the sequence of SEQ ID NO: 1 or 4 is a conservative alteration positioned within the ligand-binding pocket. The ActRIIB polypeptide or ActRIIB-based GDF trap polypeptide as above, wherein at least one alteration with respect to the sequence of SEQ ID NO: 1 or 4 is an alteration at one or more positions selected from the group consisting of K74, R40, Q53, K55, F82, and L79. The ActRIIB polypeptide or ActRIIB-based GDF trap polypeptide above, wherein the ActRIIB polypeptide or ActRIIB-based GDF trap polypeptide is a fusion protein further comprising one or more heterologous portion. Any of the above ActRIIB polypeptides or ActRIIB-based GDF trap polypeptides, or fusion proteins thereof, may be produced as a homodimer. Any of the above ActRIIB fusion proteins or ActRIIB-based GDF trap fusion proteins may have a heterologous portion that comprises a constant region from an IgG heavy chain, such as an Fc domain.

In certain embodiments, a preferred ActRIIB polypeptide, for use in accordance with the methods disclosed herein, comprises an amino acid sequence that comprises, consists of, or consists essentially of, the amino acid sequence of SEQ ID NOs: 2, 3, 5, 6, 29, 31, or 49, and polypeptides that are at least 80%, 85%, 90%, 95%, 96%, 97%, 98%, or 99% identical to any of the foregoing. An ActRIIB polypeptide may include a functional fragment of a natural ActRIIB polypeptide, such as one comprising at least 10, 20 or 30 amino acids of a sequence selected from SEQ ID NOs: 2, 3, 5, 6, 29, 31, or 49 or a sequence of SEQ ID NO: 2 or 5, lacking the C-terminal 1, 2, 3, 4, 5 or 10 to 15 amino acids and lacking 1, 2, 3, 4 or 5 amino acids at the N-terminus. A preferred polypeptide will comprise a truncation relative to SEQ ID NO: 2 or 5 of between 2 and 5 amino acids at the N-terminus and no more than 3 amino acids at the C-terminus. A preferred GDF trap for use in accordance with the methods described herein consists of, or consists essentially of, the amino acid sequence of SEQ ID NO:29.

A general formula for an active (e.g., ligand binding) ActRIIA polypeptide is one that comprises a polypeptide that starts at amino acid 30 and ends at amino acid 110 of SEQ ID NO:9. Accordingly, ActRIIA polypeptides and ActRIIA-based GDF traps of the present disclosure may comprise, consist, or consist essentially of a polypeptide that is at least 80%, 85%, 90%, 95%, 96%, 97%, 98%, 99%, or 100% identical to amino acids 30-110 of SEQ ID NO:9. Optionally, ActRIIA polypeptides and ActRIIA-based GDF trap polypeptides of the present disclosure comprise, consists, or consist essentially of a polypeptide that is at least 80%, 85%, 90%, 95%, 96%, 97%, 98%, 99%, or 100% identical to amino acids amino acids 12-82 of SEQ ID NO:9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115) or SEQ ID NO:9, respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO:9. Any of the foregoing ActRIIA polypeptides or ActRIIA-based GDF trap polypeptides may be produced as a homodimer. Any of the foregoing ActRIIA polypeptides or ActRIIA-based GDF trap polypeptides may further comprise a heterologous portion that comprises a constant region from an IgG heavy chain, such as an Fc domain. Any of the above ActRIIA polypeptides or ActRIIA-based GDF trap polypeptides, including homodimer and/or fusion proteins thereof, may bind to and/or inhibit signaling by activin (e.g., activin A, activin B, activin C, or activin AB) in a cell-based assay. Any of the above ActRIIA polypeptides or ActRIIA-based GDF trap polypeptides, including homodimer and/or fusion proteins thereof, may bind to and/or inhibit signaling by GDF11 and/or GDF8 in a cell-based assay. Optionally, any of the above ActRIIA polypeptides or ActRIIB-based GDF trap polypeptides, including homodimer and/or fusion proteins thereof, may bind to and/or inhibit signaling of one or more of activin B, activin C, activin E, GDF7, and Nodal in a cell-based assay.

In certain embodiments, preferred ActRIIA polypeptides and ActRIIA-based GDF-trap polypeptides, for use in accordance with the methods disclosed herein, comprise an amino acid sequence that comprises, consists of, or consists essentially of, the amino acid sequence of SEQ ID NOs: 9, 10, 22, 26, or 28, and polypeptides that are at least 80%, 85%, 90%, 95%, 96%, 97%, 98%, or 99% identical to any of the foregoing. An ActRIIA polypeptide or ActRIIA-based GDF-trap polypeptide may include a functional fragment of a natural ActRIIA polypeptide, such as one comprising at least 10, 20 or 30 amino acids of a sequence selected from SEQ ID NOs: 9, 10, 22, 26, or 28 or a sequence of SEQ ID NO:10, lacking the C-terminal 1, 2, 3, 4, 5 or 10 to 15 amino acids and lacking 1, 2, 3, 4 or 5 amino acids at the N-terminus. A preferred polypeptide will comprise a truncation relative to SEQ ID NO:10 of between 2 and 5 amino acids at the N-terminus and no more than 3 amino acids at the C-terminus. A preferred ActRIIA polypeptide for use in the methods described herein consists of, or consists essentially of, the amino acid sequence of SEQ ID NO: 26 or 28.

An ActRII polypeptide (e.g. an ActRIIA or ActRIIB polypeptide) or GDF trap polypeptide of the disclosure may include one or more alterations (e.g., amino acid additions, deletions, substitutions, or combinations thereof) in the amino acid sequence of an ActRII polypeptide (e.g., in the ligand-binding domain) relative to a naturally occurring ActRII polypeptide. The alteration in the amino acid sequence may, for example, alter glycosylation of the polypeptide when produced in a mammalian, insect, or other eukaryotic cell or alter proteolytic cleavage of the polypeptide relative to the naturally occurring ActRII polypeptide.

Optionally, ActRII polypeptides (e.g. an ActRIIA or ActRIIB polypeptides) and GDF trap polypeptides of the disclosure comprise one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

In some embodiments, an ActRII polypeptide (e.g. an ActRIIA or ActRIIB polypeptide) or GDF trap polypeptide of the disclosure may be a fusion protein that has, as one domain, an ActRII polypeptide or GDF trap polypeptide (e.g., a ligand-binding domain of an ActRII receptor, optionally with one or more sequence variations) and one or more additional heterologous domains that provide a desirable property, such as improved pharmacokinetics, easier purification, targeting to particular tissues, etc. For example, a domain of a fusion protein may enhance one or more of in vivo stability, in vivo half-life, uptake/administration, tissue localization or distribution, formation of protein complexes, multimerization of the fusion protein, and/or purification. ActRII polypeptide and GDF trap fusion proteins may include an immunoglobulin Fc domain (wild-type or mutant) or a serum albumin. In certain embodiments, an ActRII polypeptide and GDF trap fusion protein comprises a relatively unstructured linker positioned between the Fc domain and the ActRII or GDF trap domain. This unstructured linker may correspond to the roughly 15 amino acid unstructured region at the C-terminal end of the extracellular domain of ActRII or GDF trap (the "tail"), or it may be an artificial sequence of between 3 and 5, 15, 20, 30, 50 or more amino acids that are relatively free of secondary structure. A linker may be rich in glycine and proline residues and may, for example, contain repeating sequences of threonine/serine and glycines [e.g., $TG_4$ (SEQ ID NO:52), $TG_3$ (SEQ ID NO:53), or $SG_4$ (SEQ ID NO:54) singlets or repeats] or a series of three glycines. A fusion protein may include a purification subsequence, such as an epitope tag, a FLAG tag, a polyhistidine sequence, and a GST fusion. In certain embodiments, an ActRII fusion protein or GDF trap fusion comprises a leader sequence. The leader sequence may be a native ActRII leader sequence (e.g., a native ActRIIA or ActRIIB leader sequence) or a heterologous leader sequence. In certain embodiments, the leader sequence is a tissue plasminogen activator (TPA) leader sequence. In some embodiment, an ActRII fusion protein or GDF trap fusion protein comprises an amino acid sequence as set forth in the formula A-B-C. The B portion is an N- and C-terminally truncated ActRII or GDF trap polypeptide as described herein. The A and C portions may be independently zero, one, or more than one amino acids, and both A and C portions are heterologous to B. The A and/or C portions may be attached to the B portion via a linker sequence.

Optionally, ActRII polypeptides (e.g., ActRIIA and ActRIIB polypeptides) or GDF trap polypeptides, including variants and fusion proteins thereof, to be used in accordance with the methods disclosed herein bind to one or more ActRIIB ligands (e.g., activin A, activin B, activin AB, activin C, activin E, GDF11, GDF8, BMP6, BMP7, and/or Nodal) with a Kd less than 10 micromolar, less than 1 micromolar, less than 100 nanomolar, less than 10 nanomolar, or less than 1 nanomolar. Optionally, such ActRII polypeptides or GDF trap polypeptides inhibit ActRII signaling, such as ActRIIA and/or ActRIIB intracellular signal transduction events triggered by an ActRII ligand (e.g., SMAD 2/3 and/or SMAD 1/5/8 signaling).

In certain aspects, the disclosure provides pharmaceutical preparations comprising an ActRII antagonist of the present disclosure (e.g., an ActRIIA polypeptide, an ActRIIB polypeptide, a GDF trap polypeptide) and a pharmaceutically acceptable carrier. A pharmaceutical preparation may also include one or more additional compounds such as a compound that is used to treat a disorder or condition described herein (e.g., an additional compound that increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1 mutations in a subject in need thereof). Preferably, a pharmaceutical preparation of the disclosure is substantially pyrogen-free. In general, it is preferable that an ActRIIA polypeptide, an ActRIIB polypeptide, or a GDF trap polypeptide be expressed in a mammalian cell line that mediates suitably natural glycosylation of the polypeptide so as to diminish the likelihood of an unfavorable immune response in a patient. Human and CHO cell lines have been used successfully, and it is expected that other common mammalian expression vectors will be useful. In some embodiments, preferable ActRIIA polypeptides, ActRIIB polypeptides, and GDF trap polypeptides are glycosylated and have a glycosylation pattern that is obtainable from a mammalian cell, preferably a CHO cell. In certain embodiments, the disclosure provides packaged pharmaceuticals comprising a pharmaceutical preparation described herein and labeled for use in one or more of increasing red blood cell levels and/or hemoglobin in a mammal (preferably a human), treating or preventing anemia in a mammal (preferably a human), treating sideroblastic anemia or MDS in a mammal (preferably a human), and/or treating or preventing one or more complications of sideroblastic anemia or MDS (e.g., anemia, vaso-occlusive crisis, etc.) in a mammal (preferably a human) or treat or prevent a disorder associated with SF3B1 mutations in a mammal (preferably a human).

In certain aspects, the disclosure provides nucleic acids encoding an ActRII polypeptide (e.g., an ActRIIA or ActRIIB polypeptide) or GDF trap polypeptide. An isolated polynucleotide may comprise a coding sequence for a soluble ActRII polypeptide or GDF trap polypeptide, such as described herein. For example, an isolated nucleic acid may include a sequence coding for an ActRII polypeptide or GDF trap comprising an extracellular domain (e.g., ligand-binding domain) of an ActRII polypeptide having one or more sequence variations and a sequence that would code for part or all of the transmembrane domain and/or the cytoplasmic domain of an ActRII polypeptide, but for a stop codon positioned within the transmembrane domain or the cytoplasmic domain, or positioned between the extracellular domain and the transmembrane domain or cytoplasmic domain. For example, an isolated polynucleotide coding for a GDF trap may comprise a full-length ActRII polynucleotide sequence such as SEQ ID NO: 1, 4, or 9 or having one or more variations, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRII. Nucleic acids disclosed herein may be operably linked to a promoter for expression, and the disclosure provides cells transformed with such recombinant polynucleotides. Preferably the cell is a mammalian cell, such as a CHO cell.

In certain aspects, the disclosure provides methods for making an ActRII polypeptide or a GDF trap. Such a method may include expressing any of the nucleic acids disclosed herein (e.g., SEQ ID NO: 8, 13, 27, 32, 39, 42, 46, or 48) in a suitable cell, such as a Chinese hamster ovary (CHO) cell. Such a method may comprise: a) culturing a cell under conditions suitable for expression of the GDF trap polypeptide, wherein said cell is transformed with a GDF trap expression construct; and b) recovering the GDF trap polypeptide so expressed. GDF trap polypeptides may be recovered as crude, partially purified or highly purified fractions using any of the well-known techniques for obtaining protein from cell cultures.

In certain aspects, the present disclosure relates to an antibody, or combination of antibodies, that antagonize ActRII activity (e.g., inhibition of ActRIIA and/or ActRIIB signaling transduction, such as SMAD 2/3 and/or SMAD 1/5/8 signaling). In particular, the disclosure provides methods of using an antibody ActRII antagonist, or combination of antibody ActRII antagonists, to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In certain embodiments, a preferred antibody ActRII antagonist of the disclosure is an antibody, or combination of antibodies, that binds to and/or inhibits activity of at least GDF11 (e.g., GDF11-mediated activation of ActRIIA and/or ActRIIB signaling transduction, such as SMAD 2/3 signaling). Optionally, the antibody, or combination of antibodies, further binds to and/or inhibits activity of GDF8 (e.g., GDF8-mediated activation of ActRIIA and/or ActRIIB signaling transduction, such as SMAD 2/3 signaling), particularly in the case of a multispecific antibody that has binding affinity for both GDF11 and GDF8 or in the context of a combination of one or more anti-GDF11 antibody and one or more anti-GDF8 antibody. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF11 and/or GDF8 further binds to and/or inhibits activity of one of more of activin A, activin B, activin AB, activin C, activin E, BMP6, BMP7, and Nodal (e.g., activation of ActRIIA or ActRIIB signaling transduction, such as SMAD 2/3 and/or SMAD 1/5/8 signaling), particularly in the case of a multispecific antibody that has binding affinity for multiple ActRII ligands or in the context of a combination multiple antibodies—each having binding affinity for a different ActRII ligand.

In part, the disclosure demonstrates that ActRII antagonists may be used in combination (e.g., administered at the same time or different times, but generally in such a manner as to achieve overlapping pharmacological effects) with EPO receptor activators to increase red blood cell levels (erythropoiesis) or, as examples, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof. In part, the disclosure demonstrates that a GDF trap can be administered in combination with an EPO receptor activator to synergistically increase formation of red blood cells in a patient, particularly in sideroblastic anemia or MDS patients. Thus, the effect of this combined treatment can be significantly greater than the sum of the effects of the ActRII antagonists and the EPO receptor activator when administered separately at their respective doses. In certain embodiments, this synergism may be advantageous since it enables target levels of red blood cells to be attained with lower doses of an EPO receptor activator, thereby avoiding potential adverse effects or other problems associated with higher levels of EPO receptor activation. Accordingly, in certain embodiments, the methods of the present disclosure (e.g., methods of increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof) comprise administering a patient in need thereof one or more ActRII antagonists (e.g., ActRIIA polypeptides, ActRIIB polypeptides, and/or GDF trap polypeptides) in combination with one or more EPO receptor activators.

An EPO receptor activator may stimulate erythropoiesis by directly contacting and activating EPO receptor. In certain embodiments, the EPO receptor activator is one of a class of compounds based on the 165 amino-acid sequence of native EPO and generally known as erythropoiesis-stimulating agents (ESAs), examples of which are epoetin alfa, epoetin beta, epoetin delta, and epoetin omega. In other embodiments, ESAs include synthetic EPO proteins (SEPs) and EPO derivatives with nonpeptidic modifications conferring desirable pharmacokinetic properties (lengthened circulating half-life), examples of which are darbepoetin alfa and methoxy-polyethylene-glycol epoetin beta. In certain embodiments, an EPO receptor activator may be an EPO receptor agonist that does not incorporate the EPO polypeptide backbone or is not generally classified as an ESA. Such EPO receptor agonists may include, but are not limited to, peptidic and nonpeptidic mimetics of EPO, agonistic antibodies targeting EPO receptor, fusion proteins comprising an EPO mimetic domain, and erythropoietin receptor extended-duration limited agonists (EREDLA).

In certain embodiments, an EPO receptor activator may stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. In part, the disclosure provides increased erythropoiesis in a patient by combined treatment with a GDF trap and an indirect EPO receptor activator with HIF stabilizing properties, such as a prolyl hydroxylase inhibitor.

In certain instances, when administering a GDF trap polypeptide for these other therapeutic indications, it may be desirable to monitor the effects on red blood cells during administration of the ActRII antagonist, or to determine or adjust the dosing of the ActRII antagonist, in order to reduce undesired effects on red blood cells. For example, increases in red blood cell levels, hemoglobin levels, or hematocrit levels may cause increases in blood pressure.

BRIEF DESCRIPTION OF THE DRAWINGS

This patent or patent application filed contains at least one drawing executed in color. Copies of this patent or patent application publication with color drawing(s) will be provided by the Office upon request and payment of the necessary fee.

FIG. 1 shows an alignment of extracellular domains of human ActRIIA (SEQ ID NO: 56) and human ActRIIB (SEQ ID NO: 2) with the residues that are deduced herein, based on composite analysis of multiple ActRIIB and ActRIIA crystal structures, to directly contact ligand indicated with boxes.

FIG. 3 shows the purification of ActRIIA-hFc expressed in CHO cells. The protein purifies as a single, well-defined peak as visualized by sizing column (top panel) and Coomassie stained SDS-PAGE (bottom panel) (left lane: molecular weight standards; right lane: ActRIIA-hFc).

FIG. 5A shows red blood cell (RBC) counts. FIG. 5B shows hemoglobin levels. Statistical significance is relative to baseline for each treatment group. At day 57, two monkeys remained in each group.

FIG. 6A shows red blood cell (RBC) counts. FIG. 6B shows hemoglobin levels. Statistical significance is relative to baseline for each treatment group. At day 57, two monkeys remained in each group.

FIG. 7A shows absolute reticulocyte counts. FIG. 7B shows the percentage of reticulocytes relative to RBCs. Statistical significance is relative to baseline for each group. At day 57, two monkeys remained in each group.

FIG. 8A shows absolute reticulocyte counts. FIG. 8B shows the percentage of reticulocytes relative to RBCs. Statistical significance is relative to baseline for each group. At day 57, two monkeys remained in each group.

FIG. 16 shows the full amino acid sequence for the GDF trap ActRIIB(L79D 20-134)-hFc (SEQ ID NO:38), including the TPA leader sequence (double underlined), ActRIIB extracellular domain (residues 20-134 in SEQ ID NO: 1; underlined), and hFc domain. The aspartate substituted at position 79 in the native sequence is double underlined and highlighted, as is the glycine revealed by sequencing to be the N-terminal residue in the mature fusion protein.

FIGS. 17A and 17B show a nucleotide sequence encoding ActRIIB(L79D 20-134)-hFc. SEQ ID NO:39 corresponds to the sense strand, and SEQ ID NO:40 corresponds to the antisense strand. The TPA leader (nucleotides 1-66) is double underlined, and the ActRIIB extracellular domain (nucleotides 76-420) is underlined.

FIG. 18 shows the full amino acid sequence for the truncated GDF trap ActRIIB(L79D 25-131)-hFc (SEQ ID NO:41), including the TPA leader (double underlined), truncated ActRIIB extracellular domain (residues 25-131 in SEQ ID NO:1; underlined), and hFc domain. The aspartate substituted at position 79 in the native sequence is double underlined and highlighted, as is the glutamate revealed by sequencing to be the N-terminal residue in the mature fusion protein.

FIGS. 19A and 19B shows a nucleotide sequence encoding ActRIIB(L79D 25-131)-hFc. SEQ ID NO:42 corresponds to the sense strand, and SEQ ID NO:43 corresponds to the antisense strand. The TPA leader (nucleotides 1-66) is double underlined, and the truncated ActRIIB extracellular domain (nucleotides 76-396) is underlined. The amino acid sequence for the ActRIIB extracellular domain (residues 25-131 in SEQ ID NO: 1) is also shown (SEQ ID NO:45).

FIG. 20 shows the amino acid sequence for the truncated GDF trap ActRIIB(L79D 25-131)-hFc without a leader (SEQ ID NO:44). The truncated ActRIIB extracellular domain (residues 25-131 in SEQ ID NO:1) is underlined. The aspartate substituted at position 79 in the native sequence is double underlined and highlighted, as is the glutamate revealed by sequencing to be the N-terminal residue in the mature fusion protein.

FIG. 21 shows the amino acid sequence for the truncated GDF trap ActRIIB(L79D 25-131) without the leader, hFc domain, and linker (SEQ ID NO:45). The aspartate substituted at position 79 in the native sequence is underlined and highlighted, as is the glutamate revealed by sequencing to be the N-terminal residue in the mature fusion protein.

FIGS. 22A and 22B shows an alternative nucleotide sequence encoding ActRIIB(L79D 25-131)-hFc. SEQ ID NO:46 corresponds to the sense strand, and SEQ ID NO:47 corresponds to the antisense strand. The TPA leader (nucleotides 1-66) is double underlined, the truncated ActRIIB extracellular domain (nucleotides 76-396) is underlined, and substitutions in the wild-type nucleotide sequence of the extracellular domain are double underlined and highlighted (compare with SEQ ID NO:42, FIGS. 19A and 19B). The amino acid sequence for the ActRIIB extracellular domain (residues 25-131 in SEQ ID NO:1) is also shown (SEQ ID NO:45).

FIG. 23 shows nucleotides 76-396 (SEQ ID NO:48) of the alternative nucleotide sequence shown in FIGS. 22A and 22B (SEQ ID NO:46). The same nucleotide substitutions indicated in FIGS. 22A and 22B are also underlined and highlighted here. SEQ ID NO:48 encodes only the truncated ActRIIB extracellular domain (corresponding to residues 25-131 in SEQ ID NO:1) with a L79D substitution, e.g., ActRIIB(L79D 25-131).

on the absolute change in hematocrit from baseline in cynomolgus monkey. VEH=vehicle. Data are means±SEM. n=4-8 per group.

Figure 26:
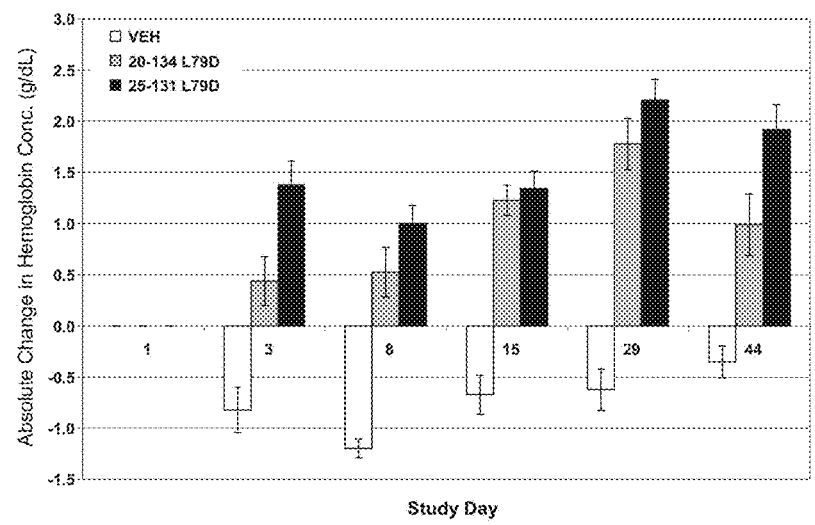

FIG. 26 shows the effect of treatment with ActRIIB(L79D 20-134)-hFc (gray) or ActRIIB(L79D 25-131)-hFc (black) on the absolute change in hemoglobin concentration from baseline in cynomolgus monkey. VEH=vehicle. Data are means±SEM. n=4-8 per group.

Figure 27:
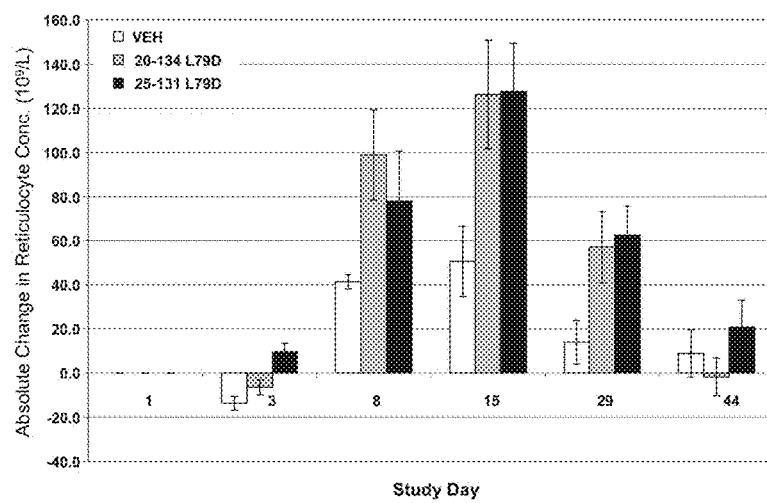

FIG. 27 shows the effect of treatment with ActRIIB(L79D 20-134)-hFc (gray) or ActRIIB(L79D 25-131)-hFc (black) on the absolute change in circulating reticulocyte concentration from baseline in cynomolgus monkey. VEH=vehicle. Data are means±SEM. n=4-8 per group.

Figure 28:
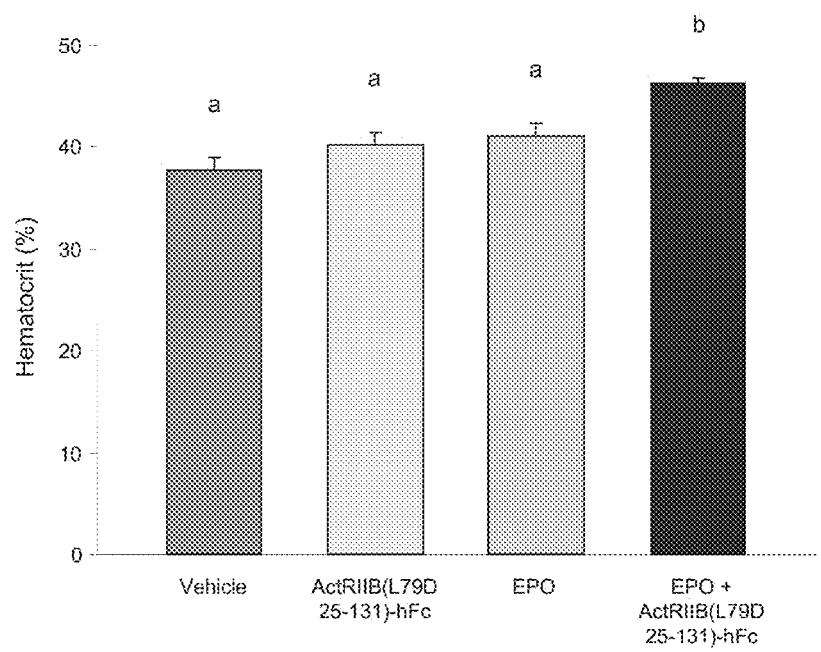

FIG. 28 shows the effect of combined treatment with erythropoietin (EPO) and ActRIIB(L79D 25-131)-hFc for 72 hours on hematocrit in mice. Data are means±SEM (n=4 per group), and means that are significantly different from each other (p<0.05, unpaired t-test) are designated by different letters. Combined treatment increased hematocrit by 23% compared to vehicle, a synergistic increase greater than the sum of the separate effects of EPO and ActRIIB(L79D 25-131)-hFc.

Figure 29:
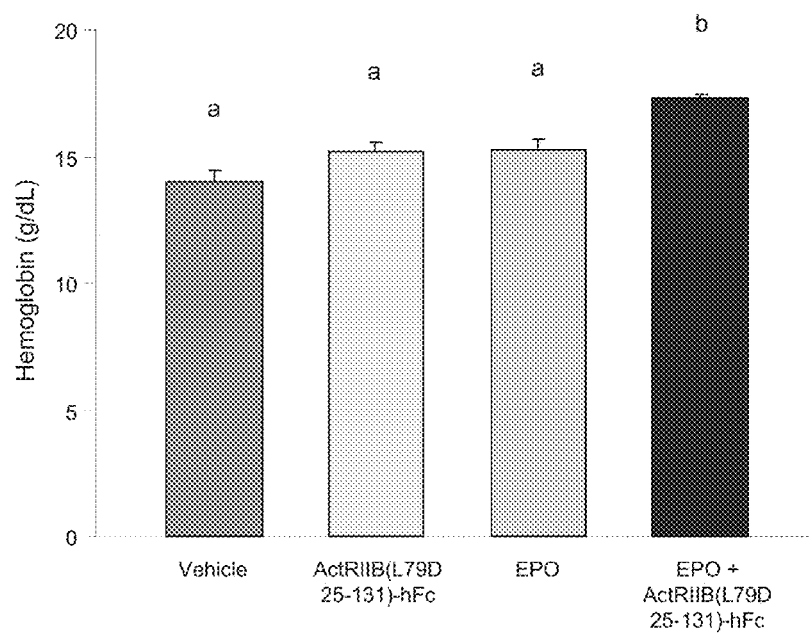

FIG. 29 shows the effect of combined treatment with EPO and ActRIIB(L79D 25-131)-hFc for 72 hours on hemoglobin concentrations in mice. Data are means±SEM (n=4 per group), and means that are significantly different from each other (p<0.05) are designated by different letters. Combined treatment increased hemoglobin concentrations by 23% compared to vehicle, which was also a synergistic effect.

Figure 30:
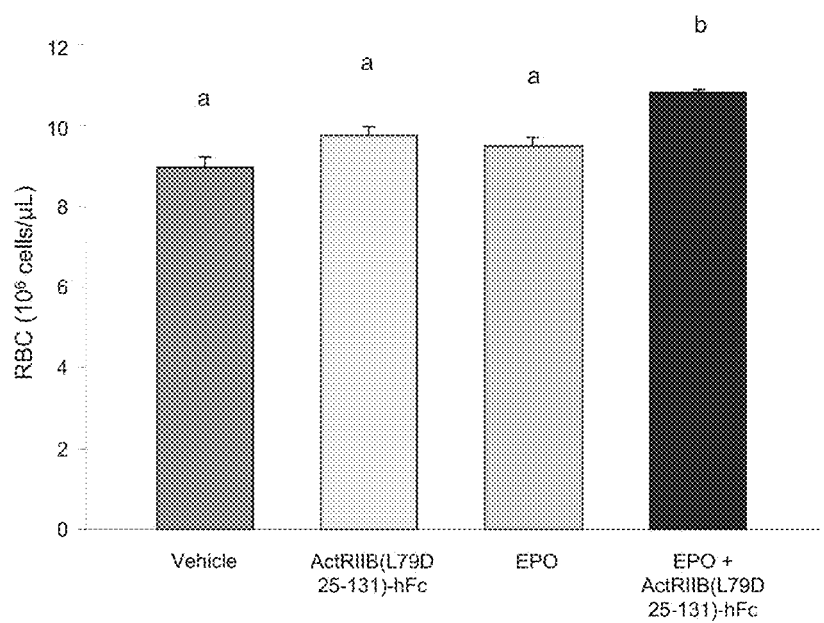

FIG. 30 shows the effect of combined treatment with EPO and ActRIIB(L79D 25-131)-hFc for 72 hours on red blood cell concentrations in mice. Data are means±SEM (n=4 per group), and means that are significantly different from each other (p<0.05) are designated by different letters. Combined treatment increased red blood cell concentrations by 20% compared to vehicle, which was also a synergistic effect.

Figure 31:
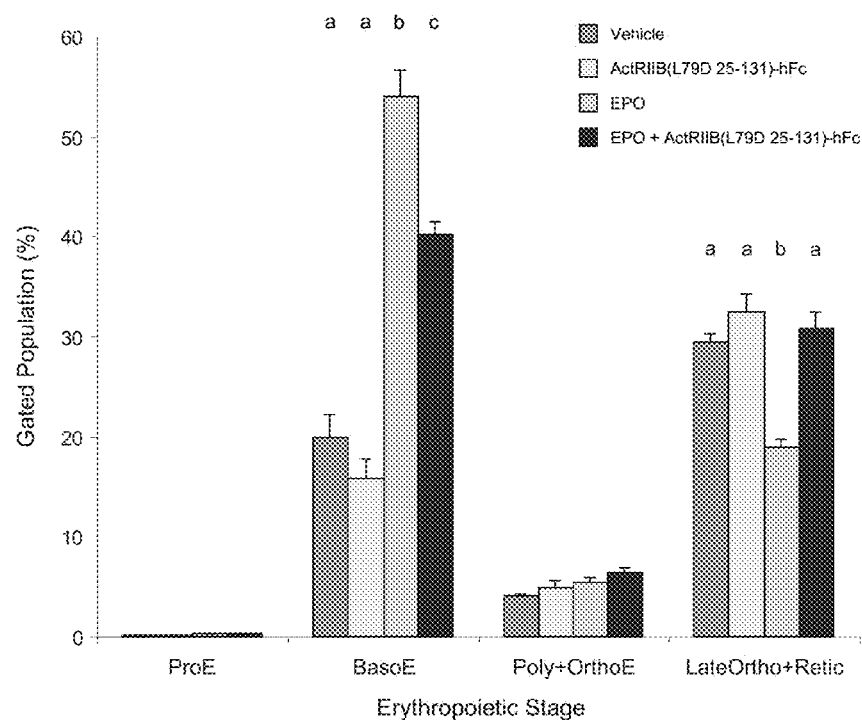

FIG. 31 shows the effect of combined treatment with EPO and ActRIIB(L79D 25-131)-hFc for 72 hours on numbers of erythropoietic precursor cells in mouse spleen. Data are means±SEM (n=4 per group), and means that are significantly different from each other (p<0.01) are designated by different letters. Whereas EPO alone increased the number of basophilic erythroblasts (BasoE) dramatically at the expense of late-stage precursor maturation, combined treatment increased BasoE numbers to a lesser but still significant extent while supporting undiminished maturation of late-stage precursors.

FIG. 32 shows that a GDF trap can mitigate ineffective erythropoiesis and ameliorate anemia at multiple stages of disease severity in a mouse model of MDS. (A) RBC numbers and hemoglobin concentrations (top) and morphological enumeration of hematopoietic precursors in bone marrow (bottom) in wild-type (Wt) mice treated with vehicle (Tris-buffered saline, TBS, n=5), MDS mice treated with TBS (n=5), and MDS mice treated with ActRIIB(L79D 25-131)-mFc (RAP-536, 10 mg/kg, n=6) twice weekly for 8 weeks ending at approximately 6 months of age (early stage). *P<0.05, **P<0.01, vs. TB S-treated MDS mice; ####P<0.001 vs. wild-type mice. (B) Same endpoints as in panel A in MDS mice treated with RAP-536 (10 mg/kg, twice weekly, n=5) or TBS (n=4) for 7 weeks ending at approximately 12 months of age (late stage). *P<0.05 vs. TBS-treated MDS mice. Data are means±SEM.

DETAIL DESCRIPTION OF THE INVENTION

1. Overview

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [see, e.g., Grobet et al. (1997) Nat Genet. 17(1):71-4]. Furthermore, in humans, inactive alleles of GDF8 are associated with increased muscle mass and, reportedly, exceptional strength [see, e.g., Schuelke et al. (2004) N Engl J Med, 350:2682-8].

TGF-β signals are mediated by heteromeric complexes of type I and type II serine/threonine kinase receptors, which phosphorylate and activate downstream SMAD proteins (e.g., SMAD proteins 1, 2, 3, 5, and 8) upon ligand stimulation [see, e.g., Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for activation of type I receptors. Type I and II activin receptors form a stable complex after ligand binding, resulting in phosphorylation of type I receptors by type II receptors.

Two related type II receptors (ActRII), ActRIIA and ActRIIB, have been identified as the type II receptors for activins [see, e.g., Mathews and Vale (1991) Cell 65:973-982; and Attisano et al. (1992) Cell 68: 97-108]. Besides activins, ActRIIA and ActRIIB can biochemically interact with several other TGF-β family proteins including, for example, BMP6, BMP7, Nodal, GDF8, and GDF11 [see, e.g., Yamashita et al. (1995) J. Cell Biol. 130:217-226; Lee and McPherron (2001) Proc. Natl. Acad. Sci. USA 98:9306-9311; Yeo and Whitman (2001) Mol. Cell 7: 949-957; and Oh et al. (2002) Genes Dev. 16:2749-54]. ALK4 is the primary type I receptor for activins, particularly for activin A, and ALK-7 may serve as a receptor for other activins as well, particularly for activin B. In certain embodiments, the present disclosure relates to antagonizing a ligand of an ActRII receptor (also referred to as an ActRII ligand) with one or more inhibitor agents disclosed herein, particularly inhibitor agents that can antagonize one or more of activin A, activin B, activin C, activin E, GDF11 and/or GDF8.

Activins are dimeric polypeptide growth factors that belong to the TGF-beta superfamily. There are three principal activin forms (A, B, and AB) that are homo/heterodimers of two closely related β subunits ($β_A,β_A$, $β_B,β_B$, and $β_Aβ_B$, respectively). The human genome also encodes an activin C and an activin E, which are primarily expressed in the liver, and heterodimeric forms containing $β_C$ or $β_E$ are also known.

In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al.

(1991) Proc Soc Ep Biol Med. 198:500-512; Dyson et al. (1997) Curr Biol. 7:81-84; and Woodruff (1998) Biochem Pharmacol. 55:953-963]. Moreover, erythroid differentiation factor (EDF) isolated from the stimulated human monocytic leukemic cells was found to be identical to activin A [Murata et al. (1988) PNAS, 85:2434]. It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the PA subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a PAPA homodimer or a PAN heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $\beta_B$ subunit.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as SMAD proteins. Studies support the idea that ActRIIA and ActRIIB serve as type II receptors for Nodal [see, e.g., Sakuma et al. (2002) Genes Cells. 2002, 7:401-12]. It is suggested that Nodal ligands interact with their co-factors (e.g., cripto) to activate activin type I and type II receptors, which phosphorylate SMAD2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway SMADs, SMAD2 and SMAD3. Further evidence has shown that the extracellular cripto protein is required for Nodal signaling, making it distinct from activin or TGF-beta signaling.

Growth and differentiation factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle [McPherron et al., Nature (1997) 387:83-90]. Similar increases in skeletal muscle mass are evident in naturally occurring mutations of GDF8 in cattle [see, e.g., Ashmore et al. (1974) Growth, 38:501-507; Swatland and Kieffer (1994) J. Anim. Sci. 38:752-757; McPherron and Lee (1997) Proc. Natl. Acad. Sci. USA 94:12457-12461; and Kambadur et al. (1997) Genome Res. 7:910-915] and, strikingly, in humans [see, e.g., Schuelke et al. (2004) N Engl J Med 350:2682-8]. Studies have also shown that muscle wasting associated with HIV-infection in humans is accompanied by increases in GDF8 protein expression [see, e.g., Gonzalez-Cadavid et al. (1998) PNAS 95:14938-43]. In addition, GDF8 can modulate the production of muscle-specific enzymes (e.g., creatine kinase) and modulate myoblast cell proliferation [see, e.g. international patent application publication no. WO 00/43781]. The GDF8 propeptide can noncovalently bind to the mature GDF8 domain dimer, inactivating its biological activity [see, e.g., Miyazono et al. (1988) J. Biol. Chem., 263: 6407-6415; Wakefield et al. (1988) J. Biol. Chem., 263: 7646-7654; and Brown et al. (1990) Growth Factors, 3: 35-43]. Other proteins which bind to GDF8 or structurally related proteins and inhibit their biological activity include follistatin, and potentially, follistatin-related proteins [see, e.g., Gamer et al. (1999) Dev. Biol., 208: 222-232].

Growth and differentiation factor-11 (GDF11), also known as BMP11, is a secreted protein [McPherron et al. (1999) Nat. Genet. 22: 260-264]. GDF11 is expressed in the tail bud, limb bud, maxillary and mandibular arches, and dorsal root ganglia during mouse development [see, e.g., Nakashima et al. (1999) Mech. Dev. 80: 185-189]. GDF11 plays a unique role in patterning both mesodermal and neural tissues [see, e.g., Gamer et al. (1999) Dev Biol., 208:222-32]. GDF11 was shown to be a negative regulator of chondrogenesis and myogenesis in developing chick limb [see, e.g., Gamer et al. (2001) Dev Biol. 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [see, e.g., Wu et al. (2003) Neuron. 37:197-207].

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB However, BMP7 and activin recruit distinct type I receptors into heteromeric receptor complexes. The major BMP7 type I receptor observed was ALK2, while activin bound exclusively to ALK4 (ActRIIB) BMP7 and activin elicited distinct biological responses and activated different SMAD pathways [see, e.g., Macias-Silva et al. (1998) J Biol Chem. 273:25628-36].

As demonstrated herein, ActRII polypeptides (e.g., ActRIIA and ActRIIB polypeptides) can be used to increase red blood cell levels in vivo. In certain examples, it is shown that a GDF trap polypeptide (specifically a variant ActRIIB polypeptide) is characterized by unique biological properties in comparison to a corresponding sample of a wild-type (unmodified) ActRII polypeptide. This GDF trap is characterized, in part, by substantial loss of binding affinity for activin A, and therefore significantly diminished capacity to antagonize activin A activity, but retains near wild-type levels of binding and inhibition of GDF11. In vivo, the GDF trap is more effective at increasing red blood cell levels as compared to the wild-type ActRIIB polypeptide and has beneficial effects in a variety of models for anemia. It should be noted that hematopoiesis is a complex process, regulated by a variety of factors, including erythropoietin, G-CSF, and iron homeostasis. The terms "increase red blood cell levels" and "promote red blood cell formation" refer to clinically observable metrics, such as hematocrit, red blood cell counts, and hemoglobin measurements, and are intended to be neutral as to the mechanism by which such changes occur.

The data of the present disclosure therefore indicate that the observed biological activity of an ActRII polypeptide, with respect to red blood cell levels, is not dependent on activin A inhibition. However, it is to be noted that the unmodified ActRIIB polypeptide, which retains activin A binding, still demonstrates the capacity to increase red blood cells in vivo. Furthermore, an ActRIIB or ActRIIA polypeptide that retains activin A inhibition may be more desirable in some applications, in comparison to a GDF trap having diminished binding affinity for activin A, where more modest gains in red blood cell levels are desirable and/or where some level of off-target activity is acceptable (or even desirable).

Accordingly, the methods of the present disclosure, in general, are directed to the use of one or more ActRII antagonist agents described herein, optionally in combination with one or more supportive therapies, to increase red blood cell formation in a subject in need thereof, treat or prevent an anemia in a subject in need thereof, to treat myelodysplastic syndrome, to treat sideroblastic anemia in a subject in need thereof, and to treat or prevent one or more complications of sideroblastic anemia or myelodysplastic syndrome (e.g., anemia, blood transfusion requirement, iron overload, neutropenia, splenomegaly, progression to acute myeloid leukemia), and, optionally, in a subgroup of patients with ring sideroblasts and/or one or more mutations in the SF3B1, DNMT3A, and/or TET2 gene in bone marrow cells. Another subgroup of patients that are identified as being particularly likely to respond to an ActRII antagonist is patients that have failed prior treatment with EPO therapy or other EPO receptor activator therapy.

As evidenced herein, the ActRII antagonist agents described may be used in combination with an EPO receptor activator or in patients that have failed treatment with EPO receptor activators. EPO is a glycoprotein hormone involved in the growth and maturation of erythroid progenitor cells into erythrocytes. EPO is produced by the liver during fetal life and by the kidney in adults. Decreased production of EPO, which commonly occurs in adults as a consequence of renal failure, leads to anemia. EPO has been produced by genetic engineering techniques based on expression and secretion of the protein from a host cell transfected with the EPO gene. Administration of such recombinant EPO has been effective in the treatment of anemia. For example, Eschbach et al. (1987, N Engl J Med 316:73) describe the use of EPO to correct anemia caused by chronic renal failure.

Effects of EPO are mediated through its binding to, and activation of, a cell surface receptor belonging to the cytokine receptor superfamily and designated the EPO receptor. The human and murine EPO receptors have been cloned and expressed [see, e.g., D'Andrea et al. (1989) Cell 57:277; Jones et al. (1990) Blood 76:31; Winkelman et al. (1990) Blood 76:24; and U.S. Pat. No. 5,278,065]. The human EPO receptor gene encodes a 483-amino-acid transmembrane protein comprising an extracellular domain of approximately 224 amino acids and exhibits approximately 82% amino acid sequence identity with the murine EPO receptor (see, e.g., U.S. Pat. No. 6,319,499). The cloned, full-length EPO receptor expressed in mammalian cells (66-72 kDa) binds EPO with an affinity ($K_D$=100-300 nM) similar to that of the native receptor on erythroid progenitor cells. Thus, this form is thought to contain the main EPO binding determinant and is referred to as the EPO receptor. By analogy with other closely related cytokine receptors, the EPO receptor is thought to dimerize upon agonist binding. Nevertheless, the detailed structure of the EPO receptor, which may be a multimeric complex, and its specific mechanism of activation are not completely understood (see, e.g., U.S. Pat. No. 6,319,499).

Activation of the EPO receptor results in several biological effects. These include increased proliferation of immature erythroblasts, increased differentiation of immature erythroblasts, and decreased apoptosis in erythroid progenitor cells [see, e.g., Liboi et al. (1993) Proc Natl Acad Sci USA 90:11351-11355; Koury et al. (1990) Science 248:378-381]. The EPO receptor signal transduction pathways mediating proliferation and differentiation appear to be distinct [see, e.g., Noguchi et al. (1988) Mol Cell Biol 8:2604; Patel et al. (1992) J Biol Chem, 267:21300; and Liboi et al. (1993) Proc Natl Acad Sci USA 90:11351-11355]. Some results suggest that an accessory protein may be required for mediation of the differentiation signal [see, e.g., Chiba et al. (1993) Nature 362:646; and Chiba et al. (1993) Proc Natl Acad Sci USA 90:11593]. However, there is controversy regarding the role of accessory proteins in differentiation since a constitutively activated form of the receptor can stimulate both proliferation and differentiation [see, e.g., Pharr et al. (1993) Proc Natl Acad Sci USA 90:938].

EPO receptor activators include small molecule erythropoiesis-stimulating agents (ESAs) as well as EPO-based compounds. An example of the former is a dimeric peptide-based agonist covalently linked to polyethylene glycol (proprietary names Hematide™ and Omontys®), which has shown erythropoiesis-stimulating properties in healthy volunteers and in patients with both chronic kidney disease and endogenous anti-EPO antibodies [see, e.g., Stead et al. (2006) Blood 108:1830-1834; and Macdougall et al. (2009) N Engl J Med 361:1848-1855]. Other examples include nonpeptide-based ESAs [see, e.g., Qureshi et al. (1999) Proc Natl Acad Sci USA 96:12156-12161].

EPO receptor activators also include compounds that stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. Therefore, inhibitors of HIF prolyl hydroxylase enzymes are being investigated for EPO-inducing activity in vivo. Other indirect activators of EPO receptor include inhibitors of GATA-2 transcription factor [see, e.g., Nakano et al. (2004) Blood 104:4300-4307], which tonically inhibits EPO gene expression, and inhibitors of hemopoietic cell phosphatase (HCP or SHP-1), which functions as a negative regulator of EPO receptor signal transduction [see, e.g., Klingmuller et al. (1995) Cell 80:729-738].

As described herein, patients that exhibit ring sideroblasts may be particularly suited to treatment with ActRII antagonists. Sideroblastic anemias can be classified broadly into congenital (inherited) and acquired forms, which can be further subdivided as shown in Table 1.

TABLE 1

Classification of Sideroblastic Anemias*

| Class | Gene | Anemia Severity | Iron Homeostasis |
|---|---|---|---|
| Congenital | | | |
| Nonsyndromic | | | |
| X-linked | ALAS2 | Mild to severe | Iron overload |
| SLC25A38 deficiency | SLC25A38 | Severe | Iron overload |
| Glutaredoxin 5 deficiency | GLRX5 | Mild to severe | Iron overload |
| Erythropoietic protoporphyria | FECH | Mild | — |
| Syndromic | | | |
| X-linked with ataxia | ABCB7 | Mild to moderate | — |
| SIFD | Unknown | Severe | Iron overload |
| Pearson marrow- pancreas Syndrome | mtDNA | Severe | — |
| Myopathy, lactic acidosis, and sideroblastic anemia (MLASA) | PUS1/ YARS2 | Mild to severe | — |
| Thiamine-responsive megaloblastic anemia (TRMA) | SLC19A2 | Severe | — |
| Syndromic/nonsyndromic of unknown cause | Unknown | Variable | — |
| Acquired | | | |
| Clonal/Neoplastic | | | |
| MDS** | Variable | Mild to severe | Iron overload |
| Metabolic | | | |
| Alcoholism | — | Variable | — |
| Drug-induced | — | Variable | — |
| Copper deficiency (zinc toxicity) | — | Variable | — |
| Hypothermia | — | Variable | — |

*See Bottomley et al., 2014, Hematol Oncol Clin N Am 28:653-670.
**See table below for MDS subclassifications according to the World Health Organization.

MDS represent the most common class of acquired bone-marrow-failure syndromes in adults. Although MDS are increasingly well understood from a biological standpoint, improved pathologic insight has not yet translated into highly effective or curative therapies for most patients suffering from these disorders. Increasing failure of cellular differentiation in MDS is associated with evolution to secondary acute myeloid leukemia (AML), which is currently defined by the WHO as having at least 20% myeloblasts in the blood or marrow, or the presence of one of several AML-defining karyotypic abnormalities regardless of blast proportion [see, e.g., Vardiman et al. (2009) Blood 114:937-951]. AML is ultimately diagnosed in as many as 30% of MDS patients. Since the biological heterogeneity that underlies MDS translates into wide variations in clinical outcomes, prognostic classification schemes have been developed to predict the natural course of MDS and to counsel patients [Zeidan et al (2013) Curr Hematol Malig Rep 8:351-360]. The International Prognostic Scoring System (IPSS) is an example of one such classification that categorizes patients according to risk profile, ranging from Low (median survival of 5.7 years) to Intermediate 1 (median survival of 3.5 years) to Intermediate 2 (median survival of 1.2 years) to High (median survival of 0.4 years). An alternate system referred to as IPSS-R may also be used for patient stratification. From a patient's perspective, the prognosis helps define the severity of disease and sets expectations as to how it is likely to impact them. From a physician's standpoint, the prognosis provides a means of staging the disease in a manner that can be used to help direct therapy. Notably, such schemes do not typically take patient comorbidities into account and are not intended to predict clinical benefit in relation to a specific therapy.

Additional MDS classification systems have been proposed to facilitate appropriate treatment and management of patients with MDS. Classification has evolved over several decades to incorporate progress in understanding these complex syndromes. The French-American-British (FAB) classification scheme for MDS was proposed in 1982 [Bennett et al. (1982) Br J Haematol 51:189-199] and served as the basis for a modified classification system established by the WHO in 2001. As summarized in Table 2 below, the current version of the WHO classification (revised in 2008) is based on (1) the percentage of myeloblasts in the bone marrow and peripheral blood, (2) the type and degree of dysplasia, (3) the presence of ring sideroblasts, and (4) the presence of cytogenetic abnormalities. Thus, ring sideroblasts are characteristic of RARS but can also be present in other subtypes of MDS [see, e.g., Juneja et al. (1983) J Clin Pathol 36:566-569; Malcovati et al. (2013) Best Pract Res Clin Haematol 26:377-385]. Depending on the MDS subtype, anemia can occur, for example, in the presence or absence of ring sideroblasts, alone or in combination with abnormally low numbers of neutrophils (neutropenia), low numbers of platelets (thrombocytopenia), or elevated levels of platelets (thrombocytosis). Refractory anemia with ring sideroblasts associated with marked thrombocytosis (RARS-T) is currently included as a provisional entry in the WHO classification (Table 2) within the group of MDS neoplasms unclassifiable (MDS-U). RARS-T is defined as anemia with dysplastic ineffective erythropoiesis and ring sideroblasts≥15% of erythroid precursors, no blasts in peripheral blood and <5% in the bone marrow, and thrombocytosis with a platelet count≥450×10$^9$/L [Malcovati et al. (2013) Best Pract Res Clin Haematol 26:377-385]. Due to a compromised immune system, patients with neutropenia may be at serious risk of infection and even sepsis, and it is therefore important to treat this condition. Patients with thrombocytopenia are at increased risk of internal hemorrhage, and depending on severity it may also be beneficial to treat this condition.

TABLE 2

2008 WHO Classification System for MDS*

| MDS Subtype | Blood Findings | Bone Marrow Findings |
|---|---|---|
| Refractory cytopenia with unilineage dysplasia (RCUD): (a) refractory anemia, (b) | Predominantly unicytopenia | Unilineage dysplasia: ≥10% of cells in one myeloid lineage <5% blasts |

TABLE 2-continued

2008 WHO Classification System for MDS*

| MDS Subtype | Blood Findings | Bone Marrow Findings |
|---|---|---|
| refractory neutropenia, or (c) refractory thrombocytopenia | | <15% of erythroid precursors are ring sideroblasts |
| Refractory anemia with ring sideroblasts (RARS) | Anemia<br>No blasts | ≥15% of erythroid precursors are ring sideroblasts<br>Erythroid dysplasia only<br><5% blasts |
| Refractory cytopenia with multilineage dysplasia (RCMD) | Cytopenia(s)<br>No or rare blasts (<1%)<br>No Auer rods<br><1 × $10^9$ per L monocytes | Dysplasia in ≥10% of cells in ≥2 myeloid lineages (neutrophil and/or erythroid precursors and/or megakaryocytes)<br><5% blasts<br>No Auer rods<br>±15% ring sideroblasts |
| Refractory anemia with excess blasts-1 (RAEB-1) | Cytopenia(s)<br><5% blasts<br>No Auer rods<br><1 × $10^9$ per L monocytes | Unilineage or multilineage dysplasia<br>5%-9% blasts<br>No Auer rods |
| Refractory anemia with excess blasts-1 (RAEB-2) | Cytopenia(s)<br>5%-19% blasts<br>Auer rods ±<br><1 × $10^9$ per L monocytes | Unilineage or multilineage dysplasia<br>10%-19% blasts<br>Auer rods ± |
| Myelodysplastic syndrome-unclassified (MDS-U) ** | Cytopenias<br><1% blasts | Unequivocal dysplasia in <10% of cells in one or more myeloid lineages when accompanied by a cytogenetic abnormality considered as presumptive evidence for a diagnosis of MDS<br><5% blasts |
| MDS associated with isolated del(5q) | Anemia<br>Usually normal or increased platelet count<br>No or rare blasts (<1%) | Normal-to-increased megakaryocytes with hypolobated nuclei<br><5% blasts<br>Isolated del(5q) cytogenetic abnormality<br>No Auer rods |

*From Vardiman et al (2009) Blood 114:937-951
**Includes refractory anemia with ring sideroblasts associated with marked thrombocytosis (RARS-T)

In one embodiment of the disclosure, ActRII antagonists are useful for treating anemia in patients, including MDS patients or patients with sideroblastic anemia, in whom more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% of erythroid precursors are ring sideroblasts, e.g., in refractory anemia with ring sideroblasts (RARS), RARS associated with marked thrombocytosis (RARS-T), or refractory cytopenia with multilineage dysplasia (RCMD, also known as RCMD-RS in patients where ring sideroblasts are prominent).

Anemia occurs frequently in MDS. Approximately 80% of MDS patients present with anemia, and a substantial percentage of them become dependent on blood transfusions during the course of their disease [Steensma et al. (2006) Mayo Clin Proc 81:104-130]. Some MDS subtypes are characterized by "ineffective erythropoiesis", in which there is impaired differentiation (maturation) of late-stage erythroid precursor cells despite EPO-stimulated hyperproliferation of early-stage erythroid progenitor cells in response to tissue hypoxia. Thus, a key sign of ineffective erythropoiesis is persistent anemia in spite of elevated levels of endogenous EPO. Ineffective erythropoiesis occurs frequently in the RARS subtype of MDS but not the RAEB subtype, which is characterized by relative hypoproliferation of the erythroid marrow [Cazzola et al. (1982) Br J Haematol 50:55-62]. Circulating levels of hepcidin, a critical regulator of iron homeostasis, are about an order of magnitude lower in RARS than RAEB [Santini et al. (2011) PLoS One 6:e23109]. Since low levels of hepcidin promote iron absorption, the inappropriately low levels of hepcidin measured in disorders such as RARS and thalassemia are thought to account for iron overload observed in these disorders even in the absence of blood transfusions.

Chronic red blood cell transfusions alleviate anemia but expose patients to multiple risks, including infectious disease, allergic or hemolytic reactions, and exacerbation of iron overload [Rawn (2008) Curr Opin Anaesthesiol 21:664-668; Özcan et al. (2013) Expert Rev Hematol 6:165-189]. As systemic iron levels increase, the body increases ferritin production for iron storage and reduces transferrin receptor production to reduce iron entry into cells. When the iron-binding capacity of circulating transferrin is exceeded, iron is found in the plasma as non-transferrin bound iron (NTBI). In MDS, levels of non-transferrin bound iron are higher in low-risk than high-risk subtypes and highest in RARS [Santini et al. (2011) PLoS One 6:e23109]. Since iron cannot be actively secreted from the body, it initially accumulates in the reticuloendothelial macrophages and is later deposited primarily in parenchymal cells of the heart, liver, and endocrine glands [Siah et al. (2006) Clin Biochem Rev 27:5-16]. Under conditions of iron overload, non-transferrin bound iron changes to its redox-active form known as labile plasma iron, which is transported into cells where it promotes formation of reactive oxygen species. These highly toxic molecules adversely impact hematopoiesis and particularly damage cardiac, hepatic, and endocrine tissues.

The MDS patient population consists mainly of elderly with comorbid conditions—including a propensity for cardiac failure, infection, hemorrhage, and hepatic cirrhosis—and iron overload may rapidly exacerbate such pre-existing conditions. Compared to MDS patients at high risk of developing AML, patients at low or intermediate-1 risk may be more prone to iron overload due to their longer life expectancy. For these reasons, iron chelation therapy to reduce iron burden is considered advisable in patients with low- or intermediate-1 risk MDS subtypes who have a long life expectancy and are anticipated to receive more than 20 RBC transfusions [Temraz et al. (2014) Crit Rev Oncol Hematol 91:64-73].

Novel sequencing techniques have led in the past few years to identification of dozens of genes that are recurrently mutated in MDS. A 2013 list of such genes classified by type is shown in Table 3. One or more such mutations can be found in almost all patients with MDS, and knowing the nature of the genes involved has improved understanding of how MDS develops and evolves, although it has not yet had an impact on treatment. Whole-genome sequencing applied to MDS patient samples has identified an entirely novel class of cancer-associated genes encoding mRNA splicing (spliceosome) factors. The first such gene identified in MDS was SF3B1, which is mutated particularly frequently in patients with RARS [Papaemmanuil et al. (2011) N Engl J Med 365:1384-1395]. Other major categories of mutated genes are epigenetic (DNA methylation) regulators, transcription factors, and signaling molecules [Cazzola et al. (2013) Blood 122:4021-4034; Bejar et al. (2014) Blood 124:2793-2803]. The extent to which these mutations co-occur in MDS patients seems to vary with gene type. For example, approximately 50% of MDS patients possess one of ten genes identified to date encoding mutant splicing factors, but these mutant genes rarely co-occur in the same patient [Bejar et al. (2014) Blood 124:2793-2803]. Thus, these mutant genes are seldom redundant markers for the same individuals. Genes encoding mutant epigenetic regulators co-occur more frequently with each other and with mutant splicing factor genes in the same patient. As disclosed herein, the differential occurrence of mutant genes such as those listed in Table 3 provides a genetic signature that can assist in predicting which patients with MDS or sideroblastic anemia are likely to be either responsive or nonresponsive therapeutically to an ActRII antagonist.

TABLE 3

MDS-Associated Somatic Mutations*

| Gene | Frequency in MDS (% cases) |
| --- | --- |
| RNA Splicing | |
| SF3B1 | 14-28 |
| SRSF2 | 15 |
| U2AF1 | 8 |
| ZRSR2 | 6 |
| PRPF40B | 1 |
| SF3A1 | 1 |
| SF1 | 1 |
| U2AF65 | <1 |
| LUC7L2 | Rare |
| PRPF8 | Rare |
| Epigenetic Regulators | |
| TET2 | 19-26 |
| ASXL1 | 10-20 |
| DNMT3A | 10 |
| IDH1/IDH2 | 4-12 |
| EZH2 | 6 |
| UTX | 1 |
| ATRX | <1 |
| Transcription Factors | |
| RUNX1 | 10-20 |
| TP53 | 4-14 |
| ETV6 | 1-3 |
| PHF6 | Rare |
| WT1 | Rare |
| Signaling | |
| NRAS | 10 |
| CBL | 3 |
| JAK2 | 3 |
| FLT3 | 2-3 |

TABLE 3-continued

MDS-Associated Somatic Mutations*

| Gene | Frequency in MDS (% cases) |
| --- | --- |
| KRAS | 1-2 |
| c-KIT | 1 |
| BRAF | <1 |
| CDKN2A | <1 |
| GNAS | <1 |
| PTEN | <1 |
| PTPN11 | <1 |
| CBLB | Rare |
| MPL, CSF1R | Rare |
| Others | |
| NPM1 | 2-3 |

*From Tothova et al. (2013) Clin Cancer Res 19:1637-1643.

Among the genes listed in Table 3, the gene encoding splicing factor 3B1 (SF3B1) has been implicated recently as critical in MDS, particularly in the RARS, RARS-T, and RCMD-RS subtypes [Malcovati et al. (2011) Blood 118:6239-6246; Dolatshad et al. (2014) Leukemia doi: 10.1038/leu.2014.331 epub ahead of print]. Somatic mutations in SF3B1 also occur in hematologic cancers including chronic lymphocytic leukemia (CLL), and acute myeloid leukemia (AML) as well as in breast cancer, pancreatic cancer, gastric cancer, prostate cancer, and uveal melanoma [Malcovati et al. (2011) Blood 118:6239-6246; Wang et al. (2011) N Engl J Med 365:2497-2506; The Cancer Genome Atlas Network (2012) Nature 490:61-70; Biankin et al. (2012) Nature 491:399-405; Chesnais et al. (2012) Oncotarget 3:1284-1293; Furney et al. (2013) Cancer Discov 3:1122-1129; Je et al. (2013) Int J Cancer 133:260-266]. A spectrum of SF3B1 mutations, many clustered at a few locations in the protein, have been identified in clinical samples or in cell lines exposed to high concentrations of pladienolide [Webb et al. (2013) Drug Discov Today 18:43-49]. SF3B1 mutations identified in MDS include, for example, K182E, E491G, R590K, E592K, R625C, R625G, N626D, N626S, H662Y, T663A, K666M, K666Q, K666R, Q670E, G676D, V701I, I704N, I704V, G740R, A744P, D781G, and A1188V. SF3B1 mutations identified in cancer include, for example, N619K, N626H, N626Y, R630S, I704T, G740E, K741N, G742D, D894G, Q903R, R1041H, and I1241T. Finally, SF3B1 mutations found in both MDS and cancer include, for example, G347V, E622D, Y623C, R625H, R625L, H662D, H662Q, T663I, K666E, K666N, K666T, K700E, and V701F.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which they are used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

As used herein, unless otherwise stated, "does not substantially bind to X" is intended to mean that an agent has a $K_D$ that is greater than about $10^{-7}$, $10^{-6}$, $10^{-5}$, $10^{-4}$, or greater (e.g., no detectable binding by the assay used to determine the $K_D$) for "X" or has relatively modest binding for "X", e.g., about $1 \times 10^{-8}$M or about $1 \times 10^{-9}$M.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. ActRII Antagonists

The data presented herein demonstrates that antagonists (inhibitors) of ActRII (e.g., antagonist of ActRIIA and/or ActRIIB SMAD 2/3 and/or SMAD 1/5/8 signaling) can be used to increase red blood cell levels in vivo and provide other benefits to patients. In particular, such ActRII antagonists are shown herein to be effective in treating various anemias as well as various complications (e.g., disorders/conditions) of MDS and sideroblastic anemias. Accordingly, the present disclosure provides, in part, various ActRII antagonist agents that can be used, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In certain embodiments, preferred ActRII antagonists to be used in accordance with the methods disclosed herein are GDF-ActRII antagonists (e.g., antagonists of GDF-mediated ActRIIA and/or ActRIIB signaling transduction, such as SMAD 2/3 signaling), particularly GDF11- and/or GDF8-mediated ActRII signaling. In some embodiments, preferred ActRII antagonists of the present disclosure are soluble ActRII polypeptides (e.g., soluble ActRIIA and ActRIIB polypeptides) and GDF trap polypeptides, such as ActRIIA-Fc fusion proteins, ActRIIB-Fc fusion proteins, and GDF trap-Fc fusion proteins.

Although soluble ActRII polypeptides and GDF trap polypeptides of the disclosure may affect red blood cell levels and/or various complications of MDS and sideroblastic anemia through a mechanism other than GDF (e.g. GDF11 and/or GDF8) antagonism [e.g., GDF11 and/or GDF8 inhibition may be an indicator of the tendency of an agent to inhibit the activities of a spectrum of additional agents, including, perhaps, other members of the TGF-beta superfamily (e.g., activin B, activin C, activin E, BMP6, BMP7, and/or Nodal) and such collective inhibition may lead to the desired effect on, e.g., hematopoiesis], other types of GDF-ActRII antagonist are expected to be useful including, for example, anti-GDF11 antibodies; anti-GDF8 antibodies; anti-activin A, B, C and/or E antibodies, anti-ActRIIA antibodies; anti-ActRIIB antibodies; anti-ActRIIA/IM antibodies, antisense, RNAi, or ribozyme nucleic acids that inhibit the production of one or more of GDF11, GDF8, ActRIIA, and/or ActRIIB; and other inhibitors (e.g., small-molecule inhibitors) of one or more of GDF11, GDF8, ActRIIA, and/or ActRIIB, particularly agents that disrupt GDF11- and/or GDF8-ActRIIA binding and/or GDF11- and/or GDF8-ActRIIB binding as well as agents that inhibit expression of one or more of GDF11, GDF8, ActRIIA, and/or ActRIIB Optionally, GDF-ActRII antagonists of the present disclosure may bind to and/or inhibit the activity (or expression) of other ActRII ligands including, for example, activin A, activin AB, activin B, activin C, activin E, BMP6, BMP7, and/or Nodal. Optionally, a GDF-ActRII antagonist of the present disclosure may be used in combination with at least one additional ActRII antagonist agent that binds to and/or inhibits the activity (or expression) of one or more additional ActRII ligands including, for example, activin A, activin AB, activin B, activin C, activin E, BMP6, BMP7, and/or Nodal. In some embodiments, ActRII antagonists to be used in accordance with the methods disclosed herein do not substantially bind to and/or inhibit activin A (e.g., activin A-mediated activation of ActRIIA and/or ActRIIB signaling transduction, such as SMAD 2/3 signaling).

hepatomegaly, splenomegaly, progression to acute myeloid lymphoma) and or treat or prevent a disorder associated with SF3B1, DNMT3A, and/or TET2 mutations in a subject in need thereof. As used herein the term "ActRII" refers to the family of type II activin receptors. This family includes both the activin receptor type IIA and the activin receptor type IIB.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Optionally, ActRIIB polypeptides of the present disclosure can be used to increase red blood cell levels in a subject. Numbering of amino acids for all ActRIIB-related polypeptides described herein is based on the numbering of the human ActRIIB precursor protein sequence provided below (SEQ ID NO:1), unless specifically designated otherwise.

The human ActRIIB precursor protein sequence is as follows:

```
                                                              (SEQ ID NO: 1)
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

A. ActRII Polypeptides and GDF Traps

In certain aspects, the present disclosure relates to ActRII polypeptides. In particular, the disclosure provides methods of using ActRII polypeptides, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, The signal peptide is indicated with single underline; the extracellular domain is indicated in bold font; and the potential, endogenous N-linked glycosylation sites are indicated with double underline.

The processed soluble (extracellular) human ActRIIB polypeptide sequence is as follows:

```
                                                              (SEQ ID NO: 2)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT.
```

In some embodiments, the protein may be produced with an "SGR . . . " sequence at the N-terminus. The C-terminal "tail" of the extracellular domain is indicated by single underline. The sequence with the "tail" deleted (a 415 sequence) is as follows:

(SEQ ID NO: 3)
GRGEAETRECIYYNANWELERTNQSGLERCEGEQDKRLHCYASWRNSSGT

IELVKKGCWLDDFNCYDRQECVATEENPQVYFCCCEGNFCNERFTHL

PEA.

A form of ActRIIB with an alanine at position 64 of SEQ ID NO:1 (A64) is also reported in the literature [see, e.g., Hilden et al. (1994) Blood, 83(8): 2163-2170]. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

(SEQ ID NO: 4)
```
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI.
```

The signal peptide is indicated by single underline and the extracellular domain is indicated by bold font.

The processed soluble (extracellular) ActRIIB polypeptide sequence of the alternative A64 form is as follows:

(SEQ ID NO: 5)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

GGPEVTYEPPPTAPT.

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)
GRGEAETRECIYYNANWELERTNQSGLERCEGEQDKRLHCYASWANSSGT

IELVKKGCWLDDFNCYDRQECVATEENPQVYFCCCEGNFCNERFTHL

PEA.

The nucleic acid sequence encoding human ActRIIB precursor protein is shown below (SEQ ID NO: 7), consisting of nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)
```
  1 ATGACGGCGC CTGGGTGGC CCTCGCCCTC CTCTGGGGAT CGCTGTGCGC

51 CGGCTCTGGG CGTGGGGAGG CTGAGACACG GGAGTGCATC TACTACAACG
```

-continued

```
 101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC.
```

A nucleic acid sequence encoding processed soluble (extracellular) human ActRIIB polypeptide is as follows (SEQ ID NO: 8). The sequence as shown provides an arginine at position 64, and may be modified to provide an alanine instead.

(SEQ ID NO: 8)
```
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT
```

```
251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC.
```

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Optionally, ActRIIA polypeptides of the present disclosure can be used to increase red blood cell levels in a subject. Numbering of amino acids for all ActRIIA-related polypeptides described herein is based on the numbering of the human ActRIIA precursor protein sequence provided below (SEQ ID NO:9), unless specifically designated otherwise.

The human ActRIIA precursor protein sequence is as follows:

The signal peptide is indicated by single underline; the extracellular domain is indicated in bold font; and the potential, endogenous N-linked glycosylation sites are indicated by double underline.

The processed soluble (extracellular) human ActRIIA polypeptide sequence is as follows:

```
                                                  (SEQ ID NO: 10)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP
```

The C-terminal "tail" of the extracellular domain is indicated by single underline. The sequence with the "tail" deleted (a Δ15 sequence) is as follows:

```
                                                  (SEQ ID NO: 11)

IEIVKQGCWLDDINCYDRTDCVEKKDSPEVYFCCCEGNMCNEKFSYFPEM
```

The nucleic acid sequence encoding human ActRIIA precursor protein is shown below (SEQ ID NO: 12), as follows nucleotides 159-1700 of Genbank Reference Sequence NM_001616.4. The signal sequence is underlined.

```
                                                   (SEQ ID NO: 9)
  1 MGAAAKLAFA VFLISCSSGA ILGRSETQEC LFFNANWEKD RTNQTGVEPC

51 YGDKDKRRHC FATWKNISGS IEIVKQGCWL DDINCYDRTD CVEKKDSPEV

101 YFCCCEGNMC NEKFSYFPEM EVTQPTSNPV TPKPPYYNIL LYSLVPLMLI

151 AGIVICAFWV YRHHKMAYPP VLVPTQDPGP PPPSPLLGLK PLQLLEVKAR

201 GRFGCVWKAQ LLNEYVAVKI FPIQDKQSWQ NEYEVYSLPG MKHENILQFI

251 GAEKRGTSVD VDLWLITAFH EKGSLSDFLK ANVVSWNELC HIAETMARGL

301 AYLHEDIPGL KDGHKPAISH RDIKSKNVLL KNNLTACIAD FGLALKFEAG

351 KSAGDTHGQV GTRRYMAPEV LEGAINFQRD AFLRIDMYAM GLVLWELASR

401 CTAADGPVDE YMLPFEEEIG QHPSLEDMQE VVVHKKKRPV LRDYWQKHAG

451 MAMLCETIEE CWDHDAEARL SAGCVGERIT QMQRLTNIIT TEDIVTVVTM

501 VTNVDFPPKE SSL
```

(SEQ ID NO: 12)
```
   1 atgggagctg ctgcaaagtt ggcgtttgcc gtctttctta tctcctgttc
  51 ttcaggtgct atacttggta gatcagaaac tcaggagtgt cttttcttta
 101 atgctaattg ggaaaaagac agaaccaatc aaactggtgt tgaaccgtgt
 151 tatggtgaca agataaacg gcggcattgt tttgctacct ggaagaatat
 201 ttctggttcc attgaaatag tgaaacaagg ttgttggctg atgatatca
 251 actgctatga caggactgat tgtgtagaaa aaaagacag ccctgaagta
 301 tattttttgtt gctgtgaggg caatatgtgt aatgaaaagt tttcttattt
 351 tccggagatg gaagtcacac agcccacttc aaatccagtt acacctaagc
 401 caccctatta caacatcctg ctctattcct tggtgccact tatgttaatt
 451 gcggggattg tcatttgtgc attttgggtg tacaggcatc acaagatggc
 501 ctaccctcct gtacttgttc caactcaaga cccaggacca cccccacctt
 551 ctccattact aggtttgaaa ccactgcagt tattagaagt gaaagcaagg
 601 ggaagatttg gttgtgtctg gaaagcccag ttgcttaacg aatatgtggc
 651 tgtcaaaata tttccaatac aggacaaaca gtcatggcaa aatgaatacg
 701 aagtctacag tttgcctgga atgaagcatg agaacatatt acagttcatt
 751 ggtgcagaaa acgaggcac cagtgttgat gtggatcttt ggctgatcac
 801 agcatttcat gaaaagggtt cactatcaga ctttcttaag gctaatgtgg
 851 tctcttggaa tgaactgtgt catattgcag aaaccatggc tagaggattg
 901 gcatattac atgaggatat acctggccta aaagatggcc acaaacctgc
 951 catatctcac agggacatca aaagtaaaaa tgtgctgttg aaaaacaacc
1001 tgacagcttg cattgctgac tttgggttgg ccttaaaatt tgaggctggc
1051 aagtctgcag gcgataccca tggacaggtt ggtacccgga ggtacatggc
1101 tccagaggta ttagagggtg ctataaactt ccaaagggat gcattttga
1151 ggatagatat gtatgccatg ggattagtcc tatgggaact ggcttctcgc
1201 tgtactgctg cagatggacc tgtagatgaa tacatgttgc catttgagga
1251 ggaaattggc cagcatccat ctcttgaaga catgcaggaa gttgttgtgc
1301 ataaaaaaaa gaggcctgtt ttaagagatt attggcagaa acatgctgga
1351 atggcaatgc tctgtgaaac cattgaagaa tgttgggatc acgacgcaga
1401 agccaggtta tcagctggat gtgtaggtga agaattacc cagatgcaga
1451 gactaacaaa tattattacc acagaggaca ttgtaacagt ggtcacaatg
1501 gtgacaaatg ttgactttcc tcccaaagaa tctagtcta
```

The nucleic acid sequence encoding processed soluble (extracellular) human ActRIIA polypeptide is as follows:

(SEQ ID NO: 13)
```
   1 atacttggta gatcagaaac tcaggagtgt cttttcttta atgctaattg
  51 ggaaaaagac agaaccaatc aaactggtgt tgaaccgtgt tatggtgaca
 101 agataaacg gcggcattgt tttgctacct ggaagaatat ttctggttcc
 151 attgaaatag tgaaacaagg ttgttggctg atgatatca actgctatga
 201 caggactgat tgtgtagaaa aaaagacag ccctgaagta tattttttgtt
```

```
251 gctgtgaggg caatatgtgt aatgaaaagt tttcttattt tccggagatg 301 gaagtcacac agcccacttc aaatccagtt acacctaagc caccc.
```

Figure 2:
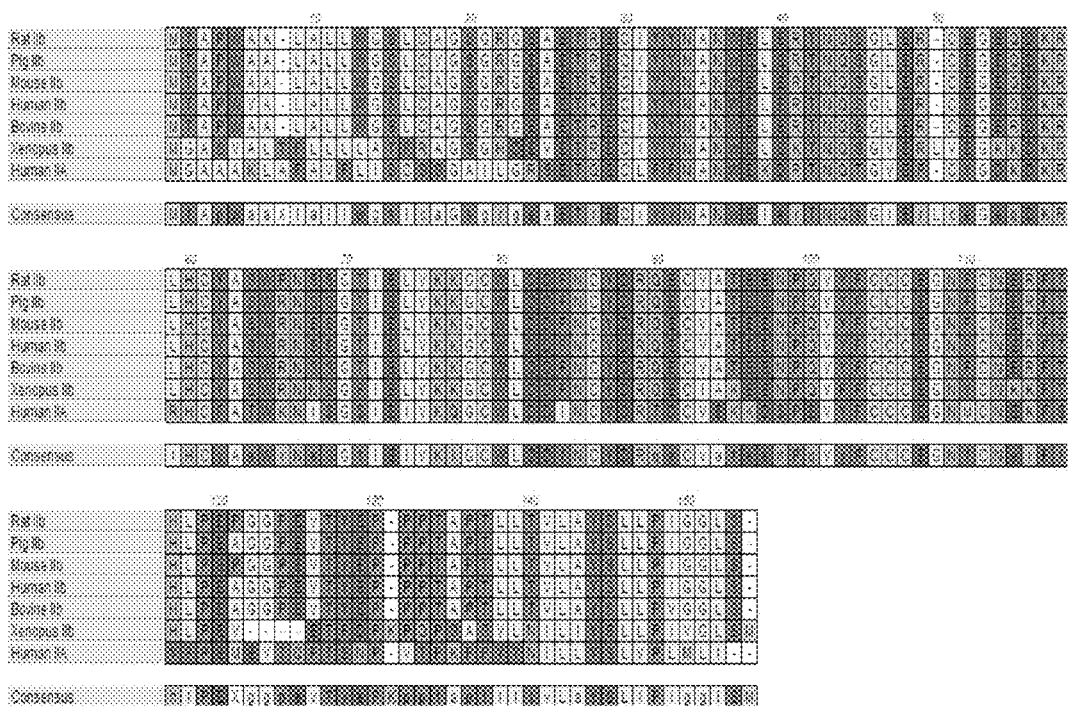
FIG. 2 shows a multiple sequence alignment of various vertebrate ActRIIB proteins and human ActRIIA (SEQ ID NOs: 57-63 and 69).

An alignment of the amino acid sequences of human ActRIIB soluble extracellular domain and human ActRIIA soluble extracellular domain are illustrated in FIG. 1. This alignment indicates amino acid residues within both receptors that are believed to directly contact ActRII ligands. FIG. 2 depicts a multiple-sequence alignment of various vertebrate ActRIIB proteins and human ActRIIA. From these alignments it is possible to predict key amino acid positions within the ligand-binding domain that are important for normal ActRII-ligand binding activities as well as to predict amino acid positions that are likely to be tolerant to substitution without significantly altering normal ActRII-ligand binding activities.

In other aspects, the present disclosure relates to GDF trap polypeptides (also referred to as "GDF traps") which may be used, for example, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) in a subject in need thereof.

In some embodiments, GDF traps of the present disclosure are soluble, variant ActRII polypeptides (e.g., ActRIIA and ActRIIB polypeptides) that comprise one or more mutations (e.g., amino acid additions, deletions, substitutions, and combinations thereof) in the extracellular domain (also referred to as the ligand-binding domain) of an ActRII polypeptide (e.g., a "wild-type" ActRII polypeptide) such that the variant ActRII polypeptide has one or more altered ligand-binding activities than the corresponding wild-type ActRII polypeptide. In preferred embodiments, GDF trap polypeptides of the present disclosure retain at least one similar activity as a corresponding wild-type ActRII polypeptide (e.g., an ActRIIA or ActRIIB polypeptide). For example, a GDF trap may bind to and/or inhibit (e.g. antagonize) the function of one or more ActRII ligands (e.g., inhibit ActRII ligand-mediated activation of the ActRIIA and/or ActRIIB signaling transduction, such as SMAD 2/3 and/or SMAD 1/5/8 signaling pathway). In some embodiments, GDF traps of the present disclosure bind to and/or inhibit one or more of activin A, activin B, activin AB, activin C, activin E, Nodal, GDF8, GDF11, BMP6 and/or BMP7).

In certain embodiments, GDF trap polypeptides of the disclosure have elevated binding affinity for one or more specific ActRII ligands (e.g., GDF8, GDF11, BMP6, Nodal, and/or BMP7). In other embodiments, GDF trap polypeptides of the disclosure have decreased binding affinity for one or more specific ActRII ligands (e.g., activin A, activin B, activin AB, activin C, and/or activin E). In still other embodiments, GDF trap polypeptides of the disclosure have elevated binding affinity for one or more specific ActRII ligands and decreased binding affinity for one or more different/other ActRII ligands. Accordingly, the present disclosure provides GDF trap polypeptides that have an altered binding specificity for one or more ActRII ligands.

In certain preferred embodiments, GDF traps of the present disclosure are designed to preferentially bind to and antagonize GDF11 and/or GDF8 (also known as myostatin), e.g., in comparison to a wild-type ActRII polypeptide. Optionally, such GDF11 and/or GDF8-binding traps may further bind to and/or antagonize one or more of Nodal, GDF8, GDF11, BMP6 and/or BMP7. Optionally, such GDF11 and/or GDF8-binding traps may further bind to and/or antagonize one or more of activin B, activin C, activin E, Nodal, GDF8, GDF11, BMP6 and/or BMP7. Optionally, such GDF11 and/or GDF8-binding traps may further bind to and/or antagonize one or more of activin A, activin A/B, activin B, activin C, activin E, Nodal, GDF8, GDF11, BMP6 and/or BMP7. In certain embodiments, GDF traps of the present disclosure have diminished binding affinity for activins (e.g., activin A, activin A/B, activin B, activin C, activin E), e.g., in comparison to a wild-type ActRII polypeptide. In certain preferred embodiments, a GDF trap polypeptide of the present disclosure has diminished binding affinity for activin A.

For example, the disclosure provides GDF trap polypeptides that preferentially bind to and/or antagonize GDF8/GDF11 relative to activin A. As demonstrated by the Examples of the disclosure, such GDF trap polypeptides are more potent activators of erythropoiesis in vivo in comparison to ActRII polypeptides that retain high binding affinity for activin A. Furthermore, these non-activin-A-binding GDF trap polypeptides demonstrate decreased effects on other tissues. Therefore, such GDF traps may be useful for increasing red blood cell levels in a subject while reducing potential off-target effects associated with binding/antagonizing activin A. However, such selective GDF trap polypeptides may be less desirable in some applications wherein more modest gains in red blood cell levels may be needed for therapeutic effect and wherein some level of off-target effect is acceptable (or even desirable).

Amino acid residues of the ActRIIB proteins (e.g., E39, K55, Y60, K74, W78, L79, D80, and F101) are in the ActRIIB ligand-binding pocket and help mediated binding to its ligands including, for example, activin A, GDF11, and GDF8. Thus the present disclosure provides GDF trap polypeptides comprising an altered-ligand binding domain (e.g., a GDF8/GDF11-binding domain) of an ActRIIB receptor which comprises one or more mutations at those amino acid residues.

Optionally, the altered ligand-binding domain can have increased selectivity for a ligand such as GDF11 and/or GDF8 relative to a wild-type ligand-binding domain of an ActRIIB receptor. To illustrate, one or more mutations may be selected that increase the selectivity of the altered ligand-binding domain for GDF11 and/or GDF8 over one or more activins (activin A, activin B, activin AB, activin C, and/or activin A), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

As a specific example, the positively-charged amino acid residue Asp (D80) of the ligand-binding domain of ActRIIB can be mutated to a different amino acid residue to produce a GDF trap polypeptide that preferentially binds to GDF8, but not activin. Preferably, the D80 residue with respect to SEQ ID NO:1 is changed to an amino acid residue selected from the group consisting of: an uncharged amino acid residue, a negative amino acid residue, and a hydrophobic amino acid residue. As a further specific example, the hydrophobic residue L79 of SEQ ID NO:1 can be altered to confer altered activin-GDF11/GDF8 binding properties. For example, an L79P substitution reduces GDF11 binding to a greater extent than activin binding. In contrast, replacement of L79 with an acidic amino acid [an aspartic acid or glutamic acid; an L79D or an L79E substitution] greatly reduces activin A binding affinity while retaining GDF11 binding affinity. In exemplary embodiments, the methods described herein utilize a GDF trap polypeptide which is a variant ActRIIB polypeptide comprising an acidic amino acid (e.g., D or E) at the position corresponding to position 79 of SEQ ID NO: 1, optionally in combination with one or more additional amino acid substitutions, additions, or deletions.

As will be recognized by one of skill in the art, most of the described mutations, variants or modifications described herein may be made at the nucleic acid level or, in some cases, by post-translational modification or chemical synthesis. Such techniques are well known in the art and some of which are described herein.

In certain embodiments, the present disclosure relates to ActRII polypeptides (ActRIIA and ActRIIB polypeptides) which are soluble ActRII polypeptides. As described herein, the term "soluble ActRII polypeptide" generally refers to polypeptides comprising an extracellular domain of an ActRII protein. The term "soluble ActRII polypeptide," as used herein, includes any naturally occurring extracellular domain of an ActRII protein as well as any variants thereof (including mutants, fragments, and peptidomimetic forms) that retain a useful activity (e.g., a GDF trap polypeptide as described herein). Other examples of soluble ActRII polypeptides comprise a signal sequence in addition to the extracellular domain of an ActRII or GDF trap protein. For example, the signal sequence can be a native signal sequence of an ActRIIA or ActRIIB protein, or a signal sequence from another protein including, for example, a tissue plasminogen activator (TPA) signal sequence or a honey bee melittin (HBM) signal sequence.

In part, the present disclosure identifies functionally active portions and variants of ActRII polypeptides that can be used as guidance for generating and using ActRIIA polypeptides, ActRIIB polypeptides, and GDF trap polypeptides within the scope of the methods described herein.

ActRII proteins have been characterized in the art in terms of structural and functional characteristics, particularly with respect to ligand binding [see, e.g., Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; and U.S. Pat. Nos. 7,709,605, 7,612,041, and 7,842,663].

For example, Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO:1, "ActRIIB(20-119)-Fc", has reduced binding to GDF-11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar but somewhat reduced activity relative to the wild-type, even though the proline knot region is disrupted. Thus, ActRIIB extracellular domains that stop at amino acid 134, 133, 132, 131, 130 and 129 (with respect to present SEQ ID NO:1) are all expected to be active, but constructs stopping at 134 or 133 may be most active. Similarly, mutations at any of residues 129-134 (with respect to SEQ ID NO:1) are not expected to alter ligand-binding affinity by large margins. In support of this, mutations of P129 and P130 (with respect to SEQ ID NO:1) do not substantially decrease ligand binding. Therefore, an ActRIIB polypeptide or an ActRIIB-based GDF trap polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides and ActRIIB-based GDF traps ending at 128 (with respect to present SEQ ID NO:1) or later should retain ligand binding activity. ActRIIB polypeptides and ActRIIB-based GDF traps ending at or between 119 and 127 (e.g., 119, 120, 121, 122, 123, 124, 125, 126, or 127), with respect to SEQ ID NO:1, will have an intermediate binding ability. Any of these forms may be desirable to use, depending on the clinical or experimental setting.

At the N-terminus of ActRIIB, it is expected that a protein beginning at amino acid 29 or before (with respect to present SEQ ID NO:1) will retain ligand-binding activity. Amino acid 29 represents the initial cysteine. An alanine-to-asparagine mutation at position 24 (with respect to present SEQ ID NO:1) introduces an N-linked glycosylation sequence without substantially affecting ligand binding (see, e.g., U.S. Pat. No. 7,842,663). This confirms that mutations in the region between the signal cleavage peptide and the cysteine cross-linked region, corresponding to amino acids 20-29, are well tolerated. In particular, ActRIIB polypeptides and ActRIIB-based GDF traps beginning at position 20, 21, 22, 23, and 24 (with respect to present SEQ ID NO:1) should retain general ligand-biding activity, and ActRIIB polypeptides and ActRIIB-based GDF traps beginning at positions 25, 26, 27, 28, and 29 (with respect to present SEQ ID NO:1) are also expected to retain ligand-biding activity. Data shown herein as well as in, e.g., U.S. Pat. No. 7,842,663 demonstrates that, surprisingly, an ActRIIB construct beginning at 22, 23, 24, or 25 will have the most activity.

Taken together, an active portion (e.g., ligand-binding activity) of ActRIIB comprises amino acids 29-109 of SEQ ID NO:1. Therefore ActRIIB polypeptides and ActRIIB-based GDF traps of the present disclosure may, for example, comprise an amino acid sequence that is at least 80%, 85%, 90%, 95%, 96%, 97%, 98%, 99%, or 100% identical to a portion of ActRIIB beginning at a residue corresponding to amino acids 20-29 (e.g., beginning at amino acid 20, 21, 22, 23, 24, 25, 26, 27, 28, or 29) of SEQ ID NO: 1 and ending at a position corresponding to amino acids 109-134 (e.g., ending at amino acid 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, ActRIIB-based GDF trap polypeptides of the present disclosure do not comprise or consist of amino acids 29-109 of SEQ ID NO:1. Other examples include polypeptides that begin at a position from 20-29 (e.g., position 20, 21, 22, 23, 24, 25, 26, 27, 28, or 29) or 21-29 (e.g., position 21, 22, 23, 24, 25, 26, 27, 28, or 29) and end at a position from 119-134 (e.g., 119, 120, 121, 122, 123, 124, 125, 126, 127, 128, 129, 130, 131, 132, 133, or 134), 119-133 (e.g., 119, 120, 121, 122, 123, 124, 125, 126, 127, 128, 129, 130, 131, 132, or 133), 129-134 (e.g., 129, 130, 131, 132, 133, or 134), or 129-133 (e.g., 129, 130, 131, 132, or 133) of SEQ ID NO: 1. Other examples include constructs that begin at a position from 20-24 (e.g., 20, 21, 22, 23, or 24), 21-24 (e.g., 21, 22, 23, or 24), or 22-25 (e.g., 22, 22, 23, or 25) and end at a position from 109-134 (e.g., 109, 110, 111, 112, 113, 114, 115, 116, 117, 118, 119, 120, 121, 122, 123, 124, 125, 126, 127, 128, 129, 130, 131, 132, 133, or 134), 119-134 (e.g., 119, 120, 121, 122, 123, 124, 125, 126, 127, 128, 129, 130, 131, 132, 133, or 134) or 129-134 (e.g., 129, 130, 131, 132, 133, or 134) of SEQ ID NO: 1. Variants within these ranges are also contemplated, particularly those having at least 80%, 85%, 90%, 95%, 96%, 97%, 98%, 99%, or 100% identity to the corresponding portion of SEQ ID NO: 1. In some embodiments, the ActRIIB polypeptides and ActRIIB-based GDF traps comprise a polypeptide having an amino acid sequence that is at least 80%, 85%, 90%, 95%, 96%, 97%, 98%, 99%, or 100% identical to amino acid residues 25-131 of SEQ ID NO: 1. In certain embodiments, ActRIIB-based GDF trap polypeptides do not comprise or consist of amino acids 25-131 of SEQ ID NO: 1.

The disclosure includes the results of an analysis of composite ActRIIB structures, shown in FIG. 1, demonstrating that the ligand-binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an ActRIIB polypeptide and ActRIIB-based GDF trap polypeptide of the disclosure is one that comprises an amino acid sequence that is at least 80%, 85%, 90%, 95%, 96%, 97%, 98%, 99%, or 100% identical to amino acids 29-109 of SEQ ID NO: 1, optionally beginning at a position ranging from 20-24 (e.g., 20, 21, 22, 23, or 24) or 22-25 (e.g., 22, 23, 24, or 25) and ending at a position ranging from 129-134 (e.g., 129, 130, 131, 132, 133, or 134), and comprising no more than 1, 2, 5, 10 or 15 conservative amino acid changes in the ligand-binding pocket, and zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO:1). An asparagine-to-alanine alteration at position 65 (N65A) actually improves ligand binding in the A64 background, and is thus expected to have no detrimental effect on ligand binding in the R64 background (see, e.g., U.S. Pat. No. 7,842,663). This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 (see, e.g., U.S. Pat. No. 7,842,663).

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant polypeptide and ActRIIB-based GDF trap useful in accordance with the presently disclosed methods may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

It has been previously demonstrated that the addition of a further N-linked glycosylation site (N-X-S/T) is well-tolerated relative to the ActRIIB(R64)-Fc form (see, e.g., U.S. Pat. No. 7,842,663). Therefore, N-X-S/T sequences may be generally introduced at positions outside the ligand binding pocket defined in FIG. 1 in ActRIIB polypeptide and ActRIIB-based GDF traps of the present disclosure. Particularly suitable sites for the introduction of non-endogenous N-X-S/T sequences include amino acids 20-29, 20-24, 22-25, 109-134, 120-134 or 129-134 (with respect to SEQ ID NO:1). N-X-S/T sequences may also be introduced into the linker between the ActRIIB sequence and an Fc domain or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO:1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO:1) are contemplated. Likewise, in an A24N variant, an S26T alteration may be used. Accordingly, an ActRIIB polypeptide and ActRIIB-based GDF trap polypeptide of the present disclosure may be a variant having one or more additional, non-endogenous N-linked glycosylation consensus sequences as described above.

The variations described herein may be combined in various ways. Additionally, the results of the mutagenesis program described herein indicate that there are amino acid positions in ActRIIB that are often beneficial to conserve. With respect to SEQ ID NO:1, these include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in the ActRIIB polypeptides and ActRIIB-based GDF traps disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K), all with respect to SEQ ID NO:1.

A general formula for an active (e.g., ligand binding) ActRIIA polypeptide is one that comprises a polypeptide that starts at amino acid 30 and ends at amino acid 110 of SEQ ID NO:9. Accordingly, ActRIIA polypeptides and ActRIIA-based GDF traps of the present disclosure may comprise a polypeptide that is at least 80%, 85%, 90%, 95%, 96%, 97%, 98%, 99%, or 100% identical to amino acids 30-110 of SEQ ID NO:9. In some embodiments, ActRIIA-based GDF traps of the present disclosure do not comprise or consist of amino acids 30-110 of SEQ ID NO:9. Optionally, ActRIIA polypeptides and ActRIIA-based GDF trap polypeptides of the present disclosure comprise a polypeptide that is at least 80%, 85%, 90%, 95%, 96%, 97%, 98%, 99%, or 100% identical to amino acids amino acids 12-82 of SEQ ID NO:9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO:9.

In certain embodiments, functionally active fragments of ActRII polypeptides (e.g. ActRIIA and ActRIIB polypeptides) and GDF trap polypeptides of the present disclosure can be obtained by screening polypeptides recombinantly produced from the corresponding fragment of the nucleic acid encoding an ActRII polypeptide or GDF trap polypeptide (e.g., SEQ ID NOs: 7, 8, 12, 13, 27, 32, 39, 40, 42, 46, and 48). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII receptors and/or one or more ActRII ligands (e.g., GDF11, GDF8, activin A, activin B, activin AB, activin C, activin E, BMP6, BMP7, and/or Nodal).

In some embodiments, an ActRIIA polypeptide of the present disclosure is a polypeptide comprising an amino acid sequence that is at least 75% identical to an amino acid sequence selected from SEQ ID NOs: 9, 10, 11, 22, 26, and 28. In certain embodiments, the ActRIIA polypeptide comprises an amino acid sequence that is at least 80%, 85%, 90%, 95%, 97%, 98%, 99% or 100% identical to an amino acid sequence selected from SEQ ID NOs: 9, 10, 11, 22, 26, and 28. In certain embodiments, the ActRIIA polypeptide consists essentially of, or consists of, an amino acid sequence that is at least 80%, 85%, 90%, 95%, 97%, 98%, 99% or 100% identical to an amino acid sequence selected from SEQ ID NOs: 9, 10, 11, 22, 26, and 28.

In some embodiments, an ActRIIB polypeptide of the present disclosure is a polypeptide comprising an amino acid sequence that is at least 75% identical to an amino acid sequence selected from SEQ ID NOs: 1, 2, 3, 4, 5, 6, 29, 31, and 49. In certain embodiments, the ActRIIB polypeptide comprises an amino acid sequence that is at least 80%, 85%, 90%, 95%, 97%, 98%, 99% or 100% identical to an amino acid sequence selected from SEQ ID NOs: 1, 2, 3, 4, 5, 6, 29, 31, and 49. In certain embodiments, the ActRIIB polypeptide consists essentially of, or consists of, an amino acid sequence that is at least 80%, 85%, 90%, 95%, 97%, 98%, 99% or 100% identical to an amino acid sequence selected from SEQ ID NOs: 1, 2, 3, 4, 5, 6, 29, 31, and 49.

In some embodiments, a GDF trap polypeptide of the present disclosure is a variant ActRIIB polypeptide comprising an amino acid sequence that is at least 75% identical to an amino acid sequence selected from SEQ ID NOs: 1, 2, 3, 4, 5, 6, 29, 30, 31, 36, 37, 38, 41, 44, 45, 49, 50, and 51. In certain embodiments, the GDF trap comprises an amino acid sequence that is at least 80%, 85%, 90%, 95%, 97%, 98%, 99% or 100% identical to an amino acid sequence selected from SEQ ID NOs: 1, 2, 3, 4, 5, 6, 29, 30, 31, 36, 37, 38, 41, 44, 45, 49, 50, and 51. In certain embodiments, the GDF trap comprises an amino acid sequence that is at least 80%, 85%, 90%, 95%, 97%, 98%, 99% or 100% identical to an amino acid sequence selected from SEQ ID NOs: 1, 2, 3, 4, 5, 6, 29, 30, 31, 36, 37, 38, 41, 44, 45, 49, 50, and 51, wherein the position corresponding to L79 of SEQ ID NO:1, 4, or 49 is an acidic amino acids (a D or E amino acid residue). In certain embodiments, the GDF trap consists essentially of, or consists of, an amino acid sequence that at least 80%, 85%, 90%, 95%, 97%, 98%, 99% or 100% identical to an amino acid sequence selected from SEQ ID NOs: 36, 37, 38, 41, 44, 45, 50, and 51. In certain embodiments, the GDF trap does not comprise or consists of an amino acid sequence selected from SEQ ID NOs: 1, 2, 3, 4, 5, 6, 29, and 31.

In some embodiments, a GDF trap polypeptide of the present disclosure is a variant ActRIIA polypeptide comprising an amino acid sequence that is at least 75% identical to an amino acid sequence selected from SEQ ID NOs: 9, 10, 11, 22, 26, 28, 29, and 31. In certain embodiments, the GDF trap comprises an amino acid sequence that is at least 80%, 85%, 90%, 95%, 97%, 98%, 99% or 100% identical to an amino acid sequence selected from SEQ ID NOs: 9, 10, 11, 22, 26, 28, 29, and 31. In certain embodiments, the GDF trap consists essentially of, or consists of, an amino acid sequence that at least 80%, 85%, 90%, 95%, 97%, 98%, 99% or 100% identical to an amino acid sequence selected from SEQ ID NOs: 9, 10, 11, 22, 26, 28, 29, and 31. In certain embodiments, the GDF trap does not comprise or consists of an amino acid sequence selected from SEQ ID NOs: 9, 10, 11, 22, 26, 28, 29, and 31.

In some embodiments, the present disclosure contemplates making functional variants by modifying the structure of an ActRII polypeptide (e.g. and ActRIIA or ActRIIB polypeptide) or a GDF trap for such purposes as enhancing therapeutic efficacy, or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations)

will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more ligands, such as GDF11, activin A, activin B, activin AB, activin C, activin E, GDF8, BMP6, and BMP7, as compared to the unmodified or a wild-type polypeptide.

In certain embodiments, the present disclosure contemplates specific mutations of ActRII polypeptides and GDF trap polypeptides of the present disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, ActRII polypeptides and GDF trap polypeptides of the present disclosure for use in humans may be expressed in a mammalian cell line that provides proper glycosylation, such as HEK293 or CHO cell lines, although other mammalian expression cell lines are expected to be useful as well.

This disclosure further contemplates a method of generating mutants, particularly sets of combinatorial mutants of ActRII polypeptides and GDF trap polypeptides of the present disclosure, as well as truncation mutants. Pools of combinatorial mutants are especially useful for identifying ActRII and GDF trap sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ActRII polypeptides and GDF trap polypeptides may be screened for ability to bind to an ActRII receptor, to prevent binding of an ActRII ligand (e.g., GDF11, GDF8, activin A, activin B, activin AB, activin C, activin E, BMP7, BMP6, and/or Nodal) to an ActRII polypeptide, or to interfere with signaling caused by an ActRII ligand.

The activity of an ActRII polypeptides or GDF trap polypeptides may also be tested in a cell-based or in vivo assay. For example, the effect of an ActRII polypeptide or GDF trap polypeptide on the expression of genes involved in hematopoiesis may be assessed. This may, as needed, be performed in the presence of one or more recombinant ActRII ligand proteins (e.g., GDF11, GDF8, activin A, activin B, activin AB, activin C, activin E, BMP7, BMP6, and/or Nodal), and cells may be transfected so as to produce an ActRII polypeptide or GDF trap polypeptide, and optionally, an ActRII ligand. Likewise, an ActRII polypeptide or GDF trap polypeptide may be administered to a mouse or other animal, and one or more blood measurements, such as an RBC count, hemoglobin, or reticulocyte count may be assessed using art-recognized methods.

Combinatorial-derived variants can be generated which have a selective or generally increased potency relative to a reference ActRII polypeptide or GDF trap polypeptide. Such variants, when expressed from recombinant DNA constructs, can be used in gene therapy protocols. Likewise, mutagenesis can give rise to variants which have intracellular half-lives dramatically different than the corresponding unmodified ActRII polypeptide or GDF trap polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter ActRII polypeptide or GDF trap polypeptide levels by modulating the half-life of the polypeptide. For instance, a short half-life can give rise to more transient biological effects and, when part of an inducible expression system, can allow tighter control of recombinant ActRII polypeptide or GDF trap polypeptide levels within the cell. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRII or GDF trap sequences. For instance, a mixture of synthetic oligonucleotides can be enzymatically ligated into gene sequences such that the degenerate set of potential ActRII or GDF trap polypeptide encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-

289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815.

Alternatively, other forms of mutagenesis can be utilized to generate a combinatorial library. For example, ActRII polypeptides or GDF trap polypeptides of the present disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [see, e.g., Gustin et al. (1993) Virology 193:653-660; and Brown et al. (1992) Mol. Cell Biol. 12:2644-2652; McKnight et al. (1982) Science 232:316], by saturation mutagenesis [see, e.g., Meyers et al., (1986) Science 232:613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ActRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides or GDF trap polypeptides of the disclosure. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ActRII ligand (e.g., GDF11, GDF8, activin A, activin B, activin AB, activin C, activin E, BMP7, BMP6, and/or Nodal) binding assays and/or ActRII ligand-mediated cell signaling assays.

In certain embodiments, ActRII polypeptides or GDF trap polypeptides of the present disclosure may further comprise post-translational modifications in addition to any that are naturally present in the ActRII (e.g. an ActRIIA or ActRIIB polypeptide) or GDF trap polypeptide. Such modifications include, but are not limited to, acetylation, carboxylation, glycosylation, phosphorylation, lipidation, and acylation. As a result, the ActRII polypeptide or GDF trap polypeptide may contain non-amino acid elements, such as polyethylene glycols, lipids, polysaccharide or monosaccharide, and phosphates. Effects of such non-amino acid elements on the functionality of a ligand trap polypeptide may be tested as described herein for other ActRII or GDF trap variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ActRII polypeptides or GDF trap polypeptides.

In certain aspects, ActRII polypeptides or GDF trap polypeptides of the present disclosure include fusion proteins having at least a portion (domain) of an ActRII polypeptide (e.g., an ActRIIA or ActRIIB polypeptide) or GDF trap polypeptide and one or more heterologous portions (domains). Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ligand trap polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRII polypeptide or a GDF trap polypeptide is fused with a domain that stabilizes the polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

In certain embodiments, the present disclosure provides ActRII or GDF trap fusion proteins comprising the following IgG1 Fc domain sequence:

```
                                                    (SEQ ID NO: 14)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPVPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK.
```

In other embodiments, the present disclosure provides ActRII or GDF trap fusion proteins comprising the following variant of the IgG1 Fc domain:

```
                                                    (SEQ ID NO: 64)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

In still other embodiments, the present disclosure provides ActRII or GDF trap fusion proteins comprising the following variant of the IgG1 Fc domain:

```
                                                    (SEQ ID NO: 15)
  1 THTCPPCPAP ELLGGPSVFL FPPKPKDTLM ISRTPEVTCV VVD(A)VSHEDPE

51 VKFNWYVDGV EVHNAKTKPR EEQYNSTYRV VSVLTVLHQD WLNGKEYKCK(A)

101 VSNKALPVPI EKTISKAKGQ PREPQVYTLP PSREEMTKNQ VSLTCLVKGF

151 YPSDIAVEWE SNGQPENNYK TTPPVLDSDG PFFLYSKLTV DKSRWQQGNV

201 FSCSVMHEAL HN(A)HYTQKSLS LSPGK.
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MEW class I-related Fc-receptor (FcRN) relative to a wild-type IgG1 Fc domain.

In certain other embodiments, the present disclosure provides ActRII or GDF trap fusion proteins comprising variants of the IgG2 Fc domain, including the following:

```
                                                    (SEQ ID NO: 65)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

It is understood that different elements of the fusion proteins may be arranged in any manner that is consistent with the desired functionality. For example, an ActRII polypeptide domain or GDF trap polypeptide domain may be placed C-terminal to a heterologous domain, or alternatively, a heterologous domain may be placed C-terminal to an ActRII polypeptide domain or GDF trap polypeptide domain. The ActRII polypeptide domain or GDF trap polypeptide domain and the heterologous domain need not be adjacent in a fusion protein, and additional domains or amino acid sequences may be included C- or N-terminal to either domain or between the domains.

For example, an ActRII or GDF trap fusion protein may comprise an amino acid sequence as set forth in the formula A-B-C. The B portion corresponds to an ActRII polypeptide domain or a GDF trap polypeptide domain. The A and C portions may be independently zero, one, or more than one amino acid, and both the A and C portions when present are heterologous to B. The A and/or C portions may be attached to the B portion via a linker sequence. Exemplary linkers include short polypeptide linkers such as 2-10, 2-5, 2-4, 2-3 glycine residues, such as, for example, a Gly-Gly-Gly linker. Other suitable linkers are described herein above [e.g., a TGGG linker (SEQ ID NO: 53)]. In certain embodiments, an ActRII or GDF trap fusion protein comprises an amino acid sequence as set forth in the formula A-B-C, wherein A is a leader (signal) sequence, B consists of an ActRII or GDF polypeptide domain, and C is a polypeptide portion that enhances one or more of in vivo stability, in vivo half-life, uptake/administration, tissue localization or distribution, formation of protein complexes, and/or purification. In certain embodiments, an ActRII or GDF trap fusion protein comprises an amino acid sequence as set forth in the formula A-B-C, wherein A is a TPA leader sequence, B consists of an ActRII or GDF polypeptide domain, and C is an immunoglobulin Fc domain. Preferred fusion proteins comprises the amino acid sequence set forth in any one of SEQ ID NOs: 22, 26, 29, 31, 36, 38, 41, 44, and 51.

In certain embodiments, ActRII polypeptides or GDF trap polypeptides of the present disclosure contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide domain or a GDF trap polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In preferred embodiments, ActRII polypeptides and GDF traps to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [see, e.g., Flatman et al., (2007) J. Chromatogr. B 848:79-87].

In certain embodiments, ActRII polypeptides and GDF traps of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides of the disclosure, including fragments or variants thereof, may be recombinantly produced using various expression systems [e.g., E. coli, Chinese Hamster Ovary (CHO) cells, COS cells, baculovirus] as is well known in the art. In a further embodiment, the modified or unmodified polypeptides of the disclosure may be produced by digestion of recombinantly produced full-length ActRII or GDF trap polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such polypeptides may be produced from recombinantly produced full-length ActRII or GDF trap polypeptides using chemical cleavage (e.g., cyanogen bromide, hydroxylamine, etc.).

Any of the ActRII polypeptides disclosed herein (e.g., ActRIIA or ActRIIB polypeptides) can be combined with one or more additional ActRII antagonist agents of the disclosure to achieve the desired effect (e.g., increase red blood cell levels and/or hemoglobin in a subject in need thereof, treat or prevent an anemia, treat MDS or sideroblastic anemias, treat or prevent one or more complications of MDS or sideroblastic anemias s). For example, an ActRII polypeptide disclosed herein can be used in combination with i) one or more additional ActRII polypeptides disclosed herein, ii) one or more GDF traps disclosed herein; iii) one or more ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody); iv) one or more small-molecule ActRII antagonists disclosed herein (e.g., a small-molecule antagonist of one or more of GDF11, GDF8, activin A, activin B, activin AB, activin C, activin E, BMP6, BMP7, Nodal, ActRIIA, and/or ActRIIB); v) one or more of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

Similarly, any of the GDF traps disclosed herein can be combined with one or more additional ActRII antagonist agents of the disclosure to achieve the desired effect (e.g., increase red blood cell levels and/or hemoglobin in a patient in need thereof, treat or prevent an anemia, treat MDS or sideroblastic anemias, treat or prevent one or more complications of MDS or sideroblastic anemias). For example, a GDF trap disclosed herein can be used in combination with i) one or more additional GDF traps disclosed herein, ii) one or more ActRII polypeptides disclosed herein (e.g., ActRIIA or ActRIIB polypeptides) disclosed herein; iii) one or more ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody); iv) one or more small-molecule ActRII antagonists disclosed herein (e.g., a small-molecule antagonist of one or more of GDF11, GDF8, activin A, activin B, activin AB, activin C, activin E, BMP6, BMP7, Nodal, ActRIIA, and/or ActRIIB); v) one or more of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

B. Nucleic Acids Encoding ActRII Polypeptides and GDF Traps

In certain embodiments, the present disclosure provides isolated and/or recombinant nucleic acids encoding the ActRII polypeptides and GDF trap polypeptides (including fragments, functional variants, and fusion proteins thereof) disclosed herein. For example, SEQ ID NO:12 encodes the naturally occurring human ActRIIA precursor polypeptide, while SEQ ID NO:13 encodes the processed extracellular domain of ActRIIA. In addition, SEQ ID NO:7 encodes a naturally occurring human ActRIIB precursor polypeptide (the R64 variant described above), while SEQ ID NO:8 encodes the processed extracellular domain of ActRIIB (the R64 variant described above). The subject nucleic acids may be single-stranded or double stranded. Such nucleic acids may be DNA or RNA molecules. These nucleic acids may be used, for example, in methods for making ActRII-based ligand trap polypeptides of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII polypeptides and GDF traps of the present disclosure are understood to include nucleic acids that are variants of any one of SEQ ID NOs: 7, 8, 12, 13, 27, 32, 39, 40, 42, 43, 46, 47, and 48. Variant nucleotide sequences include sequences that differ by one or more nucleotide substitutions, additions, or deletions including allelic variants, and therefore, will include coding sequence that differ from the nucleotide sequence designated in any one of SEQ ID NOs: 7, 8, 12, 13, 27, 32, 39, 40, 42, 43, 46, 47, and 48.

In certain embodiments, ActRII polypeptides and GDF traps of the present disclosure are encoded by isolated or recombinant nucleic acid sequences that are at least 80%, 85%, 90%, 95%, 97%, 98%, or 99% identical to SEQ ID NOs: 7, 8, 12, 13, 27, 32, 39, 40, 42, 43, 46, 47, and 48 In some embodiments, GDF traps of the present disclosure are not encoded by nucleic acid sequences that comprise or consist of any one of nucleotide sequences corresponding to any one of SEQ ID NOs: 7, 8, 12, 13, 27, and 32. One of ordinary skill in the art will appreciate that nucleic acid sequences that are at least 80%, 85%, 90%, 95%, 97%, 98%, or 99% identical to the sequences complementary to SEQ ID NOs: 7, 8, 12, 13, 27, 32, 39, 42, 47, and 48, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 7, 8, 12, 13, 27, 32, 39, 40, 42, 43, 46, 47, and 48, complement sequences of SEQ ID NOs: 7, 8, 12, 13, 27, 32, 39, 40, 42, 43, 46, 47, and 48, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 27, 32, 39, 40, 42, 43, 46, 47, and 48 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding an ActRII polypeptide or a GDF trap and operably linked to at least one regulatory sequence. Regulatory sequences are art-recognized and are selected to direct expression of the ActRII or GDF trap polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRII or GDF trap polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII or GDF trap polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRII or GDF trap polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII or GDF trap polypeptides. The host cell may be any prokaryotic or eukaryotic cell. For example, an ActRII or GDF trap polypeptide of the disclosure may be expressed in bacterial cells such as E. coli, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII and GDF trap polypeptides. For example, a host cell transfected with an expression vector encoding an ActRII or GDF trap polypeptide can be cultured under appropriate conditions to allow expression of the ActRII or GDF trap polypeptide to occur. The polypeptide may be secreted and isolated from a mixture of cells and medium containing the polypeptide. Alternatively, the ActRII or GDF trap polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII or GDF trap polypeptides, and affinity purification with an agent that binds to a domain fused to the ActRII or GDF trap polypeptide (e.g., a protein A column may be used to purify an ActRII-Fc or GDF Trap-Fc fusion protein). In some embodiments, the ActRII or GDF trap polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII-Fc or GDF trap-Fc protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII or GDF trap polypeptide, can allow purification of the expressed fusion protein by affinity chromatography using a $Ni^{2+}$ metal resin. The purification leader sequence can then be subsequently removed by treatment with enterokinase to provide the purified ActRII or GDF trap polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

C. Antibody Antagonists

In certain aspects, the present disclosure relates to an antibody, or combination of antibodies, that antagonize ActRII activity (e.g., inhibition of ActRIIA and/or ActRIIB signaling transduction, such as SMAD 2/3 and/or SMAD 1/5/8 signaling). Such antibodies may bind to and inhibit one or more ligands (e.g., GDF8, GDF11, activin A, activin B, activin C, activin E, BMP6, BMP7 or Nodal) or one or more receptors (e.g., ActRIIA, ActRIIB, ALK4, ALK5). In particular, the disclosure provides methods of using an antibody ActRII antagonist, or combination of antibody ActRII antagonists, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In certain embodiments, a preferred antibody ActRII antagonist of the disclosure is an antibody, or combination of antibodies, that binds to and/or inhibits activity of at least GDF11 (e.g., GDF11-mediated activation of ActRIIA and/or ActRIIB signaling transduction, such as SMAD 2/3 signaling). Optionally, the antibody, or combination of antibodies, further binds to and/or inhibits activity of GDF8 (e.g., GDF8-mediated activation of ActRIIA and/or ActRIIB signaling transduction, such as SMAD 2/3 signaling), particularly in the case of a multispecific antibody that has binding affinity for both GDF11 and GDF8 or in the context of a combination of one or more anti-GDF11 antibodies and one or more anti-GDF8 antibodies. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF11 and/or GDF8 further binds to and/or inhibits activity of one of more of activin A, activin B, activin AB, activin C, activin E, BMP6, BMP7, and Nodal (e.g., activation of ActRIIA or ActRIIB SMAD 2/3 and/or SMAD 1/5/8 signaling), particularly in the case of a multispecific antibody that has binding affinity for multiple ActRII ligands or in the context of a combination of multiple antibodies—each having binding affinity for a different ActRII ligand.

In certain aspects, an ActRII antagonist of the present disclosure is an antibody, or combination of antibodies, that binds to and/or inhibits activity of at least GDF8 (e.g., GDF8-mediated activation of ActRIIA and/or ActRIIB signaling transduction, such as SMAD 2/3 signaling). Optionally, the antibody, or combination of antibodies, further binds to and/or inhibits activity of GDF11 (e.g., GDF11-mediated activation of ActRIIA and/or ActRIIB signaling transduction, such as SMAD 2/3 signaling), particularly in the case of a multispecific antibody that has binding affinity for both GDF8 and GDF11 or in the context of a combination of one or more anti-GDF8 antibodies and one or more anti-GDF11 antibodies. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF8 and/or GDF11 further binds to and/or inhibits activity of one of more of activin A, activin B, activin AB, activin C, activin E, BMP6, BMP7, and Nodal (e.g., activation of ActRIIA or ActRIIB signaling transduction, such as SMAD 2/3 and/or SMAD 1/5/8 signaling), particularly in the case of a multispecific antibody that has binding affinity for multiple ActRII ligands or in the context of a combination multiple antibodies—each having binding affinity for a different ActRII ligand.

In another aspect, an ActRII antagonist of the present disclosure is an antibody, or combination of antibodies, that binds to and/or inhibits activity of an ActRII receptor (e.g. an ActRIIA or ActRIIB receptor). In preferred embodiments, an anti-ActRII receptor antibody (e.g. an anti-ActRIIA or anti-ActRIIB receptor antibody), or combination of antibodies, of the disclosure binds to an ActRII receptor and prevents binding and/or activation of the ActRII receptor by at least GDF11 (e.g., GDF11-mediated activation of ActRIIA and/or ActRIIB signaling transduction, such as SMAD 2/3 signaling). Optionally, an anti-ActRII receptor antibody, or combination of antibodies, of the disclosure further prevents binding and/or activation of the ActRII receptor by GDF8. Optionally, an anti-ActRII receptor antibody, or combination of antibodies, of the disclosure does not substantially inhibit activin A from binding to and/or activating an ActRII receptor. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by one or more of activin A, activin B, activin AB, activin C, activin E, BMP6, BMP7, and Nodal.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies.

Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134.

Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516.

Antibody fragments can be made by various techniques, including but not limited to proteolytic digestion of an intact antibody as well as production by recombinant host cells (e.g., E. coli or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, $IgG_1$, $IgG_2$, $IgG_3$, $IgG_4$, $IgA_1$, and $IgA_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. GDF11, GDF8, ActRIIA, ActRIIB, etc.) with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radio-labeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NETS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PB ST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophotometer (Aviv Instruments) or a 8000-series SLM-AMINCO® spectrophotometer (ThermoSpectronic) with a stirred cuvette.

As used herein, anti-GDF11 antibody generally refers to an antibody that is capable of binding to GDF11 with sufficient affinity such that the antibody is useful as a diagnostic and/or therapeutic agent in targeting GDF11. In certain embodiments, the extent of binding of an anti-GDF11 antibody to an unrelated, non-GDF11 protein is less than about 10%, 9%, 8%, 7%, 6%, 5%, 4%, 3%, 2%, or less than 1% of the binding of the antibody to GDF11 as measured, for example, by a radioimmunoassay (MA). In certain embodiments, an anti-GDF11 antibody binds to an epitope of GDF11 that is conserved among GDF11 from different species. In certain preferred embodiments, an anti-GDF11 antibody of the present disclosure is an antagonist antibody that can inhibit GDF11 activity. For example, an anti-GDF11 antibody of the disclosure may inhibit GDF11 from binding to a cognate receptor (e.g., ActRIIA or ActRIIB receptor) and/or inhibit GDF11-mediated signal transduction (activation) of a cognate receptor, such as SMAD2/3 signaling by ActRIIA and/or ActRIIB receptors. In some embodiments, anti-GDF11 antibodies of the present disclosure do not substantially bind to and/or inhibit activity of activin A. It should be noted that GDF11 has high sequence homology to GDF8 and therefore antibodies that bind and/or to GDF11, in some cases, may also bind to and/or inhibit GDF8.

An anti-GDF8 antibody refers to an antibody that is capable of binding to GDF8 with sufficient affinity such that the antibody is useful as a diagnostic and/or therapeutic agent in targeting GDF8. In certain embodiments, the extent of binding of an anti-GDF8 antibody to an unrelated, non-GDF8 protein is less than about 10%, 9%, 8%, 7%, 6%, 5%, 4%, 3%, 2%, or less than 1% of the binding of the antibody to GDF8 as measured, for example, by a radioimmunoassay (MA). In certain embodiments, an anti-GDF8 antibody binds to an epitope of GDF8 that is conserved among GDF8 from different species. In preferred embodiments, an anti-GDF8 antibody of the present disclosure is an antagonist antibody that can inhibit GDF8 activity. For example, an anti-GDF8 antibody of the disclosure may inhibit GDF8 from binding to a cognate receptor (e.g., ActRIIA or ActRIIB receptor) and/or inhibit GDF8-mediated signal transduction (activation) of a cognate receptor, such as SMAD2/3 signaling by ActRIIA and/or ActRIIB receptors. In some embodiments, anti-GDF8 antibodies of the present disclosure do not substantially bind to and/or inhibit activity of activin A. It should be noted that GDF8 has high sequence homology to GDF11 and therefore antibodies that bind and/or to GDF8, in many cases, may also bind to and/or inhibit GDF11.

An anti-ActRIIA antibody refers to an antibody that is capable of binding to ActRIIA with sufficient affinity such that the antibody is useful as a diagnostic and/or therapeutic agent in targeting ActRIIA. In certain embodiments, the extent of binding of an anti-ActRIIA antibody to an unrelated, non-ActRIIA protein is less than about 10%, 9%, 8%, 7%, 6%, 5%, 4%, 3%, 2%, or less than 1% of the binding of the antibody to ActRIIA as measured, for example, by a radioimmunoassay (MA). In certain embodiments, an anti-ActRIIA antibody binds to an epitope of ActRIIA that is conserved among ActRIIA from different species. In preferred embodiments, an anti-ActRIIA antibody of the present disclosure is an antagonist antibody that can inhibit ActRIIA activity. For example, an anti-ActRIIA antibody of the present disclosure may inhibit one or more ActRIIA ligands selected from activin A, activin B, activin AB, activin C, activin E, GDF11, GDF8, activin A, BMP6, and BMP7 from binding to the ActRIIA receptor and/or inhibit one of these ligands from activating ActRIIA signaling (e.g., SMAD2/3 and/or SMAD 1/5/8 ActRIIA signaling). In preferred embodiments, anti-ActRIIA antibodies of the present disclosure inhibit GDF11 from binding to the ActRIIA receptor and/or inhibit GDF11 from activating ActRIIA signaling. Optionally, anti-ActRIIA antibodies of the disclosure further inhibit GDF8 from binding to the ActRIIA receptor and/or inhibit GDF8 from activating ActRIIA signaling. Optionally, anti-ActRIIA antibodies of the present disclosure do not substantially inhibit activin A from binding to the ActRIIA receptor and/or do not substantially inhibit activin A-mediated activation of ActRIIA signaling. In some embodiments, an anti-ActRIIA antibody of the disclosure that inhibits GDF11 and/or GDF8 from binding to and/or activating an ActRIIA receptor further inhibits one or more of activin A, activin B, activin AB, activin C, activin E, activin A, GDF8, BMP6, and BMP7 from binding to and/or activating the ActRIIA receptor.

An anti-ActRIIB antibody refers to an antibody that is capable of binding to ActRIIB with sufficient affinity such that the antibody is useful as a diagnostic and/or therapeutic agent in targeting ActRIIB In certain embodiments, the extent of binding of an anti-ActRIIB antibody to an unrelated, non-ActRIIB protein is less than about 10%, 9%, 8%, 7%, 6%, 5%, 4%, 3%, 2%, or less than 1% of the binding of the antibody to ActRIIB as measured, for example, by a radioimmunoassay (MA). In certain embodiments, an anti-ActRIIB antibody binds to an epitope of ActRIIB that is conserved among ActRIIB from different species. In preferred embodiments, an anti-ActRIIB antibody of the present disclosure is an antagonist antibody that can inhibit ActRIIB activity. For example, an anti-ActRIIB antibody of the present disclosure may inhibit one or more ActRIIB ligands selected from activin A, activin B, activin AB, activin C, activin E, GDF11, GDF8, activin A, BMP6, and BMP7 from binding to the ActRIIB receptor and/or inhibit one of these ligands from activating ActRIIB signaling (e.g., SMAD2/3 and/or SMAD 1/5/8 ActRIIB signaling). In preferred embodiments, anti-ActRIIB antibodies of the present disclosure inhibit GDF11 from binding to the ActRIIB receptor and/or inhibit GDF11 from activating ActRIIB signaling. Optionally, anti-ActRIIB antibodies of the disclosure further inhibit GDF8 from binding to the ActRIIB receptor and/or inhibit GDF8 from activating ActRIIB signaling. Optionally, anti-ActRIIB antibodies of the present disclosure do not substantially inhibit activin A from binding to the ActRIIB receptor and/or do not substantially inhibit activin A-mediated activation of ActRIIB signaling. In some embodiments, an anti-ActRIIB antibody of the disclosure that inhibits GDF11 and/or GDF8 from binding to and/or activating an ActRIIB receptor further inhibits one or more of activin A, activin B, activin AB, activin C, activin E, activin A, GDF8, BMP6, and BMP7 from binding to and/or activating the ActRIIB receptor.

The nucleic acid and amino acid sequences of human GDF11, GDF8, activin A, activin B, activin AB, activin C, activin E, GDF8, BMP6, BMP7, ActRIIB, and ActRIIA are well known in the art and thus antibody antagonists for use in accordance with this disclosure may be routinely made by the skilled artisan based on the knowledge in the art and teachings provided herein.

In certain embodiments, an antibody provided herein (e.g., an anti-GDF11 antibody, an anti-GDF8 antibody, an anti-ActRIIA antibody, or an anti-ActRIIB antibody) is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein (e.g., an anti-GDF11 antibody, an anti-GDF8 antibody, an anti-ActRIIA antibody, or an anti-ActRIIB antibody) is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et cd., (1997) J. Biol. Chem. 272:10678-10684; and Rosok et cd., (1996) J. Biol. Chem. 271:22611-22618].

In certain embodiments, an antibody provided herein (e.g., an anti-GDF11 antibody, an anti-GDF8 antibody, an anti-ActRIIA antibody, or an anti-ActRIIB antibody) is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen (e.g., a GDF11 polypeptide, GDF8 polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein (e.g., an anti-GDF11 antibody, an anti-activin B antibody, an anti-ActRIIA antibody, or an anti-ActRIIB antibody) may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., GDF11, activin B, ActRIIA, or ActRIIB) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/

0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

In certain embodiments, a multispecific antibody of the present disclosure comprises two or more binding specificities, with at least one of the binding specificities being for a GDF11 epitope, and optionally one or more additional binding specificities being for an epitope on a different ActRII ligand (e.g., GDF8, activin A, activin B, activin AB, activin C, activin E, BMP6 BMP7 and/or Nodal) and/or an ActRII receptor (e.g., an ActRIIA and/or ActRIIB receptor). In certain embodiments, multispecific antibodies may bind to two or more different epitopes of GDF11. Preferably a multispecific antibody of the disclosure that has binding affinity, in part, for a GDF11 epitope can be used to inhibit a GDF11 activity (e.g., the ability to bind to and/or activate an ActRIIA and/or ActRIIB receptor), and optionally inhibit the activity of one or more different ActRII ligands (e.g., GDF8, activin A, activin B, activin AB, activin C, activin E, BMP6, BMP7 and/or Nodal) and/or an ActRII receptor (e.g., an ActRIIA or ActRIIB receptor). In certain preferred embodiments, multispecific antibodies of the present disclosure that bind to and/or inhibit GDF11 further bind to and/or inhibit at least GDF8. Optionally, multispecific antibodies of the disclosure that bind to and/or inhibit GDF11 do not substantially bind to and/or substantially inhibit activin A. In some embodiments, multispecific antibodies of the disclosure that bind to and/or inhibit GDF11 and GDD8 further bind to and/or inhibit one or more of activin A, activin B, activin AB, activin C, activin E, BMP6, BMP7 and/or Nodal.

In certain embodiments, a multispecific antibody of the present disclosure comprises two or more binding specificities, with at least one of the binding specificities being for a GDF8 epitope, and optionally one or more additional binding specificities being for an epitope on a different ActRII ligand (e.g., GDF11, activin A, activin B, activin AB, activin C, activin E, BMP6, BMP7 and/or Nodal) and/or an ActRII receptor (e.g., an ActRIIA and/or ActRIIB receptor). In certain embodiments, multispecific antibodies may bind to two or more different epitopes of GDF8. Preferably a multispecific antibody of the disclosure that has binding affinity, in part, for an GDF8 epitope can be used to inhibit an GDF8 activity (e.g., the ability to bind to and/or activate an ActRIIA and/or ActRIIB receptor), and optionally inhibit the activity of one or more different ActRII ligands (e.g., GDF11, activin A, activin B, activin AB, activin C, activin E, BMP6, BMP7 and/or Nodal) and/or an ActRII receptor (e.g., an ActRIIA or ActRIIB receptor). In certain preferred embodiments, multispecific antibodies of the present disclosure that bind to and/or inhibit GDF8 further bind to and/or inhibit at least GDF11. Optionally, multispecific antibodies of the disclosure that bind to and/or inhibit GDF8 do not substantially bind to and/or substantially inhibit activin A. In some embodiments, multispecific antibodies of the disclosure that bind to and/or inhibit GDF8 and GDF11 further bind to and/or inhibit one or more of activin A, activin B, activin AB, activin C, activin E, BMP6, BMP7 and/or Nodal.

Engineered antibodies with three or more functional antigen binding sites, including "octopus antibodies," are also included herein (see, e.g., US 2006/0025576A1).

In certain embodiments, the antibodies disclosed herein (e.g., an anti-GDF11 antibody, an anti-activin B antibody, an anti-ActRIIA antibody, or an anti-ActRIIB antibody) are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11 or GDF8, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the GDF11 or GDF8 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 or GDF8 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11 or GDF8, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 or GDF8 polypeptide, and monoclonal antibodies isolated from a culture comprising such hybridoma cells.

In certain embodiments, one or more amino acid modifications may be introduced into the Fc region of an antibody provided herein (e.g., an anti-GDF11 antibody, an anti-activin B antibody, an anti-ActRIIA antibody, or an anti-ActRIIB antibody), thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure (e.g., an anti-GDF11 antibody, an anti-activin B antibody, an anti-ActRIIA antibody, or an anti-ActRIIB antibody) with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (GDF11, GDF8, ActRIIA, and/or ActRIIB binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

Any of the ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody) can be combined with one or more additional ActRII antagonist agents of the disclosure to achieve the desired effect. For example, an ActRII antagonist antibody disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody) can be used in combination with i) one or more additional ActRII antagonist antibodies disclosed herein, ii) one or more ActRII polypeptides disclosed herein (e.g., ActRIIA and/or ActRIIB polypeptides), iii) one or more GDF traps disclosed herein; iv) one or more small-molecule ActRII antagonist disclosed herein (e.g., a small molecule antagonist of one or more of GDF11, GDF8, activin A, activin B, activin AB, activin C, activin E, BMP6, BMP7, Nodal, ActRIIA, and/or ActRIIB); v) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

D. Small-Molecule Antagonists

In another aspect, the present disclosure relates to a small molecule, or combination of small molecules, that antagonizes ActRII activity (e.g., inhibition of ActRIIA and/or ActRIIB signaling transduction, such as SMAD 2/3 and/or SMAD 1/5/8 signaling). In particular, the disclosure provides methods of using a small-molecule antagonist, or combination of antibody antagonists, of ActRII, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In some embodiments, a preferred ActRII antagonist of the present disclosure is a small-molecule antagonist, or combination of small-molecule antagonists, that direct or indirect inhibits at least GDF11 activity. Optionally, such a small-molecule antagonist, or combination of small-molecule antagonists, may further inhibit, either directly or indirectly, GDF8. Optionally, a small-molecule antagonist, or combination of small-molecule antagonists, of the present disclosure does not substantially inhibit activin A activity. In some embodiments, a small-molecule antagonist, or combination of small-molecule antagonists, of the present disclosure that inhibits, either directly or indirectly, GDF11 and/or GDF8 activity further inhibits, either directly or indirectly, activity of one or more of activin A, activin B, activin AB, activin C, activin E, BMP6, BMP7, Nodal, ActRIIA, and ActRIIB In certain embodiments, a small-molecule antagonist, or combination of small-molecule antagonists, of the present disclosure is an indirect inhibitor of one or more of GDF11, GDF8, activin A, activin B, activin AB, activin C, activin E, BMP6, Nodal, ActRIIA, and ActRIIB For example, a small-molecule antagonist, or combination of small-molecule antagonists, of the present disclosure may inhibit the expression (e.g., transcription, translation, cellular secretion, or combinations thereof) of at least GDF11. Optionally, such a small-molecule antagonist, or combination of small-molecule antagonists, may further inhibit expression of GDF8. Optionally, a small-molecule antagonist, or combinations of small-molecule antagonists, of the disclosure does not substantially inhibit the expression of activin A. In some embodiments, a small-molecule antagonist, or combination of small-molecule antagonists, of the disclosure that inhibits expression of GDF11 and/or GDF8 may further inhibit the expression of one or more of activin A, activin B, activin AB, activin C, activin E, BMP6, BMP7, Nodal, ActRIIA, and ActRIIB In other embodiments, a small-molecule antagonist, or combination of small-molecule antagonists, of the present disclosure is direct inhibitor of one or more of GDF11, GDF8, activin A, activin B, activin AB, activin C, activin E, BMP6, BMP7, Nodal, ActRIIA, and ActRIIB For example, a preferred small-molecule antagonist, or combination of small-molecule antagonists, of the present disclosure directly binds to and inhibits at least GDF11 activity (e.g. inhibits the ability GDF11 to bind to an ActRIIA and/or ActRIIB receptor; inhibits GDF11-mediated activation of the ActRIIA and/or ActRIIB signaling transduction, such as SMAD 2/3 signaling). Optionally, a small-molecule antagonist, or combinations of small-molecule antagonists, of the disclosure may further bind to and inhibit GDF8 activity (e.g. inhibits the ability of GDF8 to bind to an ActRIIA and/or ActRIIB receptor; inhibits GDF8-mediated activation of the ActRIIA and/or ActRIIB signaling transduction, such as SMAD 2/3 signaling). Optionally, a small-molecule antagonist, or combinations of small-molecule antagonists, of the disclosure does not substantially bind to or inhibit activin A activity (e.g. the ability of activin A to bind to an ActRIIA and/or ActRIIB receptor; activin A-mediated activation of the ActRIIA and/or ActRIIB signaling transduction, such as SMAD 2/3 signaling pathway). In some embodiments, a small-molecule antagonist, or combinations of small-molecule antagonists, of the disclosure that binds to and inhibits the activity of GDF11 and/or GDF8 further binds to and inhibits the activity of one or more of activin A, activin B, activin AB, activin C, activin E, BMP6, BMP7, Nodal, ActRIIA, and ActRIIB In some embodiments, a small-molecule antagonist, or combination of small-molecule antagonists, of the present disclosure directly binds to and inhibits at least GDF8 activity (e.g. inhibits the ability GDF8 to bind to an ActRIIA and/or ActRIIB receptor; inhibits GDF8-mediated activation of the ActRIIA and/or ActRIIB signaling transduction, such as SMAD 2/3 signaling). Optionally, a small-molecule antagonist, or combinations of small-molecule antagonists, of the disclosure may further bind to and inhibit GDF11 activity (e.g. inhibit the ability of GDF11 to bind to an ActRIIA and/or ActRIIB receptor; inhibit GDF11-mediated activation of the ActRIIA and/or ActRIIB signaling transduction, such as SMAD 2/3 signaling). Optionally, a small-molecule antagonist, or combinations of small-molecule antagonists, of the disclosure does not substantially bind to or inhibit activin A activity (e.g. the ability of activin A to bind to an ActRIIA and/or ActRIIB receptor; activin A-mediated activation of the ActRIIA and/or ActRIIB signaling transduction, SMAD 2/3 signaling). In some embodiments, a small-molecule antagonist, or combinations of small-molecule antagonists, of the disclosure that binds to and inhibits the activity of GDF8 and/or GDF11 further binds to and inhibits the activity of one or more of activin A, activin B, activin AB, activin C, activin E, BMP6, BMP7, Nodal, ActRIIA, and ActRIIB In some embodiments, a small-molecule antagonist, or combination of small-molecule antagonists, of the present disclosure directly binds to and inhibits at least ActRIIA activity (e.g. ActRII ligand-mediated activation of ActRIIA signaling transduction, such as SMAD 2/3 signaling). For example, a preferred small-molecule antagonist, or combination of small-molecule antagonists, of the disclosure binds to an ActRIIA receptor and inhibits at least GDF11 from binding to and/or activating the ActRIIA receptor. Optionally, such a small-molecule antagonist, or combination of small-molecule antagonists, may further inhibit GDF8 from binding to and/or activating the ActRIIA receptor. Optionally, a small-molecule antagonist, or combination of small-molecule antagonists, of the disclosure does not substantially inhibit activin A from binding to and/or activating an ActRIIA receptor. In some embodiments, a small-molecule antagonist, or combination of small-molecule antagonists, of the disclosure that inhibits GDF11 and/or GDF8 from binding to and/or activating the ActRIIA receptor further inhibits one or more of activin A, activin B, activin AB, activin C, activin E, BMP6, BMP7, and Nodal from binding to/and or activating the ActRIIA receptor.

In some embodiments, a small-molecule antagonist, or combination of small-molecule antagonists, of the present disclosure directly binds to and inhibits at least ActRIIB activity (e.g. ActRII ligand-mediated activation of ActRIIB signaling transduction, such as SMAD 2/3 signaling). For example, a preferred small-molecule antagonist, or combination of small-molecule antagonists, of the disclosure binds to an ActRIIB receptor and inhibits at least GDF11 from binding to and/or activating the ActRIIB receptor. Optionally, such a small-molecule antagonist, or combination of small-molecule antagonists, may further inhibit GDF8 from binding to and/or activating the ActRIIB receptor. Optionally, a small-molecule antagonist, or combination of small-molecule antagonists, of the disclosure does not substantially inhibit activin A from binding to and/or activating an ActRIIB receptor. In some embodiments, a small-molecule antagonist, or combination of small-molecule antagonists, of the disclosure that inhibits GDF11 and/or GDF8 from binding to and/or activating the ActRIIB receptor further inhibits one or more of activin A, activin B, activin AB, activin C, activin E, BMP6, BMP7, and Nodal from binding to/and or activating the ActRIIB receptor.

Binding organic small molecule antagonists of the present disclosure may be identified and chemically synthesized using known methodology (see, e.g., PCT Publication Nos. WO 00/00823 and WO 00/39585). In general, small-molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., GDF11, GDF8, ActRIIA, and ActRIIB) Such small-molecule antagonists may be identified without undue experimentation using well-known techniques. In this regard, it is noted that techniques for screening organic small-molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

Any of the small-molecule ActRII antagonists disclosed herein (e.g., a small-molecule antagonist of one or more of GDF11, GDF8, activin A, activin B, activin AB, activin C, activin E, BMP6, BMP7, Nodal, ActRIIA, and/or ActRIIB) can be combined with one or more additional ActRII antagonist agents of the disclosure to achieve the desired effect (e.g., increase red blood cell levels and/or hemoglobin in a subject in need thereof, treat or prevent an anemia, treat MDS or sideroblastic anemias, treat or prevent one or more complications of MDS or sideroblastic anemias). For example, a small-molecule ActRII antagonist disclosed herein (e.g., a small-molecule antagonist of one or more of GDF11, GDF8, activin A, activin B, activin AB, activin C, activin E, BMP6, BMP7, Nodal, ActRIIA, and/or ActRIIB) can be used in combination with i) one or more additional small molecule ActRII antagonists disclosed herein, ii) one or more ActRII polypeptides disclosed herein (e.g., ActRIIA and/or ActRIIB polypeptides), iii) one or more GDF traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

E. Antagonist Polynucleotides

In another aspect, the present disclosure relates to a polynucleotide, or combination of polynucleotides, that antagonizes ActRII activity (e.g., inhibition of ActRIIA and/or ActRIIB signaling transduction, such as SMAD 2/3 and/or SMAD 1/5/8 signaling). In particular, the disclosure provides methods of using a polynucleotide ActRII antagonist, or combination of polynucleotide ActRII antagonists, alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof.

In some embodiments, a polynucleotide ActRII antagonist, or combination of polynucleotide ActRII antagonists, of the present disclosure can be used to inhibit the activity and/or expression on one or more of GDF11, GDF8, activin A, activin B, activin AB, activin C, activin C, activin E, BMP6, BMP7, Nodal, ActRIIA, and/or ActRIIB In certain preferred embodiments, a polynucleotide ActRII antagonist, or combination of polynucleotide ActRII antagonists, of the disclosure is a GDF-ActRII antagonist.

In some embodiments, a polynucleotide antagonist, or combination of polynucleotide antagonists, of the disclosure inhibits the activity and/or expression (e.g., transcription, translation, secretion, or combinations thereof) of at least GDF11. Optionally, such a polynucleotide antagonist, or combination of polynucleotide antagonists, may further inhibit the activity and/or expression of GDF8. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of GDF11 and/or GDF8 may further inhibit the activity and or expression of one or more of activin A, activin B, activin AB, activin C, activin E, BMP6, BMP7, Nodal, ActRIIA, and/or ActRIIB In some embodiments, a polynucleotide antagonist, or combination of polynucleotide antagonists, of the disclosure inhibits the activity and/or expression (e.g., transcription, translation, secretion, or combinations thereof) of at least GDF8. Optionally, such polynucleotide antagonist, or combination of polynucleotide antagonists, may further inhibit the activity and/or expression of GDF11. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of GDF8 and/or GDF11 may further inhibit the activity and or expression of one or more of activin A, activin B, activin AB, activin C, activin E, BMP6, BMP7, Nodal, ActRIIA, and/or ActRIIB In some embodiments, a polynucleotide antagonist, or combination of polynucleotide antagonists, of the disclosure inhibits the activity and/or expression (e.g., transcription, translation, secretion, or combinations thereof) of at least ActRIIA. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of ActRIIA may further inhibit the activity and or expression of one or more of activin A, activin B, activin AB, activin C, activin E, BMP6, BMP7, Nodal, and/or ActRIIB In some embodiments, a polynucleotide antagonist, or combination of polynucleotide antagonists, of the disclosure inhibits the activity and/or expression (e.g., transcription, translation, secretion, or combinations thereof) of at least ActRIIB Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of ActRIIB may further inhibit the activity and or expression of one or more of activin A, activin B, activin AB, activin C, activin E, BMP6, BMP7, Nodal, and/or ActRIIA.

The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human GDF11, GDF8, activin A, activin B, activin C, activin E, BMP6, BMP7, Nodal, ActRIIA, and ActRIIB are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991) Science 251:1300. The methods are based on binding of a polynucleotide to a complementary DNA or RNA. In some embodiments, the antisense nucleic acids comprise a single-stranded RNA or DNA sequence that is complementary to at least a portion of an RNA transcript of a gene disclosed herein (e.g., GDF11, GDF8, activin A, activin B, activin C, activin C, activin E, BMP6, BMP7, Nodal, ActRIIA, and ActRIIB) However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein (e.g., GDF11, GDF8, activin A, activin B, activin C, activin E, BMP6, BMP7, Nodal, ActRIIA, and ActRIIB), a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure (e.g., GDF11, GDF8, activin A, activin B, activin C, activin E, BMP6, BMP7, Nodal, ActRIIA, and ActRIIB), could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure (e.g., an GDF11, GDF8, activin A, activin B, activin C, activin E, BMP6, BMP7, Nodal, ActRIIA, and ActRIIB mRNA), antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure (e.g., a GDF11, GDF8, activin A, activin B, activin C, activin E, BMP6, BMP7, Nodal, ActRIIA, or ActRIIB antisense nucleic acid) is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more of: GDF11, GDF8, activin A, activin B, activin C, activin E, BMP6, BMP7, Nodal, ActRIIA, and ActRIIB RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA)

molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a GDF11, GDF8, activin A, activin B, activin C, activin E, BMP6, BMP7, Nodal, ActRIIA, and ActRIIB polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

Any of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB) can be combined with one or more additional ActRII antagonist agents of the disclosure to achieve the desired effect (e.g., increase red blood cell levels and/or hemoglobin in a subject in need thereof, treat or prevent an anemia, treat MDS or sideroblastic anemias, treat or prevent one or more complications of MDS or sideroblastic anemias). For example, an polynucleotide ActRII antagonist disclosed herein (e.g., a polynucleotide antagonist of one or more of GDF11, GDF8, activin A, activin B, activin AB, activin C, activin E, BMP6, BMP7, Nodal, ActRIIA, and/or ActRIIB) can be used in combination with i) one or more additional polynucleotide ActRII antagonists disclosed herein, ii) one or more ActRII polypeptides disclosed herein (e.g., ActRIIA and/or ActRIIB polypeptides), iii) one or more GDF traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

F. Other Antagonists

In other aspects, an agent for use in accordance with the methods disclosed herein is a follistatin polypeptide, which may be used alone or in combination with one or more erythropoiesis stimulating agents (e.g., EPO) or other supportive therapies [e.g., hematopoietic growth factors (e.g., G-CSF or GM-CSF), transfusion of red blood cells or whole blood, iron chelation therapy], to, e.g., increase red blood cell levels in a subject in need thereof, treat or prevent an anemia in a subject in need thereof (including, e.g., reduction of transfusion burden), treat MDS or sideroblastic anemias in a subject in need thereof, and/or treat or prevent one or more complications of MDS or sideroblastic anemias (e.g., anemia, blood transfusion requirement, neutropenia, iron overload, acute myocardial infarction, hepatic failure, hepatomegaly, splenomegaly, progression to acute myeloid lymphoma) and or treat or prevent a disorder associated with SF3B1, DNMT3A, and/or TET2 mutations in a subject in need thereof. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin activity, particularly activin A (e.g., activin-mediated activation of ActRIIA and/or ActRIIB SMAD 2/3 signaling). Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 18-20, the follistatin N-terminal domain ("FSND" SEQ ID NO:18), FSD2 (SEQ ID NO: 20), and to a lesser extent FSD1 (SEQ ID NO: 19) represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide (SEQ ID NO: 16) as described, for example, in WO2005/025601.

The human follistatin precursor polypeptide isoform FST344 is as follows:

```
              (SEQ ID NO: 16; NCBI Reference No. NP_037541.1)
  1 mvrarhqpgg lcllllllcq fmedrsaqag ncwlrqakng rcqvlyktel 51 skeeccstgr lstswteedv ndntlfkwmi fnggapncip cketcenvdc 101 gpgkkcrmnk knkprcvcap dcsnitwkgp vcgldgktyr necallkarc 151 keqpelevqy qgrckktcrd vfcpgsstcv vdqtnnaycv tcnricpepa 201 sseqylcgnd gvtyssachl rkatcllgrs iglayegkci kakscediqc 251 tggkkclwdf kvgrgrcslc delcpdsksd epvcasdnat yasecamkea 301 acssgvllev khsgscnsis edteeeeede dqdysfpiss ilew
```

The signal peptide is underlined; also underlined above are the last 27 residues which represent the C-terminal extension distinguishing this follistatin isoform from the shorter follistatin isoform FST317 shown below.

The human follistatin precursor polypeptide isoform FST317 is as follows:

```
              (SEQ ID NO: 17; NCBI Reference No. NP_006341.1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCN
```

The signal peptide is underlined.

The follistatin N-terminal domain (FSND) sequence is as follows:

```
                                            (SEQ ID NO: 18; FSND)
GNCWLRQAKNGRCQVLYKTELSKEECCSTGRLSTSWTEEDVNDNTLFKWM

IFNGGAPNCIPCK
```

The FSD1 and FSD2 sequences are as follows:

```
                                            (SEQ ID NO: 19; FSD1)
            ETCENVDCGPGKKCRMNKKNKPRCV (SEQ ID NO: 20; FSD2)
           KTCRDVFCPGSSTCVVDQTNNAYCVT
```

In other aspects, an agent for use in accordance with the methods disclosed herein is a follistatin-like related gene (FLRG), also known as follistatin-related protein 3 (FSTL3). The term "FLRG polypeptide" includes polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activin activity, particularly activin A (e.g., activin-mediated activation of ActRIIA and/or ActRIIB SMAD 2/3 signaling). Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor (follistatin-related protein 3 precursor) polypeptide is as follows:

```
              (SEQ ID NO: 21; NCBI Reference No. NP_005851.1)
  1 MRPGAPGPLWPLPWGALAWAVGFVSSMGSG NPAPGGVCWL QQGQEATCSL

51 VLQTDVTRAE CCASGNIDTA WSNLTHPGNK INLLGFLGLV HCLPCKDSCD

101 GVECGPGKAC RMLGGRPRCE CAPDCSGLPA RLQVCGSDGA TYRDECELRA

151 ARCRGHPDLS VMYRGRCRKS CEHVVCPRPQ SCVVDQTGSA HCVVCRAAPC

201 PVPSSPGQEL CGNNNVTYIS SCHMRQATCF LGRSIGVRHA GSCAGTPEEP

251 PGGESAEEEE NFV
```

The signal peptide is underlined.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

Any of the follistatin polypeptides disclosed herein may be combined with one or more additional ActRII antagonist agents of the disclosure to achieve the desired effect (e.g., increase red blood cell levels and/or hemoglobin in a subject in need thereof, treat or prevent an anemia, treat MDS or sideroblastic anemias, treat or prevent one or more complications of MDS or sideroblastic anemias). For example, a follistatin polypeptide disclosed herein can be used in combination with i) one or more additional follistatin polypeptides disclosed herein, ii) one or more ActRII polypeptides disclosed herein (e.g., ActRIIA and/or ActRIIB polypeptides), iii) one or more GDF traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); and/or one or more FLRG polypeptides disclosed herein.

Similarly, any of the FLRG polypeptides disclosed herein may be combined with one or more additional ActRII antagonist agents of the disclosure to achieve the desired effect. For example, a FLRG polypeptide disclosed herein can be used in combination with i) one or more additional FLRG polypeptides disclosed herein, ii) one or more ActRII polypeptides disclosed herein (e.g., ActRIIA and/or ActRIIB polypeptides), iii) one or more GDF traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); and/or one or more follistatin polypeptides disclosed herein.

3. Screening Assays

In certain aspects, the present disclosure relates to the use of the subject ActRII polypeptides (e.g., ActRIIA and ActRIIB polypeptides) and GDF trap polypeptides to identify compounds (agents) which are agonist or antagonists of ActRIIB polypeptides. Compounds identified through this screening can be tested to assess their ability to modulate red blood cell, hemoglobin, and/or reticulocyte levels in vivo or in vitro. These compounds can be tested, for example, in animal models.

There are numerous approaches to screening for therapeutic agents for increasing red blood cell or hemoglobin levels by targeting ActRII signaling (e.g., ActRIIA and/or ActRIIB SMAD 2/3 and/or SMAD 1/5/8 signaling). In certain embodiments, high-throughput screening of compounds can be carried out to identify agents that perturb ActRII-mediated effects on a selected cell line. In certain embodiments, the assay is carried out to screen and identify compounds that specifically inhibit or reduce binding of an ActRII polypeptide or GDF trap polypeptide to its binding partner, such as an ActRII ligand (e.g., activin A, activin B, activin AB, activin C, Nodal, GDF8, GDF11 or BMP7). Alternatively, the assay can be used to identify compounds that enhance binding of an ActRII polypeptide or GDF trap polypeptide to its binding partner such as an ActRII ligand. In a further embodiment, the compounds can be identified by their ability to interact with an ActRII polypeptide or GDF trap polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRII polypeptide or a GDF trap polypeptide and its binding partner (e.g., an ActRII ligand).

Merely to illustrate, in an exemplary screening assay of the present disclosure, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand (e.g., GDF11). Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose-response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between an ActRII polypeptide or GDF trap polypeptide and its binding protein may be detected by a variety of techniques. For instance, modulation of the formation of complexes can be quantitated using, for example, detectably labeled proteins such as radiolabeled (e.g. $^{32}P$, $^{35}S$, $^{14}C$ or $^{3}H$), fluorescently labeled (e.g., FITC), or enzymatically labeled ActRII polypeptide or GDF trap polypeptide and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ActRII polypeptide of GDF trap polypeptide and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between an ActRII polypeptide or GDF trap polypeptide and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between an ActRII polypeptide or GDF trap and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with an ActRII polypeptide or GDF trap polypeptide. The interaction between the compound and the ActRII polypeptide or GDF trap polypeptide may be covalent or non-covalent. For example, such interaction can be identified at the protein level using in vitro biochemical methods, including photo-crosslinking, radiolabeled ligand binding, and affinity chromatography [see, e.g., Jakoby W B et al. (1974) Methods in Enzymology 46:1]. In certain cases, the compounds may be screened in a mechanism-based assay, such as an assay to detect compounds which bind to an ActRII polypeptide of GDF trap polypeptide. This may include a solid-phase or fluid-phase binding event. Alternatively, the gene encoding an ActRII polypeptide or GDF trap polypeptide can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

4. Exemplary Therapeutic Uses

In certain aspects, the disclosure provides methods of treating MDS and sideroblastic anemias, particularly treating or preventing one or more subtypes or complications of MDS, with one or more ActRII antagonists, including the treatment of patients with MDS characterized by the presence of ring sideroblasts and/or one or more mutations in the SF3B1, DNMT3A, and/or TET2 genes. In particular, the disclosure provides methods for using an ActRII antagonist, or combination of ActRII antagonists, to treat or prevent one or more complications of MDS and sideroblastic anemias including, for example, anemia, neutropenia, splenomegaly, blood transfusion requirement, development of acute myeloid leukemia, iron overload, and complications of iron overload, among which are congestive heart failure, cardiac arrhythmia, myocardial infarction, other forms of cardiac disease, diabetes mellitus, dyspnea, hepatic disease, and adverse effects of iron chelation therapy.

In particular, the disclosure provides methods for using an ActRII antagonist, or combination of ActRII antagonists, to treat or prevent anemia or other complications in a subtype of MDS, including MDS patients with elevated numbers of erythroblasts (hypercellularity) in bone marrow; in MDS patients with more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% sideroblasts in bone marrow; in MDS patients with refractory anemia with ring sideroblasts (RARS); in MDS patients with refractory anemia with ring sideroblasts and thrombocytosis (RARS-T); in MDS patients with refractory cytopenia with unilineage dysplasia (RCUD); in MDS patients with refractory cytopenia with multilineage dysplasia and ring sideroblasts (RCMD-RS); in MDS patients with a somatic mutation in SF3B1, SRSF2, DNMT3A, or TET2; in MDS patients without a somatic mutation in ASXL1 or ZRSR2; in MDS patients with iron overload; and in MDS patients with neutropenia.

Also in particular, the disclosure provides methods for using an ActRII antagonist, or combination of ActRII antagonists, to treat or prevent anemia or other complications of a sideroblastic anemia, including but not limited to refractory anemia with ring sideroblasts (RARS); refractory anemia with ring sideroblasts and thrombocytosis (RARS-T); refractory cytopenia with multilineage dysplasia and ring sideroblasts (RCMD-RS); sideroblastic anemia associated with alcoholism; drug-induced sideroblastic anemia; sideroblastic anemia resulting from copper deficiency (zinc toxicity); sideroblastic anemia resulting from hypothermia; X-linked sideroblastic anemia (XLSA); SLC25A38 deficiency; glutaredoxin 5 deficiency; erythropoietic protoporphyria; X-linked sideroblastic anemia with ataxia (XLSA/A); sideroblastic anemia with B-cell immunodeficiency, fevers, and developmental delay (SIFD); Pearson marrow-pancreas syndrome; myopathy, lactic acidosis, and sideroblastic anemia (MLASA); thiamine-responsive megaloblastic anemia (TRIVIA); and syndromic/nonsyndromic sideroblastic anemia of unknown cause.

In certain aspects the disclosure provides methods for treating or preventing disorders or complications of a disorder that is associated with germ line or somatic mutations in SF3B1, DNMT3A, and/or TET2, such as myelodysplastic syndrome, chronic lymphocytic leukemia (CLL), and acute myeloid leukemia (AML) as well as in breast cancer, pancreatic cancer, gastric cancer, prostate cancer, and uveal melanoma. In certain aspects the disorder may be in a subject that has bone marrow cells that test positive for an SF3B1, DNMT3A, and/or TET2 mutation, particularly myelodysplastic syndrome, CLL and AML. Optionally a mutation in the SF3B1 gene is in an exon, intron or 5' or 3' untranslated region. Optionally a mutation in SF3B1, DNMT3A, and/or TET2 causes a change in the amino acid sequence or does not cause a change in the amino acid sequence of the protein encoded by the gene. Optionally a mutation in the SF3B1 gene causes a change in the amino acid of the protein encoded by the gene selected from the following changes: K182E, E491G, R590K, E592K, R625C, R625G, N626D, N626S, H662Y, T663A, K666M, K666Q, K666R, Q670E, G676D, V701I, I704N, I704V, G740R, A744P, D781G, A1188V, N619K, N626H, N626Y, R630S, I704T, G740E, K741N, G742D, D894G, Q903R, R1041H, I1241T, G347V, E622D, Y623C, R625H, R625L, H662D, H662Q, T663I, K666E, K666N, K666T, K700E, and V701F. Optionally a mutation in the DNMT3A gene causes a change in the amino acid of the protein encoded by the gene selected from the following changes: R882C, R882H, P904L, and P905P. Optionally a mutation in the DNMT3A gene introduces a premature stop codon. For example, in some embodiments, a mutation in the DNMT3A gene that introduces a premature stop codon is selected from the following positions: Y436X and W893X. Optionally a mutation in the TET2 gene causes a change in the amino acid of the protein encoded by the gene selected from the following changes: E47Q, Q1274R, W1291R, G1370R, N1387S, and Y1724H. Optionally a mutation in the TET2 gene introduces a premature stop codon. For example, in some embodiments, a mutation in the TET2 gene that introduces a premature stop codon is selected from the following positions: R550X, Q1009X, Y1337X, R1404X, R1516X, and Q1652X.

The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering one or more of the ActRII antagonists (e.g., an ActRIIA and/or ActRIIB antagonist) of the present disclosure in an effective amount. An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

Myelodysplastic syndromes (MDS) are a diverse collection of hematological disorders characterized by ineffective production of myeloid blood cells and risk of transformation to acute myeloid leukemia. In MDS patients, hematopoietic stem cells do not mature into healthy red blood cells, white blood cells, or platelets. MDS disorders include, for example, refractory anemia, refractory cytopenia with unilineage dysplasia (RCUD), refractory anemia with ringed sideroblasts (RARS), refractory anemia with ringed sideroblasts associated with marked thrombocytosis (RARS-T), refractory anemia with excess blasts (RAEB-1), refractory anemia with excess blasts in transformation (RAEB-2), refractory cytopenia with multilineage dysplasia (RCMD), MDS unclassified (MDS-U), and myelodysplastic syndrome associated with an isolated 5q chromosome abnormality [MDS with del(5q)].

Allogenic stem-cell transplantation is the only known potentially curative therapy for MDS. However, only a minority of patients undergo this procedure due to advanced age, medical comorbidities, and limited availability of appropriate stem cell donors. Even for those patients who proceed to allogenic stem-cell transplantation, significant treatment-related mortality and morbidity, including acute and chronic graft-versus-host-disease, and high relapse rates compromise long-term disease-free survival [Zeidan et al. (2013) Blood Rev 27:243-259]. For these reasons, the majority of patients with MDS are still managed on a non-curative intent therapeutic paradigm. Treatment is based on prognostic factors that predict survival or progression to acute myeloid leukemia. Survival of lower-risk MDS patients ranges from several months to more than a decade, and most of these patients die from causes directly related to complications of MDS [Dayyani et al. (2010) Cancer 116: 2174-2179]. Therefore, therapeutic strategies for lower-risk patients are adapted to the specific patient's situation, including severity and type of cytopenias and expected survival. Lower-risk patients have multiple therapeutic options, including treatment with growth factors, lenalidomide in the case of del(5q) syndrome, thalidomide, pomalidomide, hypomethylating agents such as azacitidine or decitibine, and potentially investigational agents. In contrast, higher-risk MDS patients who are not eligible for allogenic stem-cell transplantation are typically treated with hypomethylating agents, intensive chemotherapy, or investigational agents [Garcia-Manero et al. (2011) 29:516-523].

Since MDS manifest as irreversible defects in both quantity and quality of hematopoietic cells, most MDS patients are afflicted with chronic anemia. Approximately 80% to 90% of MDS patients develop anemia during the course of their disease, of whom at least 40% become RBC transfusion-dependent [Santini (2011) Oncologist 16:35-42; Malcovati et al. (2005) J Clin Oncol 23:7594-7603; Leitch (2011) Blood Rev 25:17-31]. Patients in higher-risk MDS groups (according to IPSS classification) are even more likely to become transfusion-dependent; for example, in one study 79% of high-risk category patients versus 39% of low-risk patients required chronic transfusions to treat or prevent severe anemia [Öscan et al. (2013) Expert Rev Hematol 6:165-189]. Low hemoglobin levels result in poor oxygenation of the brain and peripheral organs; as a result, MDS patients typically suffer from lethargy, decreased mental alertness, physical weakness, and poor concentration. These symptoms are linked to a reduced health-related quality of life. In addition, hemoglobin thresholds are independently associated with significant morbidity and mortality in MDS. In female and male patients with hemoglobin levels lower than 8 g/dL and 9 g/dL, respectively, the risk of morbidity and mortality increases, mainly due to an increased risk of cardiac complications [Malcovati et al. (2011) Haematologica 96:1433-1440]. Low hemoglobin levels and dependence on red blood cell transfusions have been associated with inferior cardiovascular outcomes and increased mortality in patients with MDS, representing a strong rationale for aggressive management of anemia in MDS [Goldberg et al. (2010) J Clin Oncol 28:2847-2852; Leitch (2011) Blood Rev 25:17-31; Oliva et al. (2011) Am J Blood Res 1:160-166; Özcan et al. (2013) Expert Rev Hematol 6:165-189].

MDS patients eventually require blood transfusions and/or treatment with erythropoietic growth factors (e.g., ESAs such as EPO) alone or in combination with a colony-stimulating factor [e.g., an analog of granulocyte colony-stimulating factor (G-CSF) such as filgrastim or an analog of granulocyte macrophage colony-stimulating factor (GM-GSF) such as sargramostim] to increase red blood cell levels. The frequency of transfusions depends on the extent of the disease and on the presence of comorbidities. Chronic transfusions are known to increase hemoglobin levels, which in turn improve brain and peripheral tissue oxygenation, thereby improving physical activity and mental alertness. However, many MDS patients develop side-effects from the use of such therapies. For example, patients who receive frequent red blood cell transfusions can develop tissue and organ damage from iron accumulation and generation of toxic reactive oxygen species. Accordingly, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator, may be used to treat patients with MDS or sideroblastic anemias. In certain embodiments, patients suffering from MDS or a siderblastic anemia may be treated using one or more ActRII antagonist agents of the disclosure (e.g., a GDF-ActRII antagonist, an ActRIIA polypeptide, an ActRIIB polypeptide, a GDF trap, etc.), optionally in combination with an EPO receptor activator. In other embodiments, patients suffering from MDS or a sideroblastic anemia may be treated using a combination of one or more ActRII antagonist agents of the disclosure (e.g., a GDF-ActRII antagonist, an ActRIIA polypeptide, an ActRIIB polypeptide, a GDF Trap, etc.) and one or more additional therapeutic agents for treating MDS including, for example, ESAs including, e.g., epoetin alfa, epoetin beta (e.g., NeoRecormon), epoetin delta (e.g., Dynepo), epoetin omega, darbepoetin alfa (e.g., Aranesp), methoxy-polyethylene-glycol epoetin beta (e.g., Micera), and synthetic erythropoiesis protein (SEP); G-CSF analogs, including filgrastim; GM-CSF analogs, including sargramostim; lenalidomide; thalidomide; pomalidomide, hypomethylating agents, including azacitidine and decitabine; iron-chelating agents, including deferoxamine (a.k.a., desferrioxamine B, desferoxamine B, DFO-B, DFOA, DFB, or desferal), deferiprone (a.k.a., Ferriprox), and deferasirox (a.k.a., bis-hydroxyphenyl-triazole, ICL670, or Exjade™).; thrombopoietin mimetics, including romiplostim and eltrombopag; chemotherapeutic agents, including cytarabine (ara-C) alone or in combination with idarubicin, topotecan, or fludarabine; immunosuppressants, including antithymocyte globulin, alemtuzumab, and cyclosporine; histone deacetylase inhibitors (HDAC inhibitors), including vorinostat, valproic acid, phenylbutyrate, entinostat, MGCD0103, and other class I nuclear HDAC inhibitors, class II non-nuclear HDAC inhibitors, pan HDAC inhibitors, and isoform-specific HDAC inhibitors; farnesyltransferase inhibitors, including as tipifarnib and lonafarnib; tumor necrosis factor-alpha (TNF-α) inhibitors, including etanercept or infliximab; inhibitors of glutathione-S-transferase (GST) P1-1, including ezatiostat; and inhitors of CD33, including gemtuzumab ozogamicin.

One or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to increase red blood cell levels, hemoglobin levels, and/or hematocrit levels in a patient with anemia (MDS or sideroblastic anemia). When monitoring hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in healthy adults, although, in terms of therapy, a lower target level may cause fewer cardiovascular side effects. See, e.g., Jacobs et al. (2000) Nephrol Dial Transplant 15, 15-19. Alternatively, hematocrit levels (percentage of the volume of a blood sample occupied by the cells) can be used as a measure of anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit or allow the reduction or elimination of red blood cell transfusions while maintaining an acceptable level of red blood cells, hemoglobin and/or hematocrit. As hemoglobin and hematocrit levels vary from person to person, optimally, the target hemoglobin and/or hematocrit level can be individualized for each patient.

Neutropenia denotes a condition of abnormally low levels of circulating granulocytes and is found in approximately 40% of MDS patients [Steensma et al. (2006) Mayo Clin Proc 81:104-130]. Common complaints of patients with neutropenia include fatigue and frequent bacterial infections, especially of the skin. However, neutropenia can also result in serious complications in patients with MDS, and infection is the most common cause of MDS-associated death. Treatment with granulocyte colony-stimulating factor (filgrastim) can help keep neutrophil counts above $1 \times 10^9$/L for severely neutropenic patients [Akhtari (2011) Oncology (Williston Park) 25:480-486], but myeloid growth factors do not clearly modify disease history and may only increase production of functionally defective neutrophils lacking bactericidal capacity [Dayyani et al. (2010) Cancer 116: 2174-2179; Steensma (2011) Semin Oncol 38:635-647]. Prophylactic antibiotics have no proven role in patients with MDS and are not recommended for patients with neutropenia related to MDS. However, neutropenic fever in MDS patients should be regarded as a medical emergency, requiring immediate administration of empiric broad-spectrum antibiotics and often hospitalization [Barzi et al. (2010) Cleve Clin J Med 77:37-44]. In some embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies such as a G-CSF or GM-CSF therapy, may be used to treat neutropenia in MDS patients. One or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to reduce the frequency of granulocyte transfusions in MDS patients.

Patients with MDS or sideroblastic anemia who receive frequent transfusions of red blood cells or whole blood are prone to develop transfusional iron overload, which may partly explain why transfusion dependency in MDS is associated with reduced likelihood of survival. Nevertheless, the use of iron chelation therapy in transfusion-dependent MDS patients remains controversial, because retrospective and registry data suggest chelated patients may live longer than unchelated patients, yet there are no prospective randomized trial data demonstrating a morbidity or mortality benefit from chelation, and currently approved agents are inconvenient (deferroxamine) or costly and poorly tolerated by many patients (deferasirox) [Steensma et al. (2013) Best Pract Res Clin Haematol 26:431-444; Lyons et al. (2014) Leuk Res 38:149-154].

In some embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to prevent or reverse complications of iron overload in patients with MDS or sideroblastic anemia. In certain aspects, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to prevent or reverse a cardiac complication of iron overload including, e.g., increased cardiac output, cardiomegaly, cardiomyopathy, left ventricular hypertrophy, acute myocardial infarction, arrhythmia, and congestive heart failure. In certain aspects, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to reduce liver iron content and/or prevent or reverse a hepatic complication of iron overload including, e.g., liver enlargement (hepatomegaly), liver fibrosis (increase in scar tissue), and cirrhosis (extensive scarring). In certain aspects, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to prevent or reverse an endocrine complication of iron overload including, e.g., diabetes mellitus.

In certain aspects, ActRII antagonist agents of the disclosure may be administered to a subject in need thereof in combination with one or more additional agents [for example, ESAs; G-CSF analogs, including filgrastim; GM-CSF analogs, including sargramostim; lenalidomide; thalidomide; pomalidomide, hypomethylating agents, including azacitidine and decitabine; iron-chelating agents, including deferoxamine and deferasirox; thrombopoietin mimetics, including romiplostim and eltrombopag; chemotherapeutic agents, including cytarabine (ara-C) alone or in combination with idarubicin, topotecan, or fludarabine; immunosuppressants, including antithymocyte globulin, alemtuzumab, and cyclosporine; histone deacetylase inhibitors (HDAC inhibitors), including vorinostat, valproic acid, phenylbutyrate, entinostat, MGCD0103, and other class I nuclear HDAC inhibitors, class II non-nuclear HDAC inhibitors, pan HDAC inhibitors, and isoform-specific HDAC inhibitors; farnesyltransferase inhibitors, including as tipifarnib and lonafarnib; tumor necrosis factor-alpha (TNF-α) inhibitors, including etanercept or infliximab; inhibitors of glutathione-S-transferase (GST) P1-1, including ezatiostat; and inhitors of CD33, including gemtuzumab ozogamicin.] or supportive therapies [e.g., red blood cell transfusion, granulocyte transfusion, thrombocyte (platelet)

transfusion] for treating MDS and sideroblastic anemia or one or more complications of MDS and sideroblastic anemia.

As used herein, "in combination with" or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more GDF11 and/or activin B antagonist agents (optionally further antagonists of one or more of GDF8, activin A, activin C, activin E, and BMP6) of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more ActRII antagonist agents of the disclosure (e.g., a GDF-ActRII antagonist, an ActRIIA polypeptide, an ActRIIB polypeptide, a GDF trap, antibody etc.), optionally combined with an EPO receptor activator and/or one or more additional therapies, may be used in combination with transfusion of either red blood cells or whole blood to treat anemia in patients with MDS or sideroblastic anemias. In patients who receive frequent transfusions of whole blood or red blood cells, normal mechanisms of iron homeostasis can be overwhelmed, eventually leading to toxic and potentially fatal accumulation of iron in vital tissues such as heart, liver, and endocrine glands. Regular red blood cell transfusions require exposure to various donor units of blood and hence a higher risk of alloimmunization. Difficulties with vascular access, availability of and compliance with iron chelation, and high cost are some of the reasons why it can be beneficial to limit the number of red blood cell transfusions. In some embodiments, the methods of the present disclosure relate to treating MDS or sideroblastic anemia in a subject in need thereof by administering a combination of an ActRII antagonist of the disclosure and one or more blood cell transfusions. In some embodiments, the methods of the present disclosure relate to treating or preventing one or more complications of MDS or sideroblastic anemia in a subject in need thereof by administering a combination of an ActRII antagonist of the disclosure and one or more red blood cell transfusions. In some embodiments, treatment with one or more ActRII antagonists of the disclosure is effective at decreasing the transfusion requirement in a patient with MDS or sideroblastic anemia, e.g., reduces the frequency and/or amount of blood transfusion required to effectively treat MDS or sideroblastic anemia or one or more their complications.

In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with one or more iron-chelating molecules to promote iron excretion in the urine and/or stool and thereby prevent or reverse tissue iron overload in patients with MDS or sideroblastic anemias. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; and Galanello et al. (2010) Ann NY Acad Sci 1202:79-86].

One or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used to increase red blood cell levels, hemoglobin levels, and/or hematocrit levels in a patient with MDS or sideroblastic anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in healthy adults, although, in terms of therapy, a lower target level may cause fewer cardiovascular side effects. See, e.g., Jacobs et al. (2000) Nephrol Dial Transplant 15, 15-19. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

One or more ActRII antagonist agents of the disclosure (e.g., a GDF-ActRII antagonist, an ActRIIA polypeptide, an ActRIIB polypeptide, a GDF trap, etc.) may be used in combination with EPO receptor activators and/or one or more additional therapies to treat anemia. The suboptimal erythropoietin response in some patients with MDS is considered one biologic rationale for treating MDS-related anemia with ESAs [Greenberg et al. (2011) J Natl Compr Canc Netw 9:30-56; Santini (2012) Semin Hematol 49:295-303]. Despite not being approved by the FDA for use in MDS-associated anemia, ESAs are in wide clinical use and are the most commonly used therapy for MDS [Casadevall et al. (2004) Blood 104:321-327; Greenberg et al. (2009) Blood 114:2393-2400]. An analysis of linked SEER-Medicare data between 2001 and 2005 found that 62% of Medicare beneficiaries with MDS received ESAs [Davidoff et al. (2013) Leuk Res 37:675-680]. Greenberg et al. (2009) Blood 114:2393-2400]. Some preclinical and clinical studies suggested that granulocyte colony-stimulating factor (G-CSF) can have synergistic effects with ESAs, and small doses of G-CSF can be tried to improve erythroid responses in some patients, especially those with RARS, either initially or in case of lack of response to sole ESA therapy [Negrin et al. (1996) Blood 87:4076-4081]. Additionally, patients with low-risk MDS and lower levels of serum EPO (<200-500 mU/mL) and those who have lower RBC transfusion requirements (<2 units/month) have higher probabilities of achieving erythroid responses with ESAs [Hellstrom-Lindberg et al. (2003) Br J Haemotol 120:1037-1046; Park et al. (2008) 111:574-582]. Therefore, one or more ActRII antagonist agents of the disclosure (e.g., a GDF-ActRII antagonist, an ActRIIA polypeptide, an ActRIIB polypeptide, a GDF trap, etc.) may be used in combination with granulocyte colony-stimulating factor (e.g., filgrastim) or granulocyte macrophage colony-stimulating factor (e.g., sargramostim) to treat anemia.

In certain embodiments, the present disclosure provides methods of treating or preventing anemia in an individual in need thereof by administering to the individual a therapeutically effective amount of one or more ActRII antagonist agents of the disclosure (e.g., a GDF-ActRII antagonist, an ActRIIA polypeptide, an ActRIIB polypeptide, a GDF trap, etc.) and a EPO receptor activator. In certain embodiments, one or more ActRII antagonist agents of the disclosure (e.g., a GDF-ActRII antagonist, an ActRIIA polypeptide, an ActRIIB polypeptide, a GDF trap, etc.) may be used in combination with EPO receptor activators to reduce the required dose of these activators in patients that are susceptible to adverse effects of ESAs. These methods may be used for therapeutic and prophylactic treatments of a patient.

One or more ActRII antagonist agents of the disclosure (e.g., a GDF-ActRII antagonist, an ActRIIA polypeptide, an ActRIIB polypeptide, a GDF trap, etc.) may be used in combination with EPO receptor activators to achieve an increase in red blood cells, particularly at lower dose ranges. This may be beneficial in reducing the known off-target effects and risks associated with high doses of EPO receptor activators. The primary adverse effects of ESAs include, for example, an excessive increase in the hematocrit or hemoglobin levels and polycythemia. Elevated hematocrit levels can lead to hypertension (more particularly aggravation of hypertension) and vascular thrombosis. Other adverse effects of ESAs which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that antagonists of the present disclosure act by a different mechanism that ESAs, these antagonists may be useful for increasing red blood cell and hemoglobin levels in patients that do not respond well to ESAs or other EPO receptor activators. For example, an ActRII antagonist of the present disclosure may be beneficial for a patient in which administration of a normal to increased (>300 IU/kg/week) dose of ESA does not result in the increase of hemoglobin level up to the target level. Patients with an inadequate response to ESAs are found in all types of anemia, but higher numbers of non-responders have been observed particularly frequently in patients with cancers and patients with end-stage renal disease. An inadequate response to ESAs can be either constitutive (observed upon the first treatment with ESA) or acquired (observed upon repeated treatment with ESA).

Lenalidomide is a thalidomide derivative approved for patients with lower-risk MDS with del5q and transfusion-dependent anemia. Pomalidomide is another thalidomide derivative. Approval of lenalidomide in the U.S. was based on results of a phase 2 trial in which transfusion independence was achieved in about two thirds of patients studied, and the mean duration of transfusion independence was 2.2 years [List et al. (2006) N Engl J Med 355:1456-1465]. Subsequently approved also in Europe [Giagounidis et al. (2014) Eur J Haematol 93:429-438], lenalidomide is considered the first-line treatment for patients with lower-risk MDS with del5q and anemia. In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with lenalidomide for treating patients with MDS.

Aberrant DNA methylation is a poor prognostic feature in MDS [Shen e al. (2010) J Clin Oncol 28:605-613]. Azacitidine and decitabine are two agents with DNA hypomethylating activity currently used to treat patients mainly with high-risk MDS [Kantarjian et al. (2007) Cancer 109:1133-1137; Fenaux et al. (2009) Lancet Oncol 10:223-232]. Since the mechanism underlying their therapeutic effects is uncertain, these agents are sometimes classified according to their chemical structure (azanucleosides) or known activity in vitro (DNA methyltransferase inhibitors). Although there is less experience with azacitidine and decitabine therapeutically in lower-risk MDS, studies indicate that azacytidine and decitabine can produce an erythroid response in 30% to 40% of ESA-resistant patients with lower-risk MDS [Lyons et al. (2009) J Clin Oncol 27:1850-1856]. Platelet responses are also observed in thrombocytopenic patients. On the basis of these results, azacitidine and decitabine are approved in the United States for the treatment of lower-risk MDS with symptomatic cytopenias. In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with azacitidine, decitabine, or another DNA methyltransferase inhibitor for treating patients with MDS.

Thrombocytopenia occurs in approximately 35% to 45% of MDS patients, who may complain of easy bruising or frequent minor mucocutaneous bleeding and may display purpura or petechiae [Steensma et al. (2006) Mayo Clin Proc 81:104-130]. In more extreme cases, increased risk of gastrointestinal bleeding or intracranial hemorrhage may occur. For thrombocytopenic patients, platelet transfusions are typically indicated when platelet levels drop to less than 10,000 platelets/μL [Slichter (2007) Hematology Am Soc Hematol Educ Program 2007:172-178]. The supportive use of platelet transfusions is transient and not always effective due to the frequency of sensitization in chronically transfusion-dependent MDS patients. There is considerable interest in using growth factors with thrombopoietic activity in the therapy of MDS. Romiplostim and eltrombopag are thrombomimetic agents approved in the United States for patients with idiopathic thrombocytopenic purpura, and romiplostim is being studied extensively in patients with MDS [Kantarjian et al. (2010) J Clin Oncol 28:437-444; Santini (2012) Semin Hematol 49:295-303]. When used as a single agent, romiplostim can significantly improve platelet counts in approximately 50% of patients with lower-risk MDS with thrombocytopenia. However, a transient increase in marrow blast percentage, sometimes to greater than 20%, can be observed in 15% of patients, consistent with the presence of thrombopoietin receptors on blast cells in MDS. Romiplostim can also significantly reduce thrombocytopenia and/or platelet transfusions in patients with MDS receiving azacitidine, decitabine, or lenalidomide, thalidomide or pomalidomide, and could become an important adjunct to those treatments [Kantarjian et al. (2010) Blood 116:3163-3170]. Eltrombopag is also being developed in MDS. In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with thrombomimetic agents such as romiplostim or eltrombopag for treating patients with MDS or sideroblastic anemias.

In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with hepcidin, a hepcidin analog, or a hepcidin receptor activator for treating patients with MDS or sideroblastic anemias, particularly for complications associated with iron overload. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. In broad terms, hepcidin reduces availability of extracellular iron, so hepcidin, hepcidin analogs, or hepcidin receptor activators may be beneficial in the treatment of patients with MDS or sideroblastic anemias, particularly for complications associated with iron overload.

Investigational agents for MDS are in development. These include single-agent inhibitors of histone deacetylase, p38MAPK inhibitors, glutathione S-transferase it inhibitors, and alemtuzumab for patients who meet criteria for immunosuppressive-based therapy [Garcia-Manero et al. (2011) J Clin Oncol 29:516-523;]. For example, high response rates have been reported in MDS patients treated with immunosuppressive therapies incorporating antithymocyte globulin or alemtuzumab [Sloand et al. (2010) J Clin Oncol 28:5166-5173]. However, such patients have generally been younger and have had a higher frequency of normal karyotypes than MDS patients overall, which limits the generalizability of those results. Investigational therapies include, for example, histone deacetylase inhibitors (HDAC inhibitors), including vorinostat, valproic acid, phenylbutyrate, entinostat, MGCD0103, and other class I nuclear HDAC inhibitors, class II non-nuclear HDAC inhibitors, pan HDAC inhibitors, and isoform-specific HDAC inhibitors; farnesyltransferase inhibitors, including as tipifarnib and lonafarnib; tumor necrosis factor-alpha (TNF-α) inhibitors, including etanercept or infliximab; inhibitors of glutathione-S-transferase (GST) P1-1, including ezatiostat; and inhitors of CD33, including gemtuzumab ozogamicin. In certain embodiments, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator and/or one or more additional therapies, may be used in combination with one or more of these investigational therapies for MDS.

Increasing evidence suggests that combined use of MDS therapeutic agents with different mechanisms of action offers substantial benefit in the form of diminished side effects, improved overall survival, and delayed progression to acute myeloid leukemia. Multiple studies indicate that when compared with traditional monotherapies, combining various medications with non-overlapping mechanisms of action and toxicities may result in significant benefit for MDS patients. A variety of combination therapies with growth factors, DNA methyltransferase inhibitors, histone deacetylase inhibitors, and immunosuppressant treatments provide encouraging data [Ornstein et al. (2012) Int J Hematol 95:26-33]. Therefore, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator, may be used to increase numbers of red blood cells in MDS patients additionally treated with a combination of two or more agents, including but not limited to growth factors, DNA methyltransferase inhibitors, histone deacetylase inhibitors, or immunosuppressant treatments.

In certain embodiments, the present disclosure provides methods for managing a patient that has been treated with, or is a candidate to be treated with, one or more one or more ActRII antagonist agents of the disclosure (e.g., a GDF-ActRII antagonist, an ActRIIA polypeptide, an ActRIIB polypeptide, a GDF trap, etc.) by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more ActRII antagonist agents of the disclosure (e.g., a GDF-ActRII antagonist, an ActRIIA polypeptide, an ActRIIB polypeptide, a GDF trap, etc.) may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more ActRII antagonist agents of the disclosure (e.g., a GDF-ActRII antagonist, an ActRIIA polypeptide, an ActRIIB polypeptide, a GDF trap, etc.), then onset of administration of the one or more antagonists of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more ActRII antagonist agents of the disclosure (e.g., a GDF-ActRII antagonist, an ActRIIA polypeptide, an ActRIIB polypeptide, a GDF trap, etc.), then the onset of administration may not be delayed. However, the dosage amount or frequency of dosing of the one or more antagonists of the disclosure may be set at an amount that would reduce the risk of an unacceptable increase in the hematologic parameters arising upon administration of the one or more antagonists of the disclosure. Alternatively, a therapeutic regimen may be developed for the patient that combines one or more ActRII antagonist agents of the disclosure (e.g., a GDF-ActRII antagonist, an ActRIIA polypeptide, an ActRIIB polypeptide, a GDF trap, etc.) with a therapeutic agent that addresses the undesirable level of the hematologic parameter. For example, if the patient has elevated blood pressure, then a therapeutic regimen may be designed involving administration of one or more ActRII antagonist agents of the disclosure (e.g., a GDF-ActRII antagonist, an ActRIIA polypeptide, an ActRIIB polypeptide, a GDF trap, etc.) and a blood pressure lowering agent. For a patient having lower than desired iron stores, a therapeutic regimen may be developed involving one or more ActRII antagonist agents of the disclosure (e.g., a GDF-ActRII antagonist, an ActRIIA polypeptide, an ActRIIB polypeptide, a GDF trap, etc.) and iron supplementation.

In one embodiment, baseline parameter(s) for one or more hematologic parameters may be established for a patient who is a candidate to be treated with one or more ActRII antagonist agents of the disclosure (e.g., a GDF-ActRII antagonist, an ActRIIA polypeptide, an ActRIIB polypeptide, a GDF trap, etc.) and an appropriate dosing regimen established for that patient based on the baseline value(s). Alternatively, established baseline parameters based on a patient's medical history could be used to inform an appropriate antagonist dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more ActRII antagonist agents of the disclosure (e.g., a GDF-ActRII antagonist, an ActRIIA polypeptide, an ActRIIB polypeptide, a GDF trap, etc.) may also be used as the relevant comparative values for monitoring any changes to the hematologic parameters during treatment with the one or more antagonists of the disclosure.

In certain embodiments, one or more hematologic parameters are measured in patients who are being treated with a one or more ActRII antagonist agents of the disclosure (e.g., a GDF-ActRII antagonist, an ActRIIA polypeptide, an ActRIIB polypeptide, a GDF trap, etc.). The hematologic parameters may be used to monitor the patient during treatment and permit adjustment or termination of the dosing with the one or more antagonists of the disclosure or additional dosing with another therapeutic agent. For example, if administration of one or more ActRII antagonist agents of the disclosure (e.g., a GDF-ActRII antagonist, an ActRIIA polypeptide, an ActRIIB polypeptide, a GDF trap, etc.) results in an increase in blood pressure, red blood cell level, or hemoglobin level, or a reduction in iron stores, then the dose of the one or more antagonists of the disclosure may be reduced in amount or frequency in order to decrease the effects of the one or more antagonists of the disclosure on the one or more hematologic parameters. If administration of one or more ActRII antagonist agents of the disclosure (e.g., a GDF-ActRII antagonist, an ActRIIA polypeptide, an ActRIIB polypeptide, a GDF trap, etc.) results in a change in one or more hematologic parameters that is adverse to the patient, then the dosing of the one or more antagonists of the disclosure may be terminated either temporarily, until the hematologic parameter(s) return to an acceptable level, or permanently. Similarly, if one or more hematologic parameters are not brought within an acceptable range after reducing the dose or frequency of administration of the one or more antagonists of the disclosure, then the dosing may be terminated. As an alternative, or in addition to, reducing or terminating the dosing with the one or more antagonists of the disclosure, the patient may be dosed with an additional therapeutic agent that addresses the undesirable level in the hematologic parameter(s), such as, for example, a blood pressure lowering agent or an iron supplement. For example, if a patient being treated with one or more ActRII antagonist agents of the disclosure (e.g., a GDF-ActRII antagonist, an ActRIIA polypeptide, an ActRIIB polypeptide, a GDF trap, etc.) has elevated blood pressure, then dosing with the one or more antagonists of the disclosure may continue at the same level and a blood-pressure-lowering agent is added to the treatment regimen, dosing with the one or more antagonist of the disclosure may be reduced (e.g., in amount and/or frequency) and a blood-pressure-lowering agent is added to the treatment regimen, or dosing with the one or more antagonist of the disclosure may be terminated and the patient may be treated with a blood-pressure-lowering agent.

6. Pharmaceutical Compositions

In certain aspects, one or more ActRII antagonist agents of the disclosure (e.g., a GDF-ActRII antagonist, an ActRIIA polypeptide, an ActRIIB polypeptide, a GDF trap, etc.) can be administered alone or as a component of a pharmaceutical formulation (also referred to as a therapeutic composition or pharmaceutical composition). A pharmaceutical formulation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

Typically, compounds will be administered parenterally [e.g., by intravenous (I.V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined, including, for example, bone or dermal collagen. Further matrices are comprised of pure proteins or extracellular matrix components. Other potential matrices are non-biodegradable and chemically defined, including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of the present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient (s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delays absorption, including, for example, aluminum monostearate and gelatin.

It is understood that the dosage regimen will be determined by the attending physician considering various factors which modify the action of the one or more of the agents of the present disclosure. The various factors include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous sarcoma virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form [see, e.g., Fraley, et al. (1981) Trends Biochem. Sci., 6:77]. Methods for efficient gene transfer using a liposome vehicle are known in the art [see, e.g., Mannino, et al. (1988) Biotechniques, 6:682, 1988].

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used, including, for example a phosphatidyl compound (e.g., phosphatidylglycerol, phosphatidylcholine, phosphatidylserine, phosphatidylethanolamine, sphingolipid, cerebroside, or a ganglioside), egg phosphatidylcholine, dipalmitoylphosphatidylcholine, and distearoylphosphatidylcholine. The targeting of liposomes is also possible based on, for example, organ specificity, cell specificity, and organelle specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1: ActRIIa-Fc Fusion Proteins

Applicants constructed a soluble ActRIIA fusion protein that has the extracellular domain of human ActRIIa fused to a human or mouse Fc domain with a minimal linker in between. The constructs are referred to as ActRIIA-hFc and ActRIIA-mFc, respectively.

ActRIIA-hFc is shown below as purified from CHO cell lines (SEQ ID NO:22):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP<u>TGGGTHTCPPCPAPELLGGPSVFLFPPKPKDTLMI</u>

<u>SRTPEVTCVVVDVSHEDPEVKFNWYVDGVEVHNAKTKPREEQYNSTYRVV</u>

<u>SVLTVLHQDWLNGKEYKCKVSNKALPVPIEKTISKAKGQPREPQVYTLPP</u>

<u>SREEMTKNQVSLTCLVKGFYPSDIAVEWESNGQPENNYKTTPPVLDSDGS</u>

<u>FFLYSKLTVDKSRWQQGNVFSCSVMHEALHNHYTQKSLSLSPGK</u>

The ActRIIA-hFc and ActRIIA-mFc proteins were expressed in CHO cell lines. Three different leader sequences were considered:

(i) Honey bee mellitin (HBML): MKFLVNVALVFMV-VYISYIYA (SEQ ID NO:23)

(ii) Tissue plasminogen activator (TPA): MDAMKRGL-CCVLLLCGAVFVSP (SEQ ID NO:24)

(iii) Native: MGAAAKLAFAVFLISCSSGA (SEQ ID NO:25).

The selected form employs the TPA leader and has the following unprocessed amino acid sequence:

(SEQ ID NO: 26)
MDAMKRGLCCVLLLCGAVFVSPGAAILGRSETQECLFFNANWEKDRTNQT

GVEPCYGDKDKRRHCFATWKNISGSIEIVKQGCWLDDINCYDRTDCVEKK

DSPEVYFCCCEGNMCNEKFSYFPEMEVTQPTSNPVTPKPPTGGGTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PVPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK

This polypeptide is encoded by the following nucleic acid sequence:

(SEQ ID NO: 27)
ATGGATGCAATGAAGAGAGGGCTCTGCTGTGTGCTGCTGCTGTGTGGAGC

AGTCTTCGTTTCGCCCGGCGCCGCTATACTTGGTAGATCAGAAACTCAGG

AGTGTCTTTTTTTAATGCTAATTGGGAAAAAGACAGAACCAATCAAACTG

GTGTTGAACCGTGTTATGGTGACAAAGATAAACGGCGGCATTGTTTTGCT

ACCTGGAAGAATATTTCTGGTTCCATTGAATAGTGAAACAAGGTTGTTGG

CTGGATGATATCAACTGCTATGACAGGACTGATTGTGTAGAAAAAAAAGA

CAGCCCTGAAGTATATTTCTGTTGCTGTGAGGGCAATATGTGTAATGAAA

AGTTTTCTTATTTTCCGGAGATGGAAGTCACACAGCCCACTTCAAATCCA

GTTACACCTAAGCCACCCACCGGTGGTGGAACTCACACATGCCCACCGTG

CCCAGCACCTGAACTCCTGGGGGGACCGTCAGTCTTCCTCTTCCCCCCAA

AACCCAAGGACACCCTCATGATCTCCCGGACCCCTGAGGTCACATGCGTG

GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AGTCCCCATCGAGAAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC

Both ActRIIA-hFc and ActRIIA-mFc were remarkably amenable to recombinant expression. As shown in FIG. 3, the protein was purified as a single, well-defined peak of protein. N-terminal sequencing revealed a single sequence of -ILGRSETQE (SEQ ID NO:34). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

Figure 4:
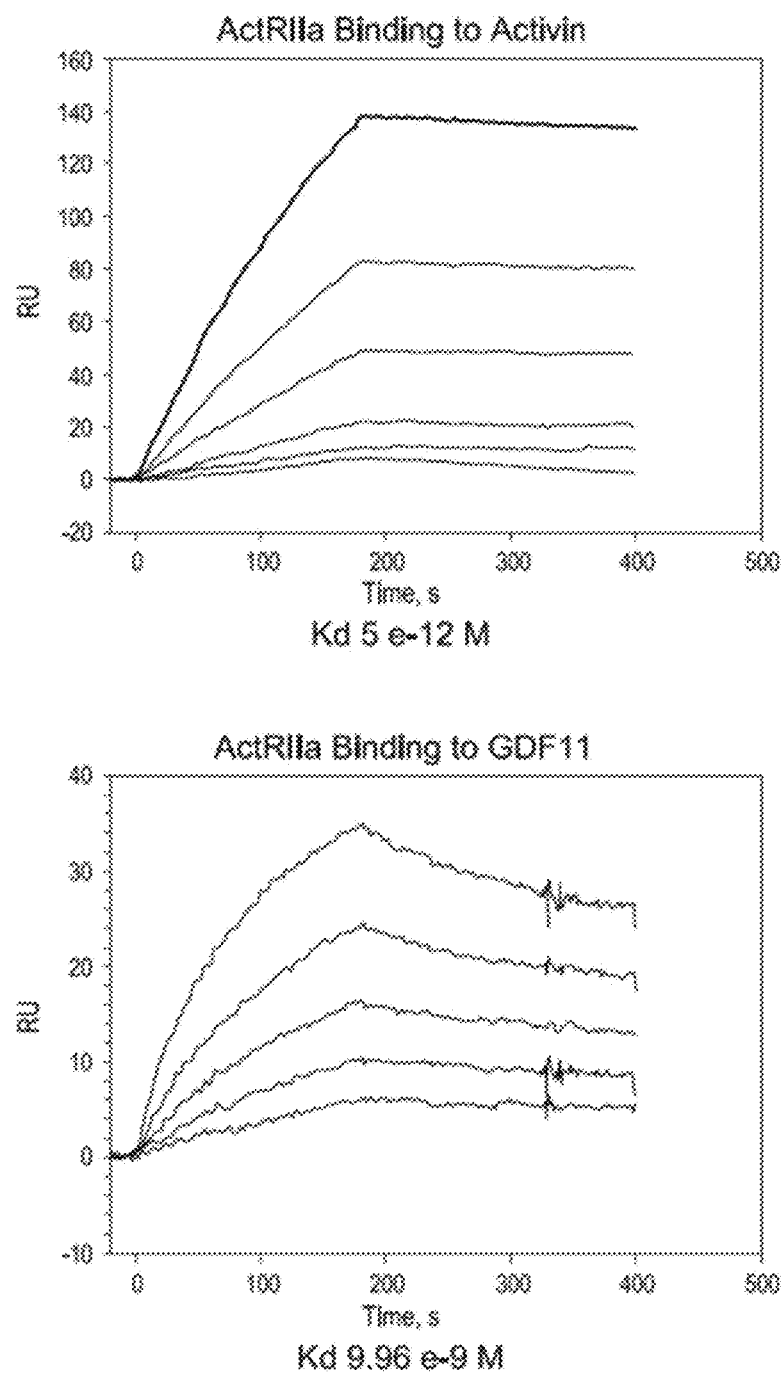
FIG. 4 shows the binding of ActRIIA-hFc to activin and GDF-11, as measured by Biacore™ assay.
Figure 5A:
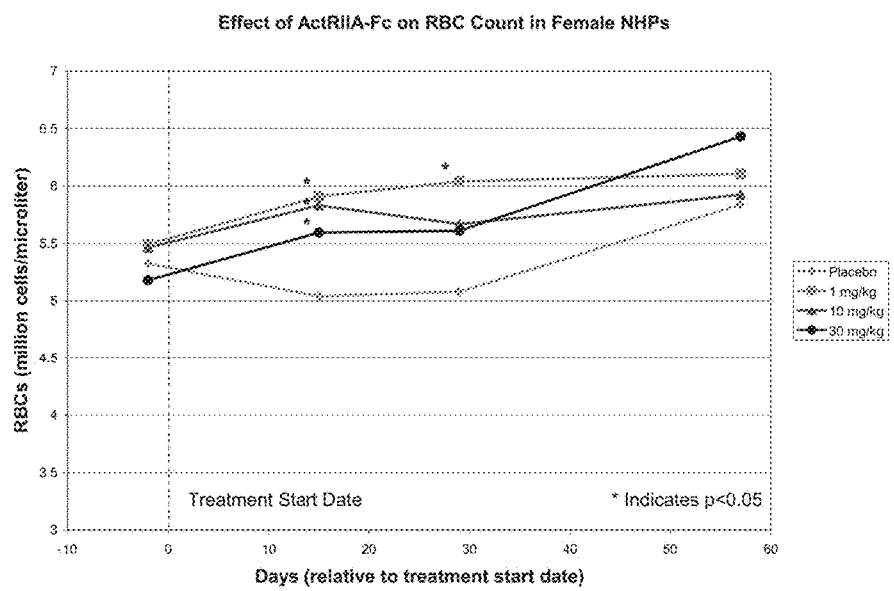
FIGS. 5A and 5B shows the effects of ActRIIA-hFc on red blood cell counts in female non-human primates (NHPs). Female cynomolgus monkeys (four groups of five monkeys each) were treated with placebo or 1 mg/kg, 10 mg/kg or 30 mg/kg of ActRIIA-hFc on day 0, day 7, day 14, and day 21.
Figure 5B:
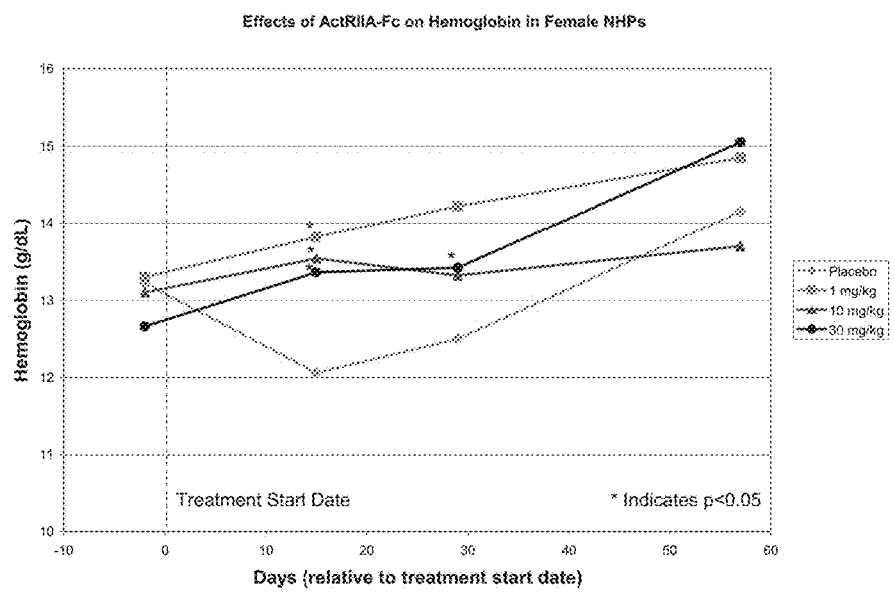
Figure 6A:
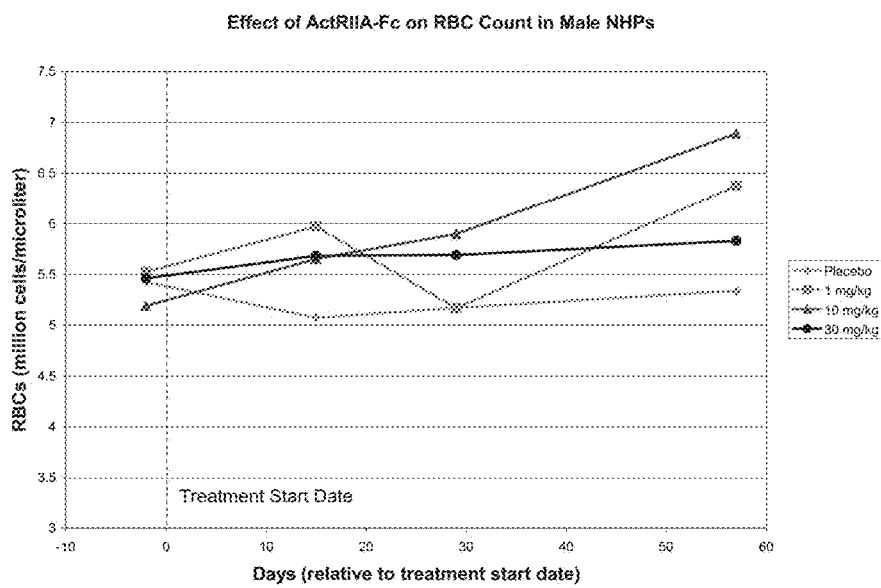
FIGS. 6A and 6B shows the effects of ActRIIA-hFc on red blood cell counts in male non-human primates. Male cynomolgus monkeys (four groups of five monkeys each) were treated with placebo or 1 mg/kg, 10 mg/kg, or 30 mg/kg of ActRIIA-hFc on day 0, day 7, day 14, and day 21.
Figure 6B:
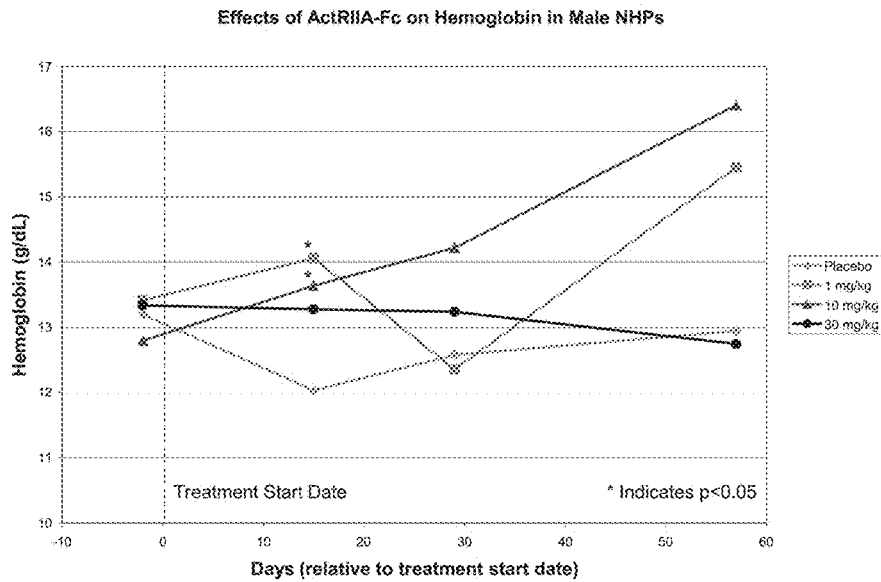
Figure 7A:
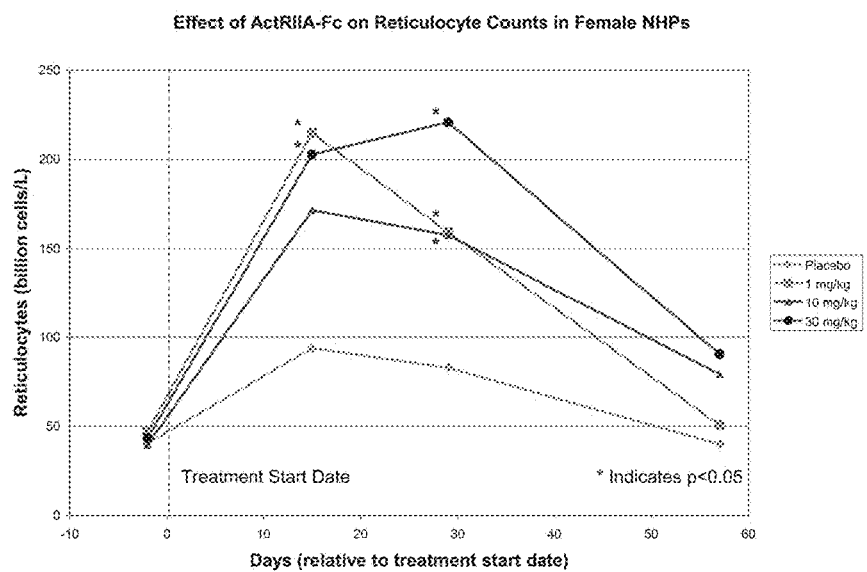
FIGS. 7A and 7B shows the effects of ActRIIA-hFc on reticulocyte counts in female non-human primates. Cynomolgus monkeys (four groups of five monkeys each) were treated with placebo or 1 mg/kg, 10 mg/kg, or 30 mg/kg of ActRIIA-hFc on day 0, day 7, day 14, and day 21.
Figure 7B:
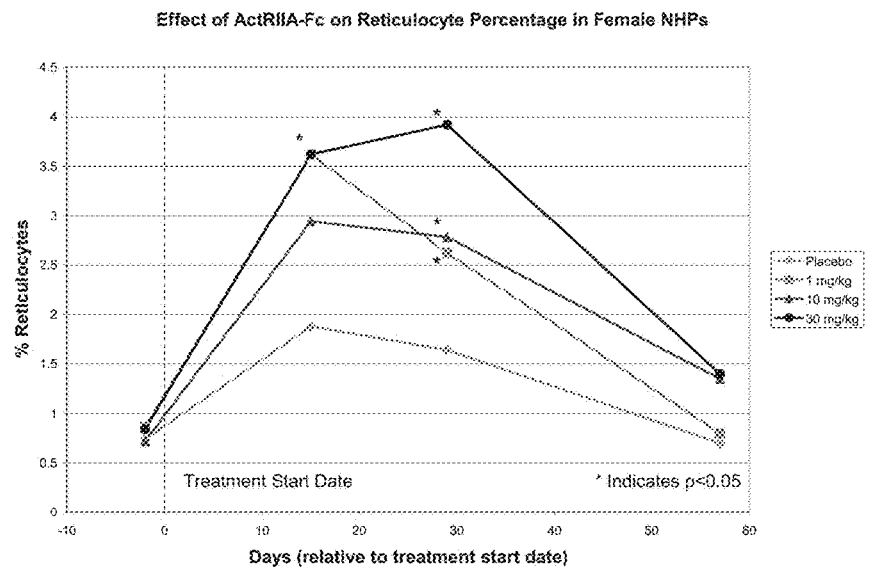
Figure 8A:
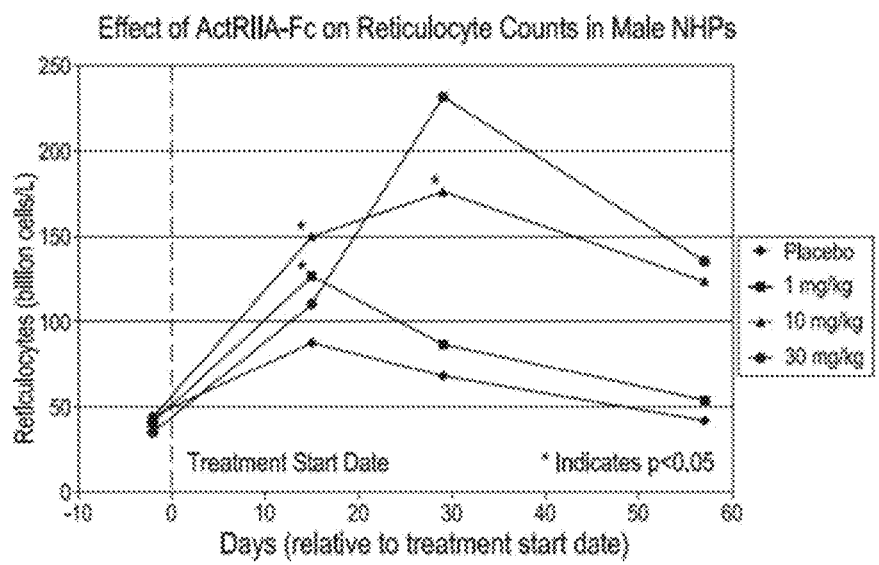
FIGS. 8A and 8B shows the effects of ActRIIA-hFc on reticulocyte counts in male non-human primates. Cynomolgus monkeys (four groups of five monkeys each) were treated with placebo or 1 mg/kg, 10 mg/kg, or 30 mg/kg of ActRIIA-hFc on day 0, day 7, day 14, and day 21.
Figure 8B:
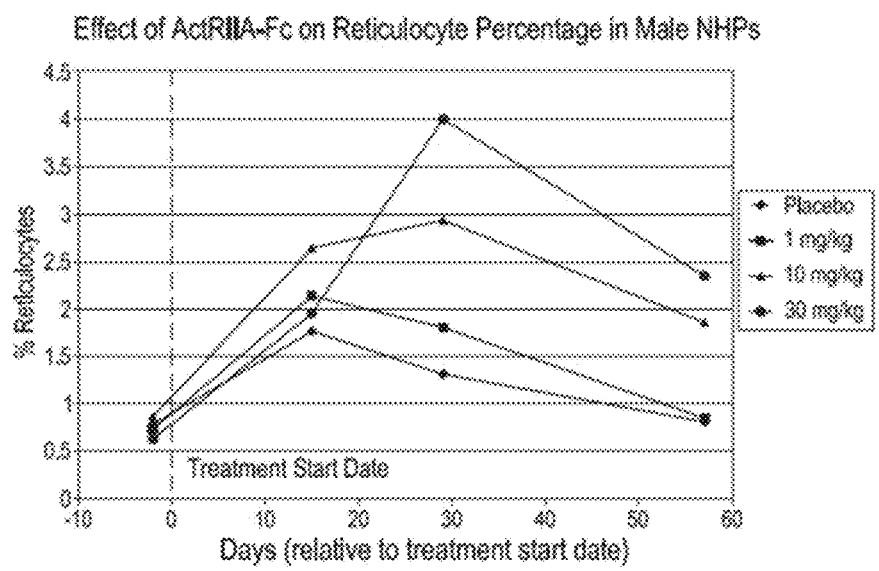

ActRIIA-hFc and ActRIIA-mFc showed a high affinity for ligands, particularly activin A. GDF-11 or activin A were immobilized on a Biacore™ CM5 chip using standard amine-coupling procedure. ActRIIA-hFc and ActRIIA-mFc proteins were loaded onto the system, and binding was measured. ActRIIA-hFc bound to activin with a dissociation constant ($K_D$) of $5 \times 10^{-12}$ and bound to GDF11 with a $K_D$ of $9.96 \times 10^{-9}$. See FIG. 4. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11 µg/ml, 110 µg/ml, or 304 µg/ml for initial administrations of 1 mg/kg, 10 mg/kg, or 30 mg/kg, respectively.) In cynomolgus monkeys, the plasma half-life was substantially greater than 14 days, and circulating levels of the drug were 25 µg/ml, 304 µg/ml, or 144 µg/ml for initial administrations of 1 mg/kg, 10 mg/kg, or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 ori/enhancer, CMV promoter), using a tissue plasminogen leader sequence of SEQ ID NO:9. The protein, purified as described above in Example 1, had a sequence of SEQ ID NO:22. The Fc portion is a human IgG1 Fc sequence, as shown in SEQ ID NO:22. Protein analysis reveals that the ActRIIA-hFc fusion protein is formed as a homodimer with disulfide bonding.

The CHO-cell-expressed material has a higher affinity for activin B ligand than that reported for an ActRIIa-hFc fusion protein expressed in human 293 cells [see, del Re et al. (2004) J Biol Chem. 279(51):53126-53135]. Additionally, the use of the TPA leader sequence provided greater production than other leader sequences and, unlike ActRIIA-Fc expressed with a native leader, provided a highly pure N-terminal sequence. Use of the native leader sequence resulted in two major species of ActRIIA-Fc, each having a different N-terminal sequence.

Example 3: ActRIIA-hFc Increases Red Blood Cell Levels in Non-Human Primates

The study employed four groups of five male and five female cynomolgus monkeys each, with three per sex per group scheduled for termination on Day 29, and two per sex per group scheduled for termination on Day 57. Each animal was administered the vehicle (Group 1) or ActRIIA-Fc at doses of 1, 10, or 30 mg/kg (Groups 2, 3 and 4, respectively) via intravenous (IV) injection on Days 1, 8, 15, and 22. The dose volume was maintained at 3 mL/kg. Various measures of red blood cell levels were assessed two days prior to the first administration and at days 15, 29, and 57 (for the remaining two animals) after the first administration.

The ActRIIA-hFc caused statistically significant increases in mean red blood cell parameters [red blood cell count (RBC), hemoglobin (HGB), and hematocrit (HCT)] for males and females, at all dose levels and time points throughout the study, with accompanying elevations in absolute and relative reticulocyte counts (ARTC; RTC). See FIGS. 5-8.

Statistical significance was calculated for each treatment group relative to the mean for the treatment group at baseline.

Notably, the increases in red blood cell counts and hemoglobin levels are roughly equivalent in magnitude to effects reported with erythropoietin. The onset of these effects is more rapid with ActRIIA-Fc than with erythropoietin.

Similar results were observed with rats and mice.

Example 4: ActRIIA-hFc Increases Red Blood Cell Levels and Markers of Bone Formation in Human Patients The ActRIIA-hFc fusion protein described in Example 1 was administered to human subjects in a randomized, double-blind, placebo-controlled study that was conducted to evaluate, primarily, the safety of the protein in healthy, postmenopausal women. Forty-eight subjects were randomized in cohorts of 6 to receive either a single dose of ActRIIA-hFc or placebo (5 active:1 placebo). Dose levels ranged from 0.01 to 3.0 mg/kg intravenously (IV) and 0.03 to 0.1 mg/kg subcutaneously (SC). All subjects were followed for 120 days. In addition to pharmacokinetic (PK) analyses, the biologic activity of ActRIIA-hFc was also assessed by measurement of biochemical markers of bone formation and resorption as well as FSH levels.

To look for potential changes, hemoglobin and RBC numbers were examined in detail for all subjects over the course of the study and compared to the baseline levels. Platelet counts were compared over the same time as the control. There were no clinically significant changes from the baseline values over time for the platelet counts.

Figure 9:
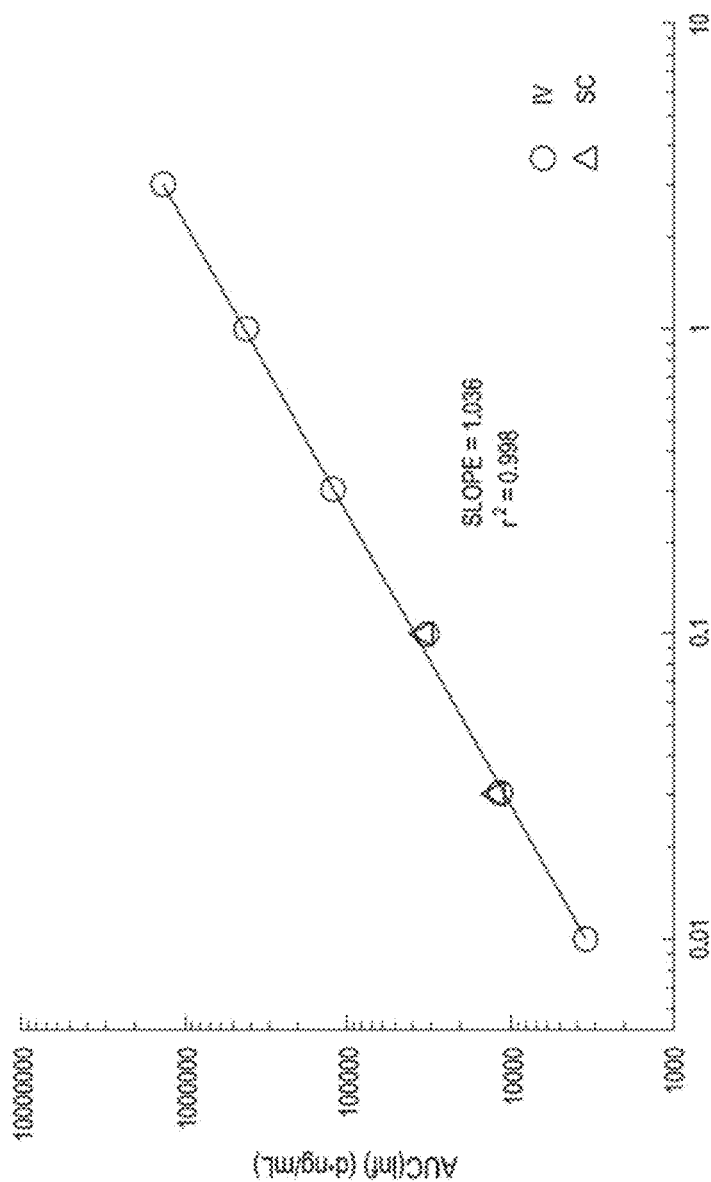
FIG. 9 shows results from the human clinical trial described in Example 5, where the area-under-curve (AUC) and administered dose of ActRIIA-hFc have a linear correlation, regardless of whether ActRIIA-hFc was administered intravenously (IV) or subcutaneously (SC).
Figure 10:
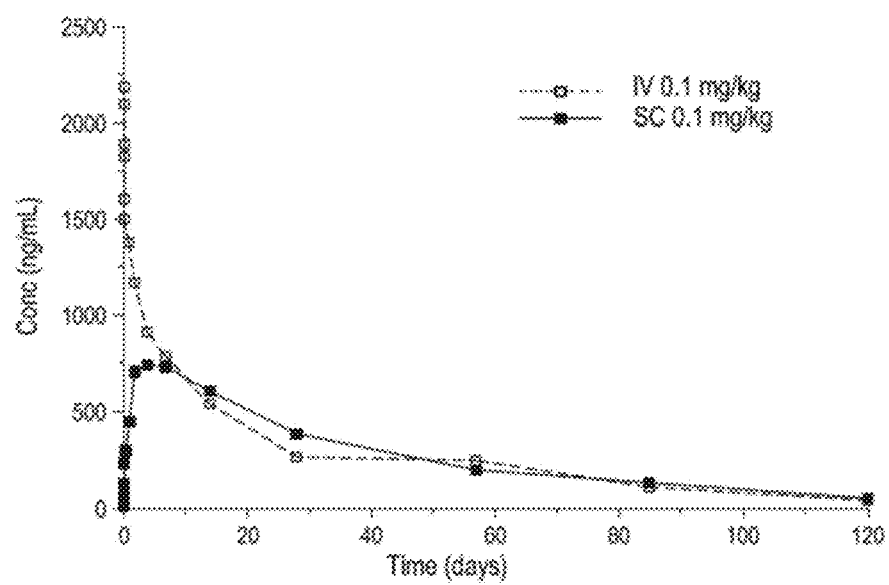
FIG. 10 shows a comparison of serum levels of ActRIIA-hFc in patients administered IV or SC.
Figure 11:
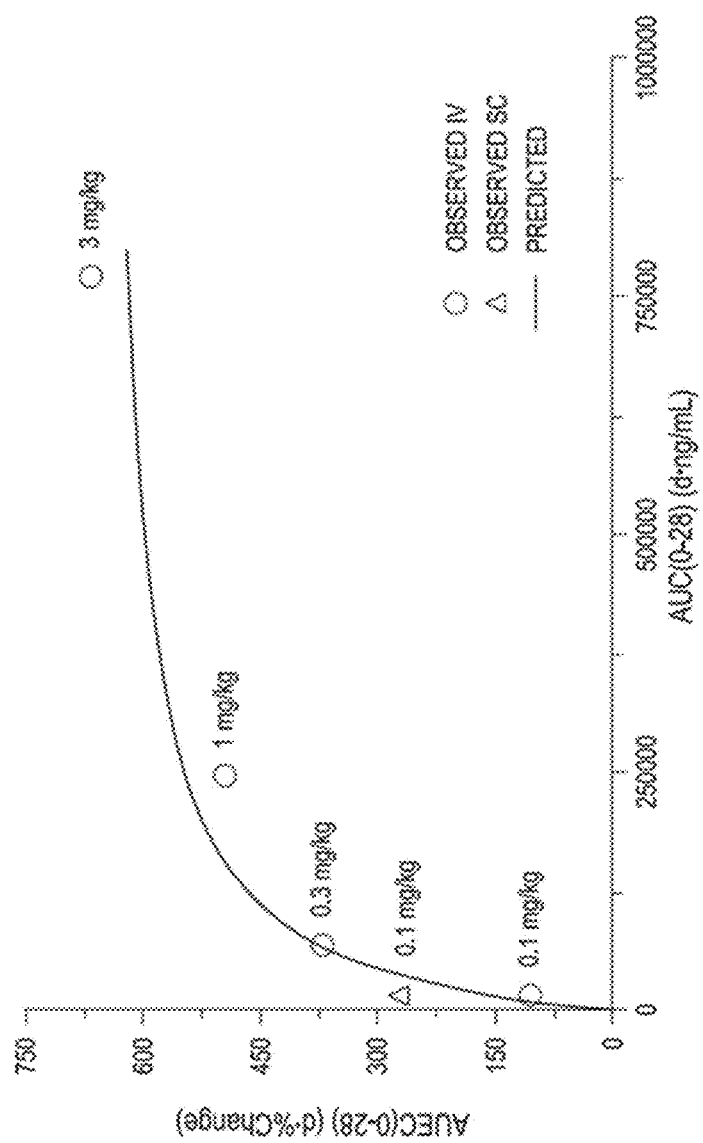
FIG. 11 shows bone alkaline phosphatase (BAP) levels in response to different dose levels of ActRIIA-hFc. BAP is a marker for anabolic bone growth.
Figure 12:
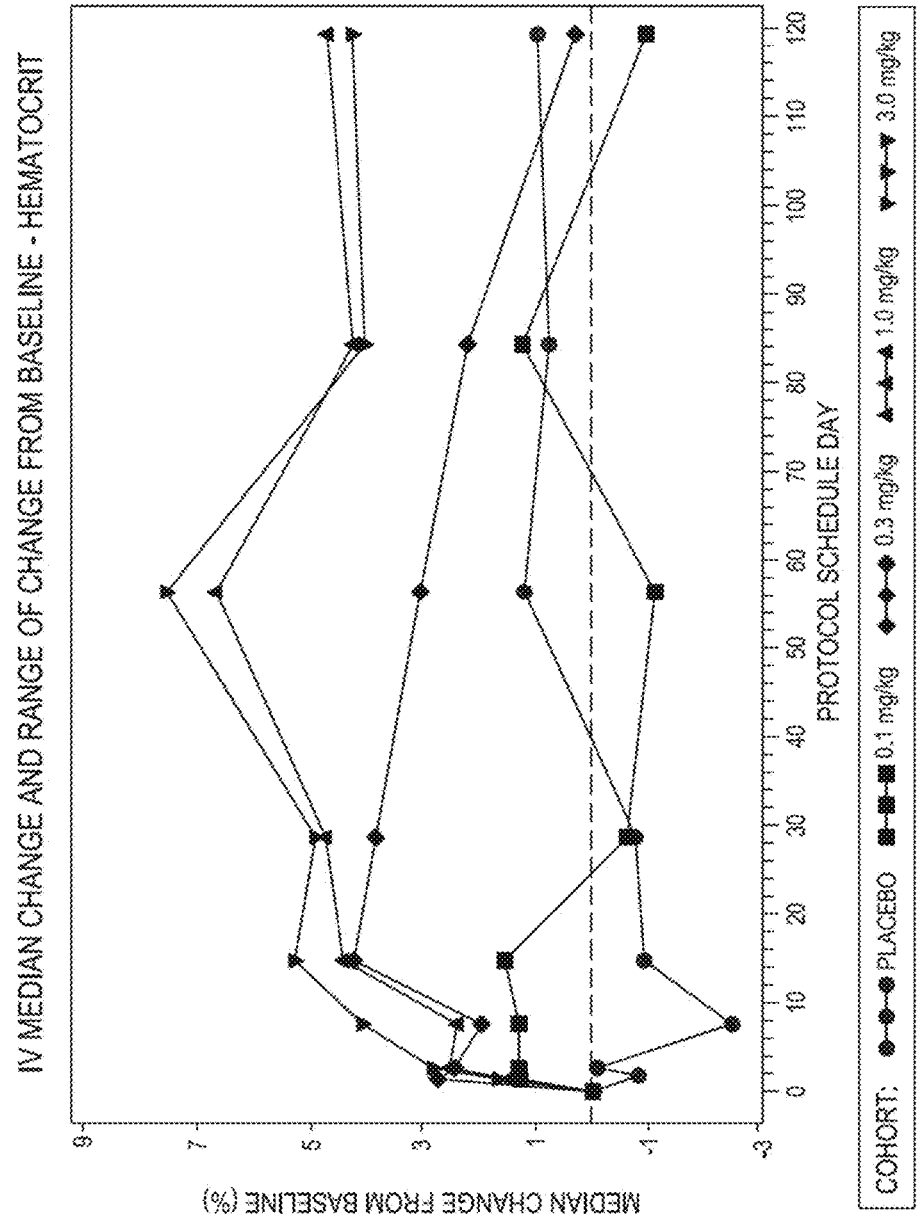
FIG. 12 depicts the median change from baseline of hematocrit levels from the human clinical trial described in Example 5. ActRIIA-hFc was administered intravenously (IV) at the indicated dosage.
Figure 13:
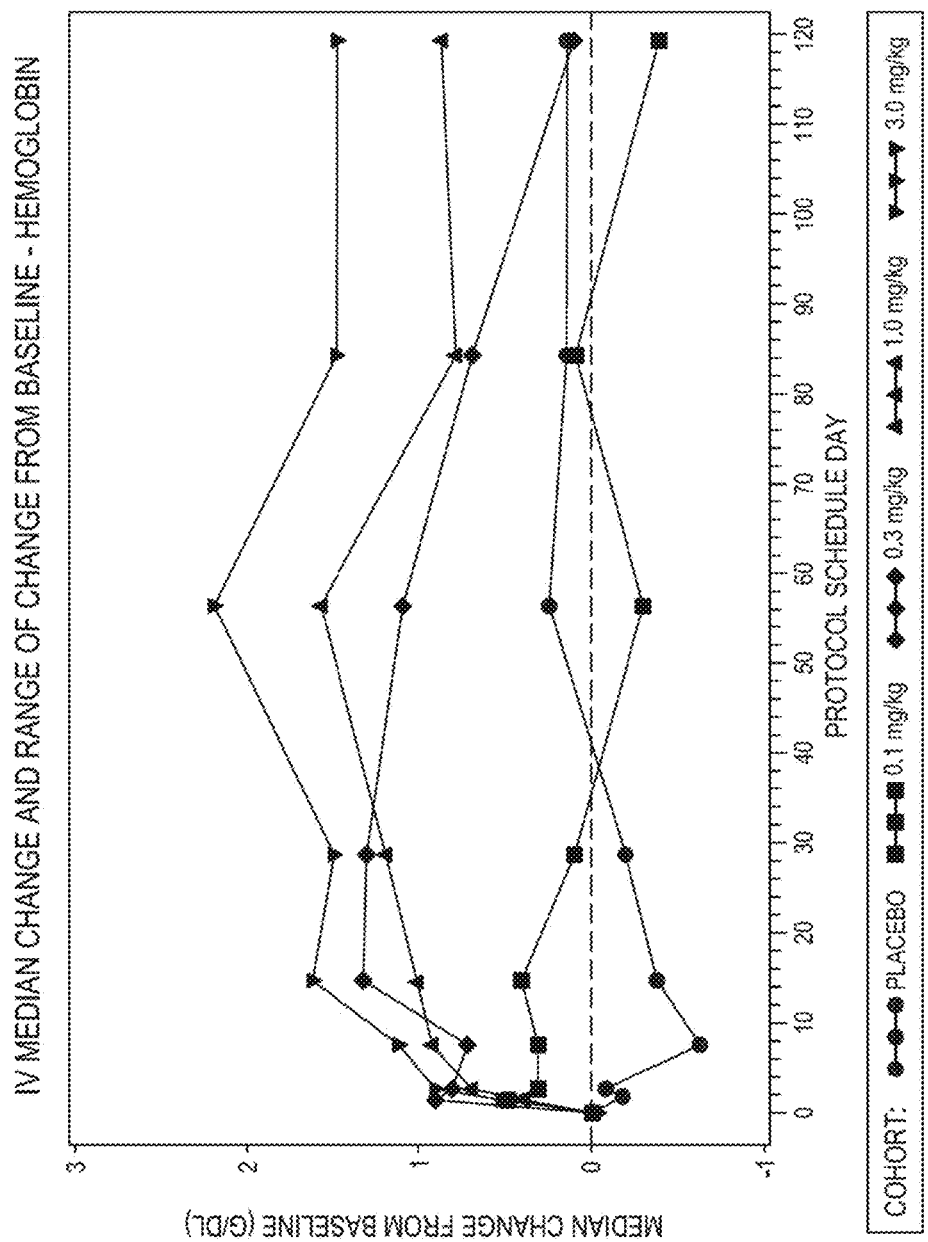
FIG. 13 depicts the median change from baseline of hemoglobin levels from the human clinical trial described in Example 5. ActRIIA-hFc was administered intravenously (IV) at the indicated dosage.
Figure 14:
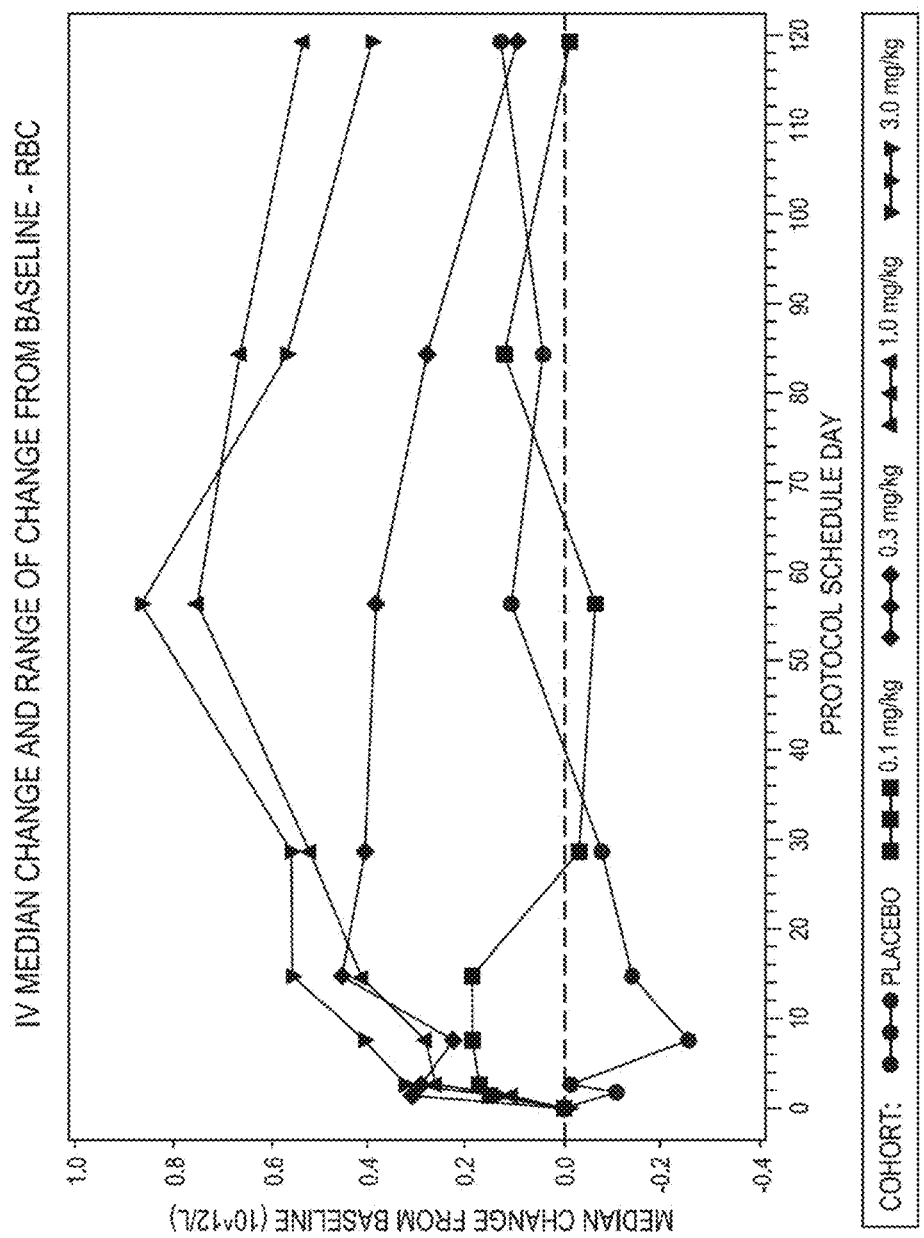
FIG. 14 depicts the median change from baseline of RBC (red blood cell) count from the human clinical trial described in Example 5. ActRIIA-hFc was administered intravenously (IV) at the indicated dosage.
Figure 15:
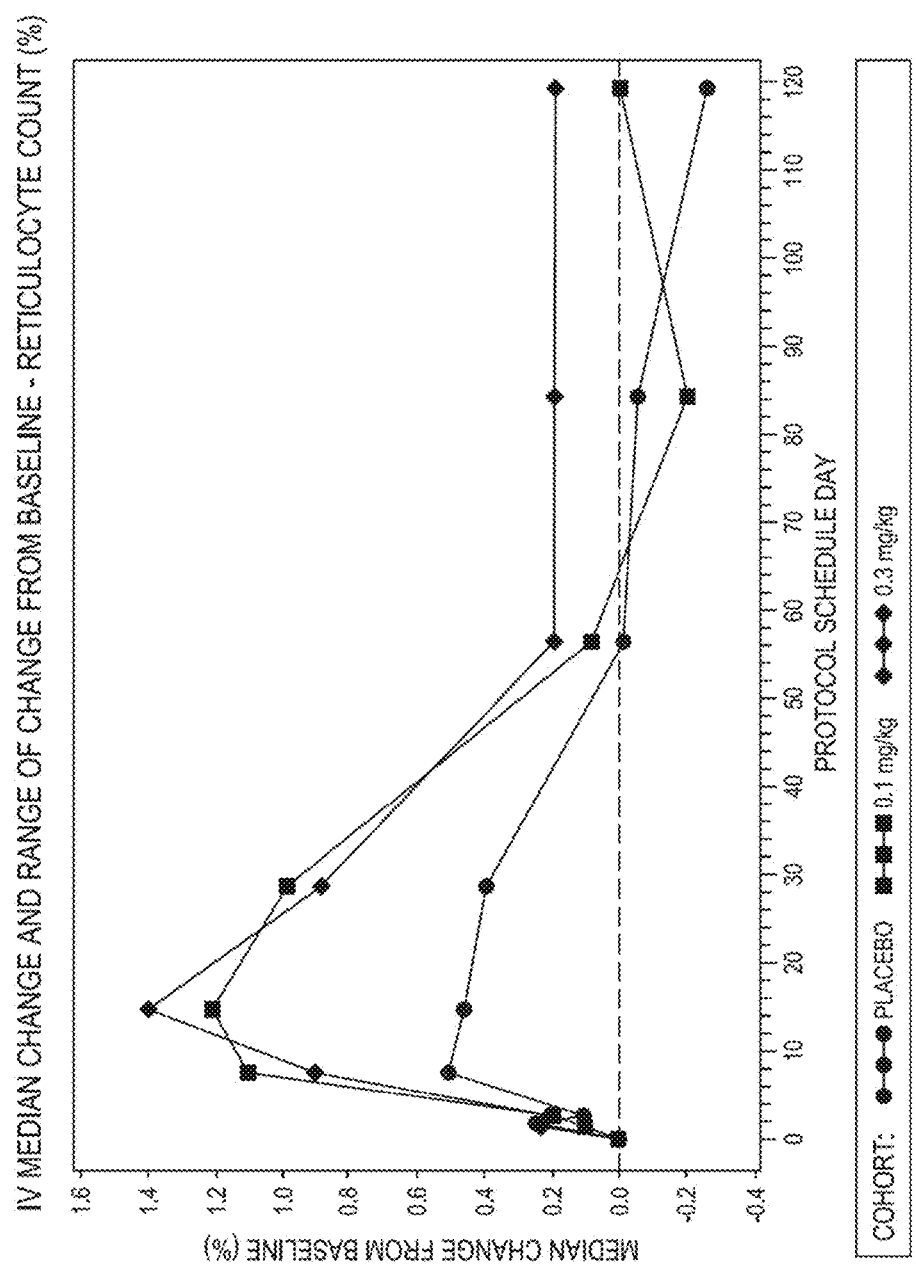
FIG. 15 depicts the median change from baseline of reticulocyte count from the human clinical trial described in Example 5. ActRIIA-hFc was administered intravenously (IV) at the indicated dosage.

Pharmacokinetic (PK) analysis of ActRIIA-hFc revealed a linear profile with dose, and a mean half-life of approximately 25-32 days. The area-under-curve (AUC) for ActRIIA-hFc was linearly related to dose, and the absorption after SC dosing was essentially complete. See FIGS. 9 and 10. These data indicate that SC is a desirable approach to dosing because it provides equivalent bioavailability and serum-half life for the drug while avoiding the spike in serum concentrations of drug associated with the first few days of IV dosing (see FIG. 10). ActRIIA-hFc caused a rapid, sustained dose-dependent increase in serum levels of bone-specific alkaline phosphatase (BAP), which is a marker for anabolic bone growth, and a dose-dependent decrease in C-terminal type 1 collagen telopeptide and tartrate-resistant acid phosphatase 5b levels, which are markers for bone resorption. Other markers such as P1NP showed inconclusive results. BAP levels showed near-saturating effects at the highest dosage of drug, indicating that half-maximal effects on this anabolic bone biomarker could be achieved at a dosage of 0.3 mg/kg, with increases ranging up to 3 mg/kg. Calculated as a relationship of pharmacodynamic effect to AUC for drug, the EC50 was 51,465 (day*ng/ml) (see FIG. 11). These bone biomarker changes were sustained for approximately 120 days at the highest dose levels tested. There was also a dose-dependent decrease in serum FSH levels consistent with inhibition of activin.

Overall, there was a very small non-drug related reduction in hemoglobin over the first week of the study probably related to study phlebotomy in the 0.01 and 0.03 mg/kg groups whether given IV or SC. The 0.1 mg/kg SC and IV hemoglobin results were stable or showed modest increases by Day 8-15. At the 0.3 mg/kg IV dose level there was a clear increase in HGB levels seen as early as Day 2 and often peaking at Day 15-29 that was not seen in the placebo-treated subjects. At the 1.0 mg/kg IV dose and the 3.0 mg/kg IV dose, mean increases in hemoglobin of greater than 1 g/dl were observed in response to the single dose, with corresponding increases in RBC counts and hematocrit. These hematologic parameters peaked at about 60 days after the dose and substantial decrease by day 120. This indicates that dosing for the purpose of increasing red blood cell levels may be more effective if done at intervals less than 120 days (i.e., prior to return to baseline), with dosing intervals of 90 days or less or 60 days or less may be desirable. For a summary of hematological changes, see FIGS. 12-15.

Overall, ActRIIA-hFc showed a dose-dependent effect on red blood cell counts and reticulocyte counts.

Example 5: Treatment of an Anemic Patient with ActRIIA-hFc

A clinical study was designed to treat patients with multiple doses of ActRIIA-hFc, at three dose levels of 0.1 mg/kg, 0.3 mg/kg, and 1.0 mg/kg, with dosing to occur every 30 days. Normal healthy subjects in the trial exhibited an increase in hemoglobin and hematocrit that is consistent with the increases seen in the Phase I clinical trial reported in Example 4, except that in some instances the hemoglobin (Hg) and hematocrit (Hct) are elevated beyond the normal range. An anemic patient with hemoglobin levels of approximately 7.5 g/dL also received two doses at the 1 mg/kg level, resulting in a hemoglobin level of approximately 10.5 g/dL after two months. The patient's anemia was a microcytic anemia, thought to be caused by chronic iron deficiency.

ActRIIA-Fc fusion proteins have been further demonstrated to be effective in increasing red blood cell levels in various models of anemia including, for example, chemotherapy-induced anemia and anemia associated with chronic kidney disease (see, e.g., U.S. Patent Application Publication No. 2010/0028331).

Example 6: Alternative ActRIIA-Fc Proteins

A variety of ActRIIA variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA. The sequence for such a construct is presented below (Fc portion underlined) (SEQ ID NO:28):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

TGGGTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPVPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

Example 7: Generation of ActRIIB-Fc Fusion Proteins

Applicants constructed a soluble ActRIIB fusion protein that has the extracellular domain of human ActRIIB fused to a human or mouse Fc domain with a minimal linker (three glycine amino acids) in between. The constructs are referred to as ActRIIB-hFc and ActRIIB-mFc, respectively.

ActRIIB-hFc is shown below as purified from CHO cell lines (SEQ ID NO:29):

GRGEAETRECIYYNANWELERTNQSGLERCEGEQDKRLHCYASWRNSSGT
IELVKKGCWLDDFNCYDRQECVATEENPQVYFCCCEGNFCNERFTHLPEA
GGPEVTYEPPPTAPTGGGTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPVPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

The ActRIIB-hFc and ActRIIB-mFc proteins were expressed in CHO cell lines. Three different leader sequences were considered:
(i) Honey bee mellitin (HBML): MKFLVNVALVFMVVYI-SYIYA (SEQ ID NO:23)
(ii) Tissue plasminogen activator (TPA): MDAMKRGLC-CVLLLCGAVFVSP (SEQ ID NO:24)
(iii) Native: MTAPWVALALLWGSLCAGS (SEQ ID NO:30).

The selected form employs the TPA leader and has the following unprocessed amino acid sequence (SEQ ID NO: 31):

MDAMKRGLCCVLLLCGAVFVSPGASGRGEAETRECIYYNANWELERTNQS
GLERCEGEQDKRLHCYASWRNSSGTIELVKKGCWLDDFNCYDRQECVATE
ENPQVYFCCCEGNFCNERFTHLPEAGGPEVTYEPPPTAPTGGGTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
VPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPGK

This polypeptide is encoded by the following nucleic acid sequence (SEQ ID NO:32):

```
A TGGATGCAAT GAAGAGAGGG CTCTGCTGTG TGCTGCTGCT
GTGTGGAGCA GTCTTCGTTT CGCCCGGCGC CTCTGGGCGT
GGGGAGGCTG AGACACGGGA GTGCATCTAC TACAACGCCA
ACTGGGAGCT GGAGCGCACC AACCAGAGCG GCCTGGAGCG
CTGCGAAGGC GAGCAGGACA AGCGGCTGCA CTGCTACGCC
TCCTGGCGCA ACAGCTCTGG CACCATCGAG CTCGTGAAGA
AGGGCTGCTG GCTAGATGAC TTCAACTGCT ACGATAGGCA
GGAGTGTGTG GCCACTGAGG AGAACCCCCA GGTGTACTTC
TGCTGCTGTG AAGGCAACTT CTGCAACGAG CGCTTCACTC
ATTTGCCAGA GGCTGGGGGC CCGGAAGTCA CGTACGAGCC
ACCCCCGACA GCCCCCACCG GTGGTGGAAC TCACACATGC
CCACCGTGCC CAGCACCTGA ACTCCTGGGG GGACCGTCAG
TCTTCCTCTT CCCCCCAAAA CCCAAGGACA CCCTCATGAT
CTCCCGGACC CCTGAGGTCA CATGCGTGGT GGTGGACGTG
AGCCACGAAG ACCCTGAGGT CAAGTTCAAC TGGTACGTGG
ACGGCGTGGA GGTGCATAAT GCCAAGACAA AGCCGCGGGA
GGAGCAGTAC AACAGCACGT ACCGTGTGGT CAGCGTCCTC
ACCGTCCTGC ACCAGGACTG GCTGAATGGC AAGGAGTACA
AGTGCAAGGT CTCCAACAAA GCCCTCCCAG TCCCCATCGA
GAAAACCATC TCCAAAGCCA AAGGGCAGCC CCGAGAACCA
CAGGTGTACA CCCTGCCCCC ATCCCGGGAG GAGATGACCA
AGAACCAGGT CAGCCTGACC TGCCTGGTCA AAGGCTTCTA
TCCCAGCGAC ATCGCCGTGG AGTGGGAGAG CAATGGGCAG
CCGGAGAACA ACTACAAGAC CACGCCTCCC GTGCTGGACT
CCGACGGCTC CTTCTTCCTC TATAGCAAGC TCACCGTGGA
CAAGAGCAGG TGGCAGCAGG GGAACGTCTT CTCATGCTCC
GTGATGCATG AGGCTCTGCA CAACCACTAC ACGCAGAAGA
GCCTCTCCCT GTCTCCGGGT AAATGA
```

N-terminal sequencing of the CHO-cell-produced material revealed a major sequence of -GRGEAE (SEQ ID NO:33). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIB-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Applicants generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO:29.

Various mutations, including N- and C-terminal truncations, were introduced into the background ActRIIB-Fc protein. Based on the data presented in Example 1, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into E. coli DH5 alpha, colonies were picked and DNAs were isolated. For murine constructs (mFc), a murine IgG2a was substituted for the human IgG1. Sequences of all mutants were verified.

All of the mutants were produced in HEK293T cells by transient transfection. In summary, in a 500 ml spinner, HEK293T cells were set up at 6×10⁵ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, a protein A column, and eluted with low pH (3.0) glycine buffer. After neutralization, these were dialyzed against PBS.

Mutants were also produced in CHO cells by similar methodology. Mutants were tested in binding assays and/or bioassays described in WO 2008/097541 and WO 2006/012627 incorporated by reference herein. In some instances, assays were performed with conditioned medium rather than purified proteins. Additional variations of ActRIIB are described in U.S. Pat. No. 7,842,663.

Example 8: ActRIIB-Fc Stimulates Erythropoiesis in Non-Human Primates

Cynomolgus monkeys were allocated into seven groups (6/sex/group) and administered ActRIIB(20-134)-hFc as a subcutaneous injection at dosages of 0.6, 3, or 15 mg/kg every 2 weeks or every 4 weeks over a 9-month period. The control group (6/sex/group) received the vehicle at the same dose volume (0.5 ml/kg/dose) as ActRIIB(20-134)-hFc-treated animals. Animals were monitored for changes in general clinical pathology parameters (e.g., hematology, clinical chemistry, coagulation, and urinalysis). Hematology, coagulation, and clinical chemistry parameters (including iron parameters, lipase, and amylase) were evaluated twice prior to initiation of dosing and on Days 59, 143, 199, 227, and on Days 267 (for groups dosed every 4 weeks) or 281 (for groups dosed every 2 weeks). The evaluations on Days 267/281 occurred 2 weeks after the final dose was administered.

Administration of ActRIIB(20-134)-hFc resulted in non-adverse, dose-related changes to hematology parameters in male and female monkeys. These changes included increased red blood cell count, reticulocyte count and red cell distribution width and decreased mean corpuscular volume, mean corpuscular hemoglobin, and platelet count. In males, RBC count was increased at all dose levels, and the magnitude of increase was generally comparable whether ActRIIB(20-134)-hFc was administered every 2 weeks or every 4 weeks. Mean RBC count was increased at all time points between Days 59 and 267/281 (except RBC count was not increased in group 2 males [0.6 mg/kg every 2 weeks] on Day 281). In females, RBC count was increased at ≥3 mg/kg every 2 weeks and the changes occurred between Days 143 and 281; at 15 mg/kg every 4 weeks mean RBC count was increased between Days 59 and 267.

These effects are consistent with a positive effect of ActRIIB(20-134)-hFc on stimulating erythropoiesis.

Example 9: Generation of a GDF Trap

Applicants constructed a GDF trap as follows. A polypeptide having a modified extracellular domain of ActRIIB (amino acids 20-134 of SEQ ID NO:1 with an L79D substitution) with greatly reduced activin A binding relative to GDF11 and/or myostatin (as a consequence of a leucine-to-aspartate substitution at position 79 in SEQ ID NO:1) was fused to a human or mouse Fc domain with a minimal linker (three glycine amino acids) in between. The constructs are referred to as ActRIIB(L79D 20-134)-hFc and ActRIIB (L79D 20-134)-mFc, respectively. Alternative forms with a glutamate rather than an aspartate at position 79 performed similarly (L79E). Alternative forms with an alanine rather than a valine at position 226 with respect to SEQ ID NO:36, below were also generated and performed equivalently in all respects tested. The aspartate at position 79 (relative to SEQ ID NO: 1, or position 60 relative to SEQ ID NO:36) is indicated with double underlining below. The valine at position 226 relative to SEQ ID NO:36 is also indicated by double underlining below.

The GDF trap ActRIIB(L79D 20-134)-hFc is shown below as purified from CHO cell lines (SEQ ID NO:36).

GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPTGGGTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPVPIEKTISKAKGQPREPQVYTLPPS

REEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

The ActRIIB-derived portion of the GDF trap has an amino acid sequence set forth below (SEQ ID NO: 37), and that portion could be used as a monomer or as a non-Fc fusion protein as a monomer, dimer, or greater-order complex.

(SEQ ID NO: 37)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPT

The GDF trap protein was expressed in CHO cell lines. Three different leader sequences were considered:
(i) Honey bee melittin (HBML): MKFLVNVALVFMVVYI-SYIYA (SEQ ID NO:23)
(ii) Tissue plasminogen activator (TPA): MDAMKRGLC-CVLLLCGAVFVSP (SEQ ID NO:24)
(iii) Native: MTAPWVALALLWGSLCAGS (SEQ ID NO:30).

The selected form employs the TPA leader and has the following unprocessed amino acid sequence:

(SEQ ID NO: 38)
MDAMKRGLCCVLLLCGAVFVSPGASGRGEAETRECIYYNANWELERTNQS

GLERCEGEQDKRLHCYASWRNSSGTIELVKKGCWDDDFNCYDRQECVATE

ENPQVYFCCCEGNFCNERFTHLPEAGGPEVTYEPPPTAPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO:68):

```
A TGGATGCAAT GAAGAGAGGG CTCTGCTGTG TGCTGCTGCT
GTGTGGAGCA GTCTTCGTTT CGCCCGGCGC CTCTGGGCGT
GGGGAGGCTG AGACACGGGA GTGCATCTAC TACAACGCCA
ACTGGGAGCT GGAGCGCACC AACCAGAGCG GCCTGGAGCG
CTGCGAAGGC GAGCAGGACA AGCGGCTGCA CTGCTACGCC
TCCTGGCGCA ACAGCTCTGG CACCATCGAG CTCGTGAAGA
AGGGCTGCTG GGACGATGAC TTCAACTGCT ACGATAGGCA
GGAGTGTGTG GCCACTGAGG AGAACCCCCA GGTGTACTTC
TGCTGCTGTG AAGGCAACTT CTGCAACGAG CGCTTCACTC
ATTTGCCAGA GGCTGGGGGC CCGGAAGTCA CGTACGAGCC
ACCCCCGACA GCCCCCACCG GTGGTGGAAC TCACACATGC
CCACCGTGCC CAGCACCTGA ACTCCTGGGG GGACCGTCAG
TCTTCCTCTT CCCCCCAAAA CCCAAGGACA CCCTCATGAT
CTCCCGGACC CCTGAGGTCA CATGCGTGGT GGTGGACGTG
AGCCACGAAG ACCCTGAGGT CAAGTTCAAC TGGTACGTGG
ACGGCGTGGA GGTGCATAAT GCCAAGACAA AGCCGCGGGA
GGAGCAGTAC AACAGCACGT ACCGTGTGGT CAGCGTCCTC
ACCGTCCTGC ACCAGGACTG GCTGAATGGC AAGGAGTACA
AGTGCAAGGT CTCCAACAAA GCCCTCCCAG TCCCCATCGA
GAAAACCATC TCCAAAGCCA AAGGGCAGCC CCGAGAACCA
CAGGTGTACA CCCTGCCCCC ATCCCGGGAG GAGATGACCA
AGAACCAGGT CAGCCTGACC TGCCTGGTCA AAGGCTTCTA
TCCCAGCGAC ATCGCCGTGG AGTGGGAGAG CAATGGGCAG
CCGGAGAACA ACTACAAGAC CACGCCTCCC GTGCTGGACT
CCGACGGCTC CTTCTTCCTC TATAGCAAGC TCACCGTGGA
CAAGAGCAGG TGGCAGCAGG GGAACGTCTT CTCATGCTCC
GTGATGCATG AGGCTCTGCA CAACCACTAC ACGCAGAAGA
GCCTCTCCCT GTCTCCGGGT AAATGA
```

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q-sepharose ion-exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF traps (ActRIIB-Fc fusion proteins modified so as to reduce the ratio of activin A binding relative to myostatin or GDF11 binding) are described in WO 2008/097541 and WO 2006/012627, incorporated by reference herein.

Example 10: Bioassay for GDF-11- and Activin-Mediated Signaling

An A-204 reporter gene assay was used to evaluate the effects of ActRIIB-Fc proteins and GDF traps on signaling by GDF-11 and activin A. Cell line: human rhabdomyosarcoma (derived from muscle). Reporter vector: pGL3 (CAGA)12 (described in Dennler et al, 1998, EMBO 17: 3091-3100). The CAGA12 motif is present in TGF-beta responsive genes (e.g., PAI-1 gene), so this vector is of general use for factors signaling through SMAD2 and 3.

Day 1: Split A-204 cells into 48-well plate.

Day 2: A-204 cells transfected with 10 ug pGL3(CAGA) 12 or pGL3(CAGA)12(10 ug)+pRLCMV (1 µg) and Fugene.

Day 3: Add factors (diluted into medium+0.1% BSA). Inhibitors need to be preincubated with factors for 1 hr before adding to cells. Six hrs later, cells were rinsed with PBS and lysed.

This is followed by a luciferase assay. In the absence of any inhibitors, activin A showed 10-fold stimulation of reporter gene expression and an ED50-2 ng/ml. GDF-11: 16 fold stimulation, ED50: ~1.5 ng/ml.

ActRIIB(20-134) is a potent inhibitor of activin A, GDF-8, and GDF-11 activity in this assay. As described below, ActRIIB variants were also tested in this assay.

Example 11: ActRIIB-Fc Variants, Cell-Based Activity

Activity of ActRIIB-Fc proteins and GDF traps was tested in a cell-based assay as described above. Results are summarized in the table below. Some variants were tested in different C-terminal truncation constructs. As discussed above, truncations of five or fifteen amino acids caused reduction in activity. The GDF traps (L79D and L79E variants) showed substantial loss of activin A inhibition while retaining almost wild-type inhibition of GDF-11.

Soluble ActRIIB-Fc Binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-134 | +++ (approx. $10^{-8}$ M $K_I$) | +++ (approx. $10^{-8}$ M $K_I$) |
| A64 | 20-134 | + (approx. $10^{-6}$ M $K_I$) | + (approx. $10^{-6}$ M $K_I$) |
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64K | 20-134 | +++ | +++ |
| R64K | 20-129 | +++ | +++ |
| R64 P129S P130A | 20-134 | +++ | +++ |
| R64N | 20-134 | + | + |

+ Poor activity (roughly $1 \times 10^{-6}$ $K_I$)
++ Moderate activity (roughly $1 \times 10^{-7}$ $K_I$)
+++ Good (wild-type) activity (roughly $1 \times 10^{-8}$ $K_I$)
++++ Greater than wild-type activity Several variants have been assessed for serum half-life in rats. ActRIIB(20-134)-Fc has a serum half-life of approximately 70 hours. ActRIIB(A24N 20-134)-Fc has a serum half-life of approximately 100-150 hours. The A24N variant has activity in the cell-based assay (above) and in vivo assays (below) that is equivalent to the wild-type molecule. Coupled with the longer half-life, this means that over time an A24N variant will give greater effect per unit of protein than the wild-type molecule. The A24N variant, and any of the other variants tested above, may be combined with the GDF trap molecules, such as the L79D or L79E variants.

Example 12: GDF-11 and Activin A Binding

Binding of certain ActRIIB-Fc proteins and GDF traps to ligands was tested in a Biacore™ assay.

The ActRIIB-Fc variants or wild-type protein were captured onto the system using an anti-hFc antibody. Ligands were injected and flowed over the captured receptor proteins. Results are summarized in the tables below.

Ligand-Binding Specificity IIB Variants.

| | GDF11 | | |
|---|---|---|---|
| Protein | Kon (1/Ms) | Koff (1/s) | KD (M) |
| ActRIIB(20-134)-hFc | 1.34e-6 | 1.13e-4 | 8.42e-11 |
| ActRIIB(A24N 20-134)-hFc | 1.21e-6 | 6.35e-5 | 5.19e-11 |
| ActRIIB(L79D 20-134)-hFc | 6.7e-5 | 4.39e-4 | 6.55e-10 |
| ActRIIB(L79E 20-134)-hFc | 3.8e-5 | 2.74e-4 | 7.16e-10 |
| ActRIIB(R64K 20-134)-hFc | 6.77e-5 | 2.41e-5 | 3.56e-11 |

| | GDF8 | | |
|---|---|---|---|
| Protein | Kon (1/Ms) | Koff (1/s) | KD (M) |
| ActRIIB(20-134)-hFc | 3.69e-5 | 3.45e-5 | 9.35e-11 |
| ActRIIB(A24N 20-134)-hFc | | | |
| ActRIIB(L79D 20-134)-hFc | 3.85e-5 | 8.3e-4 | 2.15e-9 |
| ActRIIB(L79E 20-134)-hFc | 3.74e-5 | 9e-4 | 2.41e-9 |
| ActRIIB(R64K 20-134)-hFc | 2.25e-5 | 4.71e-5 | 2.1e-10 |
| ActRIIB(R64K 20-129)-hFc | 9.74e-5 | 2.09e-4 | 2.15e-9 |
| ActRIIB(P129S, P130R 20-134)-hFc | 1.08e-5 | 1.8e-4 | 1.67e-9 |
| ActRIIB(K74A 20-134)-hFc | 2.8e-5 | 2.03e-5 | 7.18e-11 |

| | Activin A | | |
|---|---|---|---|
| Protein | Kon (1/Ms) | Koff (1/s) | KD (M) |
| ActRIIB(20-134)-hFc | 5.94e6 | 1.59e-4 | 2.68e-11 |
| ActRIIB(A24N 20-134)-hFc | 3.34e6 | 3.46e-4 | 1.04e-10 |
| ActRIIB(L79D 20-134)-hFc | | | Low binding |
| ActRIIB(L79E 20-134)-hFc | | | Low binding |
| ActRIIB(R64K 20-134)-hFc | 6.82e6 | 3.25e-4 | 4.76e-11 |
| ActRIIB(R64K 20-129)-hFc | 7.46e6 | 6.28e-4 | 8.41e-11 |
| ActRIIB(P129S, P130R 20-134)-hFc | 5.02e6 | 4.17e-4 | 8.31e-11 |

These data obtained in a cell-free assay confirm the cell-based assay data, demonstrating that the A24N variant retains ligand-binding activity that is similar to that of the ActRIIB(20-134)-hFc molecule and that the L79D or L79E molecule retains myostatin and GDF11 binding but shows markedly decreased (non-quantifiable) binding to activin A.

Other variants have been generated and tested, as reported in WO2006/012627 (incorporated herein by reference in its entirety). See, e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of activin A (ActA) binding to GDF11 binding, relative to the wild-type K74 molecule. A table of data with respect to these variants is reproduced below:

Soluble ActRIIB-Fc Variants Binding to GDF11 and Activin A (Biacore™ Assay)

| ActRIIB | ActA | GDF11 |
|---|---|---|
| WT (64A) | KD = 1.8e-7M (+) | KD = 2.6e-7M (+) |
| WT (64R) | na | KD = 8.6e-8M (+++) |
| +15tail | KD~2.6e-8M (+++) | KD = 1.9e-8M (++++) |
| E37A | * | * |
| R40A | − | − |
| D54A | − | * |
| K55A | ++ | * |
| R56A | * | * |
| K74A | KD = 4.35e-9M +++++ | KD = 5.3e-9M +++++ |
| K74Y | * | −− |
| K74F | * | −− |
| K74I | * | −− |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | −− |
| F82A | ++ | − |

* No observed binding
−− <1/5 WT binding
− ~1/2 WT binding
+ WT
++ <2x increased binding
+++ ~5x increased binding
++++ ~10x increased binding
+++++ ~40x increased binding Example 13: A GDF Trap Increases Red Blood Cell Levels In Vivo Twelve-week-old male C57BL/6NTac mice were assigned to one of two treatment groups (N=10). Mice were dosed with either vehicle or with a variant ActRIIB polypeptide ("GDF trap") [ActRIIB(L79D 20-134)-hFc] by subcutaneous injection (SC) at 10 mg/kg twice per week for 4 weeks. At study termination, whole blood was collected by cardiac puncture into EDTA containing tubes and analyzed for cell distribution using an HM2 hematology analyzer (Abaxis, Inc).

Group Designation

| Group | N | Mice | Injection | Dose (mg/kg) | Route | Frequency |
|---|---|---|---|---|---|---|
| 1 | 10 | C57BL/6 | PBS | 0 | SC | Twice/week |
| 2 | 10 | C57BL/6 | GDF trap [ActRIIB(L79D 20-134)-hFc] | 10 | SC | Twice/week |

Treatment with the GDF trap did not have a statistically significant effect on the number of white blood cells (WBC) compared to the vehicle controls. Red blood cell (RBC) numbers were increased in the treated group relative to the controls (see table below). Both the hemoglobin content (HGB) and hematocrit (HCT) were also increased due to the additional red blood cells. The average width of the red blood cells (RDWc) was higher in the treated animals, indicating an increase in the pool of immature red blood cells. Therefore, treatment with the GDF trap leads to increases in red blood cells, with no distinguishable effects on white blood cell populations.

Hematology Results

| | RBC $10^{12}$/L | HGB (g/dL) | HCT (%) | RDWc (%) |
|---|---|---|---|---|
| PBS | 10.7 ± 0.1 | 14.8 ± 0.6 | 44.8 ± 0.4 | 17.0 ± 0.1 |
| GDF trap | 12.4 ± 0.4** | 17.0 ± 0.7* | 48.8 ± 1.8* | 18.4 ± 0.2** |

\* = p < 0.05,
\*\* = p < 0.01

Example 14: A GDF Trap is Superior to ActRIIB-Fc for Increasing Red Blood Cell Levels in Vivo Nineteen-week-old male C57BL/6NTac mice were randomly assigned to one of three groups. Mice were dosed with vehicle (10 mM Tris-buffered saline, TBS), wild-type ActRIIB(20-134)-mFc, or GDF trap ActRIIB(L79D 20-134)-hFc by subcutaneous injection twice per week for three weeks. Blood was collected by cheek bleed at baseline and after three weeks of dosing and analyzed for cell distribution using a hematology analyzer (HM2, Abaxis, Inc.)

Treatment with ActRIIB-Fc or the GDF trap did not have a significant effect on white blood cell (WBC) numbers compared to vehicle controls. The red blood cell count (RBC), hematocrit (HCT), and hemoglobin levels were all elevated in mice treated with GDF trap compared to either the controls or the wild-type construct (see table below). Therefore, in a direct comparison, the GDF trap promotes increases in red blood cells to a significantly greater extent than a wild-type ActRIIB-Fc protein. In fact, in this experiment, the wild-type ActRIIB-Fc protein did not cause a statistically significant increase in red blood cells, suggesting that longer or higher dosing would be needed to reveal this effect.

Hematology Results after Three Weeks of Dosing

| | RBC ($10^{12}$/ml) | HCT % | HGB g/dL |
|---|---|---|---|
| TBS | 11.06 ± 0.46 | 46.78 ± 1.9 | 15.7 ± 0.7 |
| ActRIIB-mFc | 11.64 ± 0.09 | 49.03 ± 0.3 | 16.5 ± 1.5 |
| GDF trap | 13.19 ± 0.2** | 53.04 ± 0.8** | 18.4 ± 0.3** |

\*\* = p < 0.01

Example 15: Generation of a GDF Trap with Truncated ActRIIB Extracellular Domain As described in Example 9, a GDF trap referred to as ActRIIB(L79D 20-134)-hFc was generated by N-terminal fusion of TPA leader to the ActRIIB extracellular domain (residues 20-134 in SEQ ID NO:1) containing a leucine-to-aspartate substitution (at residue 79 in SEQ ID NO:1) and C-terminal fusion of human Fc domain with minimal linker (three glycine residues) (FIG. 16). A nucleotide sequence corresponding to this fusion protein is shown in FIGS. 17A and 17B.

A GDF trap with truncated ActRIIB extracellular domain, referred to as ActRIIB(L79D 25-131)-hFc, was generated by N-terminal fusion of TPA leader to truncated extracellular domain (residues 25-131 in SEQ ID NO:1) containing a leucine-to-aspartate substitution (at residue 79 in SEQ ID NO:1) and C-terminal fusion of human Fc domain with minimal linker (three glycine residues) (FIG. 18). A nucleotide sequence corresponding to this fusion protein is shown in FIGS. 19A and 19B.

Example 16: Selective Ligand Binding by GDF Trap with Double-Truncated ActRIIB Extracelluar Domain The affinity of GDF traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e−11) | Activin B (Kd e−11) | GDF11 (Kd e−11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF trap with a truncated extracellular domain, ActRIIB(L79D 25-131)-hFc, equaled or surpassed the ligand selectivity displayed by the longer variant, ActRIIB (L79D 20-134)-hFc, with pronounced loss of activin A binding, partial loss of activin B binding, and nearly full retention of GDF11 binding compared to ActRIIB-hFc counterparts lacking the L79D substitution. Note that truncation alone (without L79D substitution) did not alter selectivity among the ligands displayed here [compare ActRIIB (L79 25-131)-hFc with ActRIIB(L79 20-134)-hFc].

Example 17: Generation of ActRIIB(L79D 25-131)-hFc with Alternative Nucleotide Sequences To generate ActRIIB(L79D 25-131)-hFc, the human ActRIIB extracellular domain with an aspartate substitution at native position 79 (SEQ ID NO:1) and with N-terminal and C-terminal truncations (residues 25-131 in SEQ ID NO: 1) was fused N-terminally with a TPA leader sequence instead of the native ActRIIB leader and C-terminally with a human Fc domain via a minimal linker (three glycine residues) (FIG. 18). One nucleotide sequence encoding this fusion protein is shown in FIGS. 19A and 19B (SEQ ID NO: 42), and an alternative nucleotide sequence encoding exactly the same fusion protein is shown in FIGS. 22A and 22B (SEQ ID NO: 46). This protein was expressed and purified using the methodology described in Example 9.

Example 18: GDF Trap with a Truncated ActRIIB Extracellular Domain Increases Proliferation of Erythroid Progenitors in Mice ActRIIB(L79D 25-131)-hFc was evaluated to determine its effect on proliferation of erythroid progenitors. Male C57BL/6 mice (8 weeks old) were treated with ActRIIB (L79D 25-131)-hFc (10 mg/kg, s.c.; n=6) or vehicle (TBS; n=6) on Days 1 and 4, then euthanized on Day 8 for collection of spleens, tibias, femurs, and blood. Cells of the spleen and bone marrow were isolated, diluted in Iscove's modified Dulbecco's medium containing 5% fetal bovine serum, suspended in specialized methylcellulose-based medium, and cultured for either 2 or 12 days to assess levels of clonogenic progenitors at the colony-forming unit-erythroid (CFU-E) and burst forming unit-erythroid (BFU-E) stages, respectively. Methylcellulose-based medium for BFU-E determination (MethoCult M3434, Stem Cell Technologies) included recombinant murine stem cell factor, interleukin-3, and interleukin-6, which were not present in methylcellulose medium for CFU-E determination (MethoCult M3334, Stem Cell Technologies), while both media contained erythropoietin, among other constituents. For both BFU-E and CFU-E, the number of colonies were determined in duplicate culture plates derived from each tissue sample, and statistical analysis of the results was based on the number of mice per treatment group.

Spleen-derived cultures from mice treated with ActRIIB (L79D 25-131)-hFc had twice the number of CFU-E colonies as did corresponding cultures from control mice (P<0.05), whereas the number of BFU-E colonies did not differ significantly with treatment in vivo. The number of CFU-E or BFU-E colonies from bone marrow cultures also did not differ significantly with treatment. As expected, increased numbers of CFU-E colonies in spleen-derived cultures were accompanied by highly significant (P<0.001) changes in red blood cell level (11.6% increase), hemoglobin concentration (12% increase), and hematocrit level (11.6% increase) at euthanasia in mice treated with ActRIIB (L79D 25-131)-hFc compared to controls. These results indicate that in vivo administration of a GDF trap with truncated ActRIIB extracellular domain can stimulate proliferation of erythroid progenitors as part of its overall effect to increase red blood cell levels.

GDF trap fusion proteins have been further demonstrated to be effective in increasing red blood cell levels in various models of anemia including, for example, chemotherapy-induced anemia, nephrectomy-induced anemia, and in a blood loss anemia (see, e.g., International Patent Application Publication No. WO 2010/019261).

Figure 24:
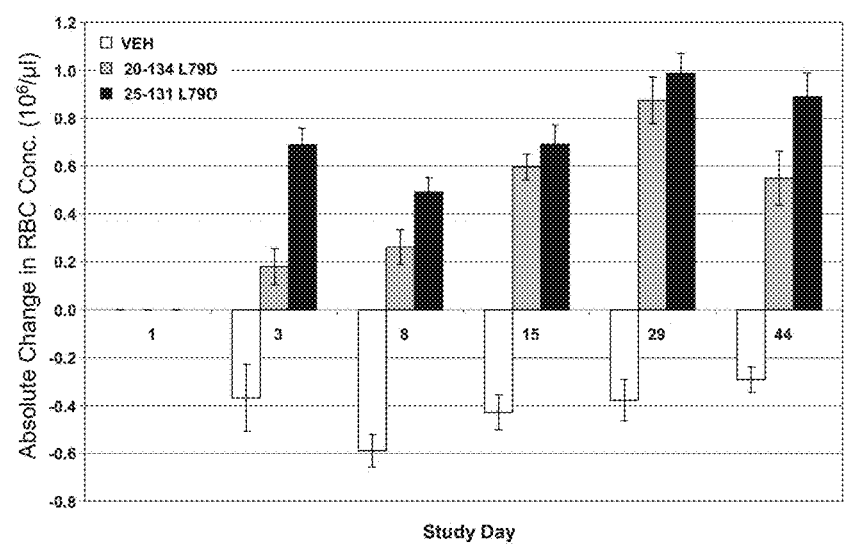
FIG. 24 shows the effect of treatment with ActRIIB(L79D 20-134)-hFc (gray) or ActRIIB(L79D 25-131)-hFc (black) on the absolute change in red blood cell concentration from baseline in cynomolgus monkey. VEH=vehicle. Data are means±SEM. n=4-8 per group.
Figure 25:
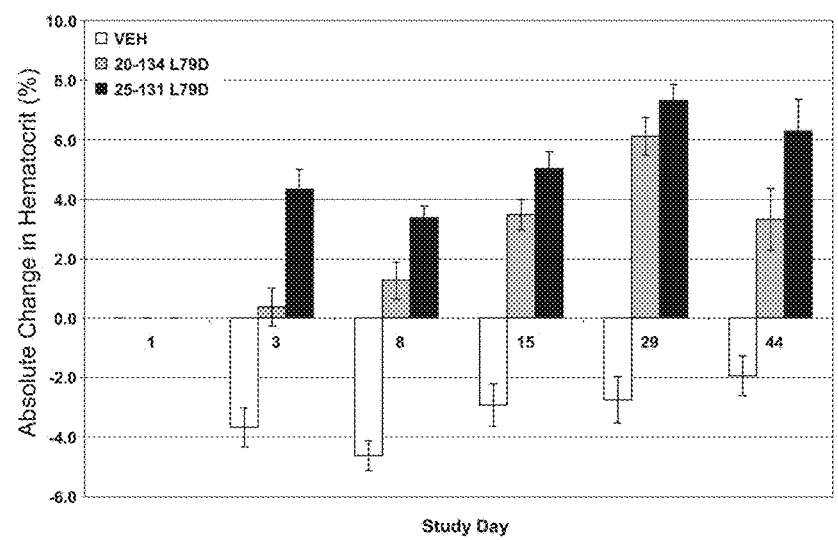
FIG. 25 shows the effect of treatment with ActRIIB(L79D 20-134)-hFc (gray) or ActRIIB(L79D 25-131)-hFc (black)

Example 19: GDF Trap with Truncated ActRIIB Extracellular Domain Increases Levels of Red Blood Cells in Non-Human Primates Two GDF Traps, ActRIIB(L79D 20-134)-hFc and ActRIIB(L79D 25-131)-hFc, were evaluated for their ability to stimulate red blood cell production in cynomolgus monkeys. Monkeys were treated subcutaneously with GDF trap (10 mg/kg; n=4 males/4 females), or vehicle (n=2 males/2 females) on Days 1 and 8. Blood samples were collected on Days 1 (pretreatment baseline), 3, 8, 15, 29, and 44, and were analyzed for red blood cell levels (FIG. 24), hematocrit (FIG. 25), hemoglobin levels (FIG. 26), and reticulocyte levels (FIG. 27). Vehicle-treated monkeys exhibited decreased levels of red blood cells, hematocrit, and hemoglobin at all post-treatment time points, an expected effect of repeated blood sampling. In contrast, treatment with ActRIIB(L79D 20-134)-hFc or ActRIIB(L79D 25-131)-hFc increased these parameters by the first post-treatment time point (Day 3) and maintained them at substantially elevated levels for the duration of the study (FIGS. 24-26). Importantly, reticulocyte levels in monkeys treated with ActRIIB (L79D 20-134)-hFc or ActRIIB(L79D 25-131)-hFc were substantially increased at Days 8, 15, and 29 compared to vehicle (FIG. 27). This result demonstrates that GDF trap treatment increased production of red blood cell precursors, resulting in elevated red blood cell levels.

Taken together, these data demonstrate that truncated GDF traps, as well as a full-length variants, can be used as selective antagonists of GDF11 and potentially related ligands to increase red blood cell formation in vivo.

Example 20: GDF Trap Derived from ActRIIB5

Others have reported an alternate, soluble form of ActRIIB (designated ActRIIB5), in which exon 4, including the ActRIIB transmembrane domain, has been replaced by a different C-terminal sequence (see, e.g., WO 2007/053775).

The sequence of native human ActRIIB5 without its leader is as follows:

```
                                     (SEQ ID NO: 49)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEGPWASTTIPSGGPEATAAAGDQGSGALWLCLEGPAHE
```

An leucine-to-aspartate substitution, or other acidic substitutions, may be performed at native position 79 (underlined) as described to construct the variant ActRIIB5(L79D), which has the following sequence:

```
                                     (SEQ ID NO: 50)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE
```

This variant may be connected to human Fc (double underline) with a TGGG linker (single underline) to generate a human ActRIIB5(L79D)-hFc fusion protein with the following sequence:

```
                                     (SEQ ID NO: 51)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHETGGGTHTCP

PCPAPELLGGPSVFLFPPKPKDTLMISRTPEVTCVVVDVSHEDPEVKFNW
```

-continued

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK.

This construct may be expressed in CHO cells.

Example 21: Effects in Mice of Combined Treatment with EPO and a GDF Trap with a Truncated ActRIIB Extracellular Domain EPO induces formation of red blood cells by increasing the proliferation of erythroid precursors, whereas GDF traps could potentially affect formation of red blood cells in ways that complement or enhance EPO's effects. Therefore, Applicants investigated the effect of combined treatment with EPO and ActRIIB(L79D 25-131)-hFc on erythropoietic parameters. Male C57BL/6 mice (9 weeks old) were given a single i.p. injection of recombinant human EPO alone (epoetin alfa, 1800 units/kg), ActRIIB(L79D 25-131)-hFc alone (10 mg/kg), both EPO and ActRIIB(L79D 25-131)-hFc, or vehicle (Tris-buffered saline). Mice were euthanized 72 h after dosing for collection of blood, spleens, and femurs.

Spleens and femurs were processed to obtain erythroid precursor cells for flow cytometric analysis. After removal, the spleen was minced in Iscove's modified Dulbecco's medium containing 5% fetal bovine serum and mechanically dissociated by pushing through a 70-μm cell strainer with the plunger from a sterile 1-mL syringe. Femurs were cleaned of any residual muscle or connective tissue and ends were trimmed to permit collection of marrow by flushing the remaining shaft with Iscove's modified Dulbecco's medium containing 5% fetal bovine serum through a 21-gauge needle connected to a 3-mL syringe. Cell suspensions were centrifuged (2000 rpm for 10 min) and the cell pellets resuspended in PBS containing 5% fetal bovine serum. Cells ($10^6$) from each tissue were incubated with anti-mouse IgG to block nonspecific binding, then incubated with fluorescently labeled antibodies against mouse cell-surface markers CD71 (transferrin receptor) and Ter119 (an antigen associated with cell-surface glycophorin A), washed, and analyzed by flow cytometry. Dead cells in the samples were excluded from analysis by counterstaining with propidium iodide. Erythroid differentiation in spleen or bone marrow was assessed by the degree of CD71 labeling, which decreases over the course of differentiation, and Ter119 labeling, which is increased during terminal erythroid differentiation beginning with the proerythroblast stage (Socolovsky et al., 2001, Blood 98:3261-3273; Ying et al., 2006, Blood 108:123-133). Thus, flow cytometry was used to determine the number of proerythroblasts ($CD71^{high}Ter119^{low}$), basophilic erythroblasts ($CD71^{high}Ter119^{high}$), polychromatophilic+orthochromatophilic erythroblasts ($CD71^{med}Ter119^{high}$), and late orthochromatophilic erythroblasts+reticulocytes ($CD71^{low}Ter119^{high}$), as described.

Combined treatment with EPO and ActRIIB(L79D 25-131)-hFc led to a surprisingly vigorous increase in red blood cells. In the 72-h time frame of this experiment, neither EPO nor ActRIIB(L79D 25-131)-hFc alone increased hematocrit significantly compared to vehicle, whereas combined treatment with the two agents led to a nearly 25% increase in hematocrit that was unexpectedly synergistic, i.e., greater than the sum of their separate effects (FIG. 28). Synergy of this type is generally considered evidence that individual agents are acting through different cellular mechanisms. Similar results were also observed for hemoglobin concentrations (FIG. 29) and red blood cell concentrations (FIG. 30), each of which was also increased synergistically by combined treatment.

Analysis of erythroid precursor levels revealed a more complex pattern. In the mouse, the spleen is considered the primary organ responsible for inducible ("stress") erythropoiesis. Flow cytometric analysis of splenic tissue at 72 h revealed that EPO markedly altered the erythropoietic precursor profile compared to vehicle, increasing the number of basophilic erythroblasts by more than 170% at the expense of late precursors (late orthochromatophilic erythroblasts+reticulocytes), which decreased by more than one third (FIG. 31). Importantly, combined treatment increased basophilic erythroblasts significantly compared to vehicle, but to a lesser extent than EPO alone, while supporting undiminished maturation of late-stage precursors (FIG. 31). Thus, combined treatment with EPO and ActRIIB(L79D 25-131)-hFc increased erythropoiesis through a balanced enhancement of precursor proliferation and maturation. In contrast to spleen, the precursor cell profile in bone marrow after combined treatment did not differ appreciably from that after EPO alone. Applicants predict from the splenic precursor profile that combined treatment would lead to increased reticulocyte levels and would be accompanied by sustained elevation of mature red blood cell levels if the experiment were extended beyond 72 h.

Taken together, these findings demonstrate that a GDF trap with a truncated ActRIIB extracellular domain can be administered in combination with EPO to synergistically increase red blood cell formation in vivo. Acting through a complementary but undefined mechanism, a GDF trap can moderate the strong proliferative effect of an EPO receptor activator alone and still permit target levels of red blood cells to be attained with lower doses of an EPO receptor activator, thereby avoiding potential adverse effects or other problems associated with higher levels of EPO receptor activation.

Example 22: Effect of a GDF Trap on Ineffective Erythropoiesis and Anemia in a Mouse Model of MDS Applicants investigated effects of the GDF trap ActRIIB(L79D 25-131)-mFc (RAP-536) in the NUP98-HOXD13 mouse model of MDS, which is characterized by abortive precursor maturation and ineffective hematopoiesis. In this model, disease severity increases with age, eventually progressing to acute myeloid leukemia in the majority of mice, and they have a mean life span of approximately 14 months. Starting at approximately 4 months of age, these mice exhibit anemia, leukopenia, ineffective erythropoiesis, and bone marrow that is normocellular to hypercellular [Lin et al. (2005) Blood 106:287-295]. To monitor the effects of chronic administration, MDS mice were treated with RAP-536 (10 mg/kg, s.c.) or vehicle twice weekly beginning at 4 months of age and continuing for 7 months, while blood samples (50 μL) were collected at baseline and monthly thereafter for complete blood count analysis. As expected, 6-month-old MDS mice developed severe anemia compared to wild-type mice (FIG. 32A), and bone marrow analyses revealed increased numbers of erythroid precursors (FIG. 32A) and a lower myeloid/erythroid (M/E) ratio [Suragani et al. (2014) Nat Med 20:408-414] in MDS mice compared to age-matched FVB wild-type mice, indicative of ineffective erythropoiesis. In 6-month-old MDS mice, treatment with RAP-536 significantly increased RBC count (by 16.9%) and hemoglobin concentration (by 12.5%) (FIG. 32A), reduced erythroid precursor cell count in bone marrow (FIG. 32A), and normalized the M/E ratio to that of wild-type mice [Suragani et al. (2014) Nat Med 20:408-414].

In MDS mice at 12 months of age, RAP-536 treatment significantly increased RBC count (by 18.3%) and hemoglobin level (by 13.0%) (FIG. 32B), reduced erythroid precursor cell count (FIG. 32B), and improved the M:E ratio [Suragani et al. (2014) Nat Med 20:408-414], as compared to vehicle. RAP-536 treatment did not affect the absolute number of myeloid precursors. Flow cytometry confirmed that RAP-536 treatment reduced erythroid hyperplasia in MDS mice at both ages. A time-course analysis in MDS mice treated with RAP-536 for 7 months showed a sustained elevation in RBC numbers for the duration of the study [Suragani et al. (2014) Nat Med 20:408-414]. Together, these results indicate that treatment with a GDF trap ameliorates anemia, erythroid hyperplasia and ineffective erythropoiesis in MDS mice regardless of disease severity.

Example 23: Cytologic and Genetic Signatures in MDS Patients Therapeutically Responsive to a GDF Trap A recombinant fusion protein containing modified activin receptor type IIB and IgG Fc [ActRIIB(L79D 25-131)-hFc, also known as luspatercept or ACE-536] is being developed for the treatment of anemias due to ineffective erythropoiesis such as myelodysplastic syndromes (MDS). Patients with MDS often have elevated levels of EPO and may be non-responsive or refractory to erythropoiesis-stimulating agents (ESAs). MDS patients have also been shown to have increased serum levels of GDF11 [Suragani et al. (2014) Nat Med 20:408-414] and increased Smad 2/3 signaling in the bone marrow [Zhou et al. (2008) Blood 112:3434-3443]. ActRIIB(L79D 25-131)-hFc binds to ligands in the TGFβ superfamily, including GDF11, inhibits Smad2/3 signaling, and promotes late-stage erythroid differentiation via a mechanism distinct from ESAs. A murine version, ActRIIB (L79D 25-131)-mFc, reduced Smad2 signaling, increased hemoglobin (Hb) levels, and decreased bone marrow erythroid hyperplasia in a mouse model of MDS [Suragani et al. (2014) Nat Med 20:408-414]. In a healthy-volunteer study, ActRIIB(L79D 25-131)-hFc was well-tolerated and increased Hb levels [Attie et al. (2014) Am J Hematol 89:766-770].

Applicants are conducting an ongoing, phase 2, multicenter, open-label, dose-finding study to evaluate the effects of ActRIIB(L79D 25-131)-hFc on anemia in patients with Low or Int-1 risk MDS who have either high transfusion burden (HTB, defined as ≥4 units RBC per 8 weeks prior to baseline) or low transfusion burden (LTB, defined as <4 units RBC per 8 weeks prior to baseline). Study outcomes include erythroid response (either Hb increase in LTB patients or reduced transfusion burden in HTB patients), safety, tolerability, pharmacokinetics, and pharmacodynamic biomarkers. Inclusion criteria include: Low or Int-1 risk MDS, age≥18 yr, anemia (defined as either being HTB patient or having baseline Hb<10.0 g/dL in LTB patient), EPO>500 U/L or nonresponsive/refractory to ESAs, no prior azacitidine or decitabine, and no current treatment with ESA, granulocyte colony-stimulating factor (G-CSF), granulocyte-macrophage colony-stimulating factor (GM-CSF), or lenalidomide, thalidomide or pomalidomide. In the dose-escalation phase, ActRIIB(L79D 25-131)-hFc was administered by subcutaneous injection once every 3 weeks in seven sequential cohorts (n=3-6) at dose levels of 0.125, 0.25, 0.5, 0.75, 1.0, 1.33 and 1.75 mg/kg for up to 5 doses with a 3-month follow-up.

Data were available for 26 patients (seven LTB/19 HTB). Median age was 71 yr (range: 27-88 yr), 50% were female, 54% had prior EPO therapy, and 15% had prior lenalidomide. Patient classification by WHO subtype was as follows: 15% RARS, 46% RCMD-RS, 15% RCMD, 15% RAEB-1 (including two patients with ≥15% ring sideroblasts) and 8% del (5q). Mean (SD) baseline Hgb for the LTB patients (n=7) was 9.1 (0.4) g/dL. Mean (SD) units RBC transfused in the 8 weeks prior to treatment was 0.9 (1.1) units for the LTB patients and 6.3 (2.4) units for the HTB patients. Two of the seven LTB patients had an increase in mean Hb≥1.5 g/dL over 8 weeks compared to baseline. Mean maximum Hb increase in the LTB patients was 0.8, 1.0, 2.2, and 3.5 g/dL in the 0.125 (n=1), 0.25 (n=1), 0.75 (n=3), and 1.75 (n=2) mg/kg dose groups, respectively. Six of the seven LTB patients achieved RBC transfusion independence (RBC-TI) for ≥8 weeks during the study. The dose levels ranging from 0.75 mg/kg to 1.75 mg/kg were deemed to be active doses. Among the five patients in the active dose groups, four (80%) achieved the pre-specified endpoint of Hgb increase of ≥1.5 g/dl for ≥2 weeks. Two patients (40%) achieved a HI-E response [International Working Group; Cheson et al. (2000) Blood 96:3671-3674; Cheson et al. (2006) Blood 108:419-425], defined as an Hgb increase of ≥1.5 g/dl for ≥8 weeks in LTB patients. In HTB patients, the HI-E response is defined as a reduction in transfusion burden of at least four units of red blood cells transfused over an 8 week period as compared to the 8 weeks prior to study start. In the active dose groups, five of 12 (42%) HTB patients met the pre-specified endpoint of a reduction of ≥4 RBC units or ≥50% reduction in RBC units transfused over an 8-week interval during the treatment period compared to the 8 weeks prior to treatment, and the same patients (five of 12, 42%) achieved a HI-E response; three of 12 (25%) of HTB patients in the active dose groups achieved RBC-TI≥8 weeks during the study. Increases in neutrophil count following study drug administration were observed in some patients. Finally, ActRIIB(L79D 25-131)-hFc was generally well tolerated. No related serious adverse events have been reported to date. The most frequent adverse events regardless of causality were: diarrhea (n=4, grade 1/2), bone pain, fatigue, muscle spasms, myalgia, and nasopharyngitis (n=3 each, grade 1/2).

Assessment of bone marrow aspirates demonstrated an association between the presence of ring sideroblasts (considered positive if ≥15% of erythroid precursors exhibited ring sideroblast morphology) and responsiveness to ActRIIB (L79D 25-131)-hFc in the active dose groups (0.75-1.75 mg/kg). The overall response rate (using HI-E criteria, described above) across both LTB and HTB patients was seven of 17 (41%). Among patients positive for ring sideroblasts at baseline, seven of 13 (54%) patients achieved a HI-E response, and notably none of the four patients negative for ring sideroblasts at baseline achieved a HI-E response.

Bone marrow aspirates from patients were also evaluated for the presence of mutations in 21 different genes that are known to harbor mutations (primarily somatic mutations) associated with MDS. Genomic DNA was isolated from bone marrow aspirates, selected coding regions of the 21 genes were amplified by polymerase chain reaction, and the DNA sequences of these regions were determined using next-generation sequencing (Myeloid Molecular Profile 21-gene panel, Genoptix, Inc., Carlsbad, Calif.). This analysis examined activated signaling genes (KIT, JAK2, NRAS, CBL, and MPL), transcription factors (RUNX1, ETV6), epigenetic genes (IDH1, IDH2, TET2, DNMT3A, EZH2, ASXL1, and SETBP1), RNA splicing genes (SF3B1, U2AF1, ZRSR2, and SRSF2), and tumor suppressors/others (TP53, NPM1, PHF6). Analysis of SF3B1 specifically targeted exons 13-16. Of these 21 MDS-associated genes evaluated, mutations in SF3B1 were more frequently detected in bone marrow cells in the responsive patients than in the nonresponsive patients. Individual SF3B1 mutations detected in these patients are shown in the following table. The same mutation sometimes occurred in multiple patients.

| Nucleotide | Nucleotide Substitution | Amino Acid Substitution | Exon |
|---|---|---|---|
| 1873 | C → T | R625C | 14 |
| 1874 | G → T | R625L | 14 |
| 1986 | C → G | H662Q | 14 |
| 2098 | A → G | K700E | 15 |
| 2342 | A → G | D781G | 16 |

In patients with SF3B1 mutations in the active dose groups, six of nine (67%) achieved HI-E responses, including all three patients that achieved transfusion independence for greater than 8 weeks. In patients not having an SF3B1 mutation, only one of eight (13%) achieved a HI-E response. Mutations in SF3B1 are frequently observed in MDS patients with ring sideroblasts and are associated with ineffective erythropoiesis.

The initial analysis of the clinical trial in process, presented above, was confirmed in a later analysis, for which data were available for 44 patients (15 LTB/29 HTB). Median age was 71 yr (range: 27-88 yr), 43% were female, 61% had prior EPO therapy, and 21% had prior lenalidomide. Mean baseline Hgb for the LTB patients (n=15) was 9.0 (range: 6.8-10.1) g/dL. Mean units RBC transfused in the 8 weeks prior to treatment was 2 (range 2-2) units for the 6 LTB patients that received transfusions and 6 (range: 4-14) units for the HTB patients. The dose levels ranging from 0.75 mg/kg to 1.75 mg/kg were deemed to be active doses. Among the 35 LTB and HTB patients in the active dose groups, 22 (63%) achieved the pre-specified endpoint of Hgb increase of ≥1.5 g/dl for ≥2 weeks for LTB patients and ≥4 unit or 50% reduction in transfusions over 8 weeks for HTB patients. 19 of 35 patients (54%) in the active dose groups achieved a HI-E response [International Working Group; Cheson et al. (2000) Blood 96:3671-3674; Cheson et al. (2006) Blood 108:419-425], defined as an Hgb increase of ≥1.5 g/dl for ≥8 weeks in LTB patients and defined as a reduction of ≥4 RBC units or ≥50% reduction in RBC units transfused over an 8-week interval during the treatment period compared to the 8 weeks prior to treatment in HTB patients. 10/28 (36%) patients in the active dose groups that had baseline transfusions achieved transfusion independence for a period of at least 8 weeks. Assessment of bone marrow aspirates demonstrated an association between the presence of ring sideroblasts (considered positive if ≥15% of erythroid precursors exhibited ring sideroblast morphology) or a mutation in the SF3B1 gene and responsiveness to ActRIIB(L79D 25-131)-hFc in the active dose groups (0.75-1.75 mg/kg). The overall response rate (using HI-E criteria, described above) across both LTB and HTB patients was 19/35 (54%). Among patients positive for ring sideroblasts at baseline, 19/30 (63%) patients achieved a HI-E response, and notably none of the four patients negative for ring sideroblasts at baseline achieved a HI-E response. Among patients positive for SF3B1 mutation at baseline, 16/22 (73%) patients achieved a HI-E response, and notably only 3/13 (23%) patients negative for SF3B1 mutation at baseline achieved a HI-E response. Finally, ActRIIB(L79D 25-131)-hFc was generally well tolerated. The most frequent adverse events regardless of causality were: diarrhea, nasopharyngitis, myalgia, bone pain, bronchitis, headache and and muscle spasms. Two possibly related serious adverse events (SAEs) were reported: grade 3 muscle pain; grade 3 worsening of general condition. One possibly related non-serious grade 3 adverse event of blast cell count increase was reported.

A further data assessment conducted at a later date extended and generally confirmed the above results. Overall, 24 of 49 patients (49%) in the active dose groups achieved an HI-E response, defined in patients with low-transfusion burden (LTB) as an increase in hemoglobin concentration of ≥1.5 g/dL for ≥8 weeks and defined in patients with high-transfusion burden (HTB) as a reduction of ≥4 RBC units, or a reduction of ≥50% RBC units, transfused over an 8-week interval during the treatment period compared to the 8 weeks prior to treatment. Fourteen of 40 patients (35%) in the active dose groups that had baseline transfusions achieved transfusion independence for a period of at least 8 weeks.

An assessment of response rate in the presence of certain somatic gene mutations was also conducted for patients in the active dose groups. Mutations in SF3B1 were detected more frequently in bone marrow cells from the responsive patients than from the nonresponsive patients. Eighteen of 30 patients (60%) in the active dose groups with an SF3B1 mutation achieved an HI-E response, whereas only 6 of 19 such patients (32%) without a mutation detected in this gene achieved an HI-E response. Individual SF3B1 mutations detected in these patients are shown in the following table. The same mutation sometimes occurred in multiple patients.

| Nucleotide | Nucleotide Change | AA Change | Exon |
|---|---|---|---|
| 1868 | A → G | Y623C | 14 |
| 1873 | C → T | R625C | 14 |
| 1874 | G → T | R625L | 14 |
| 1986 | C → G | H662Q | 14 |
| 2098 | A → G | K700E | 15 |
| 2342 | A → G | D781G | 16 |
| 2347 | G → A | E783K | 16 |

Similarly, mutations in DNMT3A were detected more frequently in bone marrow cells from responsive patients in the active dose groups than from the nonresponsive patients. Seven of 11 patients (64%) in the active dose groups with a DNMT3A mutation achieved an HI-E response, whereas 17 of 38 such patients (45%) without a mutation detected in this gene achieved an HI-E response. Individual DNMT3A mutations detected in these patients are shown in the following table (IVS refers to intronic mutations and X indicates formation of a premature stop codon).

| Nucleotide | Nucleotide Change | AA Change | Exon |
|---|---|---|---|
| 1308 | C → A | Y436X | 10 |
| IVS 2082 | +2 T → C | — | — |
| 2193_2195 | del CTT | In frame | 18 |
| 2216 | del A | Frame shift | 18 |
| IVS 2322 | +2 T → C | — | — |
| 2644 | C → T | R882C | 22 |

| Nucleotide | Nucleotide Change | AA Change | Exon |
|---|---|---|---|
| 2645 | G → A | R882H | 22 |
| 2678 | G → A | W893X | 22 |
| 2711 | C → T | P904L | 22 |
| 2714 | T → C | L905P | 22 |

Similarly, mutations in TET2 were detected more frequently in bone marrow cells from responsive patients in the active dose groups than from the nonresponsive patients. Eleven of 20 patients (55%) in the active dose groups with a TET2 mutation achieved an HI-E response, whereas 13 of 29 such patients (45%) without a mutation detected in this gene achieved an HI-E response. Individual TET2 mutations detected in these patients (excluding known polymorphisms) are shown in the following table.

| Nucleotide | Nucleotide Change | AA Change | Exon |
|---|---|---|---|
| 73 | del T | Frame shift | 1 |
| 139 | G → C | E47Q | 1 |
| 735 | del C | Frame shift | 1 |
| 1201_1202 | ins ACCACCACCAC | Frame shift | 1 |
| 1337 | del T | Frame shift | 1 |
| 1588_1591 | del CAGC | Frame shift | 1 |
| 1648 | C → T | R550X | 1 |
| 1842_1843 | ins G | Frame shift | 1 |
| 2145 | del C | Frame shift | 1 |
| 2305 | del C | Frame shift | 1 |
| 2784 | del T | Frame shift | 1 |
| 3025 | C → T | Q1009X | 1 |
| 3727_3729 | del AAA | In frame | 4 |
| 3731_3738 | del TCTACTCG | Frame shift | 4 |
| 3821 | A → G | Q1274R | 5 |
| 3854_3856 | del TCT | In frame | 5 |
| 3871 | T → A | W1291R | 5 |
| IVS 3955 | −2A → G | — | — |
| 4011 | T → A | Y1337X | 6 |
| 4108 | G → A | G1370R | 7 |
| 4109 | G → A | G1370E | 7 |
| 4160 | A → G | N1387S | 7 |
| 4209 | del T | Frame shift | 8 |
| 4210 | C → T | R1404X | 8 |
| 4211_4217 | del GAGAATT | Frame shift | 8 |
| 4546 | C → T | R1516X | 9 |
| 4954 | C → T | Q1652X | 9 |
| 5168 | del C | Frame shift | 9 |
| 5170 | T → C | Y1724H | 9 |
| 5576_5582 | del TTGGGGG | Frame shift | 9 |

Mutations in other genes were detected in bone marrow cells from responsive patients with a frequency similar to that in cells from nonresponsive patients. For example, 4 of 8 patients (50%) in the active dose groups with an ASXL1 mutation achieved an HI-E response, while a similar percentage of such patients (20 of 41, 49%) without a mutation detected in this gene achieved an HI-E response.

These results indicate that patients with MDS exhibiting ≥15% ring sideroblasts (and patients with other forms of sideroblastic anemia) and/or at least one mutation in SF3B1 are more likely to respond therapeutically to ActRIIB(L79D 25-131)-hFc than MDS patients with <15% ring sideroblasts and/or no mutation in SF3B1. Similarly, patients exhibiting exhibiting ≥15% ring sideroblasts (and patients with other forms of sideroblastic anemia) and/or at least one mutation in DNMT3A or TET2 are more likely to respond therapeutically to ActRIIB(L79D 25-131)-hFc than MDS patients with <15% ring sideroblasts and/or no mutation in DNMT3A or TET2. Based on these data, selective treatment of any of these patient subgroups is expected to greatly increase the benefit/risk ratio of treatment with ActRII inhibitors.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

SEQUENCE LISTING

```
<160> NUMBER OF SEQ ID NOS: 70

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80
```

-continued

```
Asp Phe Asn Cys Tyr Asp Arg Gln Glu Cys Val Ala Thr Glu Glu Asn
                85                  90                  95
Pro Gln Val Tyr Phe Cys Cys Glu Gly Asn Phe Cys Asn Glu Arg
            100                 105                 110
Phe Thr His Leu Pro Glu Ala Gly Pro Glu Val Thr Tyr Glu Pro
            115                 120                 125
Pro Pro Thr Ala Pro Thr Leu Leu Thr Val Leu Ala Tyr Ser Leu Leu
130                 135                 140
Pro Ile Gly Gly Leu Ser Leu Ile Val Leu Leu Ala Phe Trp Met Tyr
145                 150                 155                 160
Arg His Arg Lys Pro Pro Tyr Gly His Val Asp Ile His Glu Asp Pro
                165                 170                 175
Gly Pro Pro Pro Pro Ser Pro Leu Val Gly Leu Lys Pro Leu Gln Leu
            180                 185                 190
Leu Glu Ile Lys Ala Arg Gly Arg Phe Gly Cys Val Trp Lys Ala Gln
            195                 200                 205
Leu Met Asn Asp Phe Val Ala Val Lys Ile Phe Pro Leu Gln Asp Lys
            210                 215                 220
Gln Ser Trp Gln Ser Glu Arg Glu Ile Phe Ser Thr Pro Gly Met Lys
225                 230                 235                 240
His Glu Asn Leu Leu Gln Phe Ile Ala Ala Glu Lys Arg Gly Ser Asn
                245                 250                 255
Leu Glu Val Glu Leu Trp Leu Ile Thr Ala Phe His Asp Lys Gly Ser
            260                 265                 270
Leu Thr Asp Tyr Leu Lys Gly Asn Ile Ile Thr Trp Asn Glu Leu Cys
            275                 280                 285
His Val Ala Glu Thr Met Ser Arg Gly Leu Ser Tyr Leu His Glu Asp
            290                 295                 300
Val Pro Trp Cys Arg Gly Glu Gly His Lys Pro Ser Ile Ala His Arg
305                 310                 315                 320
Asp Phe Lys Ser Lys Asn Val Leu Leu Lys Ser Asp Leu Thr Ala Val
                325                 330                 335
Leu Ala Asp Phe Gly Leu Ala Val Arg Phe Glu Pro Gly Lys Pro Pro
            340                 345                 350
Gly Asp Thr His Gly Gln Val Gly Thr Arg Arg Tyr Met Ala Pro Glu
            355                 360                 365
Val Leu Glu Gly Ala Ile Asn Phe Gln Arg Asp Ala Phe Leu Arg Ile
370                 375                 380
Asp Met Tyr Ala Met Gly Leu Val Leu Trp Glu Leu Val Ser Arg Cys
385                 390                 395                 400
Lys Ala Ala Asp Gly Pro Val Asp Glu Tyr Met Leu Pro Phe Glu Glu
                405                 410                 415
Glu Ile Gly Gln His Pro Ser Leu Glu Glu Leu Gln Glu Val Val Val
            420                 425                 430
His Lys Lys Met Arg Pro Thr Ile Lys Asp His Trp Leu Lys His Pro
            435                 440                 445
Gly Leu Ala Gln Leu Cys Val Thr Ile Glu Glu Cys Trp Asp His Asp
450                 455                 460
Ala Glu Ala Arg Leu Ser Ala Gly Cys Val Glu Glu Arg Val Ser Leu
465                 470                 475                 480
Ile Arg Arg Ser Val Asn Gly Thr Thr Ser Asp Cys Leu Val Ser Leu
                485                 490                 495
```

```
Val Thr Ser Val Thr Asn Val Asp Leu Pro Pro Lys Glu Ser Ser Ile
            500                 505                 510
```

```
<210> SEQ ID NO 2
<211> LENGTH: 115
<212> TYPE: PRT
<213> ORGANISM: Homo sapiens

<400> SEQUENCE: 2
```

```
Gly Arg Gly Glu Ala Glu Thr Arg Glu Cys Ile Tyr Tyr Asn Ala Asn
1               5                  10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115
```

```
<210> SEQ ID NO 3
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

```
Gly Arg Gly Glu Ala Glu Thr Arg Glu Cys Ile Tyr Tyr Asn Ala Asn
1               5                  10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100
```

```
<210> SEQ ID NO 4
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

```
Met Thr Ala Pro Trp Val Ala Leu Ala Leu Leu Trp Gly Ser Leu Cys
```

-continued

```
1               5                   10                  15
Ala Gly Ser Gly Arg Gly Glu Ala Glu Thr Arg Glu Cys Ile Tyr Tyr
                20                  25                  30
Asn Ala Asn Trp Glu Leu Glu Arg Thr Asn Gln Ser Gly Leu Glu Arg
                35                  40                  45
Cys Glu Gly Glu Gln Asp Lys Arg Leu His Cys Tyr Ala Ser Trp Ala
                50                  55                  60
Asn Ser Ser Gly Thr Ile Glu Leu Val Lys Lys Gly Cys Trp Leu Asp
65                  70                  75                  80
Asp Phe Asn Cys Tyr Asp Arg Gln Glu Cys Val Ala Thr Glu Glu Asn
                85                  90                  95
Pro Gln Val Tyr Phe Cys Cys Cys Glu Gly Asn Phe Cys Asn Glu Arg
                100                 105                 110
Phe Thr His Leu Pro Glu Ala Gly Gly Pro Glu Val Thr Tyr Glu Pro
                115                 120                 125
Pro Pro Thr Ala Pro Thr Leu Leu Thr Val Leu Ala Tyr Ser Leu Leu
                130                 135                 140
Pro Ile Gly Gly Leu Ser Leu Ile Val Leu Leu Ala Phe Trp Met Tyr
145                 150                 155                 160
Arg His Arg Lys Pro Pro Tyr Gly His Val Asp Ile His Glu Asp Pro
                165                 170                 175
Gly Pro Pro Pro Ser Pro Leu Val Gly Leu Lys Pro Leu Gln Leu
                180                 185                 190
Leu Glu Ile Lys Ala Arg Gly Arg Phe Gly Cys Val Trp Lys Ala Gln
                195                 200                 205
Leu Met Asn Asp Phe Val Ala Val Lys Ile Phe Pro Leu Gln Asp Lys
                210                 215                 220
Gln Ser Trp Gln Ser Glu Arg Glu Ile Phe Ser Thr Pro Gly Met Lys
225                 230                 235                 240
His Glu Asn Leu Leu Gln Phe Ile Ala Ala Glu Lys Arg Gly Ser Asn
                245                 250                 255
Leu Glu Val Glu Leu Trp Leu Ile Thr Ala Phe His Asp Lys Gly Ser
                260                 265                 270
Leu Thr Asp Tyr Leu Lys Gly Asn Ile Ile Thr Trp Asn Glu Leu Cys
                275                 280                 285
His Val Ala Glu Thr Met Ser Arg Gly Leu Ser Tyr Leu His Glu Asp
                290                 295                 300
Val Pro Trp Cys Arg Gly Glu Gly His Lys Pro Ser Ile Ala His Arg
305                 310                 315                 320
Asp Phe Lys Ser Lys Asn Val Leu Leu Lys Ser Asp Leu Thr Ala Val
                325                 330                 335
Leu Ala Asp Phe Gly Leu Ala Val Arg Phe Glu Pro Gly Lys Pro Pro
                340                 345                 350
Gly Asp Thr His Gly Gln Val Gly Thr Arg Arg Tyr Met Ala Pro Glu
                355                 360                 365
Val Leu Glu Gly Ala Ile Asn Phe Gln Arg Asp Ala Phe Leu Arg Ile
                370                 375                 380
Asp Met Tyr Ala Met Gly Leu Val Leu Trp Glu Leu Val Ser Arg Cys
385                 390                 395                 400
Lys Ala Ala Asp Gly Pro Val Asp Glu Tyr Met Leu Pro Phe Glu Glu
                405                 410                 415
Glu Ile Gly Gln His Pro Ser Leu Glu Glu Leu Gln Glu Val Val Val
                420                 425                 430
```

```
His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
            500                 505                 510

<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 6
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95
```

Leu Pro Glu Ala
        100

<210> SEQ ID NO 7
<211> LENGTH: 1536
<212> TYPE: DNA
<213> ORGANISM: Homo sapiens

<400> SEQUENCE: 7

| | | | | | |
|---|---|---|---|---|---|
| atgacggcgc | cctgggtggc | cctcgccctc | ctctggggat | cgctgtgcgc | cggctctggg | 60 |
| cgtggggagg | ctgagacacg | ggagtgcatc | tactacaacg | ccaactggga | gctggagcgc | 120 |
| accaaccaga | gcggcctgga | gcgctgcgaa | ggcgagcagg | acaagcggct | gcactgctac | 180 |
| gcctcctggc | gcaacagctc | tggcaccatc | gagctcgtga | agaagggctg | ctggctagat | 240 |
| gacttcaact | gctacgatag | gcaggagtgt | gtggccactg | aggagaaccc | ccaggtgtac | 300 |
| ttctgctgct | gtgaaggcaa | cttctgcaac | gaacgcttca | ctcatttgcc | agaggctggg | 360 |
| ggcccggaag | tcacgtacga | gccaccccg | acagccccca | ccctgctcac | ggtgctggcc | 420 |
| tactcactgc | tgcccatcgg | gggccttttcc | ctcatcgtcc | tgctggcctt | ttggatgtac | 480 |
| cggcatcgca | agccccccta | cggtcatgtg | gacatccatg | aggaccctgg | gcctccacca | 540 |
| ccatcccctc | tggtgggcct | gaagccactg | cagctgctgg | agatcaaggc | tcggggcgc | 600 |
| tttggctgtg | tctggaaggc | ccagctcatg | aatgactttg | tagctgtcaa | gatcttccca | 660 |
| ctccaggaca | gcagtcgtg | gcagagtgaa | cgggagatct | tcagcacacc | tggcatgaag | 720 |
| cacgagaacc | tgctacagtt | cattgctgcc | gagaagcgag | gctccaacct | cgaagtagag | 780 |
| ctgtggctca | tcacggcctt | ccatgacaag | ggctccctca | cggattacct | caagggggaac | 840 |
| atcatcacat | ggaacgaact | gtgtcatgta | gcagagacga | tgtcacgagg | cctctcatac | 900 |
| ctgcatgagg | atgtgcctg | gtgccgtggc | gagggccaca | agccgtctat | tgcccacagg | 960 |
| gactttaaaa | gtaagaatgt | attgctgaag | agcgacctca | cagccgtgct | ggctgacttt | 1020 |
| ggcttggctg | ttcgatttga | gccagggaaa | cctccagggg | acacccacgg | acaggtaggc | 1080 |
| acgagacggt | acatggctcc | tgaggtgctc | gaggagccca | tcaacttcca | gagagatgcc | 1140 |
| ttcctgcgca | ttgacatgta | tgccatgggg | ttggtgctgt | gggagcttgt | gtctcgctgc | 1200 |
| aaggctgcag | acggacccgt | ggatgagtac | atgctgccct | ttgaggaaga | gattggccag | 1260 |
| caccttcgt | tggaggagct | gcaggaggtg | gtggtgcaca | agaagatgag | gcccaccatt | 1320 |
| aaagatcact | ggttgaaaca | cccgggcctg | gcccagcttt | gtgtgaccat | cgaggagtgc | 1380 |
| tgggaccatg | atgcagaggc | tcgcttgtcc | gcgggctgtg | tggaggagcg | ggtgtccctg | 1440 |
| attcggaggt | cggtcaacgg | cactacctcg | gactgtctcg | tttccctggt | gacctctgtc | 1500 |
| accaatgtgg | acctgccccc | taaagagtca | agcatc | | | 1536 |

<210> SEQ ID NO 8
<211> LENGTH: 345
<212> TYPE: DNA
<213> ORGANISM: Homo sapiens

<400> SEQUENCE: 8

| | | | | | |
|---|---|---|---|---|---|
| gggcgtgggg | aggctgagac | acgggagtgc | atctactaca | acgccaactg | ggagctggag | 60 |
| cgcaccaacc | agagcggcct | ggagcgctgc | gaaggcgagc | aggacaagcg | gctgcactgc | 120 |
| tacgcctcct | ggcgcaacag | ctctggcacc | atcgagctcg | tgaagaaggg | ctgctggcta | 180 |
| gatgacttca | actgctacga | taggcaggag | tgtgtggcca | ctgaggagaa | cccccaggtg | 240 |

```
tacttctgct gctgtgaagg caacttctgc aacgaacgct tcactcattt gccagaggct    300
gggggcccgg aagtcacgta cgagccaccc ccgacagccc ccacc                    345
```

<210> SEQ ID NO 9
<211> LENGTH: 513
<212> TYPE: PRT
<213> ORGANISM: Homo sapiens

<400> SEQUENCE: 9

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350
```

-continued

```
Ala Gly Asp Thr His Gly Gln Val Gly Thr Arg Arg Tyr Met Ala Pro
            355                 360                 365
Glu Val Leu Glu Gly Ala Ile Asn Phe Gln Arg Asp Ala Phe Leu Arg
        370                 375                 380
Ile Asp Met Tyr Ala Met Gly Leu Val Leu Trp Glu Leu Ala Ser Arg
385                 390                 395                 400
Cys Thr Ala Ala Asp Gly Pro Val Asp Glu Tyr Met Leu Pro Phe Glu
                405                 410                 415
Glu Glu Ile Gly Gln His Pro Ser Leu Glu Asp Met Gln Glu Val Val
            420                 425                 430
Val His Lys Lys Arg Pro Val Leu Arg Asp Tyr Trp Gln Lys His
        435                 440                 445
Ala Gly Met Ala Met Leu Cys Glu Thr Ile Glu Glu Cys Trp Asp His
            450                 455                 460
Asp Ala Glu Ala Arg Leu Ser Ala Gly Cys Val Gly Glu Arg Ile Thr
465                 470                 475                 480
Gln Met Gln Arg Leu Thr Asn Ile Ile Thr Thr Glu Asp Ile Val Thr
                485                 490                 495
Val Val Thr Met Val Thr Asn Val Asp Phe Pro Pro Lys Glu Ser Ser
            500                 505                 510
Leu

<210> SEQ ID NO 10
<211> LENGTH: 115
<212> TYPE: PRT
<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15
Trp Glu Lys Asp Arg Thr Asn Gln Thr Gly Val Glu Pro Cys Tyr Gly
            20                  25                  30
Asp Lys Asp Lys Arg Arg His Cys Phe Ala Thr Trp Lys Asn Ile Ser
        35                  40                  45
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
65                  70                  75                  80
Tyr Phe Cys Cys Cys Glu Gly Asn Met Cys Asn Glu Lys Phe Ser Tyr
                85                  90                  95
Phe Pro Glu Met Glu Val Thr Gln Pro Thr Ser Asn Pro Val Thr Pro
            100                 105                 110
Lys Pro Pro
        115

<210> SEQ ID NO 11
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ile Leu Gly Arg Ser Glu Thr Gln Glu Cys Leu Phe Phe Asn Ala Asn
1               5                   10                  15
Trp Glu Lys Asp Arg Thr Asn Gln Thr Gly Val Glu Pro Cys Tyr Gly
```

```
                    20                  25                  30
Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 12
<211> LENGTH: 1539
<212> TYPE: DNA
<213> ORGANISM: Homo sapiens

<400> SEQUENCE: 12
atgggagctg ctgcaaagtt ggcgtttgcc gtctttctta ctctcctgttc ttcaggtgct      60 atacttggta gatcagaaac tcaggagtgt ctttttcttta atgctaattg ggaaaaagac     120
agaaccaatc aaactggtgt tgaaccgtgt tatggtgaca agataaacg gcggcattgt      180 tttgctacct ggaagaatat ttctggttcc attgaaatag tgaaacaagg ttgttggctg     240
gatgatatca actgctatga caggactgat tgtgtagaaa aaaagacag ccctgaagta     300 tattttttgtt gctgtgaggg caatatgtgt aatgaaaagt tttcttattt tccggagatg    360
gaagtcacac agcccacttc aaatccagtt acacctaagc caccctatta caacatcctg     420
ctctattcct tggtgccact tatgttaatt gcggggattg tcatttgtgc attttgggtg     480
tacaggcatc acaagatggc ctaccctcct gtacttgttc caactcaaga cccaggacca    540
ccccaccctt ctccattact aggttttgaaa ccactgcagt tattagaagt gaaagcaagg     600
ggaagatttg gttgtgtctg aaagcccag ttgcttaacg aatatgtggc tgtcaaaata    660
tttccaatac aggacaaaca gtcatggcaa aatgaatacg aagtctacag tttgcctgga    720
atgaagcatg agaacatatt acagttcatt ggtgcagaaa acgaggcac agtgttgat    780 gtggatcttt ggctgatcac agcatttcat gaaagggtt cactatcaga ctttcttaag     840
gctaatgtgg tctcttggaa tgaactgtgt catattgcag aaaccatggc tagaggattg    900
gcatatttac atgaggatat acctggccta aaagatggcc acaaacctgc catatctcac    960
agggacatca aaagtaaaaa tgtgctgttg aaaaacaacc tgacagcttg cattgctgac   1020
tttgggttgg ccttaaaatt tgaggctggc aagtctgcag gcgataccca tggacaggtt    1080
ggtacccgga ggtacatggc tccagaggta ttagagggtg ctataaactt ccaaagggat   1140 gcattttga gatagatat gtatgccatg ggattagtcc tatgggaact ggcttctcgc      1200
tgtactgctg cagatggacc tgtagatgaa tacatgttgc catttgagga ggaaattggc    1260
cagcatccat ctcttgaaga catgcaggaa gttgttgtgc ataaaaaaaa gaggcctgtt    1320
ttaagagatt attggcagaa acatgctgga atggcaatgc tctgtgaaac cattgaagaa    1380
tgttgggatc acgacgcaga agccaggtta tcagctggat gtgtaggtga agaattacc    1440 cagatgcaga gactaacaaa tattattacc acagaggaca ttgtaacagt ggtcacaatg    1500
gtgacaaatg ttgactttcc tcccaaagaa tctagtcta                           1539

<210> SEQ ID NO 13
```

<211> LENGTH: 345
<212> TYPE: DNA
<213> ORGANISM: Homo sapiens

<400> SEQUENCE: 13

```
atacttggta gatcagaaac tcaggagtgt cttttcttta atgctaattg ggaaaaagac    60
agaaccaatc aaactggtgt tgaaccgtgt tatggtgaca agataaacg gcggcattgt   120
tttgctacct ggaagaatat ttctggttcc attgaaatag tgaaacaagg ttgttggctg   180
gatgatatca actgctatga caggactgat tgtgtagaaa aaaagacag ccctgaagta    240
tatttttgtt gctgtgaggg caatatgtgt aatgaaaagt tttcttattt tccggagatg   300
gaagtcacac agcccacttc aaatccagtt acacctaagc caccc                   345
```

<210> SEQ ID NO 14
<211> LENGTH: 225
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 14

```
Thr His Thr Cys Pro Pro Cys Pro Ala Pro Glu Leu Leu Gly Gly Pro
1               5                  10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 15
<211> LENGTH: 225
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 15

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Xaa Val Ser Asn Lys Ala Leu Pro Val Pro Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Pro Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Xaa His Tyr Thr Gln Lys Ser Leu Ser Leu Ser Pro Gly
210                 215                 220

Lys
225

<210> SEQ ID NO 16
<211> LENGTH: 344
<212> TYPE: PRT
<213> ORGANISM: Homo sapiens

<400> SEQUENCE: 16

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45
```

```
Glu Leu Ser Lys Glu Glu Cys Cys Ser Thr Gly Arg Leu Ser Thr Ser
             50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
        210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
        290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 17
<211> LENGTH: 317
<212> TYPE: PRT
<213> ORGANISM: Homo sapiens

<400> SEQUENCE: 17

Met Val Arg Ala Arg His Gln Pro Gly Gly Leu Cys Leu Leu Leu Leu
 1               5                  10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
```

```
                65                  70                  75                  80
        Phe Asn Gly Gly Ala Pro Asn Cys Ile Pro Cys Lys Glu Thr Cys Glu
                            85                  90                  95

Asn Val Asp Cys Gly Pro Gly Lys Lys Cys Arg Met Asn Lys Lys Asn
                        100                 105                 110

Lys Pro Arg Cys Val Cys Ala Pro Asp Cys Ser Asn Ile Thr Trp Lys
                    115                 120                 125

Gly Pro Val Cys Gly Leu Asp Gly Lys Thr Tyr Arg Asn Glu Cys Ala
                130                 135                 140

Leu Leu Lys Ala Arg Cys Lys Glu Gln Pro Glu Leu Glu Val Gln Tyr
        145                 150                 155                 160

Gln Gly Arg Cys Lys Lys Thr Cys Arg Asp Val Phe Cys Pro Gly Ser
                        165                 170                 175

Ser Thr Cys Val Val Asp Gln Thr Asn Asn Ala Tyr Cys Val Thr Cys
                    180                 185                 190

Asn Arg Ile Cys Pro Glu Pro Ala Ser Ser Glu Gln Tyr Leu Cys Gly
                195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
        225                 230                 235                 240

Lys Ala Lys Ser Cys Glu Asp Ile Gln Cys Thr Gly Gly Lys Lys Cys
                        245                 250                 255

Leu Trp Asp Phe Lys Val Gly Arg Gly Arg Cys Ser Leu Cys Asp Glu
                    260                 265                 270

Leu Cys Pro Asp Ser Lys Ser Asp Glu Pro Val Cys Ala Ser Asp Asn
                275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn
        305                 310                 315

<210> SEQ ID NO 18
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys
    50                  55                  60

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Glu Thr Cys Glu Asn Val Asp Cys Gly Pro Gly Lys Lys Cys Arg Met
1               5                   10                  15

Asn Lys Lys Asn Lys Pro Arg Cys Val
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25

<210> SEQ ID NO 21
<211> LENGTH: 263
<212> TYPE: PRT
<213> ORGANISM: Homo sapiens

<400> SEQUENCE: 21

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
```

```
                         245                 250                 255
Glu Glu Glu Glu Asn Phe Val
                260

<210> SEQ ID NO 22
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335
```

```
Ser Leu Ser Leu Ser Pro Gly Lys
            340

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Lys Phe Leu Val Asn Val Ala Leu Val Phe Met Val Val Tyr Ile
1               5                   10                  15

Ser Tyr Ile Tyr Ala
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Asp Ala Met Lys Arg Gly Leu Cys Cys Val Leu Leu Leu Cys Gly
1               5                   10                  15

Ala Val Phe Val Ser Pro
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Gly Ala Ala Ala Lys Leu Ala Phe Ala Val Phe Leu Ile Ser Cys
1               5                   10                  15

Ser Ser Gly Ala
            20

<210> SEQ ID NO 26
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80
```

Gln Gly Cys Trp Leu Asp Asp Ile Asn Cys Tyr Asp Arg Thr Asp Cys
            85                  90                  95

Val Glu Lys Lys Asp Ser Pro Glu Val Tyr Phe Cys Cys Lys Glu Gly
            100                 105                 110

Asn Met Cys Asn Glu Lys Phe Ser Tyr Phe Pro Glu Met Glu Val Thr
            115                 120                 125

Gln Pro Thr Ser Asn Pro Val Thr Pro Lys Pro Thr Gly Gly Gly
            130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
            245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
            275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 27
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggatgcaa tgaagagagg gctctgctgt gtgctgctgc tgtgtggagc agtcttcgtt    60
tcgcccggcg ccgctatact tggtagatca gaaactcagg agtgtctttt tttaatgcta   120
attgggaaaa agacagaacc aatcaaactg gtgttgaacc gtgttatggt gacaaagata   180
aacggcggca ttgttttgct acctggaaga atatttctgg ttccattgaa tagtgaaaca   240
aggttgttgg ctggatgata tcaactgcta tgacaggact gattgtgtag aaaaaaaaga   300 cagcccctgaa gtatatttct gttgctgtga gggcaatatg tgtaatgaaa agttttctta   360

```
tttccggag atggaagtca cacagcccac ttcaaatcca gttacaccta agccacccac    420
cggtggtgga actcacacat gcccaccgtg cccagcacct gaactcctgg ggggaccgtc    480
agtcttcctc ttccccccaa aacccaagga cacccctcatg atctcccgga cccctgaggt    540
cacatgcgtg gtggtggacg tgagccacga agaccctgag gtcaagttca actggtacgt    600
ggacggcgtg gaggtgcata atgccaagac aaagccgcgg gaggagcagt acaacagcac    660
gtaccgtgtg gtcagcgtcc tcaccgtcct gcaccaggac tggctgaatg gcaaggagta    720
caagtgcaag gtctccaaca aagccctccc agtccccatc gagaaaacca tctccaaagc    780
caaagggcag ccccgagaac cacaggtgta caccctgccc ccatcccggg aggagatgac    840
caagaaccag gtcagcctga cctgcctggt caaaggcttc tatcccagcg acatcgccgt    900
ggagtgggag agcaatgggc agccggagaa caactacaag accacgcctc ccgtgctgga    960
ctccgacggc tccttcttcc tctatagcaa gctcaccgtg gacaagagca ggtggcagca   1020
ggggaacgtc ttctcatgct ccgtgatgca tgaggctctg cacaaccact acacgcagaa   1080
gagcctctcc ctgtctccgg gtaaatgaga attc                                1114
```

<210> SEQ ID NO 28
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220
```

```
Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 29
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
```

```
                    245                 250                 255
Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Thr Ala Pro Trp Val Ala Leu Ala Leu Leu Trp Gly Ser Leu Cys
1               5                   10                  15

Ala Gly Ser

<210> SEQ ID NO 31
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175
```

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 32
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| | | | | |
|---|---|---|---|---|
| atggatgcaa | tgaagagagg | gctctgctgt | gtgctgctgc | tgtgtggagc | agtcttcgtt | 60 |
| tcgcccggcg | cctctgggcg | tggggaggct | gagacacggg | agtgcatcta | ctacaacgcc | 120 |
| aactgggagc | tggagcgcac | caaccagagc | ggcctggagc | gctgcgaagg | cgagcaggac | 180 |
| aagcggctgc | actgctacgc | ctcctggcgc | aacagctctg | gcaccatcga | gctcgtgaag | 240 |
| aagggctgct | ggctagatga | cttcaactgc | tacgataggc | aggagtgtgt | ggccactgag | 300 |
| gagaaccccc | aggtgtactt | ctgctgctgt | gaaggcaact | tctgcaacga | gcgcttcact | 360 |
| catttgccag | aggctggggg | cccggaagtc | acgtacgagc | acccccgac  | agcccccacc | 420 |
| ggtggtggaa | ctcacacatg | cccaccgtgc | ccagcacctg | aactcctggg | gggaccgtca | 480 |
| gtcttcctct | tccccccaaa | acccaaggac | accctcatga | tctcccggac | ccctgaggtc | 540 |
| acatgcgtgg | tggtggacgt | gagccacgaa | gaccctgagg | tcaagttcaa | ctggtacgtg | 600 |
| gacggcgtgg | aggtgcataa | tgccaagaca | aagccgcggg | aggagcagta | caacagcacg | 660 |
| taccgtgtgg | tcagcgtcct | caccgtcctg | caccaggact | ggctgaatgg | caaggagtac | 720 |
| aagtgcaagg | tctccaacaa | agccctccca | gtccccatcg | agaaaaccat | ctccaaagcc | 780 |
| aaagggcagc | cccgagaacc | acaggtgtac | accctgcccc | catcccggga | ggagatgacc | 840 |
| aagaaccagg | tcagcctgac | ctgcctggtc | aaaggcttct | atcccagcga | catcgccgtg | 900 |
| gagtgggaga | gcaatgggca | gccggagaac | aactacaaga | ccacgcctcc | cgtgctggac | 960 |

```
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaatga                                        1107
```

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Arg Gly Glu Ala Glu
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Leu Gly Arg Ser Glu Thr Gln Glu
1               5

<210> SEQ ID NO 35

<400> SEQUENCE: 35

000

<210> SEQ ID NO 36
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

-continued

```
Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
        180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
            245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
            325                 330                 335

Leu Ser Leu Ser Pro Gly Lys
            340
```

<210> SEQ ID NO 37
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
            85                  90                  95

Leu Pro Glu Ala Gly Gly Pro Glu Val Thr Tyr Glu Pro Pro Pro Thr
            100                 105                 110

Ala Pro Thr
        115
```

<210> SEQ ID NO 38
<211> LENGTH: 368
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 38

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 39
<211> LENGTH: 1107

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

| | |
|---|---:|
| atggatgcaa tgaagagagg gctctgctgt gtgctgctgc tgtgtggagc agtcttcgtt | 60 |
| tcgcccggcg cctctgggcg tggggaggct gagacacggg agtgcatcta ctacaacgcc | 120 |
| aactgggagc tggagcgcac caaccagagc ggcctggagc gctgcgaagg cgagcaggac | 180 |
| aagcggctgc actgctacgc ctcctggcgc aacagctctg gcaccatcga gctcgtgaag | 240 |
| aagggctgct gggatgatga cttcaactgc tacgataggc aggagtgtgt ggccactgag | 300 |
| gagaaccccc aggtgtactt ctgctgctgt gaaggcaact tctgcaacga gcgcttcact | 360 |
| catttgccag aggctggggg cccggaagtc acgtacgagc acccccgac agcccccacc | 420 |
| ggtggtggaa ctcacacatg cccaccgtgc ccagcacctg aactcctggg gggaccgtca | 480 |
| gtcttcctct tccccccaaa acccaaggac accctcatga tctcccggac ccctgaggtc | 540 |
| acatgcgtgg tggtggacgt gagccacgaa gaccctgagg tcaagttcaa ctggtacgtg | 600 |
| gacggcgtgg aggtgcataa tgccaagaca aagccgcggg aggagcagta caacagcacg | 660 |
| taccgtgtgg tcagcgtcct caccgtcctg caccaggact ggctgaatgg caaggagtac | 720 |
| aagtgcaagg tctccaacaa agccctccca gcccccatcg agaaaaccat ctccaaagcc | 780 |
| aaagggcagc cccgagaacc acaggtgtac accctgcccc catcccggga ggagatgacc | 840 |
| aagaaccagg tcagcctgac ctgcctggtc aaaggcttct atcccagcga catcgccgtg | 900 |
| gagtgggaga gcaatgggca gccggagaac aactacaaga ccacgcctcc cgtgctggac | 960 |
| tccgacggct ccttcttcct ctatagcaag ctcaccgtgg acaagagcag gtggcagcag | 1020 |
| gggaacgtct tctcatgctc cgtgatgcat gaggctctgc acaaccacta cacgcagaag | 1080 |
| agcctctccc tgtccccggg taaatga | 1107 |

<210> SEQ ID NO 40
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | |
|---|---:|
| tcatttaccc ggggacaggg agaggctctt ctgcgtgtag tggttgtgca gagcctcatg | 60 |
| catcacggag catgagaaga cgttcccctg ctgccacctg ctcttgtcca cggtgagctt | 120 |
| gctatagagg aagaaggagc cgtcggagtc cagcacggga ggcgtggtct tgtagttgtt | 180 |
| ctccggctgc ccattgctct cccactccac ggcgatgtcg ctgggataga agcctttgac | 240 |
| caggcaggtc aggctgacct ggttcttggt catctcctcc cggatgggg gcagggtgta | 300 |
| cacctgtggt tctcggggct gccctttggc tttggagatg gttttctcga tgggggctgg | 360 |
| gagggctttg ttggagacct tgcacttgta ctccttgcca ttcagccagt cctggtgcag | 420 |
| gacggtgagg acgctgacca cacggtacgt gctgttgtac tgctcctccc gcggctttgt | 480 |
| cttggcatta tgcacctcca cgccgtccac gtaccagttg aacttgacct cagggtcttc | 540 |
| gtggctcacg tccaccacca cgcatgtgac ctcaggggtc cggagatca tgaggtgtc | 600 |
| cttgggtttt gggggaaga ggaagactga cgtccccccc aggagttcag gtgctgggca | 660 |

```
cggtgggcat gtgtgagttc caccaccggt gggggctgtc gggggtggct cgtacgtgac    720
ttccgggccc ccagcctctg gcaaatgagt gaagcgctcg ttgcagaagt tgccttcaca    780
gcagcagaag tacacctggg ggttctcctc agtggccaca cactcctgcc tatcgtagca    840
gttgaagtca tcatcccagc agccttcctt cacgagctcg atggtgccag agctgttgcg    900
ccaggaggcg tagcagtgca gccgcttgtc ctgctcgcct tcgcagcgct ccaggccgct    960
ctggttggtg cgctccagct cccagttggc gttgtagtag atgcactccc gtgtctcagc   1020
ctccccacgc cagaggcgc cgggcgaaac gaagactgct ccacacagca gcagcacaca   1080
gcagagccct ctcttcattg catccat                                        1107
```

<210> SEQ ID NO 41
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Asp Ala Met Lys Arg Gly Leu Cys Cys Val Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
```

```
              275                 280                 285
Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 42
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggatgcaa tgaagagagg gctctgctgt gtgctgctgc tgtgtggagc agtcttcgtt      60
tcgcccggcg ccgctgagac acgggagtgc atctactaca acgccaactg ggagctggag     120
cgcaccaacc agagcggcct ggagcgctgc gaaggcgagc aggacaagcg gctgcactgc     180
tacgcctcct ggcgcaacag ctctggcacc atcgagctcg tgaagaaggg ctgctgggac     240
gatgacttca actgctacga taggcaggag tgtgtggcca ctgaggagaa ccccagqtg      300 tacttctgct gctgtgaagg caacttctgc aacgagcgct tcactcattt gccagaggct     360
gggggcccgg aagtcacgta cgagccaccc ccgacaggtg gtgaactcac acatgccca     420 ccgtgcccag cacctgaact cctgggggga ccgtcagtct tcctcttccc cccaaaaccc     480
aaggacaccc tcatgatctc ccggaccccct gaggtcacat gcgtggtggt ggacgtgagc     540
cacgaagacc ctgaggtcaa gttcaactgg tacgtggacg gcgtggaggt gcataatgcc     600
aagacaaagc cgcgggagga gcagtacaac agcacgtacc gtgtggtcag cgtcctcacc     660
gtcctgcacc aggactggct gaatggcaag gagtacaagt gcaaggtctc caacaaagcc     720
ctcccagccc ccatcgagaa aaccatctcc aaagccaaag gcagccccg agaaccacag      780 gtgtacaccc tgcccccatc ccgggaggag atgaccaaga accaggtcag cctgacctgc     840
ctggtcaaag gcttctatcc cagcgacatc gccgtggagt gggagagcaa tgggcagccg     900
gagaacaact acaagaccac gcctcccgtg ctggactccg acggctcctt cttcctctat     960
agcaagctca ccgtggacaa gagcaggtgg cagcagggga acgtcttctc atgctccgtg    1020
atgcatgagg ctctgcacaa ccactacacg cagaagagcc tctccctgtc cccgggtaaa    1080
tga                                                                  1083

<210> SEQ ID NO 43
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
tcatttaccc ggggacaggg agaggctctt ctgcgtgtag tggttgtgca gagcctcatg      60
```

-continued

```
catcacggag catgagaaga cgttccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcggggct gccctttggc tttggagatg gttttctcga tgggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cgggagatca tgagggtgtc    600
cttgggtttt ggggggaaga ggaagactga cggtccccc aggagttcag gtgctgggca    660
cggtgggcat gtgtgagttc caccacctgt cggggtggc tcgtacgtga cttccgggcc    720
cccagcctct ggcaaatgag tgaagcgctc gttgcagaag ttgccttcac agcagcagaa    780
gtacacctgg gggttctcct cagtggccac acactcctgc ctatcgtagc agttgaagtc    840
atcgtcccag cagcccttct tcacgagctc gatggtgcca gagctgttgc gccaggaggc    900
gtagcagtgc agccgcttgt cctgctcgcc ttcgcagcgc tccaggccgc tctggttggt    960
gcgctccagc tcccagttgg cgttgtagta gatgcactcc cgtgtctcag cggcgccggg   1020
cgaaacgaag actgctccac acagcagcag cacacagcag agccctctct tcattgcatc   1080
cat                                                                 1083
```

<210> SEQ ID NO 44
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175
```

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr
            100                 105

<210> SEQ ID NO 46
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggatgcaa tgaagagagg gctctgctgt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggggaac aggataaacg cctccattgc    180

```
tatgcgtcgt ggaggaactc ctccgggacg attgaactgg tcaagaaagg gtgctgggac      240
gacgatttca attgttatga ccgccaggaa tgtgtcgcga ccgaagagaa tccgcaggtc      300
tatttctgtt gttgcgaggg gaatttctgt aatgaacggt ttacccacct ccccgaagcc      360
ggcgggcccg aggtgaccta tgaaccccg cccaccggtg gtggaactca cacatgccca       420
ccgtgcccag cacctgaact cctgggggga ccgtcagtct tcctcttccc cccaaaaccc      480
aaggacaccc tcatgatctc ccggacccct gaggtcacat gcgtggtggt ggacgtgagc      540
cacgaagacc ctgaggtcaa gttcaactgg tacgtggacg gcgtggaggt gcataatgcc      600
aagacaaagc cgcggggagga gcagtacaac agcacgtacc gtgtggtcag cgtcctcacc      660
gtcctgcacc aggactggct gaatggcaag gagtacaagt gcaaggtctc caacaaagcc      720
ctcccagccc ccatcgagaa aaccatctcc aaagccaaag gcagccccg agaaccacag       780 gtgtacaccc tgcccccatc ccgggaggag atgaccaaga accaggtcag cctgacctgc      840
ctggtcaaag gcttctatcc cagcgacatc gccgtggagt gggagagcaa tgggcagccg      900
gagaacaact acaagaccac gcctcccgtg ctggactccg acggctcctt cttcctctat      960
agcaagctca ccgtggacaa gagcaggtgg cagcagggga acgtcttctc atgctccgtg     1020
atgcatgagg ctctgcacaa ccactacacg cagaagagcc tctccctgtc cccgggtaaa     1080
tga                                                                   1083

<210> SEQ ID NO 47
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
tcatttaccc ggggacaggg agaggctctt ctgcgtgtag tggttgtgca gagcctcatg       60
catcacggag catgagaaga cgttcccctg ctgccacctg ctcttgtcca cggtgagctt      120
gctatagagg aagaaggagc cgtcggagtc cagcacggga ggcgtggtct tgtagttgtt      180
ctccggctgc ccattgctct cccactccac ggcgatgtcg ctgggataga agcctttgac      240
caggcaggtc aggctgacct ggttcttggt catctcctcc cgggatgggg gcagggtgta      300
cacctgtggt tctcggggct gcccttttggc tttggagatg gttttctcga tgggggctgg      360
gagggctttg ttggagacct tgcacttgta ctccttgcca ttcagccagt cctggtgcag      420
gacggtgagg acgctgacca cacggtacgt gctgttgtac tgctcctccc gcggctttgt      480
cttggcatta tgcacctcca cgccgtccac gtaccagttg aacttgacct cagggtcttc      540
gtggctcacg tccaccacca cgcatgtgac ctcagggtc cgggagatca tgagggtgtc       600
cttgggtttt gggggggaaga ggaagactga cggtcccccc aggagttcag gtgctgggca      660
cggtgggcat gtgtgagttc caccaccggt gggcggggt tcataggtca cctcgggccc       720
gccggcttcg gggaggtggg taaaccgttc attacagaaa ttcccctcgc aacaacagaa      780
atagacctgc ggattctctt cggtcgcgac acattcctgg cggtcataac aattgaaatc      840
gtcgtcccag cacccttct tgaccagttc aatcgtcccg gaggagttcc tccacgacgc       900
atagcaatgg aggcgtttat cctgttcccc ctcacaccgt tcgagccgg attggttcgt       960 ccgttcgagt tcccaattag cattgtaata aatacattcg cggggtttcgg cggcgccggg     1020 cgaaacgaag actgctccac acagcagcag cacacagcag agccctctct tcattgcatc     1080
``` cat                                                                      1083

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaaacccgcg aatgtattta ttacaatgct aattgggaac tcgaacggac gaaccaatcc        60
gggctcgaac ggtgtgaggg ggaacaggat aaacgcctcc attgctatgc gtcgtggagg       120
aactcctccg ggacgattga actggtcaag aaagggtgct gggacgacga tttcaattgt       180
tatgaccgcc aggaatgtgt cgcgaccgaa gagaatccgc aggtctattt ctgttgttgc       240
gaggggaatt tctgtaatga acggtttacc cacctccccg aagccggcgg gcccgaggtg       300
acctatgaac ccccgcccac c                                                 321

<210> SEQ ID NO 49
<211> LENGTH: 141
<212> TYPE: PRT
<213> ORGANISM: Homo sapiens

<400> SEQUENCE: 49

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 50
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser

```
            35                  40                  45
Gly Thr Ile Glu Leu Val Lys Lys Gly Cys Trp Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                     85                  90                  95

Leu Pro Glu Ala Gly Gly Pro Glu Gly Pro Trp Ala Ser Thr Thr Ile
                    100                 105                 110

Pro Ser Gly Gly Pro Glu Ala Thr Ala Ala Gly Asp Gln Gly Ser
                    115                 120                 125

Gly Ala Leu Trp Leu Cys Leu Glu Gly Pro Ala His Glu
                    130                 135                 140

<210> SEQ ID NO 51
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Arg Gly Glu Ala Glu Thr Arg Glu Cys Ile Tyr Tyr Asn Ala Asn
 1               5                  10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
             35                  40                  45

Gly Thr Ile Glu Leu Val Lys Lys Gly Cys Trp Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                     85                  90                  95

Leu Pro Glu Ala Gly Gly Pro Glu Gly Pro Trp Ala Ser Thr Thr Ile
                    100                 105                 110

Pro Ser Gly Gly Pro Glu Ala Thr Ala Ala Gly Asp Gln Gly Ser
                    115                 120                 125

Gly Ala Leu Trp Leu Cys Leu Glu Gly Pro Ala His Glu Thr Gly Gly
                    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                    165                 170                 175

Ser Arg Thr Pro Glu Val Thr Cys Val Val Val Asp Val Ser His Glu
                    180                 185                 190

Asp Pro Glu Val Lys Phe Asn Trp Tyr Val Asp Gly Val Glu Val His
                    195                 200                 205

Asn Ala Lys Thr Lys Pro Arg Glu Glu Gln Tyr Asn Ser Thr Tyr Arg
        210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                    245                 250                 255
```

```
Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Gly Gly Gly Gly
1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gly Gly Gly
1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Gly Gly Gly
1               5

<210> SEQ ID NO 55

<400> SEQUENCE: 55

000

<210> SEQ ID NO 56
<211> LENGTH: 116
<212> TYPE: PRT
<213> ORGANISM: Homo sapiens
```

-continued

<400> SEQUENCE: 56

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 57
<211> LENGTH: 150
<212> TYPE: PRT
<213> ORGANISM: Rattus sp.

<400> SEQUENCE: 57

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 58
<211> LENGTH: 150
<212> TYPE: PRT
<213> ORGANISM: Sus sp.

<400> SEQUENCE: 58

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg

```
            35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
                100                 105                 110

Phe Thr His Leu Pro Glu Ala Gly Pro Glu Val Thr Tyr Glu Pro
                115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 59
<211> LENGTH: 150
<212> TYPE: PRT
<213> ORGANISM: Mus sp.

<400> SEQUENCE: 59

Met Thr Ala Pro Trp Ala Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
                100                 105                 110

Phe Thr His Leu Pro Glu Pro Gly Gly Pro Glu Val Thr Tyr Glu Pro
                115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 60
<211> LENGTH: 150
<212> TYPE: PRT
<213> ORGANISM: Homo sapiens

<400> SEQUENCE: 60

Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Arg
```

```
                50                  55                  60
Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 61
<211> LENGTH: 150
<212> TYPE: PRT
<213> ORGANISM: Bos sp.

<400> SEQUENCE: 61

Met Thr Ala Pro Trp Ala Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Arg Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Val Gly Gly Leu Ser
145                 150

<210> SEQ ID NO 62
<211> LENGTH: 150
<212> TYPE: PRT
<213> ORGANISM: Xenopus sp.

<400> SEQUENCE: 62

Met Gly Ala Ser Val Ala Leu Thr Phe Leu Leu Leu Ala Thr Phe
 1               5                  10                  15

Arg Ala Gly Ser Gly His Asp Glu Val Glu Thr Arg Glu Cys Ile Tyr
                20                  25                  30

Tyr Asn Ala Asn Trp Glu Leu Glu Lys Thr Asn Gln Ser Gly Val Glu
                35                  40                  45

Arg Leu Val Glu Gly Lys Lys Asp Lys Arg Leu His Cys Tyr Ala Ser
 50                  55                  60

Trp Arg Asn Asn Ser Gly Phe Ile Glu Leu Val Lys Lys Gly Cys Trp
```

```
                65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Glu Gly Asn Tyr Cys Asn
            100                 105                 110

Lys Lys Phe Thr His Leu Pro Glu Val Glu Thr Phe Asp Pro Lys Pro
            115                 120                 125

Gln Pro Ser Ala Ser Val Leu Asn Ile Leu Ile Tyr Ser Leu Leu Pro
            130                 135                 140

Ile Val Gly Leu Ser Met
145                 150

<210> SEQ ID NO 63
<211> LENGTH: 150
<212> TYPE: PRT
<213> ORGANISM: Homo sapiens

<400> SEQUENCE: 63

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
            130                 135                 140

Val Pro Leu Met Leu Ile
145                 150

<210> SEQ ID NO 64
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
```

```
                 65                  70                  75                  80
Val Ser Val Leu Thr Val Leu His Gln Asp Trp Leu Asn Gly Lys Glu
                     85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
                195                 200                 205

Ala Leu His Asn His Tyr Thr Gln Lys Ser Leu Ser Leu Ser Pro Gly
    210                 215                 220

Lys
225

<210> SEQ ID NO 65
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190
```

Trp Gln Gln Gly Asn Val Phe Ser Cys Ser Val Met His Glu Ala Leu
    195                 200                 205

His Asn His Tyr Thr Gln Lys Ser Leu Ser Leu Ser Pro Gly Lys
    210                 215                 220

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 66

His His His His His His
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 2 to 10 "Gly"
      residues
<220> FEATURE:
<223> OTHER INFORMATION: See specification as filed for detailed
      description of substitutions and preferred embodiments

<400> SEQUENCE: 67

Gly Gly Gly Gly Gly Gly Gly Gly Gly Gly
1               5                   10

<210> SEQ ID NO 68
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggatgcaa tgaagagagg ctctgctgt gtgctgctgc tgtgtggagc agtcttcgtt       60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggacgatga cttcaactgc tacgataggc aggagtgtgt ggccactgag     300
agaacccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gtccccatcg agaaaaccat ctccaaagcc     780

```
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107

<210> SEQ ID NO 69
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (8)..(8)
<223> OTHER INFORMATION: Thr, Ala or not present
<220> FEATURE:
<221> NAME/KEY: MOD_RES
<222> LOCATION: (121)..(121)
<223> OTHER INFORMATION: Pro, Ala, Val or Met

<400> SEQUENCE: 69

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Gly Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150

<210> SEQ ID NO 70
<211> LENGTH: 11
<212> TYPE: DNA
<213> ORGANISM: Homo sapiens

<400> SEQUENCE: 70
accaccacca c                                                         11
```

We claim:

1. A method for treating sideroblastic anemia in a human patient, comprising administering to a patient in need thereof a polypeptide comprising the amino acid sequence of SEQ ID NO: 44, and wherein the patient is on a dosing schedule that comprises administering from 0.75-1.75 mg/kg of the polypeptide to the patient, wherein the patient has bone marrow cells that test positive for one or more mutations in one or more of SF3B1, DNMT3A or TET2.

2. The method of claim 1, wherein the polypeptide consists of the amino acid sequence of SEQ ID NO: 44.

3. The method of claim 1, wherein the patient has undesirably high levels of endogenous EPO.

4. The method of claim 1, wherein the patient has previously been treated with one or more EPO receptor agonists.

5. The method of claim 4, wherein the patient has an inadequate response to the EPO receptor agonist.

6. The method of claim 4, wherein the patient is no longer responsive to the EPO receptor agonist.

7. The method of claim 4, wherein the EPO receptor agonist is EPO.

8. The method of claim 1, wherein the treatment increases red blood cell levels.

9. The method of claim 1, wherein the treatment increases hemoglobin levels.

10. The method of claim 9, wherein the treatment results in an increase in hemoglobin of ≥1.5 g/dL for ≥two weeks.

11. The method of claim 9, wherein the treatment results in an increase in hemoglobin of ≥1.5 g/dL for ≥eight weeks.

12. The method of claim 1, wherein the patient has been administered one or more blood cell transfusions prior to the start of treatment.

13. The method of claim 12, wherein the treatment decreases blood cell transfusion burden.

14. The method of claim 13, wherein the treatment decreases blood cell transfusion by ≥50% for at least four weeks relative to the equal time prior to start of treatment.

15. The method of claim 13, wherein the treatment decreases blood cell transfusion by ≥50% for at least eight weeks relative to the equal time prior to start of treatment.

16. The method of claim 1, wherein the patient is a low transfusion burden patient.

17. The method of claim 1, wherein the patient is a high transfusion burden patient.

18. The method of claim 1, wherein the patient has myelodysplastic syndrome.

19. The method of claim 18, wherein the patient has an International Prognostic Scoring System (IPSS) or IPSS-R score of low or intermediate.

20. The method of claim 1, wherein the sideroblastic anemia patient has at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% ring blasts as a percentage of bone marrow erythroid precursors in his or her bone marrow.

21. The method of claim 1, wherein the treatment increases neutrophil levels.

22. The method of claim 1, wherein the patient has bone marrow cells that test positive for one or more mutations in SF3B1.

23. The method of claim 1, wherein the patient has bone marrow cells that test positive for one or more mutations in DNMT3A.

24. The method of claim 1, wherein the patient has bone marrow cells that test positive for one or more mutations in TET2.

25. The method of claim 1, wherein the treatment decreases iron overload.

* * * * *